United States Patent
Kopczynski et al.

(10) Patent No.: US 9,808,420 B2
(45) Date of Patent: Nov. 7, 2017

(54) DRUG DELIVERY DEVICES FOR DELIVERY OF OCULAR THERAPEUTIC AGENTS

(71) Applicant: Novaer Holdings, Inc., Bedminster, NJ (US)

(72) Inventors: Casey Kopczynski, Chapel Hill, NC (US); Cheng-Wen Lin, Durham, NC (US); Chris Sutay, Raleigh, NC (US)

(73) Assignee: Novaer Holdings, INC., Bedminster, NJ (US)

( * ) Notice: Subject to any disclaimer, the term of this patent is extended or adjusted under 35 U.S.C. 154(b) by 0 days.

(21) Appl. No.: 14/978,879

(22) Filed: Dec. 22, 2015

(65) Prior Publication Data

US 2016/0106667 A1     Apr. 21, 2016

Related U.S. Application Data

(62) Division of application No. 13/642,042, filed as application No. PCT/US2011/036806 on May 17, 2011, now abandoned.

(51) Int. Cl.
*A61K 9/51* (2006.01)
*A61K 9/00* (2006.01)
*A61K 31/00* (2006.01)
*A61K 47/32* (2006.01)
*A61K 47/36* (2006.01)
*A61F 9/00* (2006.01)
*A61K 31/215* (2006.01)

(52) U.S. Cl.
CPC .......... *A61K 9/0051* (2013.01); *A61F 9/0017* (2013.01); *A61K 31/00* (2013.01); *A61K 31/215* (2013.01); *A61K 47/32* (2013.01); *A61K 47/36* (2013.01)

(58) Field of Classification Search
CPC .................................................. A61K 9/0051
See application file for complete search history.

(56) References Cited

U.S. PATENT DOCUMENTS

| | | | | |
|---|---|---|---|---|
| 4,052,505 A | * | 10/1977 | Higuchi | A61F 9/0017 424/427 |
| 2004/0208910 A1 | * | 10/2004 | Ashton | A61K 9/0024 424/427 |

* cited by examiner

*Primary Examiner* — Benjamin Packard
(74) *Attorney, Agent, or Firm* — Greenberg Traurig LLP

(57) ABSTRACT

Drug delivery devices comprising a non-bioabsorbable polymer structure configured to support a composition comprising an active agent. The devices include a plurality of portions fused together and a recess configured to support the composition. At least one of the portions includes an impermeable polymer and at least one other portion includes a rate-limiting water-permeable polymer. The rate-limiting water-permeable polymer allows for transportation of the active agent to an exterior of the device.

8 Claims, 96 Drawing Sheets

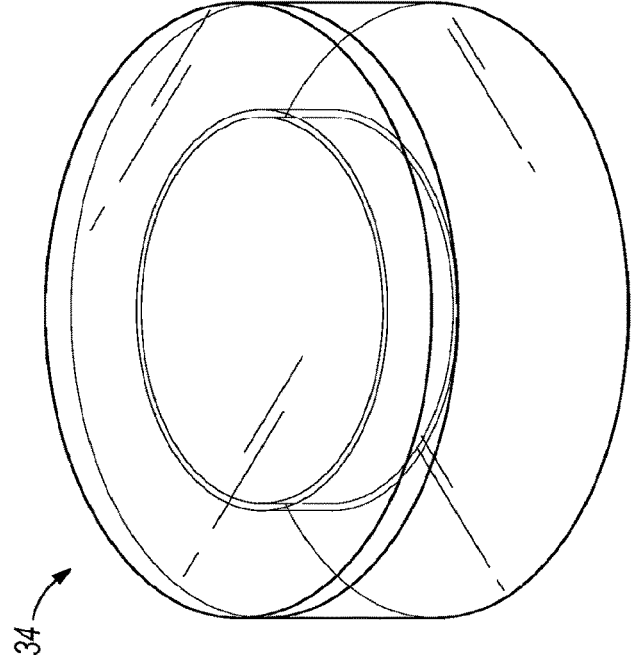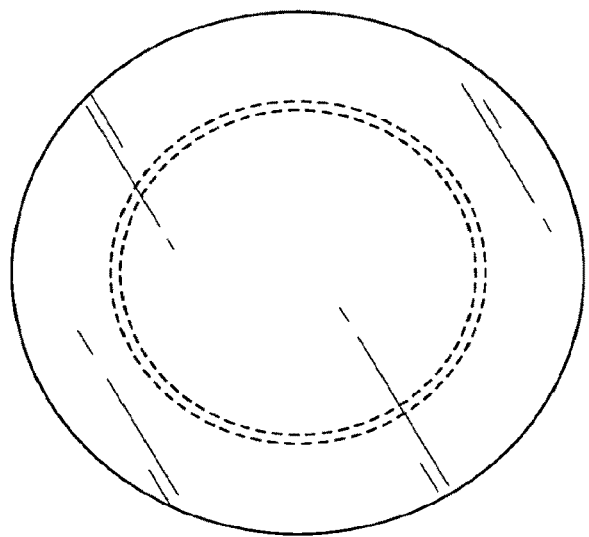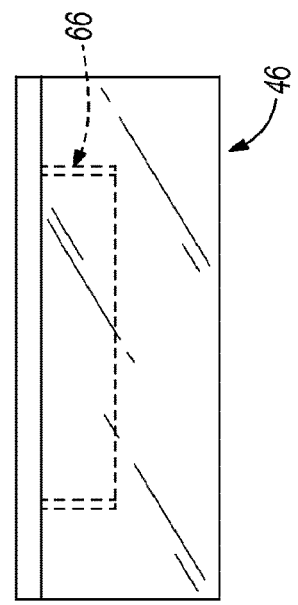
FIG. 4

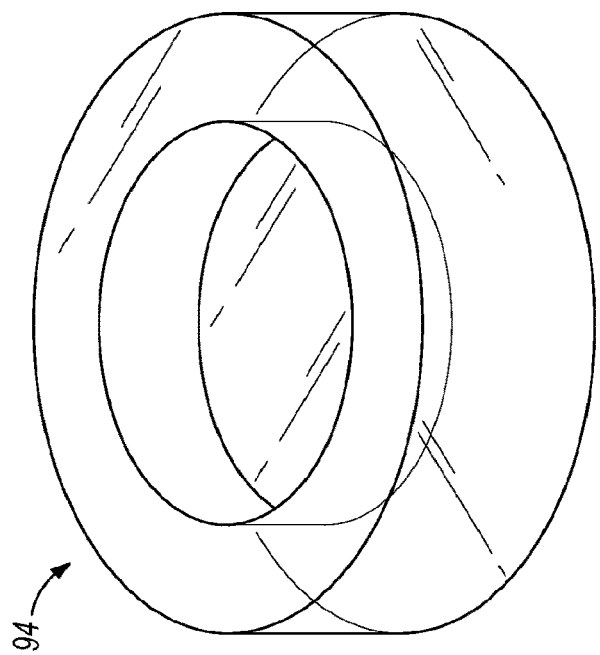
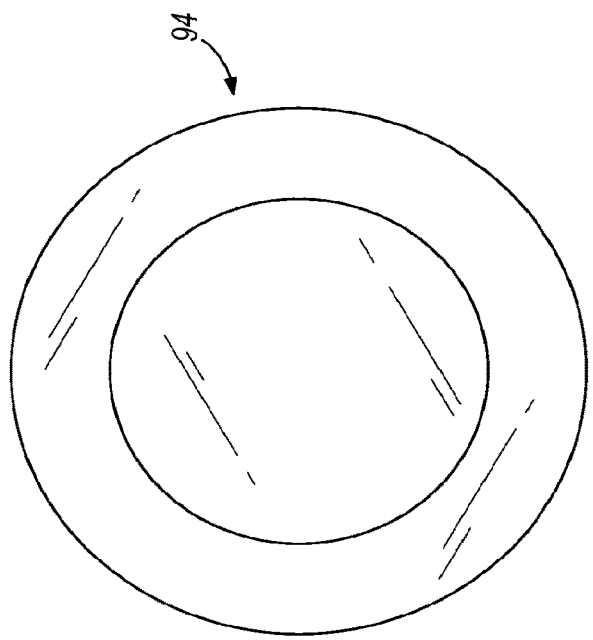
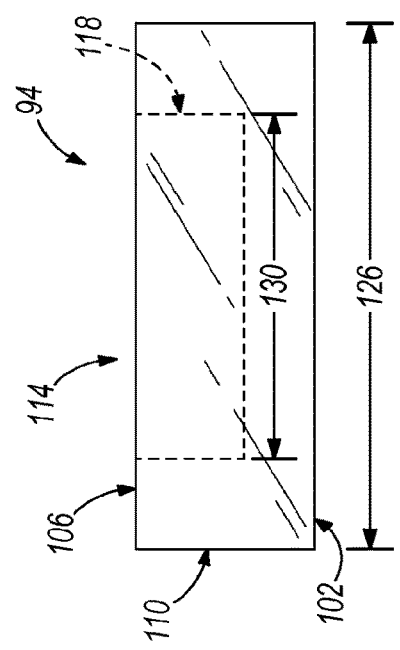
FIG. 12

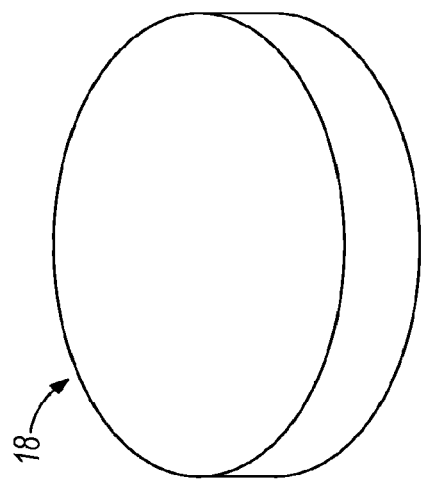
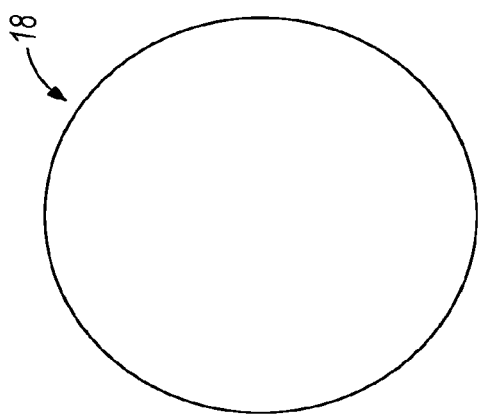
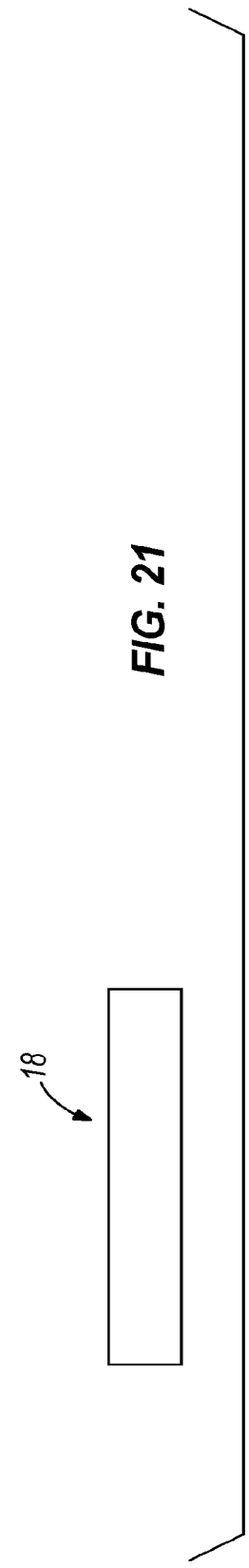
FIG. 21

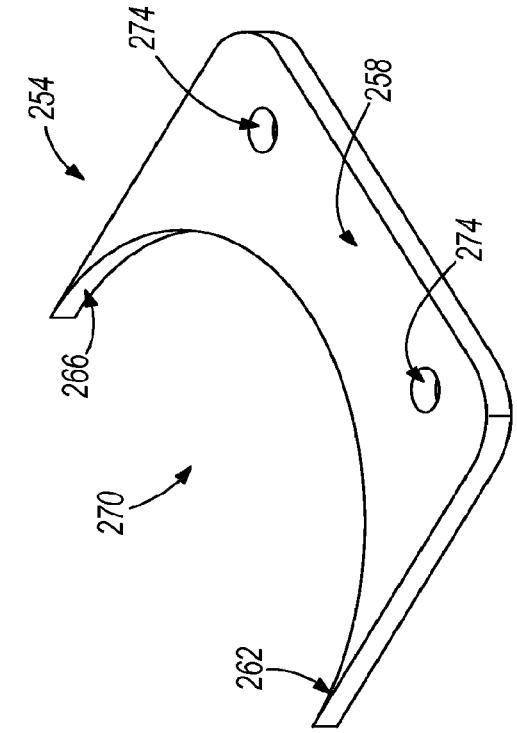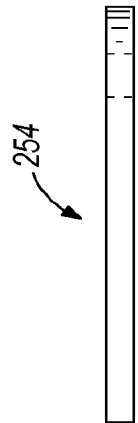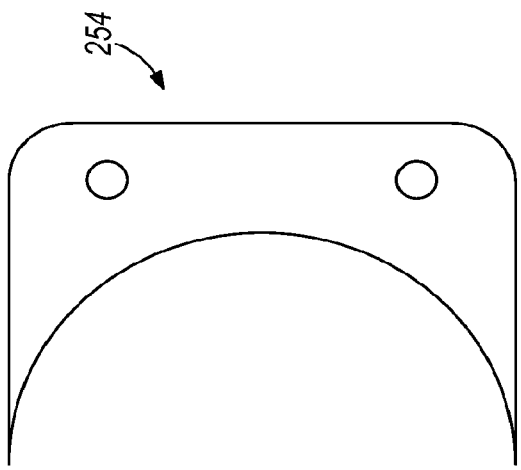
FIG. 24

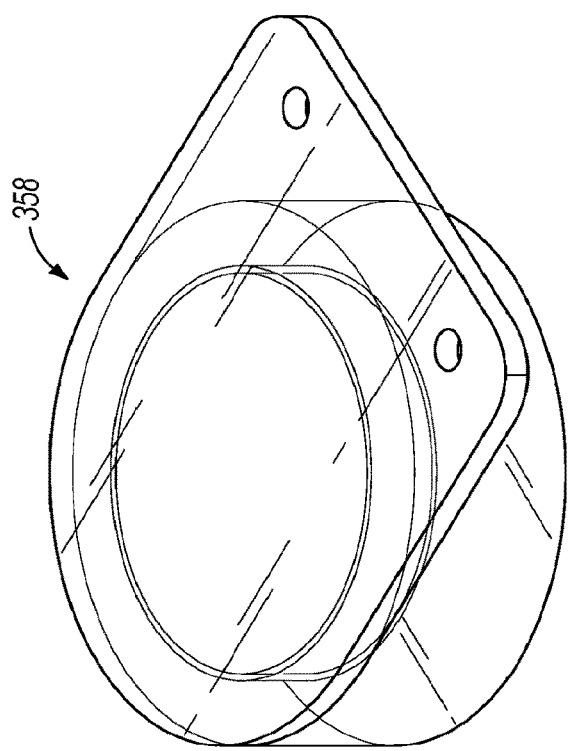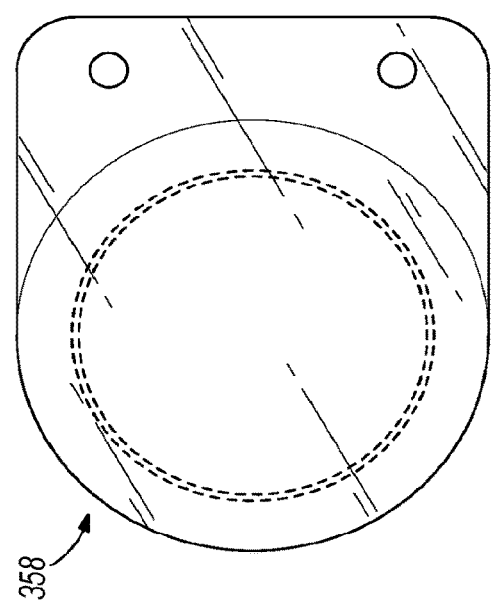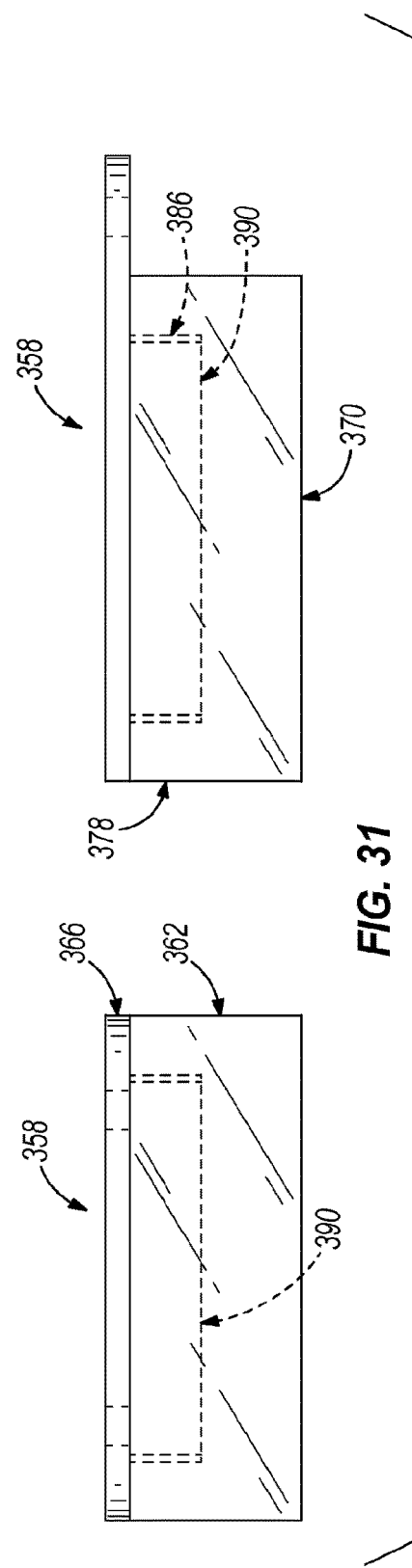
FIG. 31

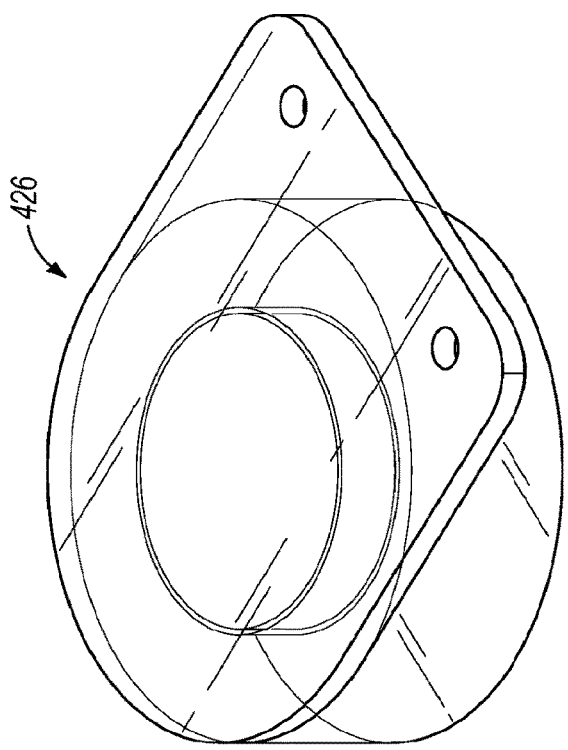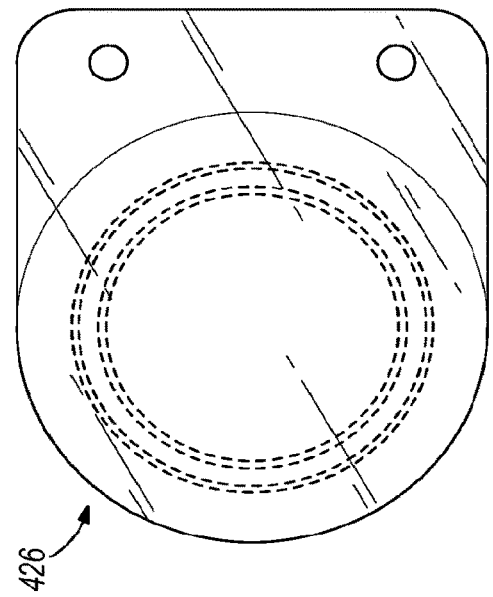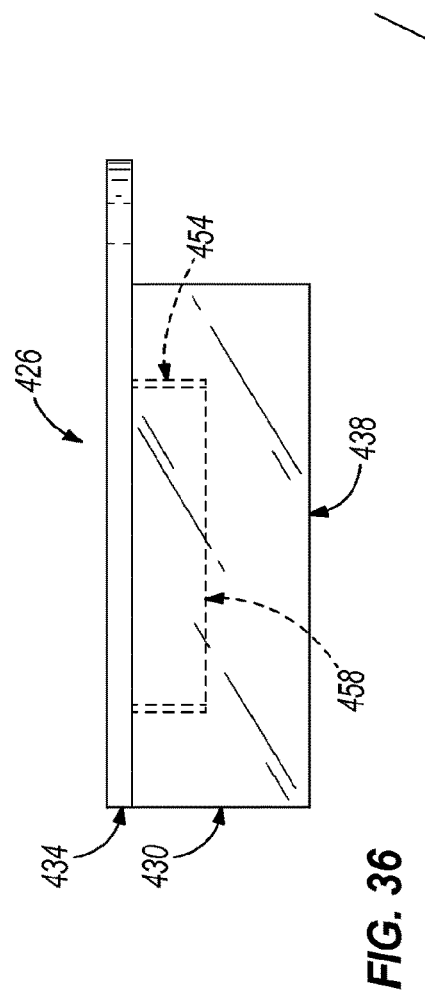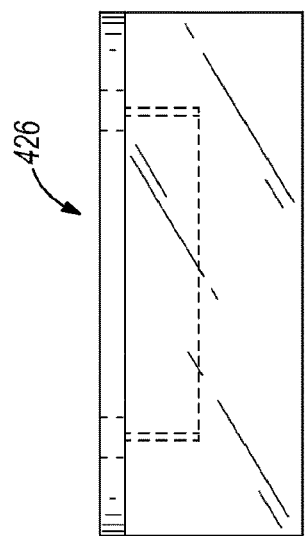
FIG. 36

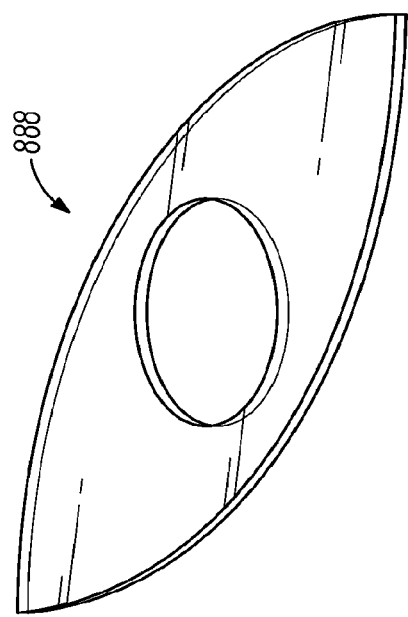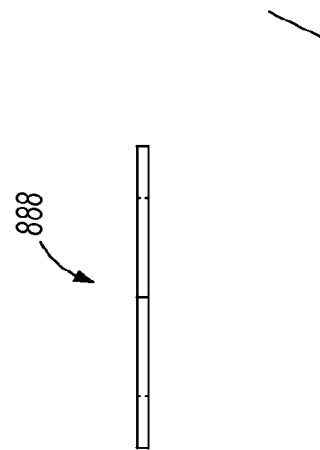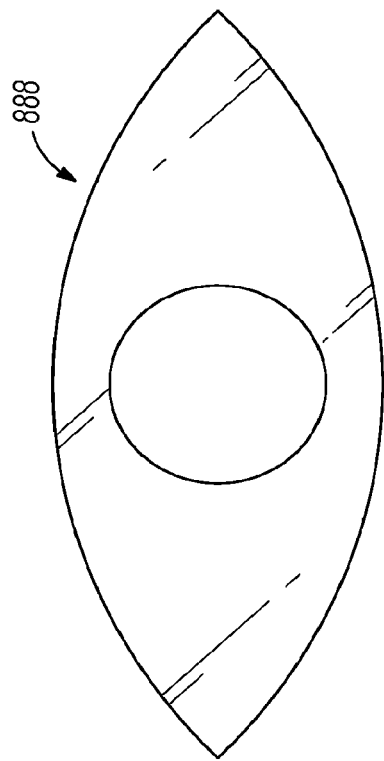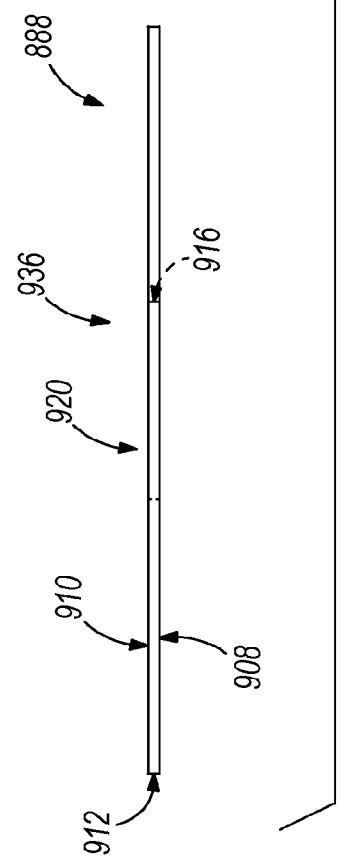
FIG. 69

The release profile of 30 mg dorzolamide HCl
drug delivery device in buffer (pH = 7.4) at 37°C The elution profile of a 30 mg ethacrynic acid sodium salt drug delivery device in buffer (pH = 7.4) at 37°C The IOP-lowering effect of 30 mg ethacrynic acid sodium salt
drug delivery device (n = 4)

The release profile of a 4 mg AR-102 free acid
drug delivery device in buffer (pH = 7.4) at 37°C The IOP-lowering effect of 30 mg AR-102 free acid drug delivery device (n = 2)

The release profile of a 5 mg latanoprost arginine salt
drug delivery device in buffer (pH = 7.4) at 37°C The IOP-lowering effect of 4 mg latanoprost drug delivery device (n = 1)

The release profile of a 30 mg dexamethasone drug delivery device in buffer (pH = 7.4) at 37°C The release profile of a 30 mg dexamethasone sodium phosphate drug delivery device in buffer (pH = 7.4) at 37°C The release profile of a 20 mg brimonidine free base
drug delivery device in buffer (pH = 7.4) at 37°C The IOP-lowering effect of 20 mg brimonidine free base drug delivery device (n = 5)

The release profile of a 30 mg brimonidine D-tartrate drug delivery device in buffer (pH = 7.4) at 37°C The release profile of a 30 mg timolol maleate implant in buffer (pH = 7.4) at 37°C Sustained IOP-lowering effect of timolol maleate
drug delivery devices in Dutch-belted rabbits (n =2)

Solubility classification of non-steroidal anti-inflammatory drugs (NSAID)

| Compound | Solubility at pH 7.4 (mg/ml) | Solubility classification |
|---|---|---|
| Diclofenac | 15.9 | High |
| Etodolac | 4.5 | High |
| Indomethacin | 1.3 | High |
| Ketorolac | >1.3 | High |
| Sulindac | >1.3 | High |
| Tolmetin | >10 | High |
| Fenoprofen | >3.1 | High |
| Flurbiprofen | 2.6 | High |
| Ibuprofen | 2.3 | High |
| Ketoprofen | >1.4 | High |
| Naproxen | >2.5 | High |
| Oxaprozin | 1.7 | High |
| Mefenamic acid | 0.1 | Low |
| Acetyle-salicylic acid | 6.4 | High |
| Diflunisal | 2.4 | High |
| Salicylic acid | >8 | High |
| Meloxicam | 0.46 | Medium |
| Piroxicam | 0.26 | Low |
| Celecoxib | 0.005 | Low |
| Rofecoxib | 0.0009 | Low |

FIG. 97

DRUG DELIVERY DEVICES FOR DELIVERY OF OCULAR THERAPEUTIC AGENTS

RELATED APPLICATIONS

This application in a non-provisional application of and claims priority to provisional patent application No. 61/345,547, filed on May 17, 2010, the entire contents of which are incorporated herein by reference.

FIELD OF THE INVENTION

The present invention relates to a drug delivery device for sustained delivery of therapeutic agents to target tissues. In particular, it relates to a non-biodegradable, drug-eluting removable device for the purpose of treating various diseases and conditions. More particularly, but not by way of limitation, this device is well-suited for episcleral or supraconjunctival delivery of pharmaceutical agents for the treatment of glaucoma and ocular hypertension.

BACKGROUND OF THE INVENTION

The delivery of therapeutic and pharmaceutical agents is a complex problem without a single universal solution. Many chronic diseases and conditions can be treated effectively by oral medications, but side effects, patient forgetfulness, and other factors often produce high rates of non-compliance with the recommended treatment. In such cases, patient outcomes can be improved using sustained delivery formulations that simplify the medication regimen (e.g., Lupron Depot® for endometriosis).

Where possible, diseases and conditions that affect only a single organ or local tissue are preferably treated by a local application. This allows for a relatively high concentration of the therapeutic agent at the site where it is most needed, and allows for minimal systemic exposure. However there are relatively few tissues that are directly accessible, with skin, hair follicles, the oral, nasal and genitourinary cavities, and eyes being candidates for direct application of therapeutic agents. Direct application of therapeutic agents to internal organs is more challenging, but has been useful in the treatment of some types of tumors.

In the treatment of ocular conditions in particular, many medications are now delivered topically to the eye as eyedrops. Despite the success of the eyedrop in treating diseases and conditions of the eye, treatment with topical eyedrops suffers from numerous drawbacks.

A significant drawback of the eyedrop is the requirement that the pharmaceutical agent be soluble in an isotonic buffered solution at a therapeutically effective concentration and be chemically stable in solution for 18 months or longer. However, solubility of useful therapeutic agents in aqueous formulation is often well below the concentration needed for effective treatment. This can sometimes be corrected by the addition of various excipients, but this increases the complexity of the formulation and often reduces tolerability of the eyedrop.

A second limitation of eyedrops is the rapid clearance of the therapeutic agent via nasolacrimal drainage from the eye surface. This results in most of the compound being delivered to the inside of the nose, where it is not needed and where, in fact, a high concentration of agent might have a detrimental effect.

A third limitation to the use of eyedrops is the observation that many therapeutically-valuable agents cause a local irritation when topically-dosed to the eye. The cornea of the eye is highly sensitive to the application of chemical agents. This irritation potential significantly limits the use of many otherwise valuable therapeutic agents.

A fourth limitation of eyedrops, which also applies to systemic drugs taken by oral, sublingual, nasal or rectal delivery routes, is the need to re-apply the therapeutic agent on a regular basis. For eyedrops, repeating application as frequently as four times a day can be necessary, and even the best agents must be reapplied on a daily basis. For many individuals, in particular the elderly, this frequent dosing becomes burdensome and leads to non-compliance with the dosing regimen, lessening the therapeutic value of the treatment.

To counter these disadvantages of eyedrop delivery, researchers have suggested various devices aimed at providing local delivery over a longer period of time. U.S. Pat. No. 5,824,072 to Wong discloses a non-biodegradable implant containing a pharmaceutical agent that diffuses through a water-impermeable polymer matrix into the target tissue. The implant is placed in the tear film or in a surgically-induced avascular region, or in direct communication with the vitreous.

U.S. Pat. No. 5,476,511 to Gwon et al. discloses a polymer implant for placement under the conjunctiva of the eye. The implant is claimed to be useful for the delivery of neovascular inhibitors for the treatment of age-related macular degeneration (AMD). Again, the pharmaceutical agent diffuses through a water-impermeable polymer matrix of the implant.

U.S. Pat. No. 5,773,019 to Aston et al. discloses a non-biodegradable implant for the delivery of steroids and immunosuppressives such as cyclosporine for the treatment of uveitis, with the drug again diffusing through the water-impermeable polymer matrix of the implant.

U.S. Pat. No. 3,854,480 to Zaffaroni discloses a drug-delivery system with a solid inner matrix formulation containing solid particles of drug surrounded by an outer polymer membrane that is permeable to the passage of the drug. While both the inner matrix and the outer wall are claimed to be permeable to the passage of drugs, the patent requires that the rate of diffusion of the outer membrane be not more than 10% of the rate of the inner matrix.

Both U.S. Pat. No. 4,281,654 to Shell, et al. and U.S. Pat. No. 4,190,642 to Gale, et al. disclose matrix polymer systems that are designed to deliver either beta-blockers or a combination of epinephrine and pilocarpine to the eye to treat glaucoma. Gale, et al. micronize their medicaments to a particle size of not more than 100 microns and these are subsequently dispersed throughout the entire polymer matrix, with no distinct cavity that contains the drug and no drug-free outer layer. In addition, both Shell and Gale require the walls surrounding these small depots be ruptured by the force of the osmotic pressure in order to release the drug by way of those formed ruptures.

All of the above-referenced patents and publications are hereby incorporated herein by reference.

SUMMARY OF THE INVENTION

In one aspect, the present invention provides an implantable device comprising a first portion including a recess configured to support a composition comprising an active agent, the first portion comprising an impermeable polymer and a second portion fused to the first portion, the second portion comprising a rate-limiting water-permeable polymer that allows for transportation of the active agent to an exterior of the device.

In one embodiment, the present invention includes a device for insert in the eye. The device comprises a first portion including a recess configured to support a composition comprising an active agent, the first portion comprising an impermeable polymer; and a second portion fused to the first portion, the second portion comprising a rate-limiting water-permeable polymer that allows for transportation of the active agent to an exterior of the device.

In another embodiment, the present invention includes a device for insert in the eye. The device comprises a first portion including a recess configured to support a composition comprising an active agent, the first portion comprising an impermeable polymer; a second portion fused to the first portion, the second portion comprising a rate-limiting water-permeable polymer that allows for transportation of the active agent to an exterior of the device; and a flange fused to the second portion.

In a further embodiment, the present invention includes a device for insert in the eye. The device comprises a first portion including a recess configured to support a composition comprising an active agent, the first portion comprising an impermeable polymer; and a second portion fused to the first portion, the second portion including a base and a flange integral with the base, the second portion comprising a rate-limiting water-permeable polymer that allows for transportation of the active agent to an exterior of the device.

In yet another embodiment, the present invention includes a device for insert in the eye. The device comprises a first portion comprising a rate-limiting water-permeable polymer; a second portion fused to the first portion, the second portion including a recess configured to support a composition comprising an active agent, the second portion comprising a rate-limiting water-permeable polymer; and a third portion fused to the second portion, the third portion comprising a rate-limiting water-permeable polymer. The rate-limiting water-permeable polymer allows for transportation of the active agent to an exterior of the device.

In another embodiment, the present invention includes a method of treating an ocular condition comprising suturing an embodiment of one of the devices disclosed herein to the conjunctiva of the eye.

In a further embodiment, the present invention includes a method of treating an ocular condition comprising implanting episclerally or supraconjunctivally a drug delivery device comprising an active agent, wherein the active agent is released at a rate of about 0.0001 to about 200 micrograms/hr.

Other aspects of the invention will become apparent by consideration of the detailed description and accompanying drawings.

BRIEF DESCRIPTION OF THE DRAWINGS

FIG. 4 illustrates several drawings of a drug delivery device according to one embodiment of the present invention.

FIG. 12 illustrates several drawings of a portion of the drug delivery device illustrated in FIG. 9.

FIG. 21 illustrates several drawings of a composition supported by the drug delivery device illustrated in FIG. 19.

FIG. 24 illustrates several drawings of a portion of the drug delivery device illustrated in FIG. 19.

FIG. 31 illustrates several drawings of a drug delivery device according to one embodiment of the present invention.

FIG. 36 illustrates several drawings of a drug delivery device according to one embodiment of the present invention.

FIG. 69 illustrates several drawings of a portion of the drug delivery device illustrated in FIG. 66.

FIG. 97 shows solubility characteristics for various active agents.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first," "second," and "third" are used herein for purposes of description and are not intended to indicate or imply relative importance or significance.

Figure 1:
FIG. 1 shows a drug delivery device according to one embodiment of the present invention.

FIG. 1 illustrates a drug delivery device 10 according to one embodiment of the present invention. The drug delivery device 10 comprises a non-bioabsorbable polymer structure 14 which encloses a composition 18 comprising an active agent. The active agent is released through the polymer structure once the drug delivery device is implanted in the desired portion of the body.

The non-bioabsorbable polymer structure 14 comprises, in one embodiment shown in FIG. 1, a mixture comprising a water-soluble polymer and a non-water soluble polymer with about 0% to about 50% by weight of the mixture being the water-soluble polymer or about 10% to about 30% by weight. Suitably, the drug delivery device 10 at least partially bioerodes when implanted in the body as the water-soluble polymer dissolves leaving a porous non-bioabsorbable polymer structure through which the active agent is released. The polymer structure 14 suitably has a thickness of about 20 micrometers to about 800 micrometers or about 40 micrometers to about 500 micrometers or about 50 micrometers to about 250 micrometers, depending on the overall size and required mechanical strength of the device 10.

The non-water soluble polymer may be selected from ethylene vinyl acetate (EVA), silicon rubber polymers, polydimethylsiloxane (PDMS), polyurethane (PU), polyesterurethanes, polyetherurethanes, polyolefins, polyethylenes (PE), low density polyethylene (LDPE), polypropylene (PP), polyetheretherketone (PEEK), polysulfone (PSF), polyphenylsulfone, polyacetals, polymethyl methacrylate (PMMA), polybutymethacrylate, plasticized polyethyleneterephthalate, polyisoprene, polyisobutylene, silicon-carbon copolymers, natural rubber, plasticized soft nylon, polytetrafluoroethylene (PTFE), or combinations thereof. Suitably, the non-water soluble polymer is EVA. The vinyl acetate content may be from about 9% to about 50% by weight (EVA-9-50). In one embodiment, the vinyl acetate content is about 40% by weight (EVA-40). Other suitable non-water soluble polymers are known to those of ordinary skill in the art.

The water-soluble polymer may be selected from dextran, cyclodextrin, poly-(L-lactic acid), polycaprolactone, poly(lactic-co-glycolic acid), poly(glycolic acid), poly(trimethylene carbonate), polydioxanone or combinations thereof. Other suitable water-soluble polymers are known to those of ordinary skill in the art.

Figure 2:
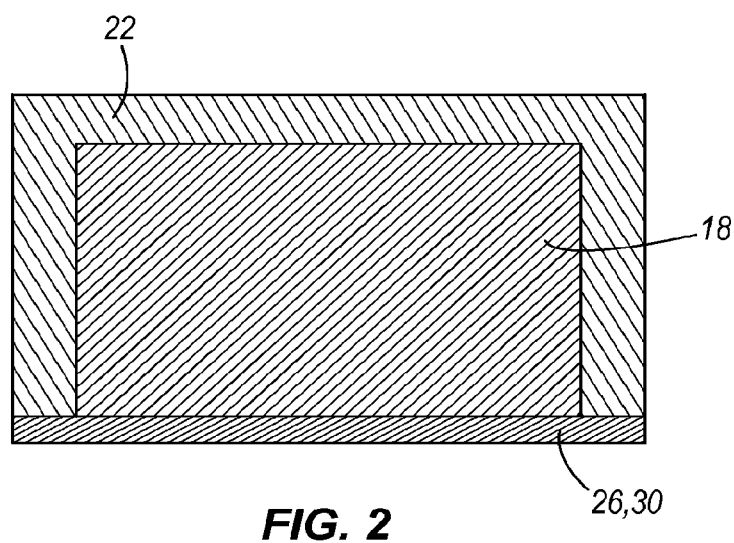
FIG. 2 shows a drug delivery device according to one embodiment of the present invention.

Alternatively, in an embodiment shown in FIG. 2, the non-bioabsorbable polymer structure 14 comprises an impermeable polymer 22 and a partially-bioerodible membrane 26. Suitably, about 0% to about 50% by weight of the polymer structure 14 is the partially-bioerodible membrane 26 or about 10% to about 30% by weight of the partially-bioerodible membrane 26. The impermeable polymer 22 does not allow the passage of the active agent and provides mechanical strength for the device 10. The impermeable polymer 22 suitably has a thickness of about 50 micrometers to about 800 micrometers or about 100 micrometers to about 250 micrometers, depending on the overall size and required mechanical strength of the device 10. The partially-bioerodible membrane 26 suitably has a thickness of about 20 micrometers to about 800 micrometers or about 40 micrometers to about 500 micrometers, depending on the overall size and required mechanical strength of the device 10.

Suitable impermeable polymers 22 include, but are not limited to, EVA-9-50, silicon rubber polymers, polydimethylsiloxane (PDMS), polyurethane (PU), polyesterurethanes, polyetherurethanes, polyolefins, polyethylenes (PE), low density polyethylene (LDPE), polypropylene (PP), polyetheretherketone (PEEK), polysulfone (PSF), polyphenylsulfone, polyacetals, polymethyl methacrylate (PMMA), polybutylmethacrylate, plasticized polyethyleneterephthalate, polyisoprene, polyisobutylene, silicon-carbon copolymers, natural rubber, plasticized soft nylon, polytetrafluoroethylene (PTFE), or combinations thereof. Other suitable impermeable polymers 22 are known to those of ordinary skill in the art.

In some embodiments, the partially-bioerodible membrane 26 comprises an impermeable polymer and a bioerodible polymer. Suitably, the partially-bioerodible membrane 26 contains about 0% to about 50% by weight of the bioerodible polymer. Suitable bioerodible polymers include, but are not limited to, dextran, cyclodextrin, poly-(L-lactic acid), polycaprolactone, poly(lactic-co-glycolic acid), poly(glycolic acid), poly(trimethylene carbonate), polydioxanone, or combinations thereof. Other suitable bioerodible polymers are known to those of ordinary skill in the art.

In another embodiment also encompassed by FIG. 2, the non-bioabsorbable polymer structure 14 comprises an impermeable polymer 22 and a rate-limiting water-permeable polymer 30. Suitably, the polymer structure contains about 0% to about 50% by weight of the rate-limiting water-permeable polymer or about 10% to about 30% by weight of the rate-limiting water-permeable polymer. The impermeable polymer 22 does not allow the passage of the active agent and provides mechanical strength for the device 10. The impermeable polymer 22 suitably has a thickness of about 50 micrometers to about 800 micrometers or about 100 micrometers to about 250 micrometers, depending on the overall size and required mechanical strength of the device 10.

Suitable impermeable polymers 22 include, but are not limited to, EVA-9-50, silicon rubber polymers, polydimethylsiloxane (PDMS), polyurethane (PU), polyesterurethanes, polyetherurethanes, polyolefins, polyethylenes (PE), low density polyethylene (LDPE), polypropylene (PP), polyetheretherketone (PEEK), polysulfone (PSF), polyphenylsulfone, polyacetals, polymethyl methacrylate (PMMA), polybutylmethacrylate, plasticized polyethyleneterephthalate, polyisoprene, polyisobutylene, silicon-carbon copolymers, natural rubber, plasticized soft nylon, polytetrafluoroethylene (PTFE), or combinations thereof. Other suitable impermeable polymers 22 are known to those of ordinary skill in the art.

The rate-limiting water-permeable polymer 30 is a polymer that allows for the passage of active agent and water or tissue fluids. The composition and/or thickness of this polymer determines the rate of release from the drug delivery device. The water-permeable polymer 30 has limited water permeability which only allows water passage into the drug core 18 at a very slow rate. Once water penetrates the polymer 30 into the enclosed drug core 18, it then serves as a solvent to dissolve the active agent to its solubility limit. Therefore, the active agent suitably has low or moderate solubility. In one embodiment, the majority of the active agent remains as a solid compressed form and the concentration of the dissolved aqueous portion remains at its solubility limit, so that the concentration gradient across the polymer remains substantially constant, given that the clearance rate is sufficient in the environment. Without wishing to be bound by theory, in one embodiment the above described mechanisms allow this polymer to provide the rate-limiting steps that allow the active agent to be released at a substantially constant rate until at least about 70% to at most about 95% of the active agent is released from the drug delivery device. The rate-limiting water-permeable polymer 30 suitably has a thickness of about 20 micrometers to about 500 micrometers, depending on the overall size and required mechanical strength of the device 10.

Suitable rate-limiting water-permeable polymers 30 may be selected from ethylene vinyl acetate with a vinyl acetate content of about 26% to about 80% by weight (EVA-26-80) or ethylene vinyl alcohol with a vinyl alcohol content of about 40% to about 80% by weight (EVOH-40-80). Suitable rate-limiting water-permeable polymers 30 may be copolymers that have both hydrophobic and hydrophilic monomers where the hydrophilic portion allows the passage of water or tissue fluids and the hydrophobic portion limits its water-permeability in order to provide the rate-limiting barrier. Other suitable rate-limiting water-permeable polymers are known to those of ordinary skill in the art.

In some embodiments, the drug delivery device 10 has a cylindrical structure. Suitably, the cylindrical structure comprises a cylindrical wall, a top and a bottom. The top and the bottom are coupled to opposite sides of the cylindrical wall. In some embodiments, the cylindrical wall and top comprise the impermeable polymer 22 and the bottom comprises the partially-bioerodible membrane 26 or rate-limiting water-permeable polymer 30. In other embodiments, drug delivery device 10 can be spherical, tubular, rod-shaped, or the like.

Figure 3:
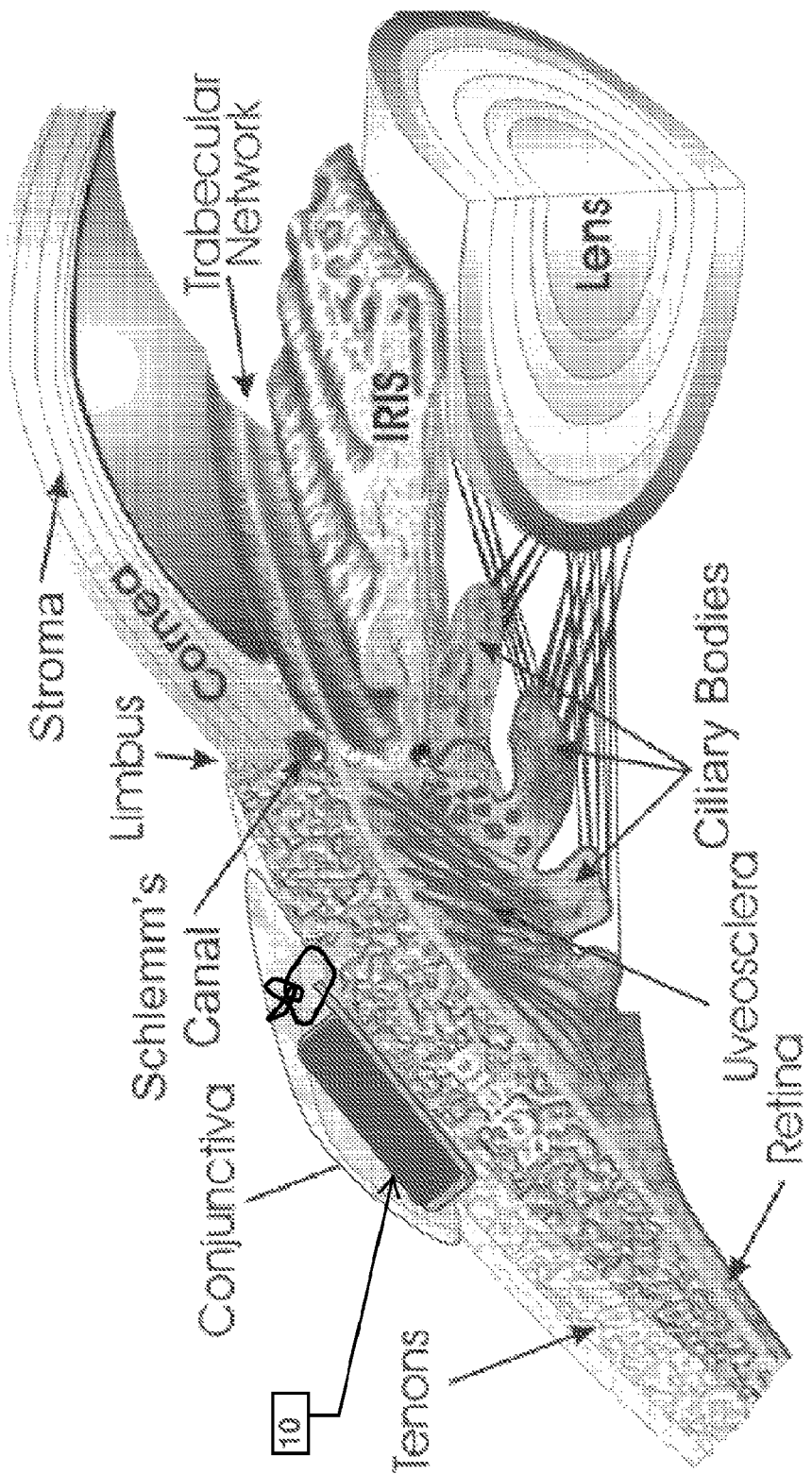
FIG. 3 illustrates a cross-sectional view of the eye with a drug delivery device according to one embodiment of the present invention inserted in the eye.
Figure 5:
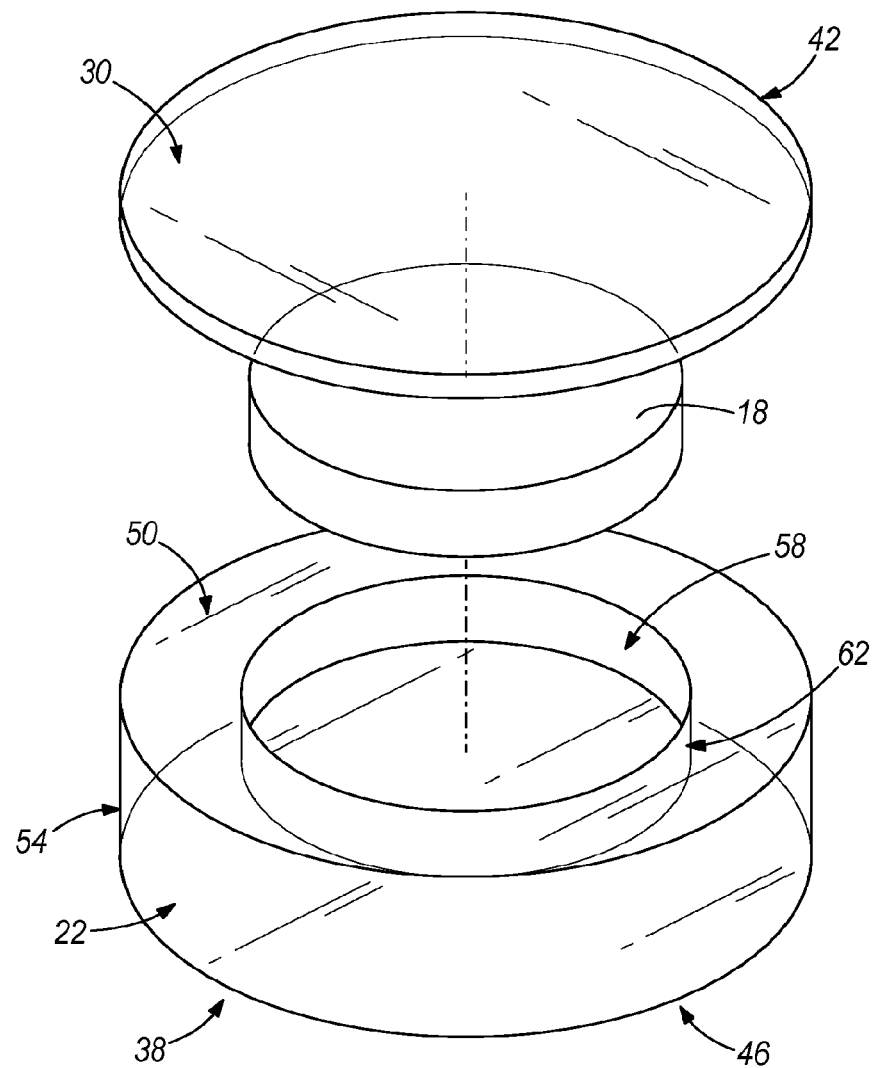
FIG. 5 is an exploded view of the drug delivery device illustrated in FIG. 4.
Figure 6:
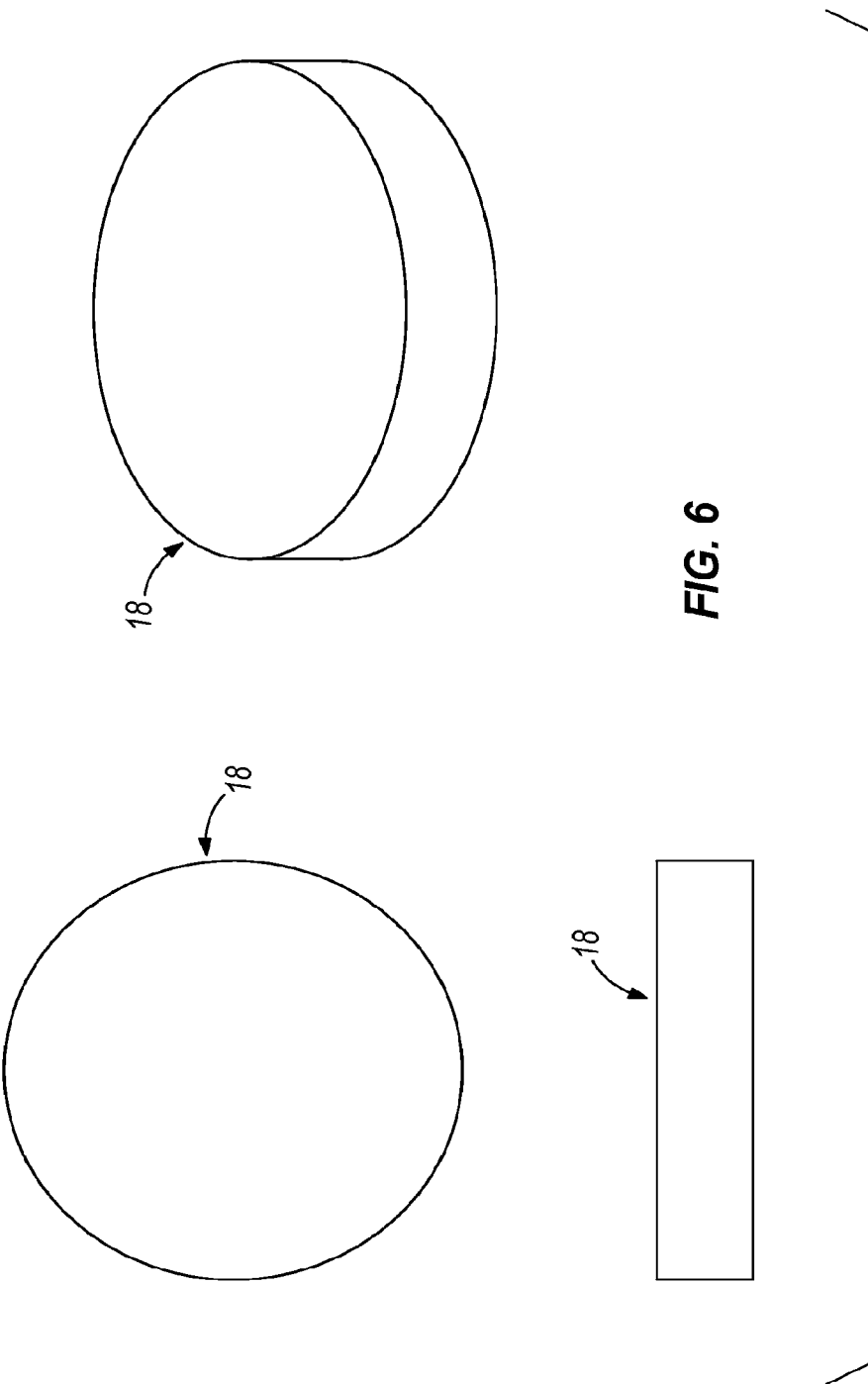
FIG. 6 illustrates several drawings of a composition supported by the drug delivery device illustrated in FIG. 4.
Figure 7:
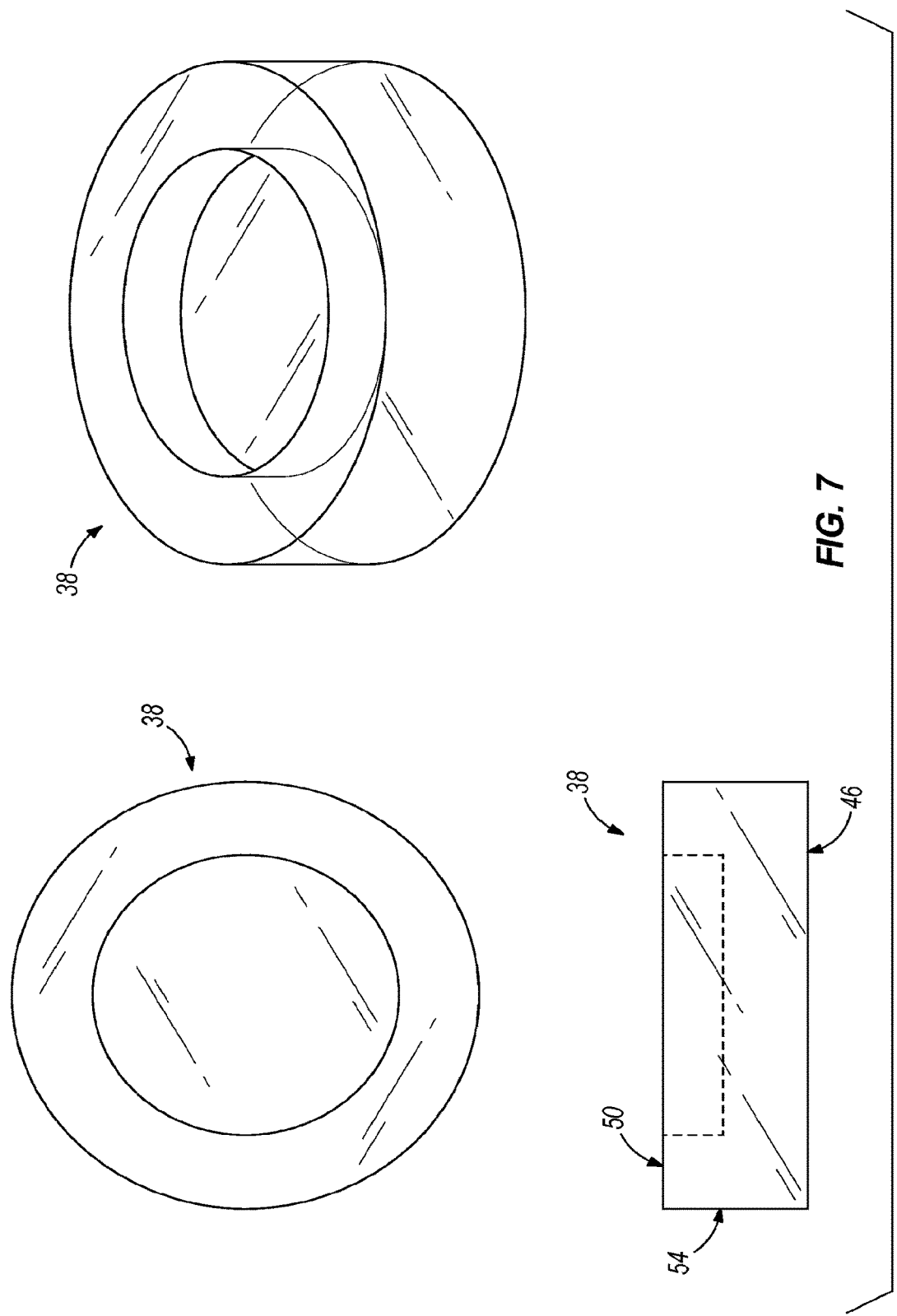
FIG. 7 illustrates several drawings of a portion of the drug delivery device illustrated in FIG. 4.
Figure 8:
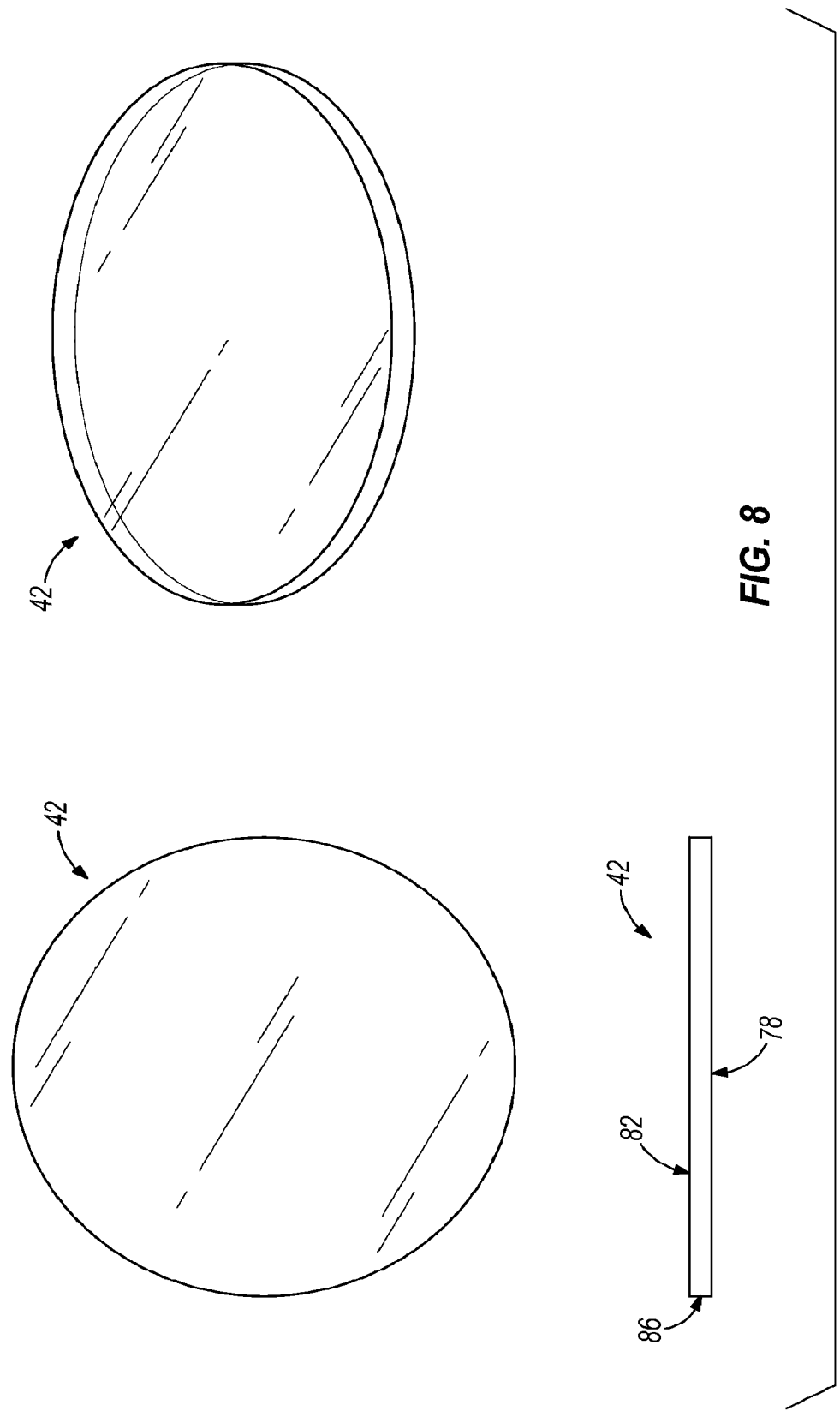
FIG. 8 illustrates several drawings of a portion of the drug delivery device illustrated in FIG. 4.
Figure 9:
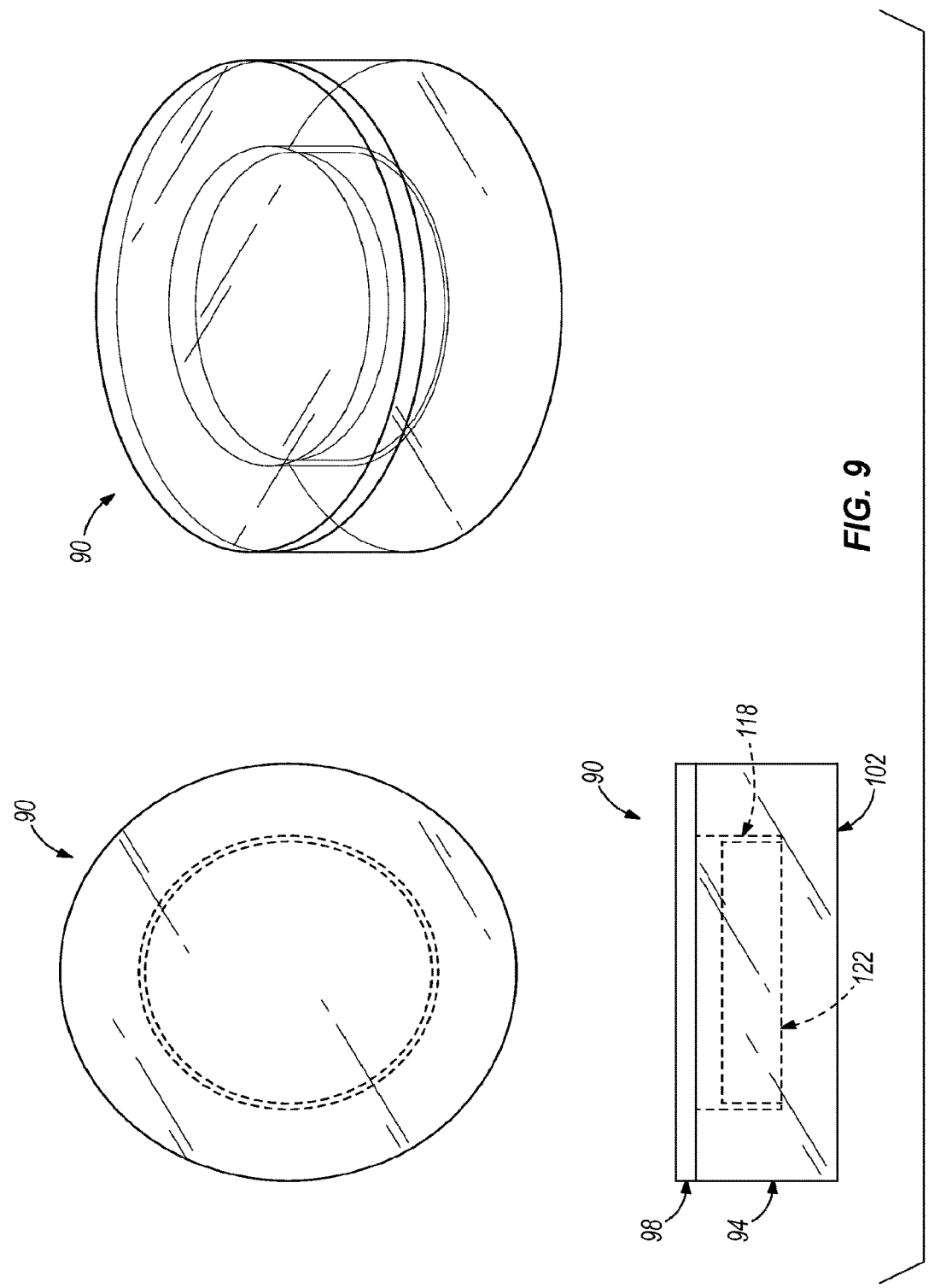
FIG. 9 illustrates several drawings of a drug delivery device according to one embodiment of the present invention.
Figure 10:
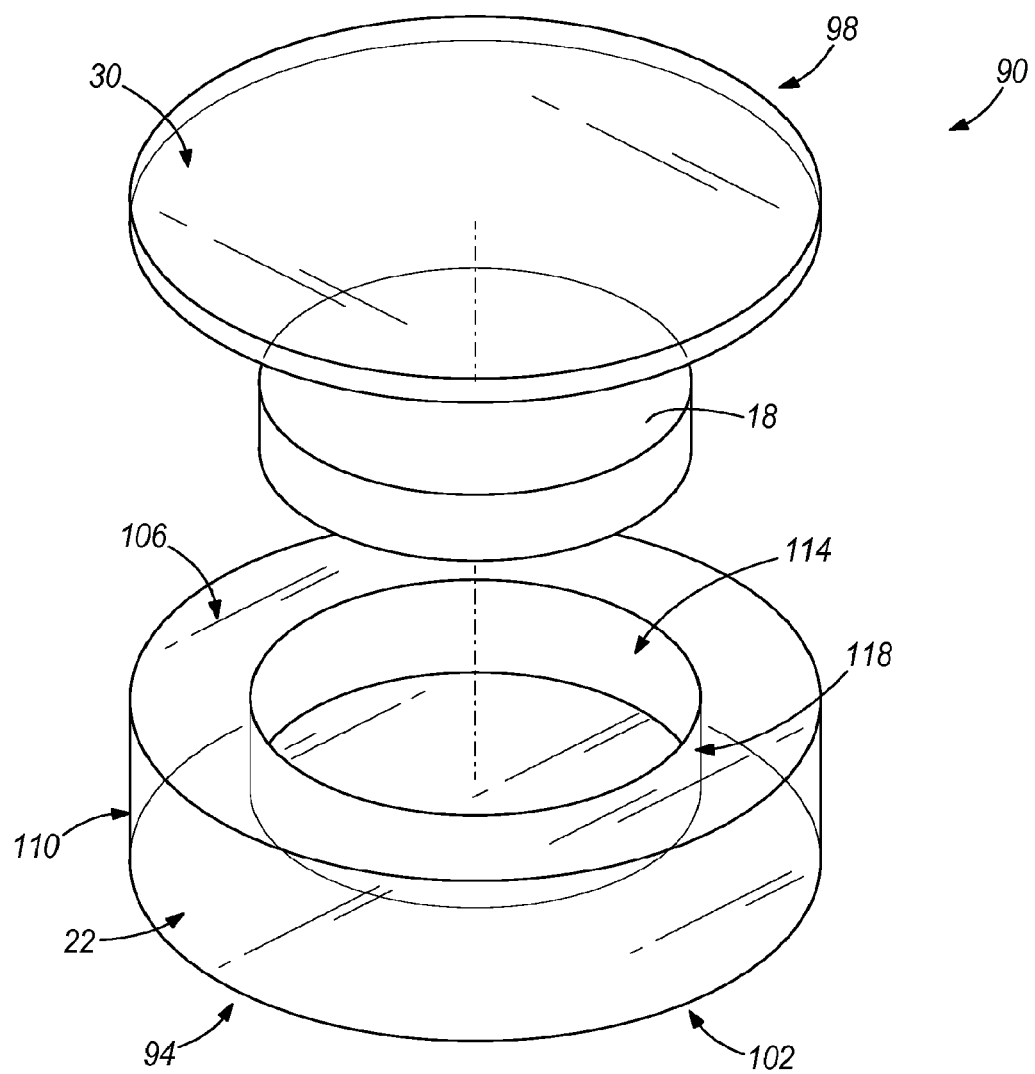
FIG. 10 is an exploded view of the drug delivery device illustrated in FIG. 9.
Figure 11:
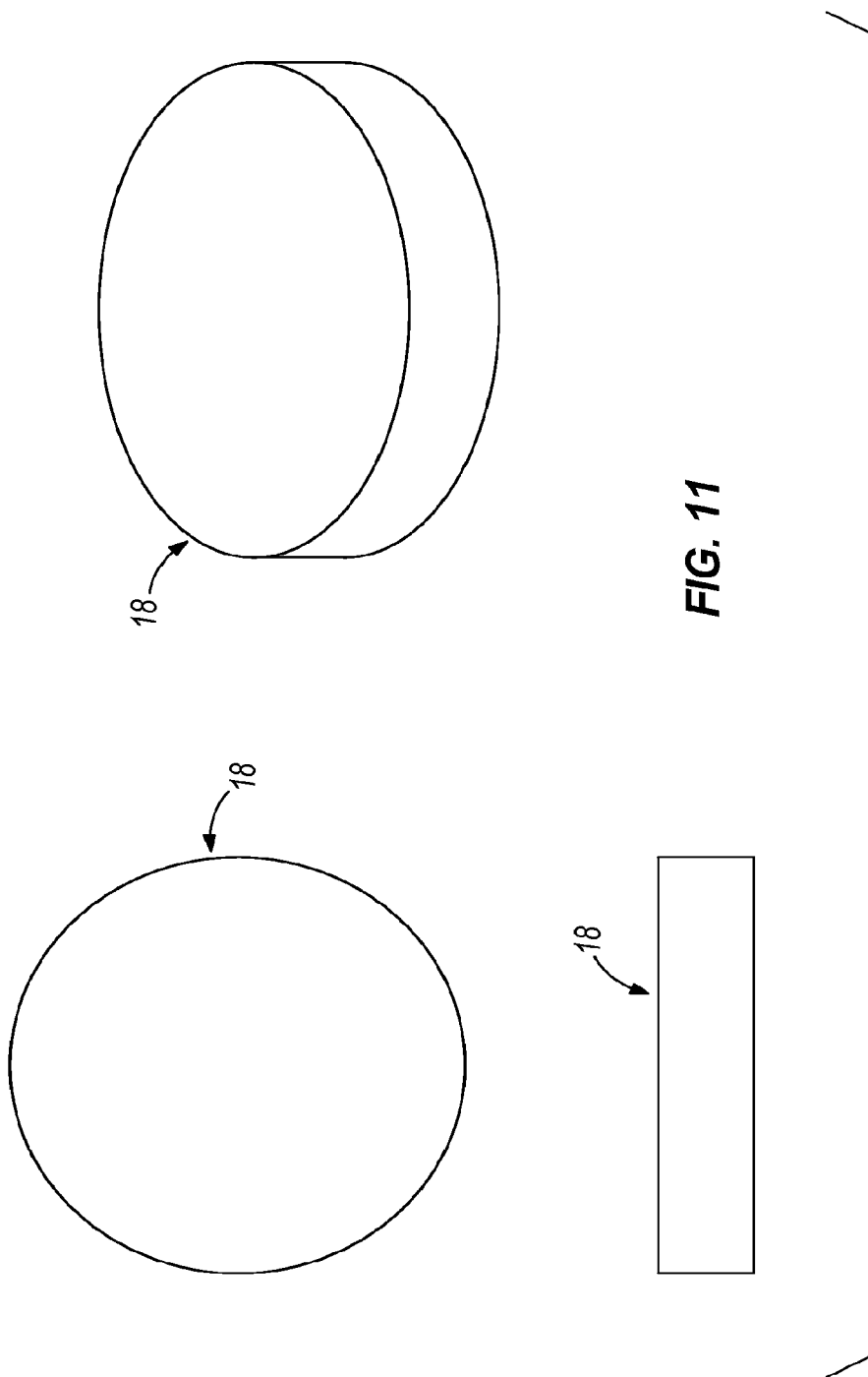
FIG. 11 illustrates several drawings of a composition supported by the drug delivery device illustrated in FIG. 9.
Figure 13:
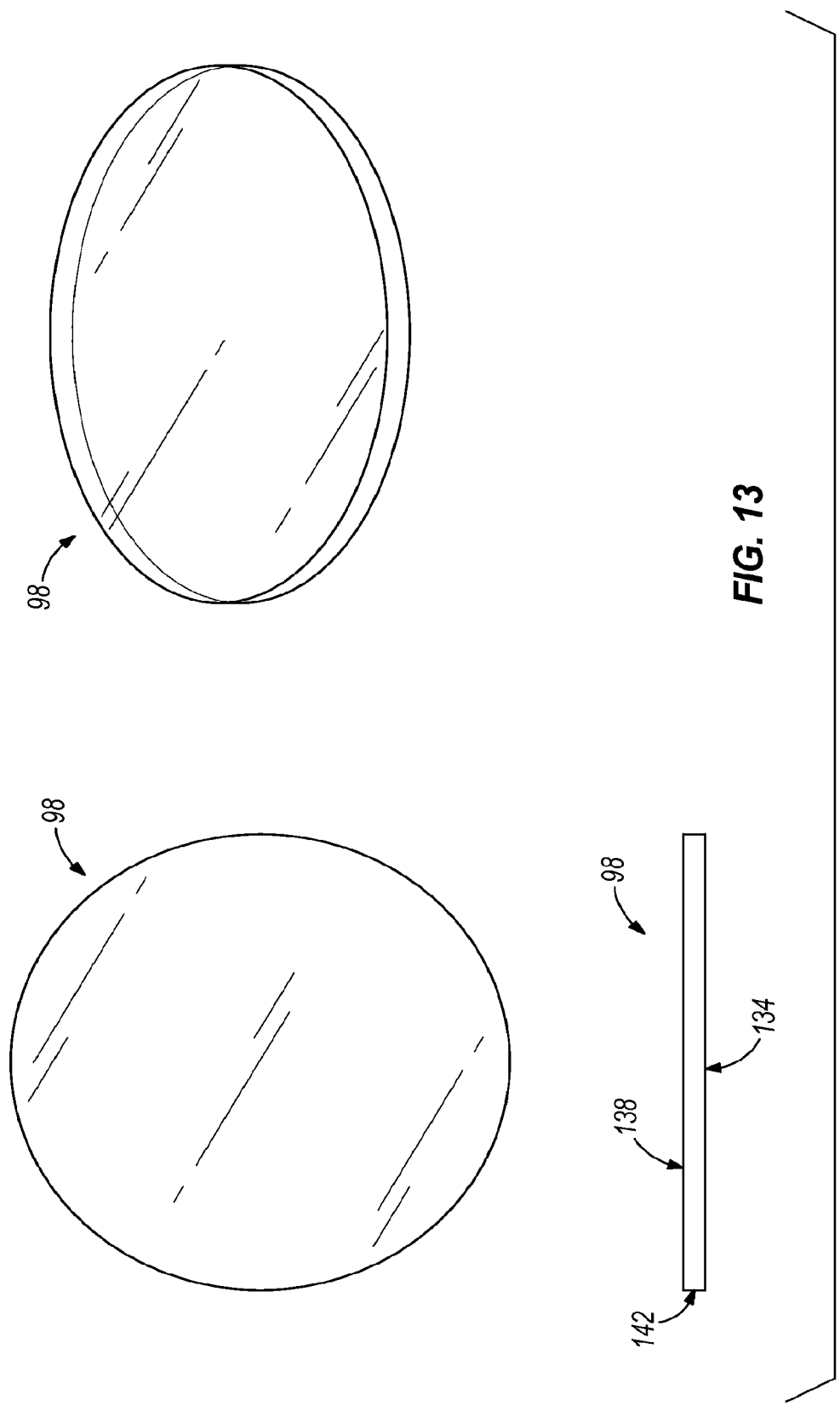
FIG. 13 illustrates several drawings of a portion of the drug delivery device illustrated in FIG. 9.
Figure 14:
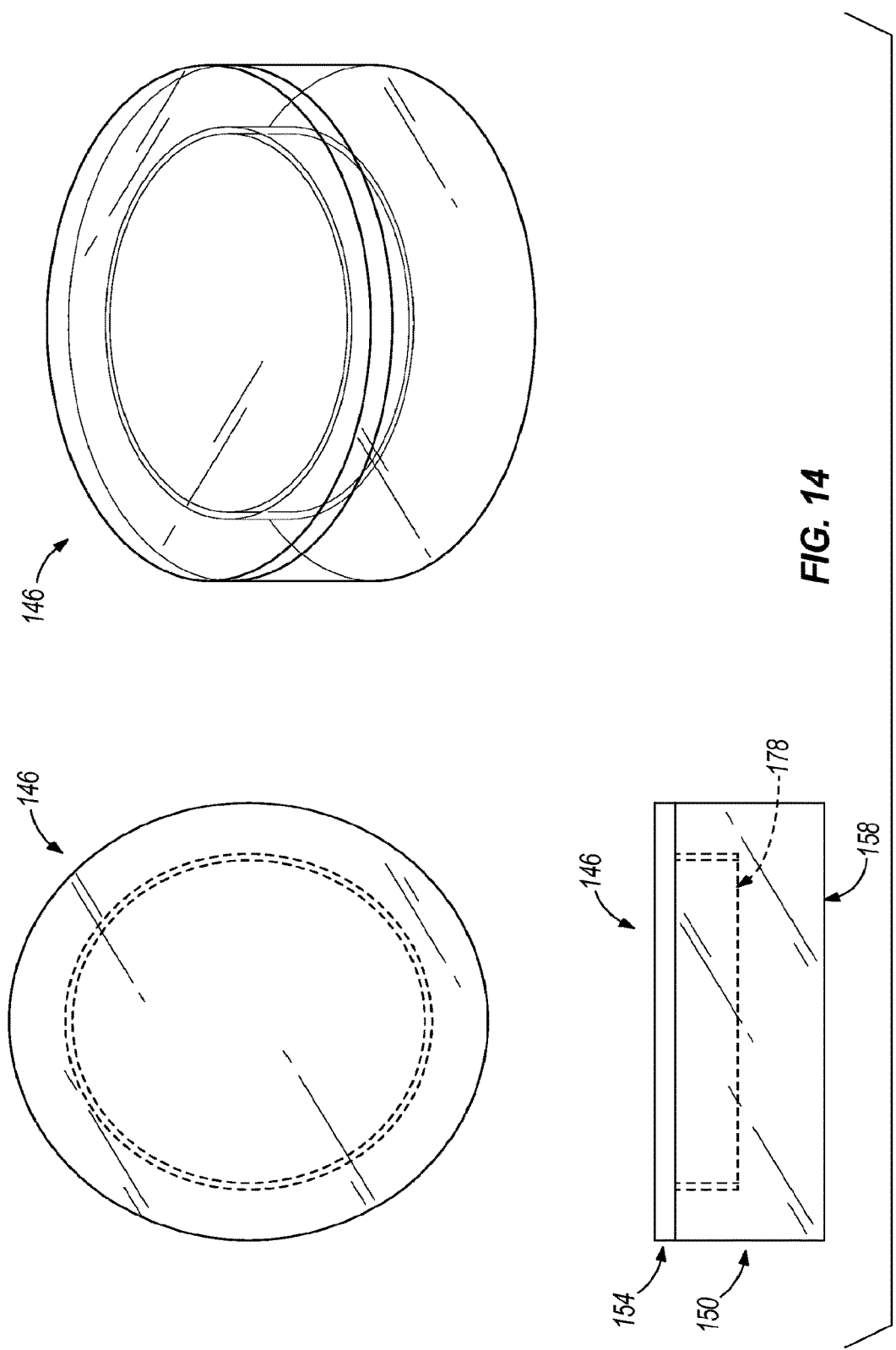
FIG. 14 illustrates several drawings of a drug delivery device according to one embodiment of the present invention.
Figure 15:
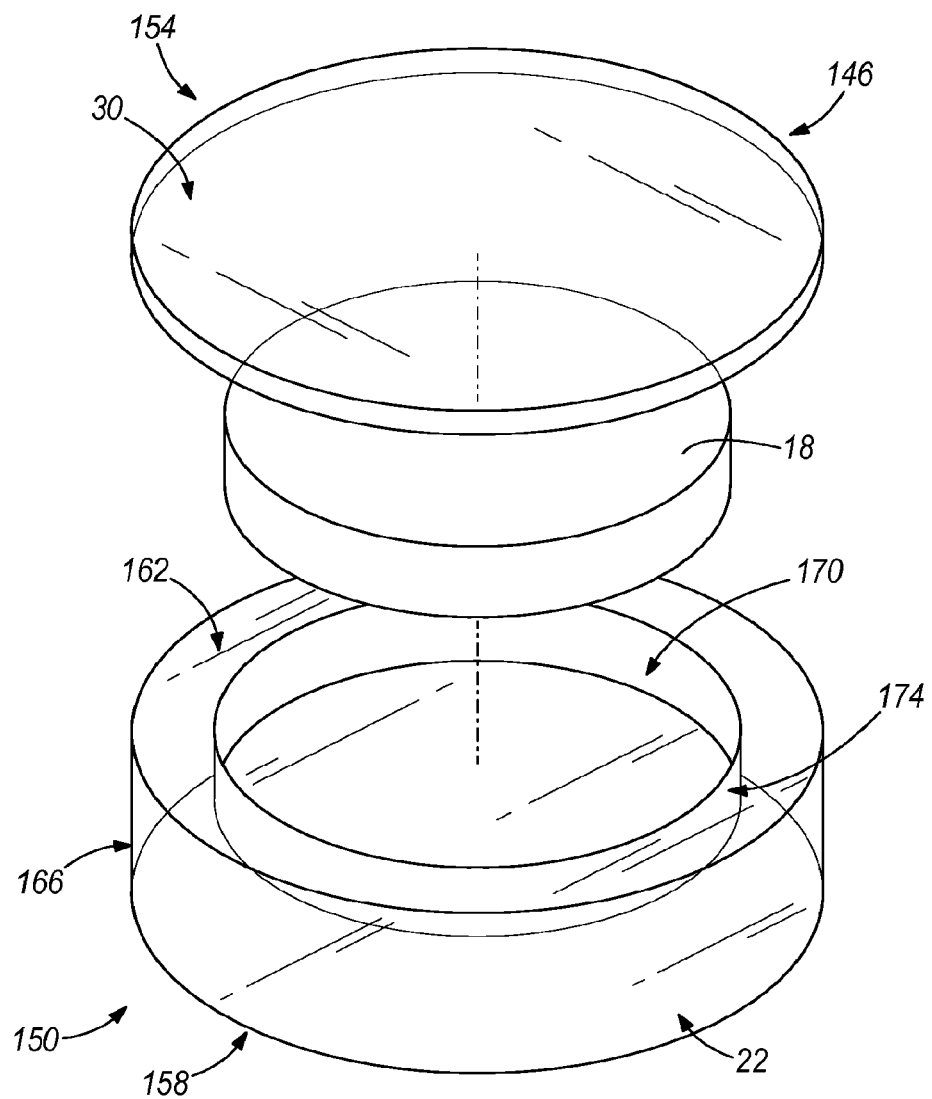
FIG. 15 is an exploded view of the drug delivery device illustrated in FIG. 14.
Figure 16:
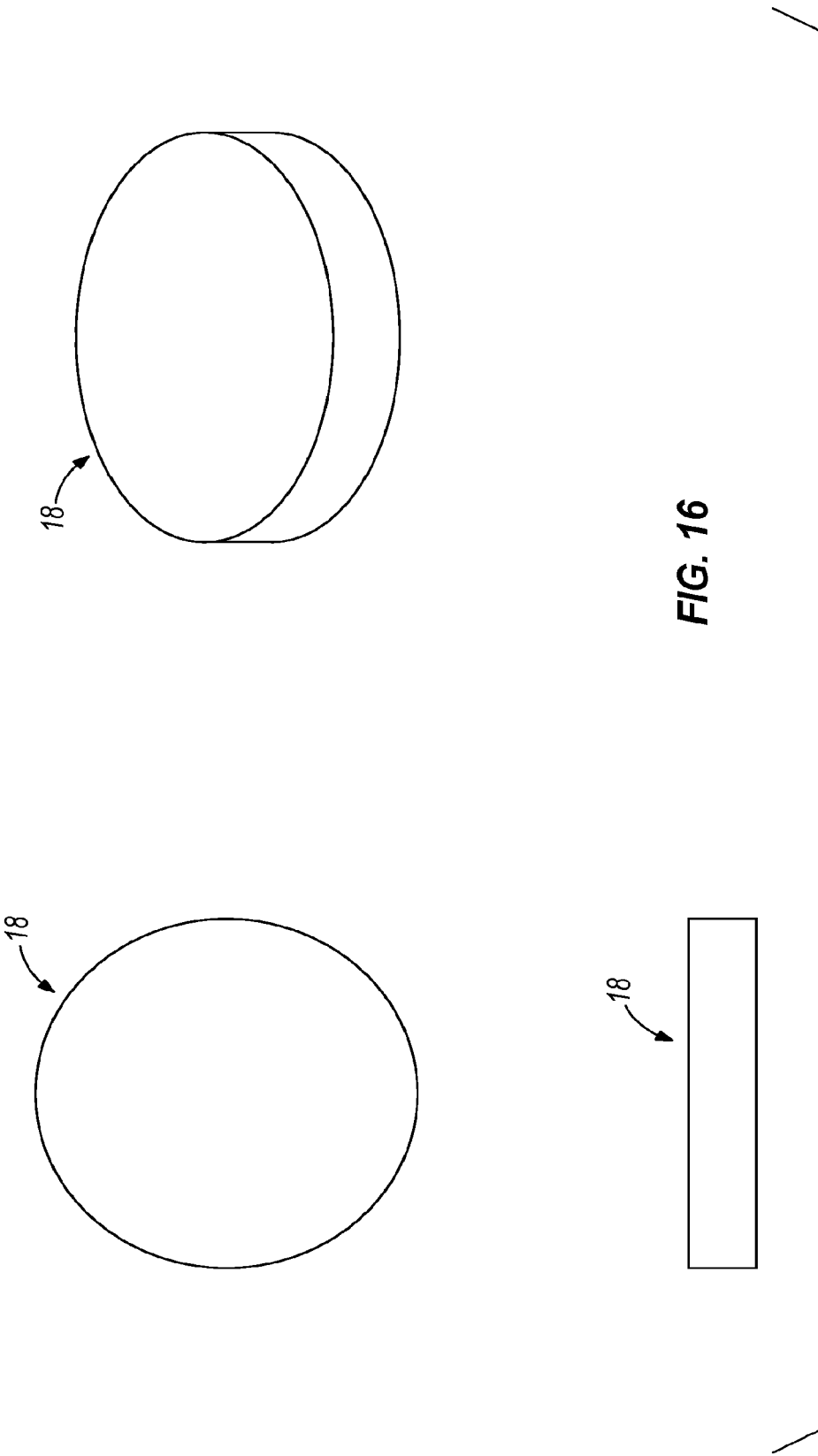
FIG. 16 illustrates several drawings of a composition supported by the drug delivery device illustrated in FIG. 14.
Figure 17:
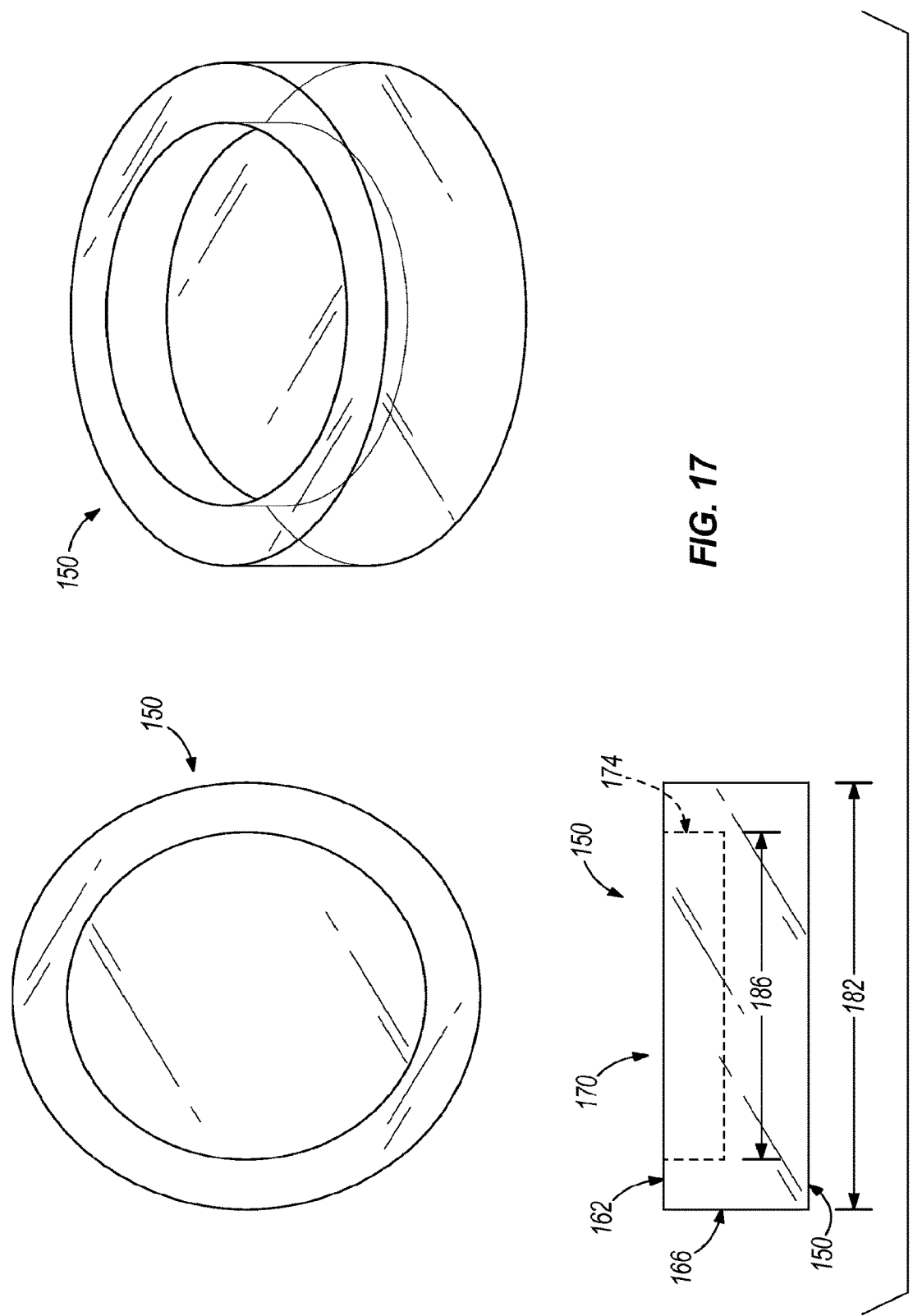
FIG. 17 illustrates several drawings of a portion of the drug delivery device illustrated in FIG. 14.
Figure 18:
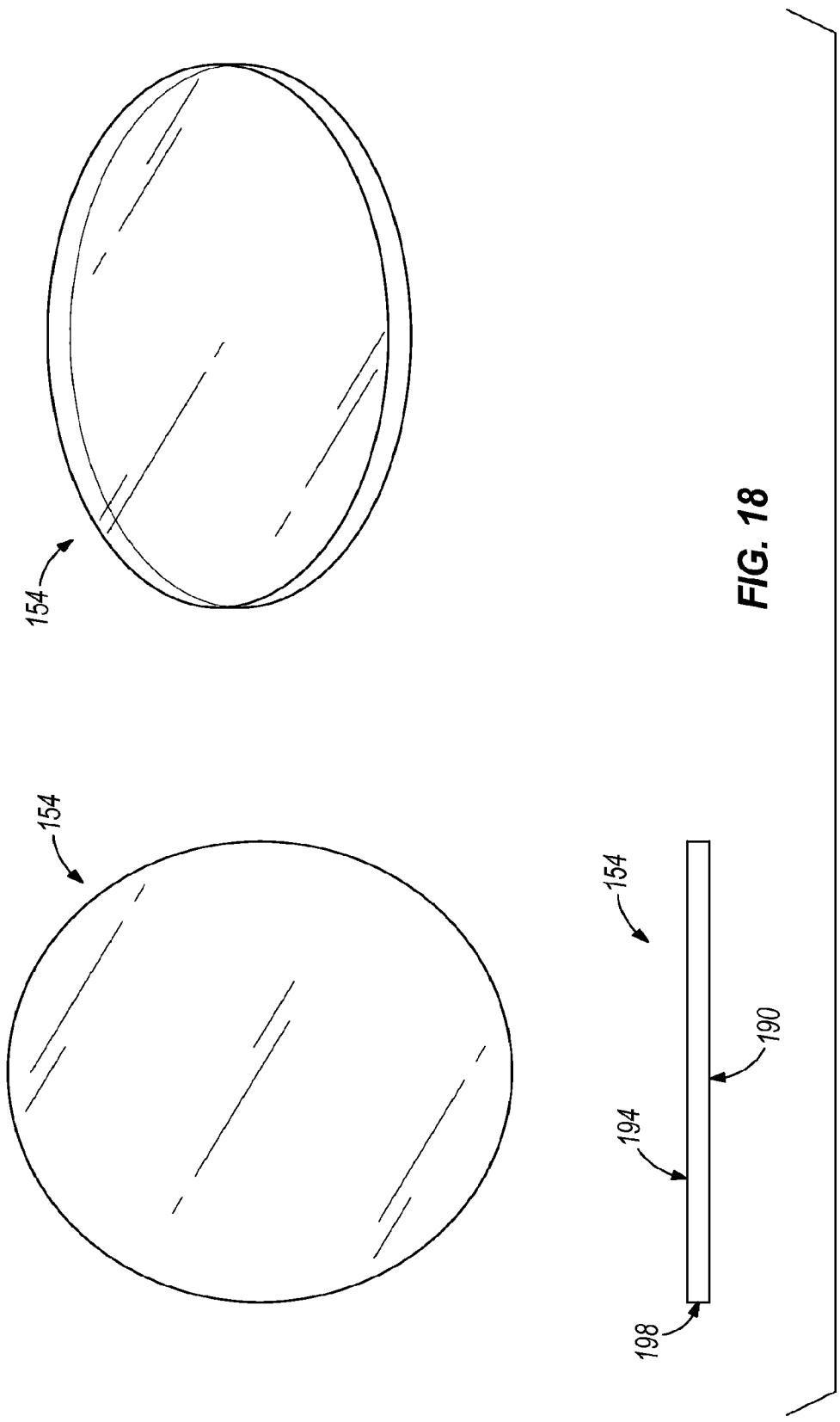
FIG. 18 illustrates several drawings of a portion of the drug delivery device illustrated in FIG. 14.
Figure 19:
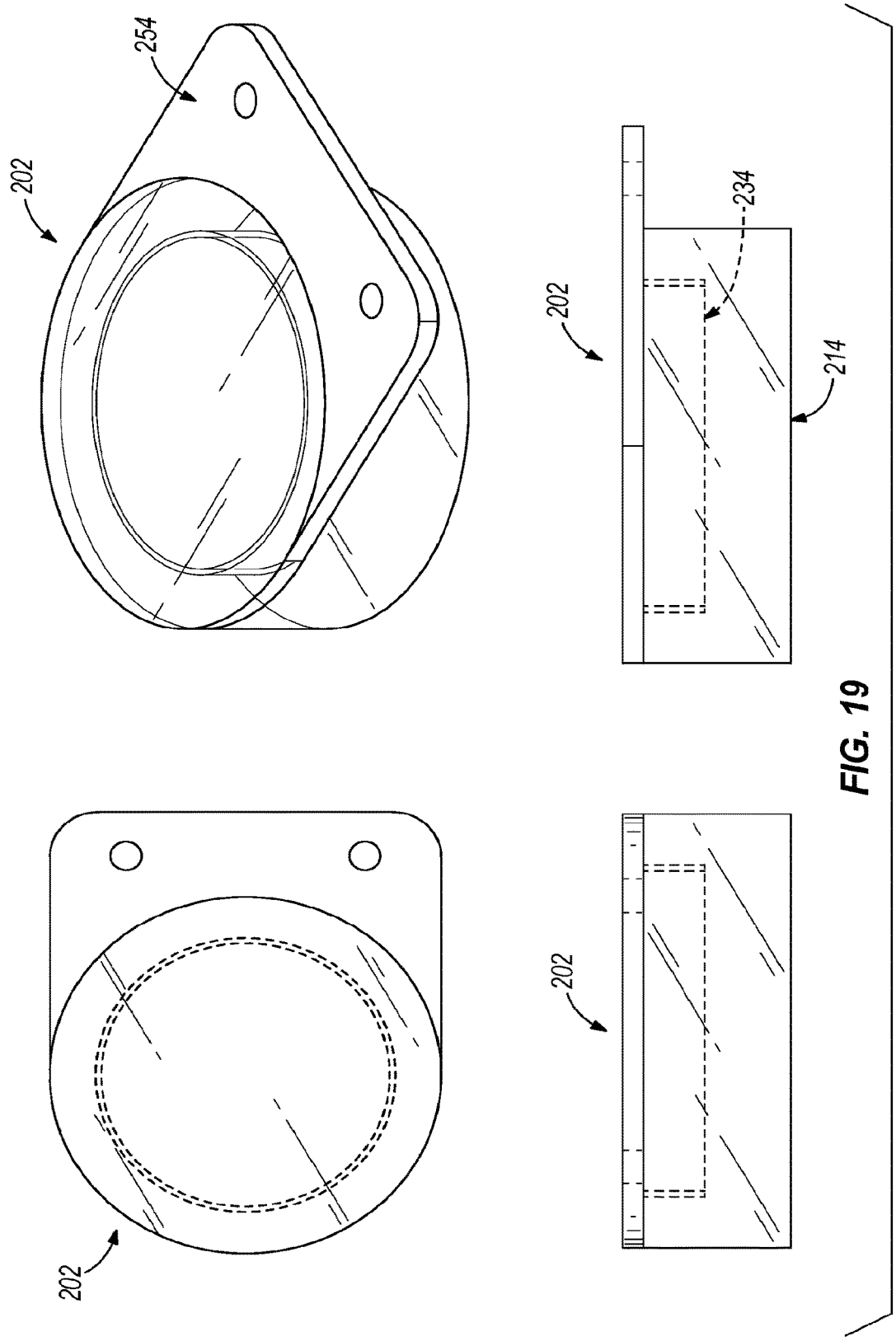
FIG. 19 illustrates several drawings of a drug delivery device according to one embodiment of the present invention.
Figure 20:
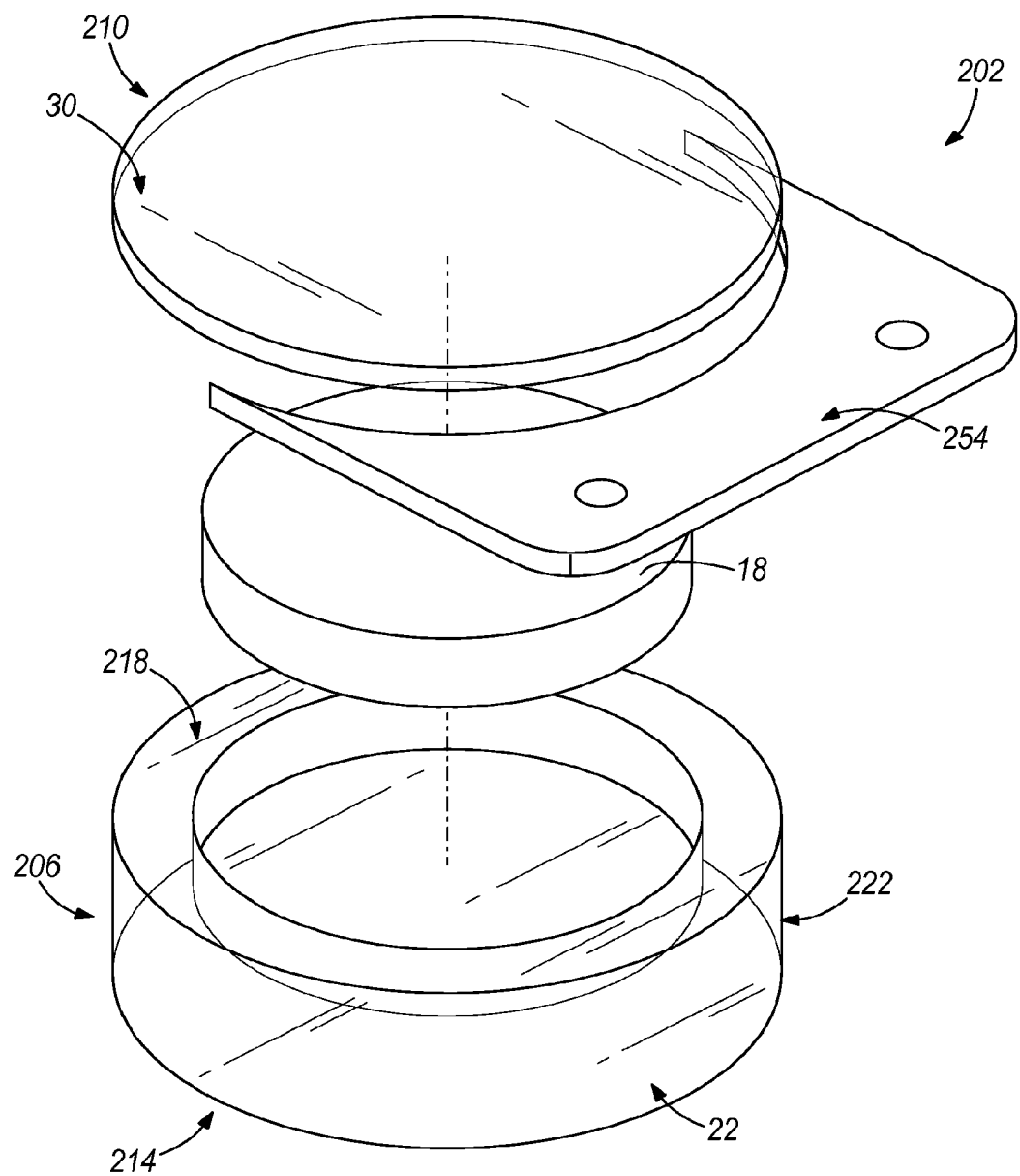
FIG. 20 is an exploded view of the drug delivery device illustrated in FIG. 19.
Figure 22:
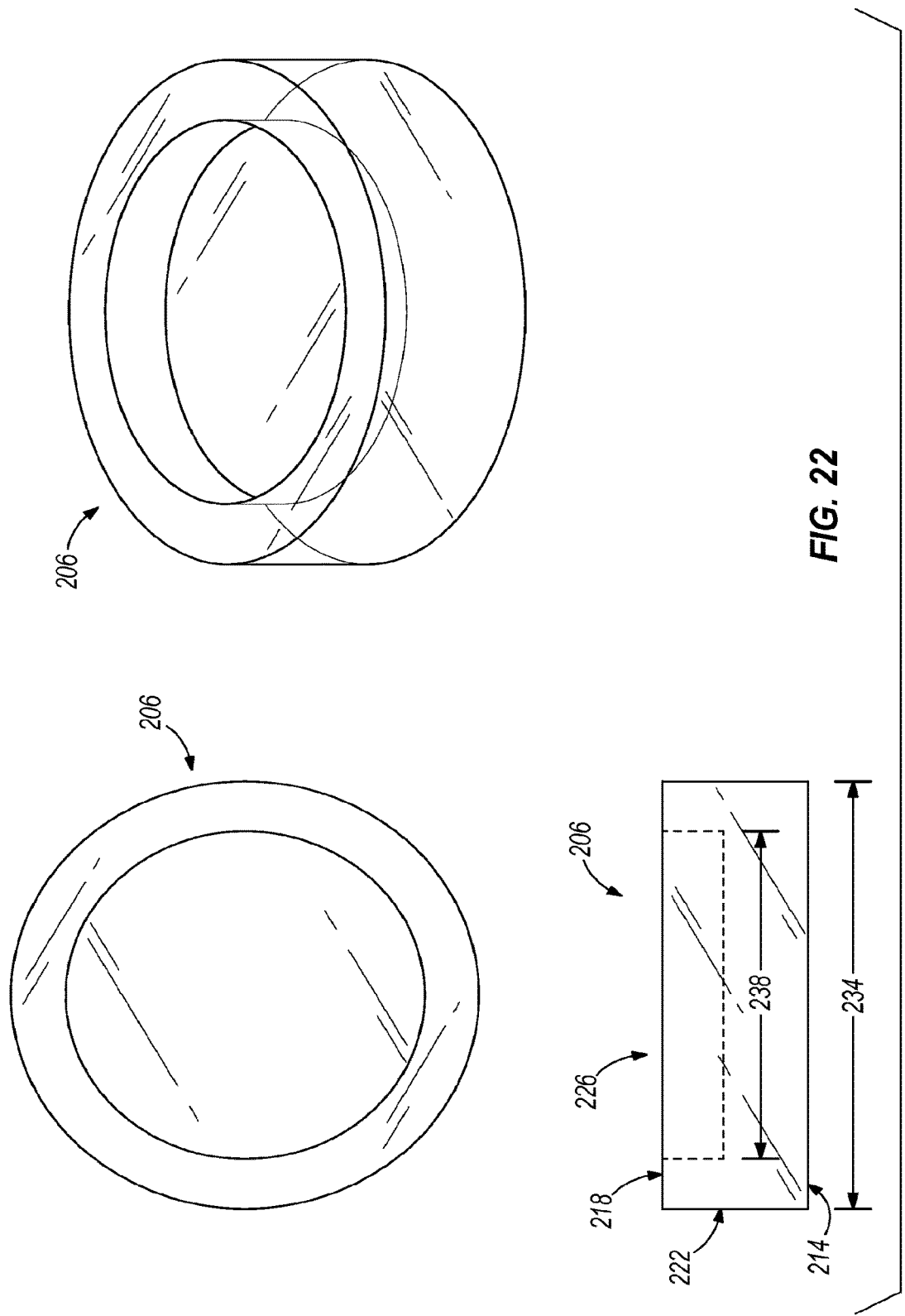
FIG. 22 illustrates several drawings of a portion of the drug delivery device illustrated in FIG. 19.
Figure 23:
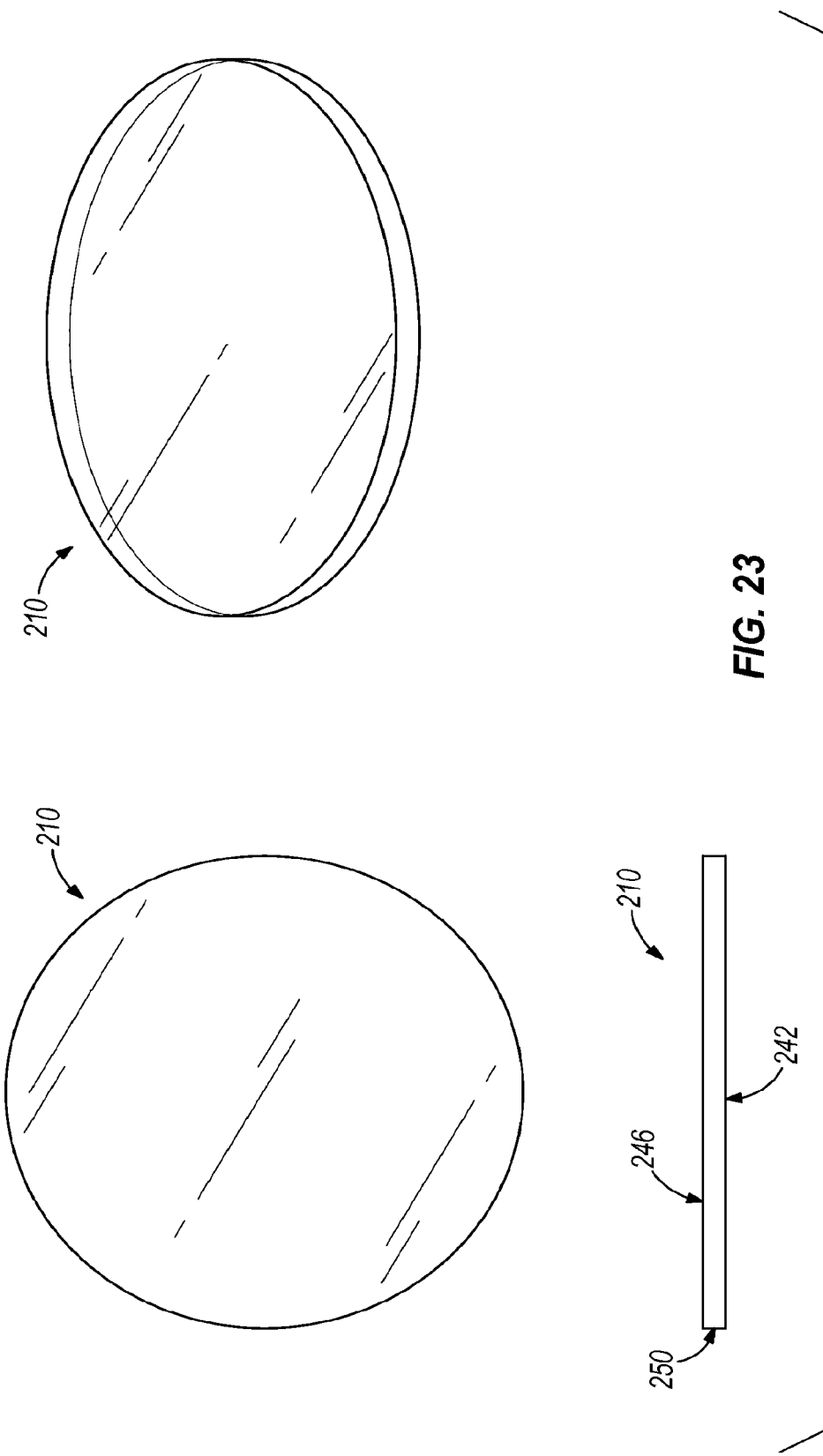
FIG. 23 illustrates several drawings of a portion of the drug delivery device illustrated in FIG. 19.
Figure 25:
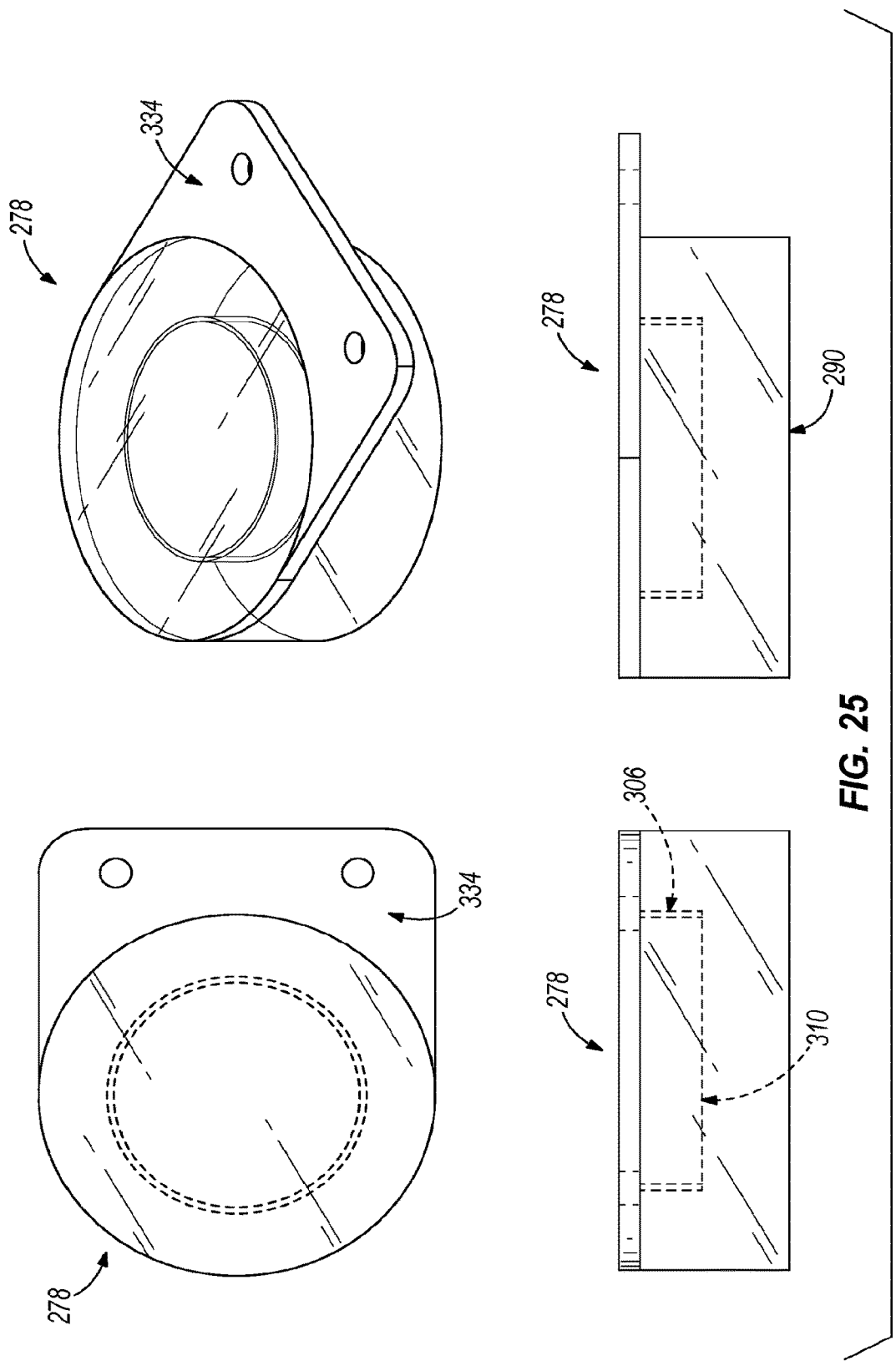
FIG. 25 illustrates several drawings of a drug delivery device according to one embodiment of the present invention.
Figure 26:
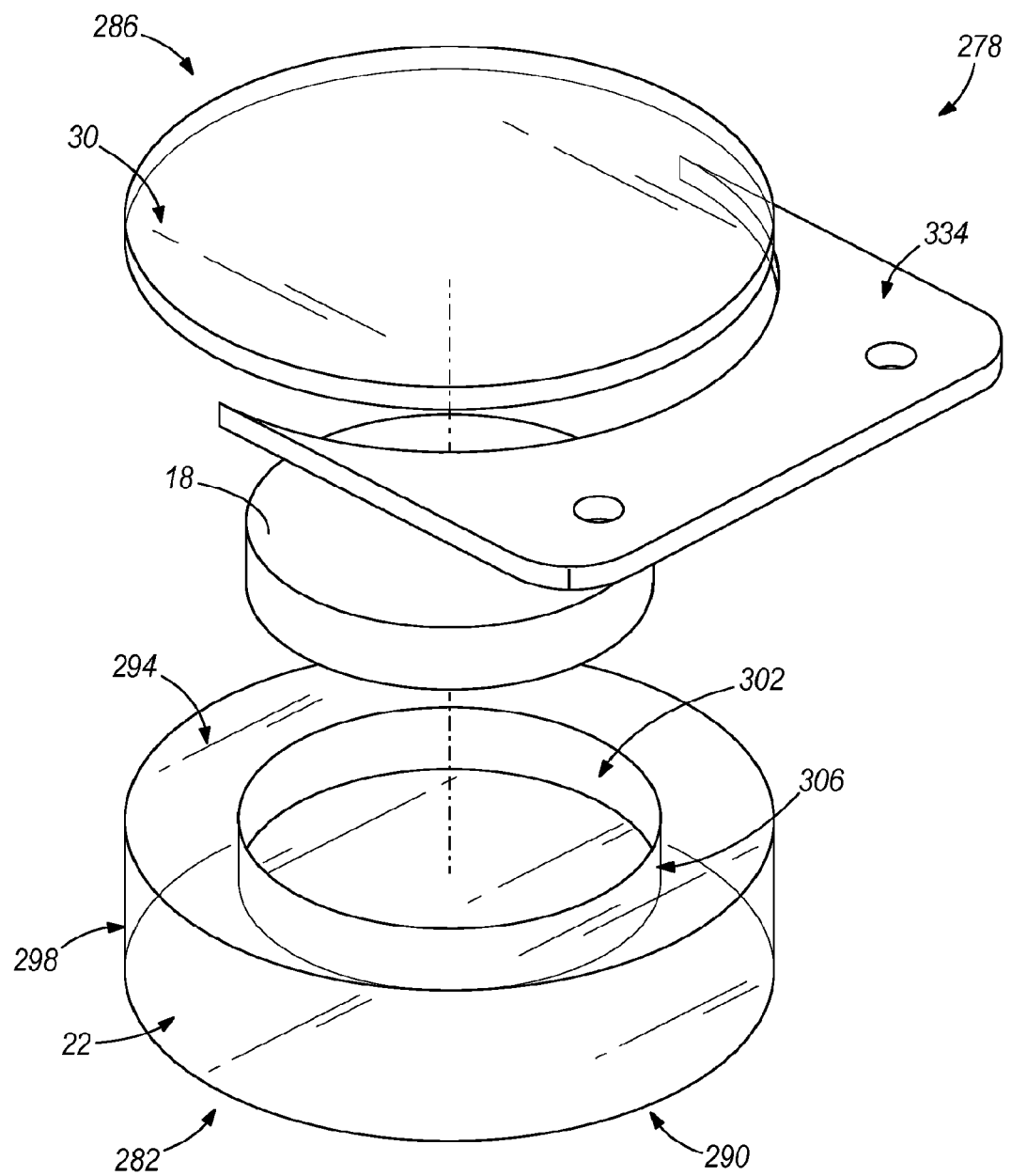
FIG. 26 is an exploded view of the drug delivery device illustrated in FIG. 25.
Figure 27:
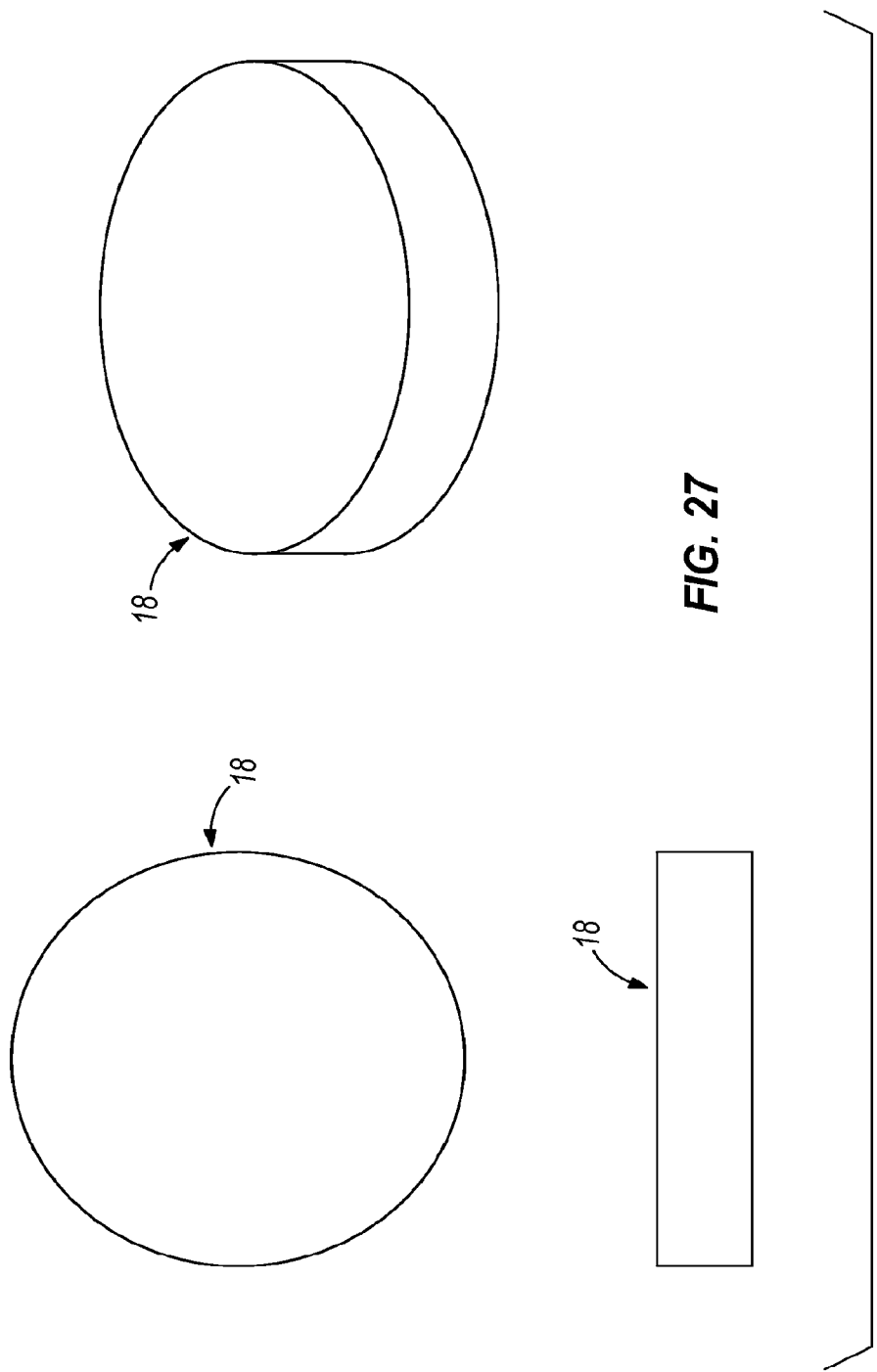
FIG. 27 illustrates several drawings of a composition supported by the drug delivery device illustrated in FIG. 25.
Figure 28:
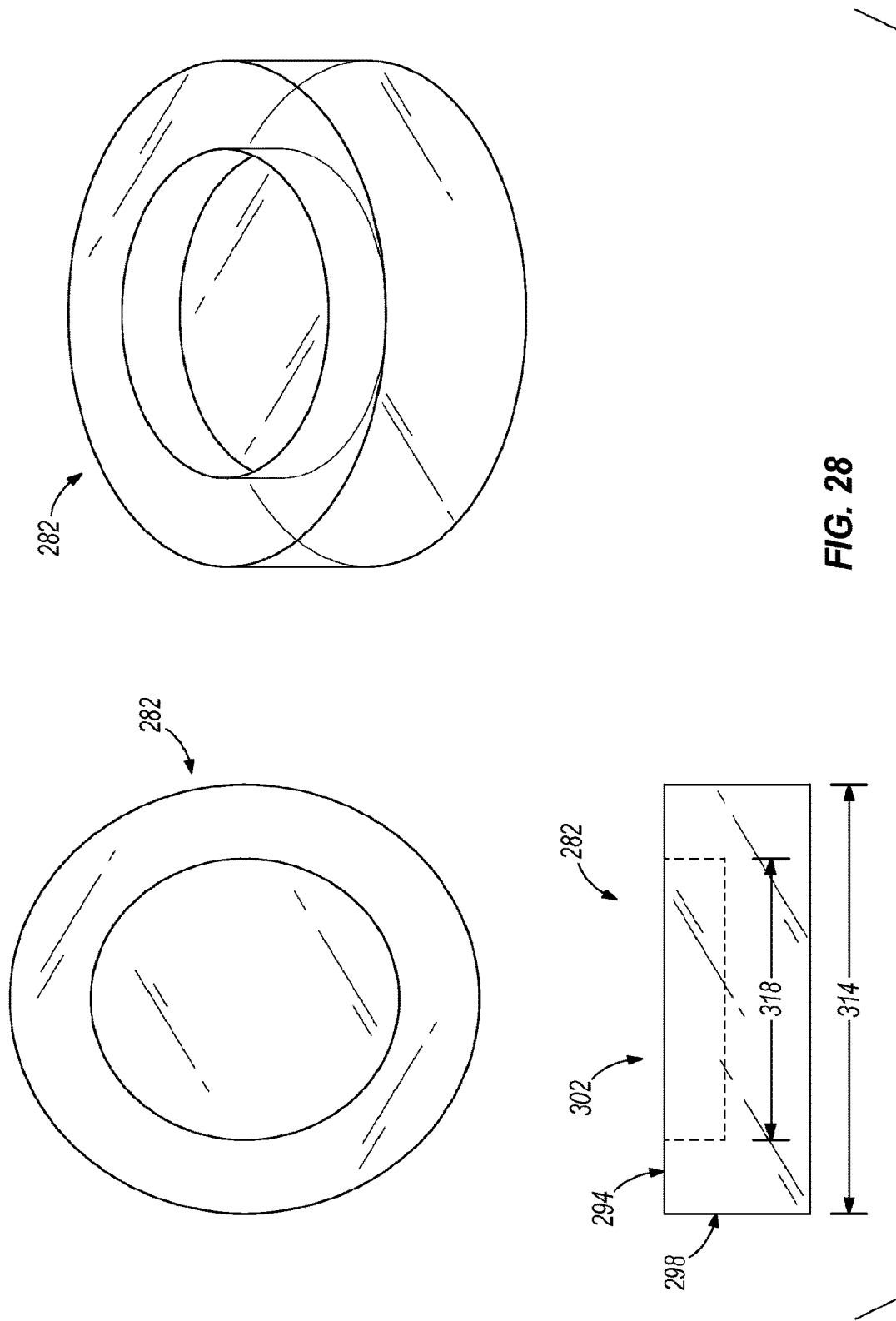
FIG. 28 illustrates several drawings of a portion of the drug delivery device illustrated in FIG. 25.
Figure 29:
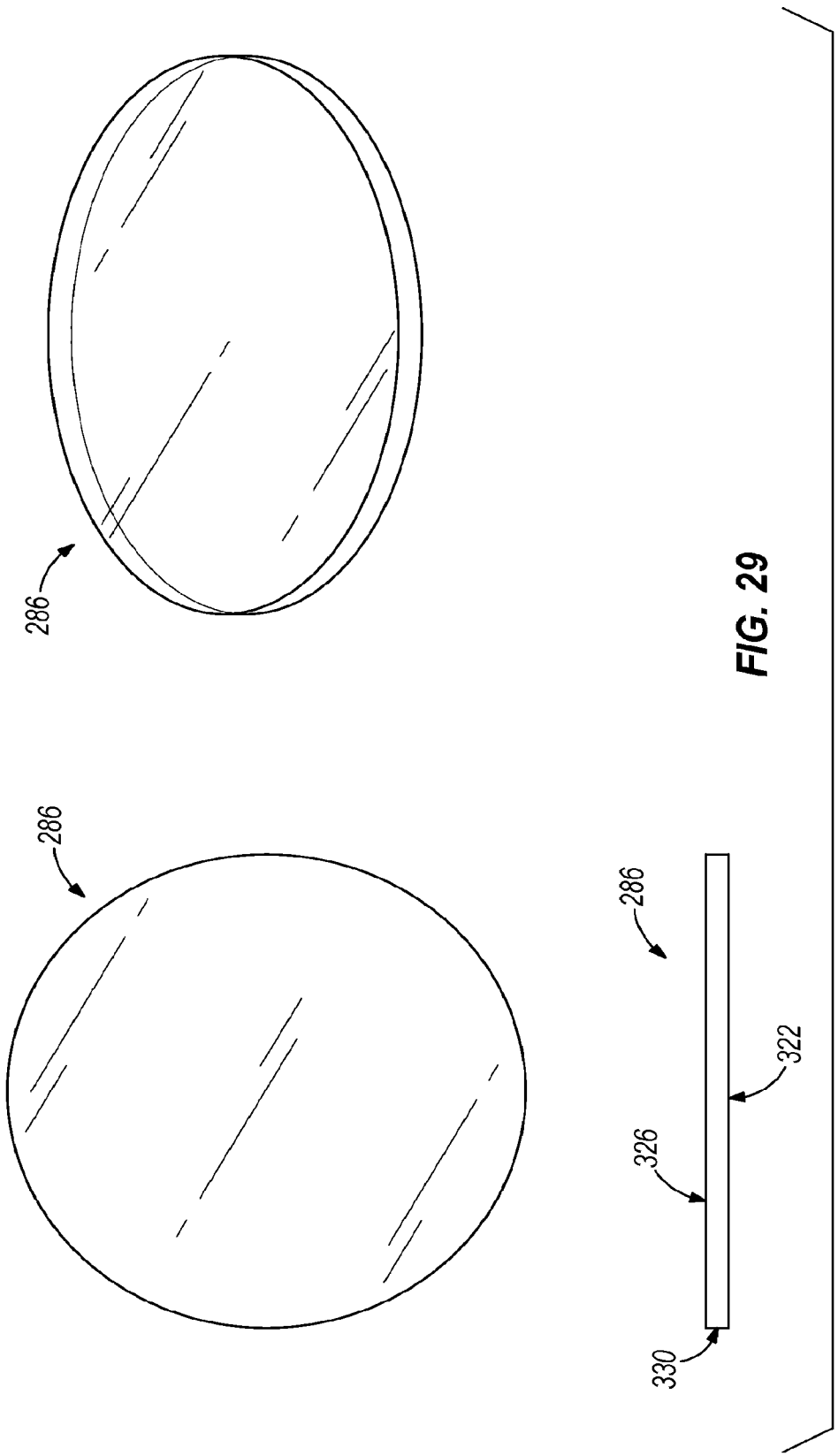
FIG. 29 illustrates several drawings of a portion of the drug delivery device illustrated in FIG. 25.
Figure 30:
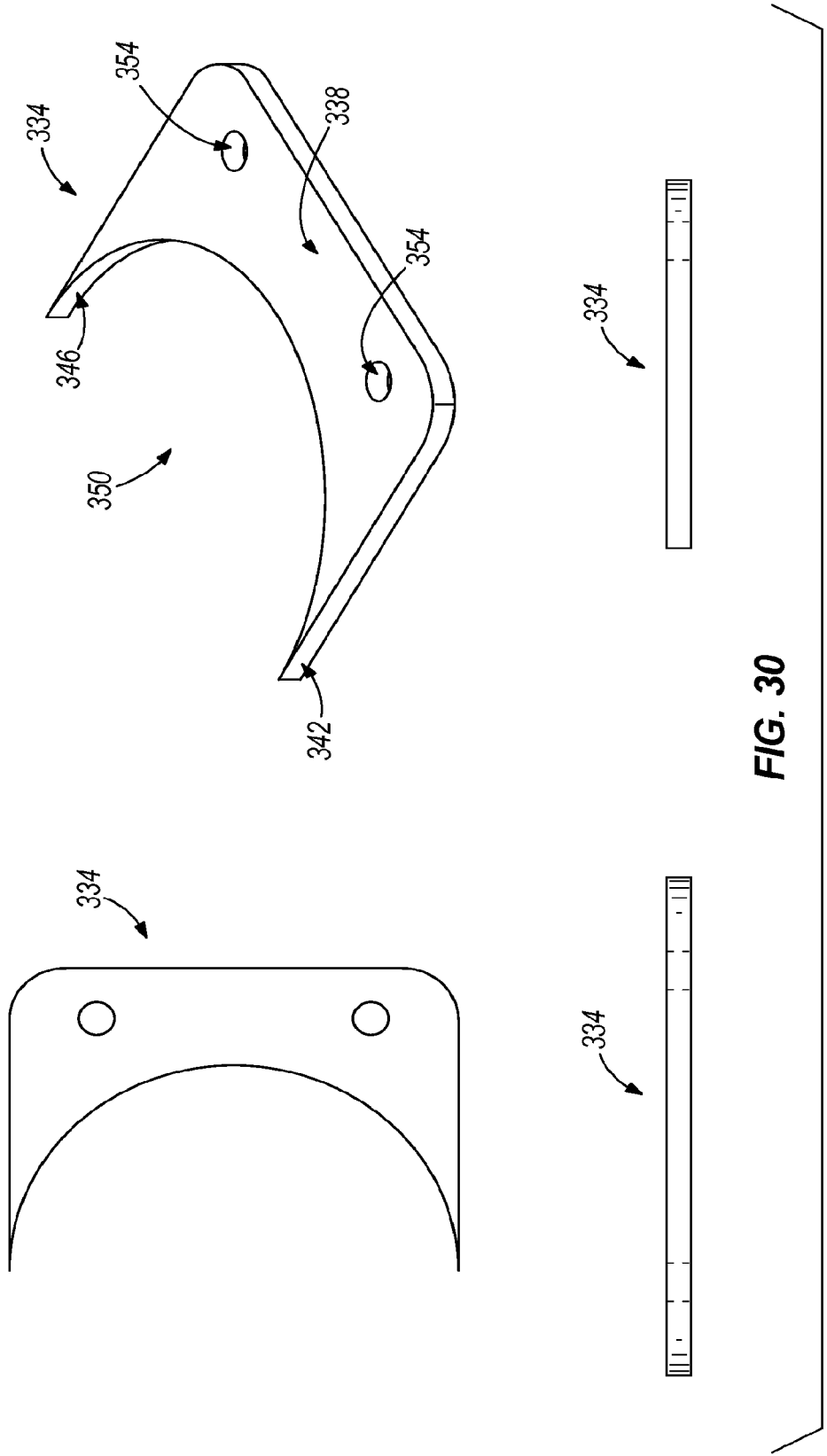
FIG. 30 illustrates several drawings of a portion of the drug delivery device illustrated in FIG. 25.
Figure 32:
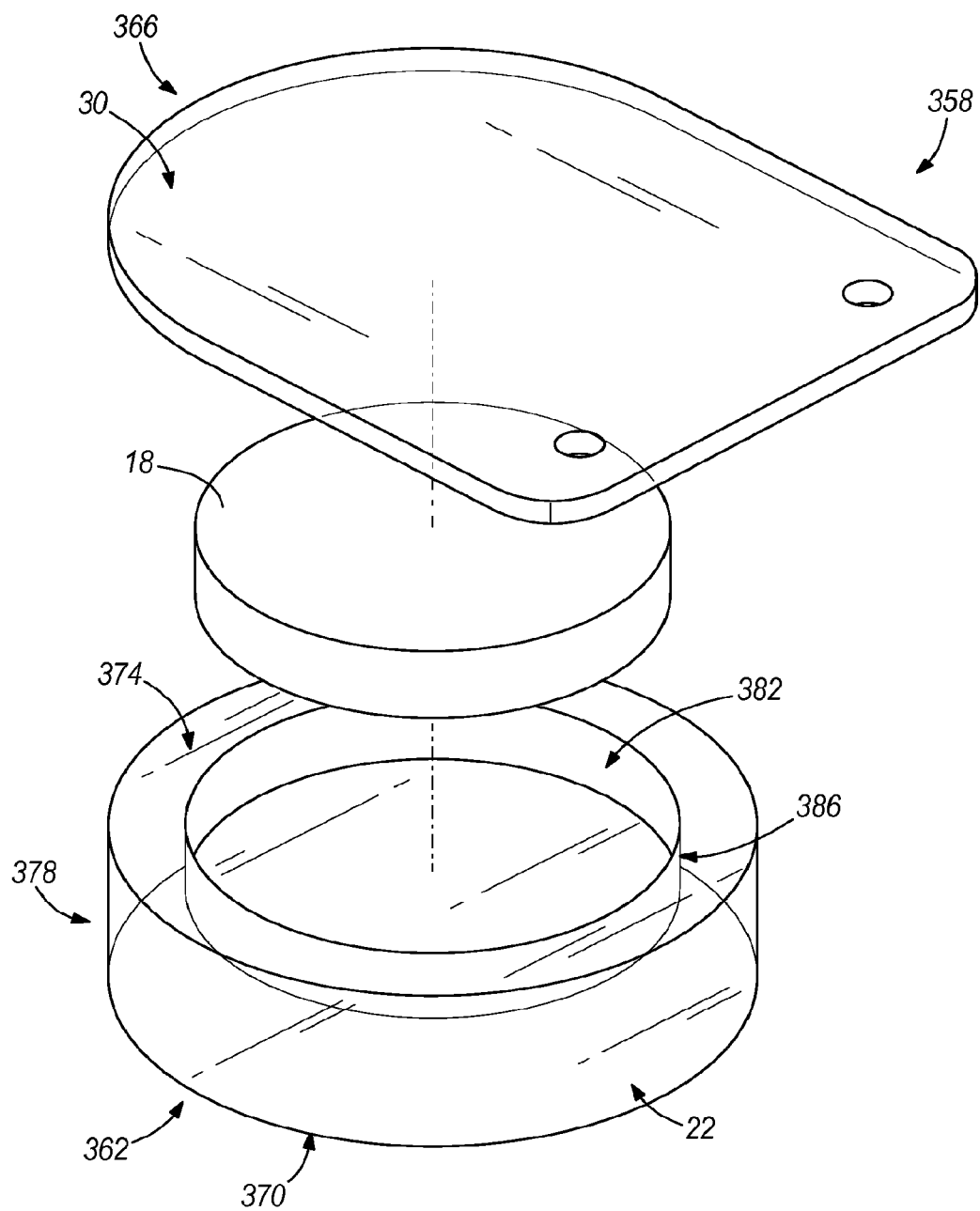
FIG. 32 is an exploded view of the drug delivery device illustrated in FIG. 31.
Figure 33:
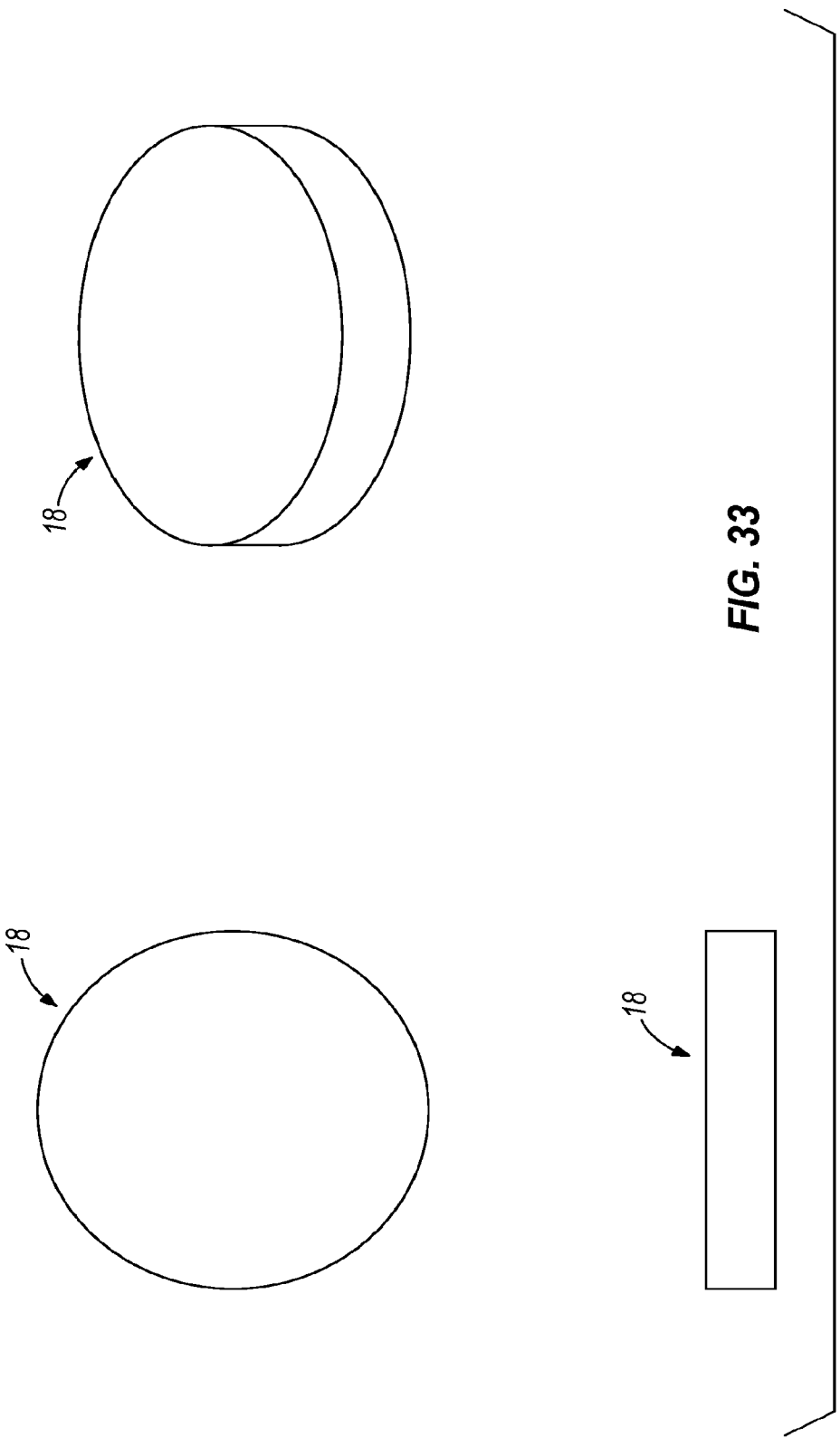
FIG. 33 illustrates several drawings of a composition supported by the drug delivery device illustrated in FIG. 31.
Figure 34:
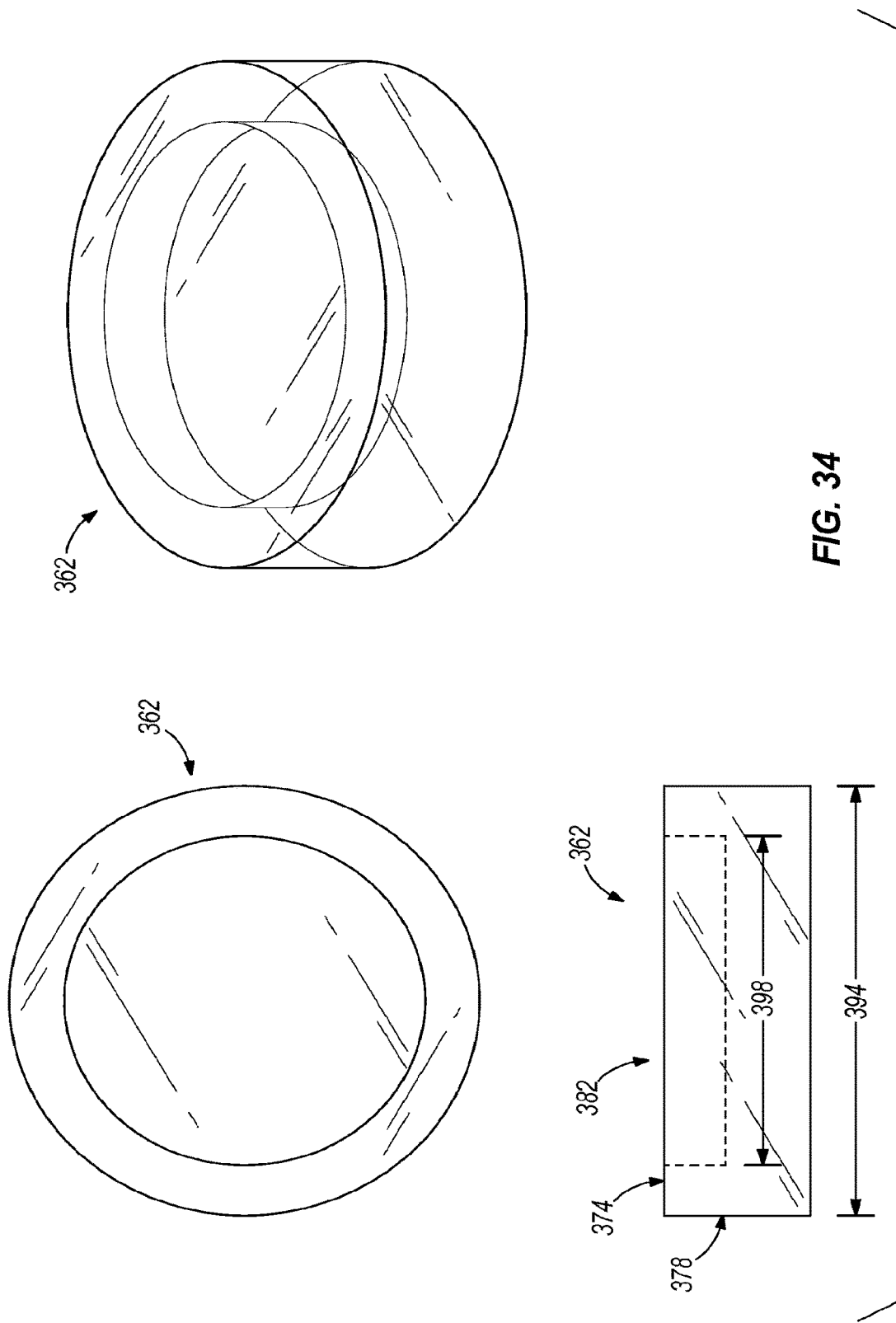
FIG. 34 illustrates several drawings of a portion of the drug delivery device illustrated in FIG. 31.
Figure 35:
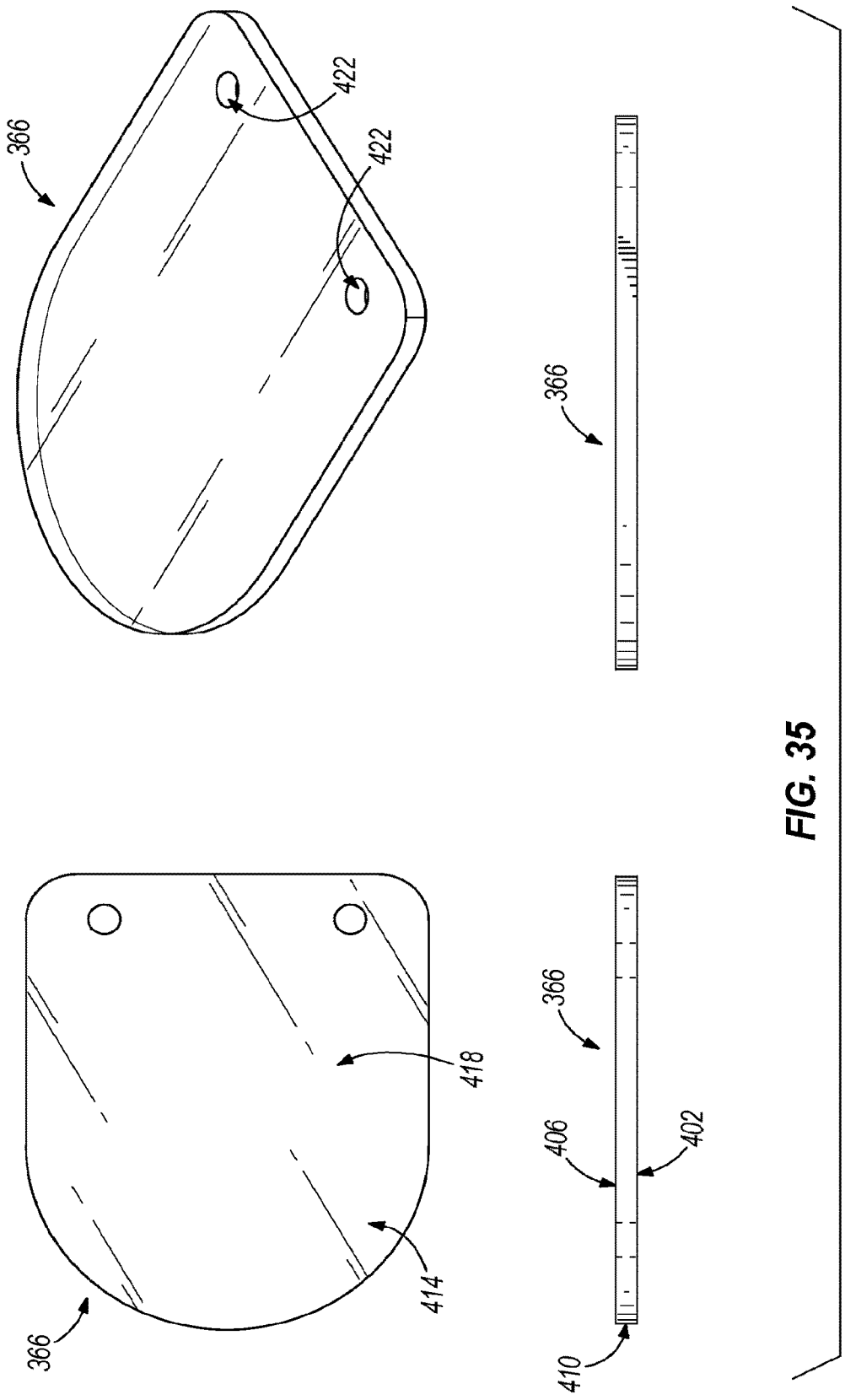
FIG. 35 illustrates several drawings of a portion of the drug delivery device illustrated in FIG. 31.
Figure 37:
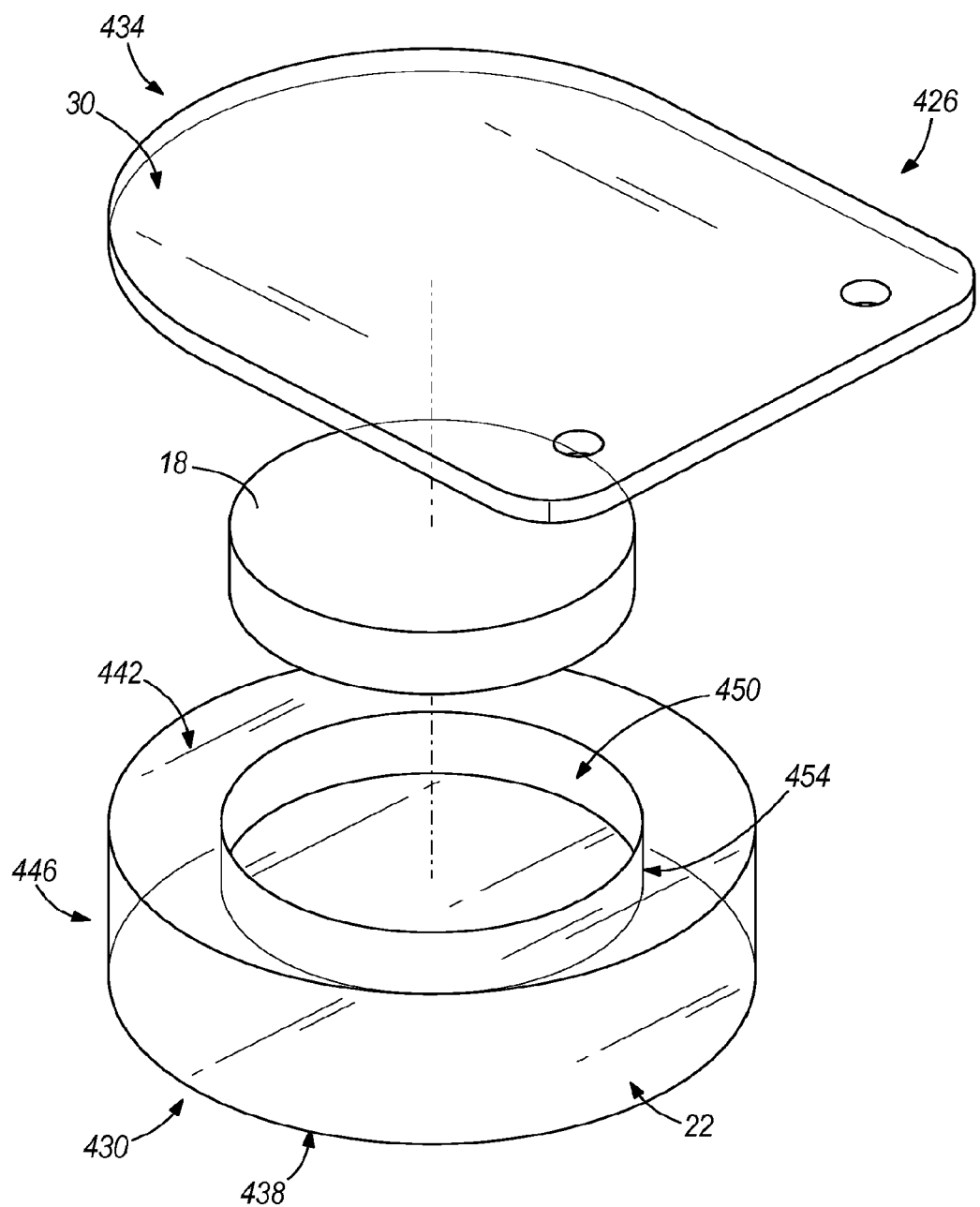
FIG. 37 is an exploded view of the drug delivery device illustrated in FIG. 36.
Figure 38:
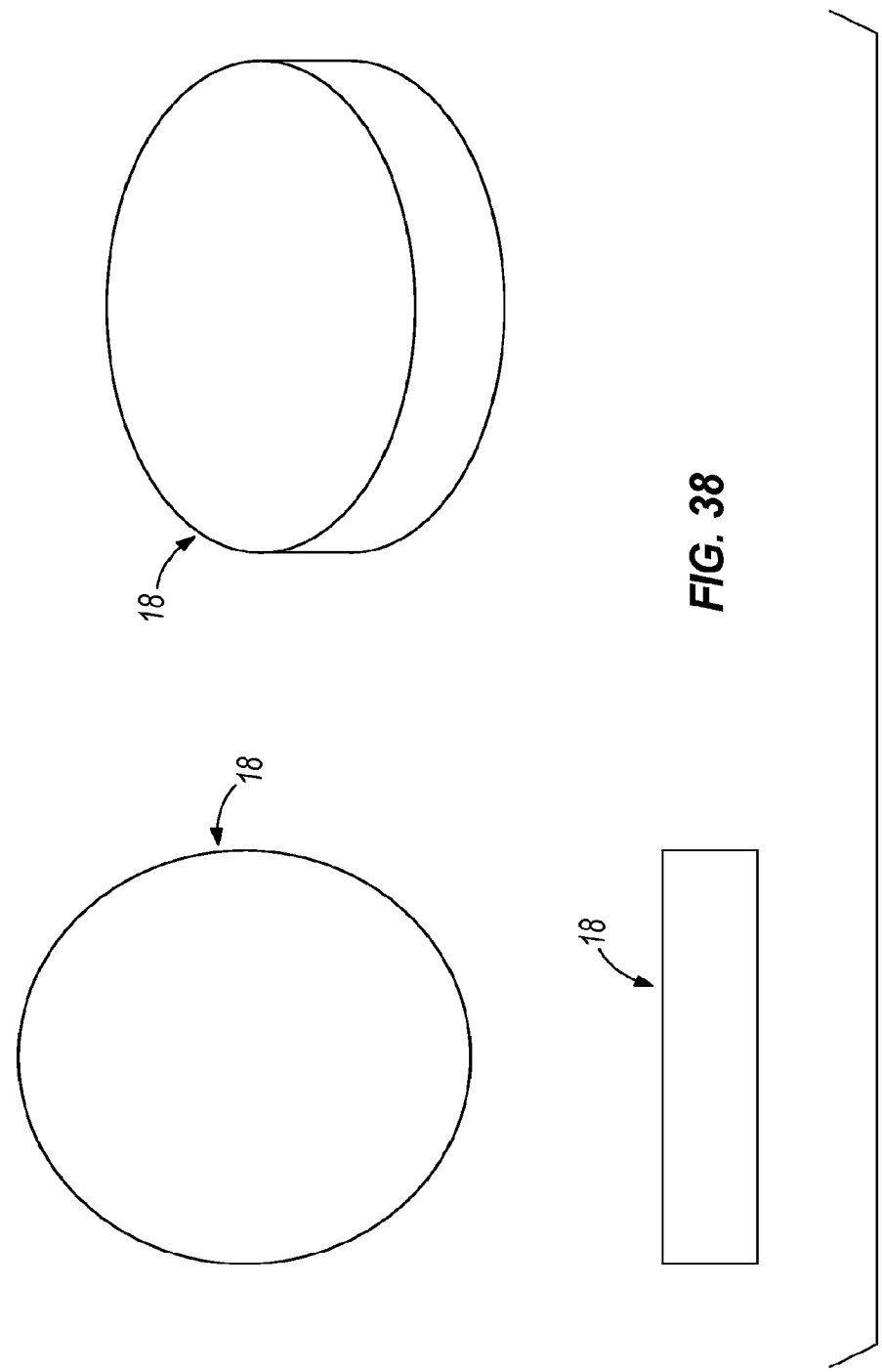
FIG. 38 illustrates several drawings of a composition supported by the drug delivery device illustrated in FIG. 36.
Figure 39:
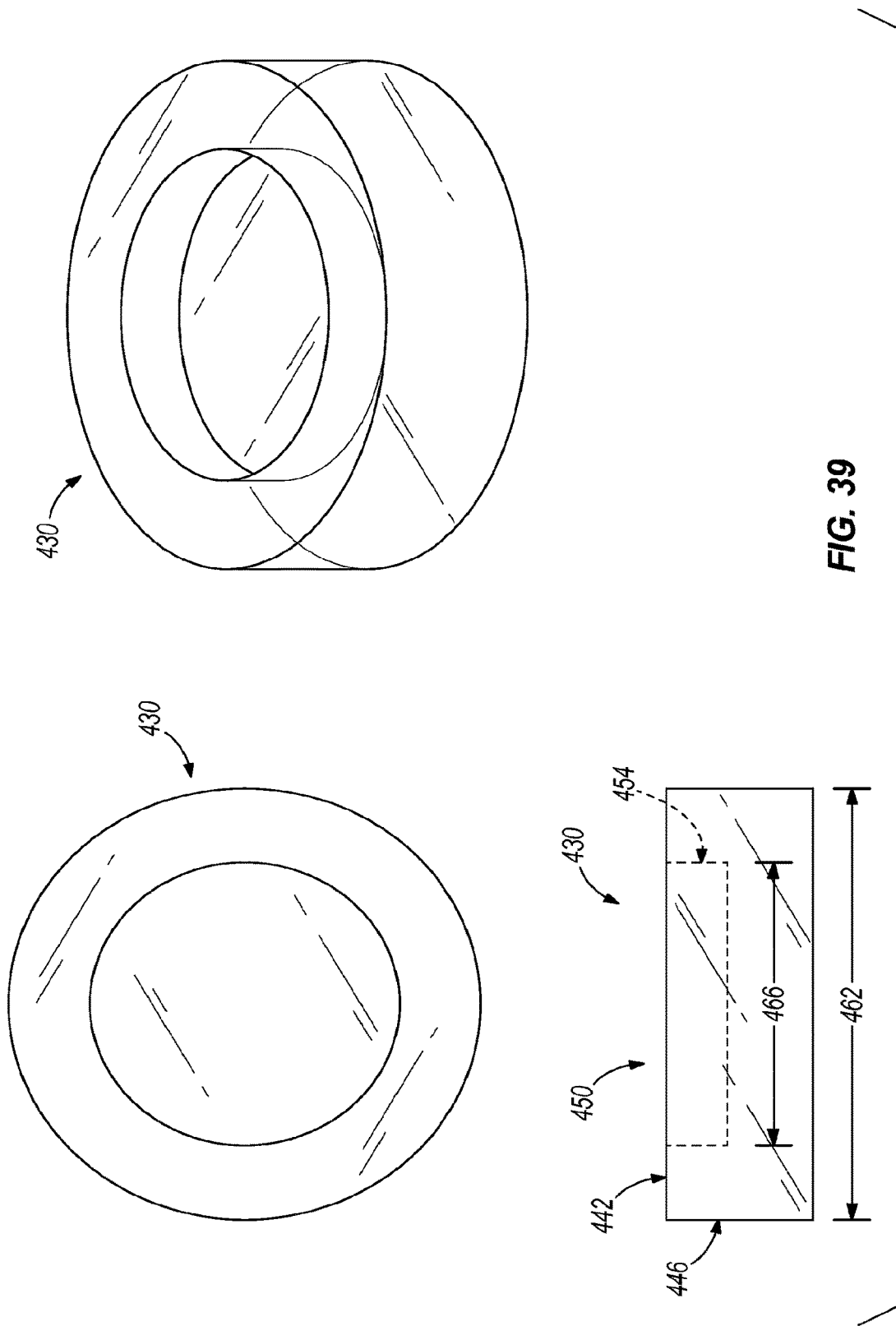
FIG. 39 illustrates several drawings of a portion of the drug delivery device illustrated in FIG. 36.
Figure 40:
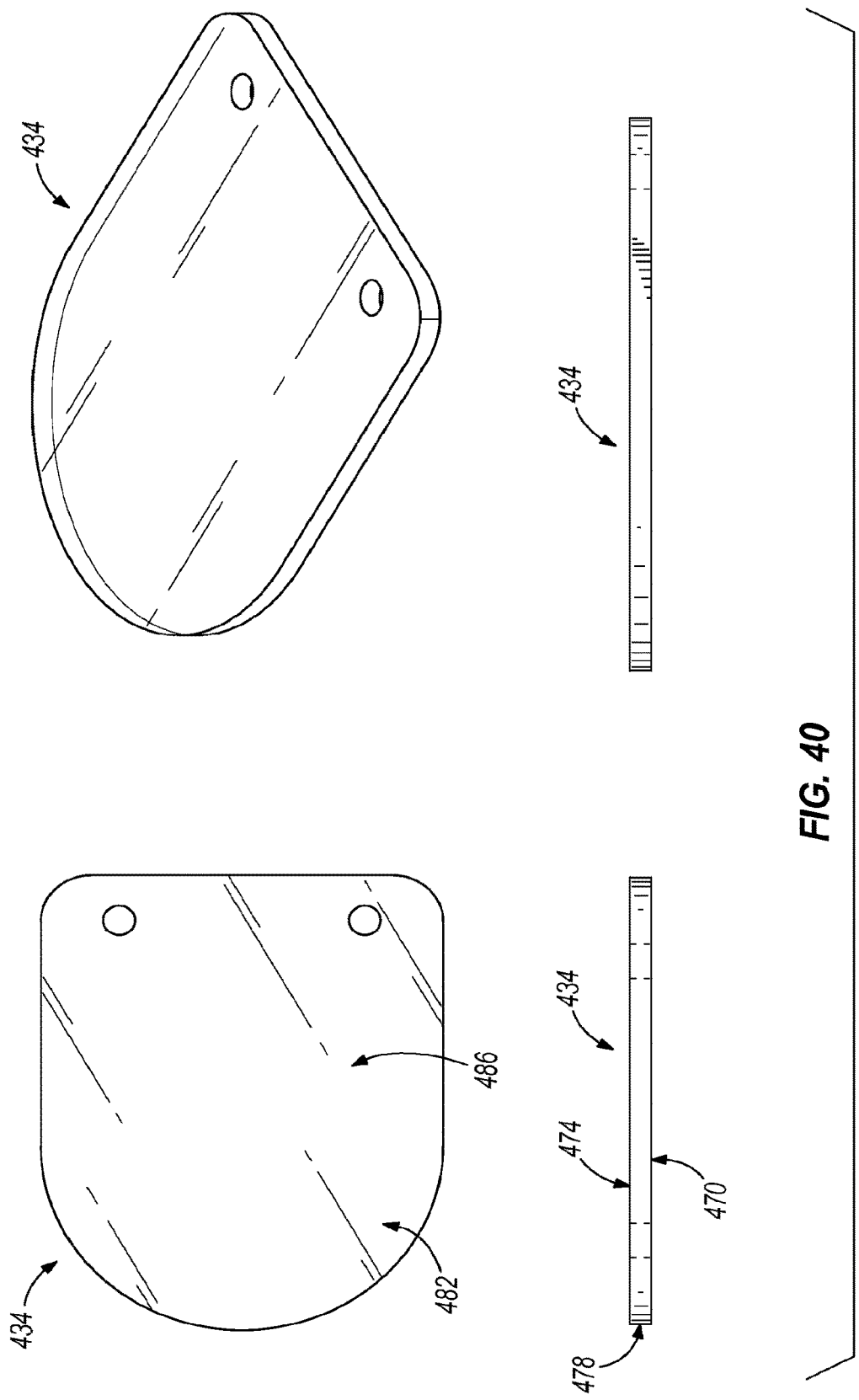
FIG. 40 illustrates several drawings of a portion of the drug delivery device illustrated in FIG. 36.
Figure 41:
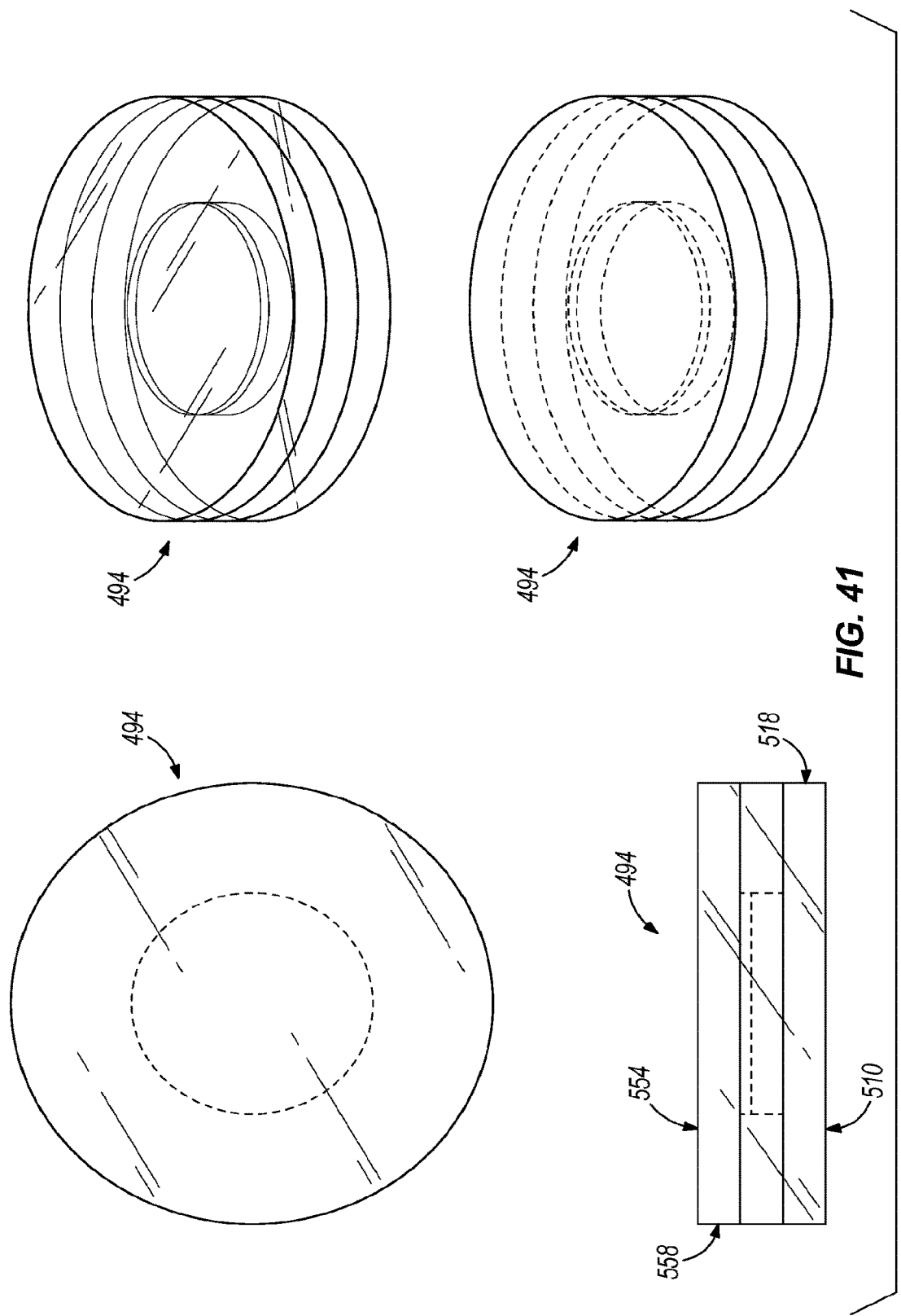
FIG. 41 illustrates several drawings of a drug delivery device according to one embodiment of the present invention.
Figure 42:
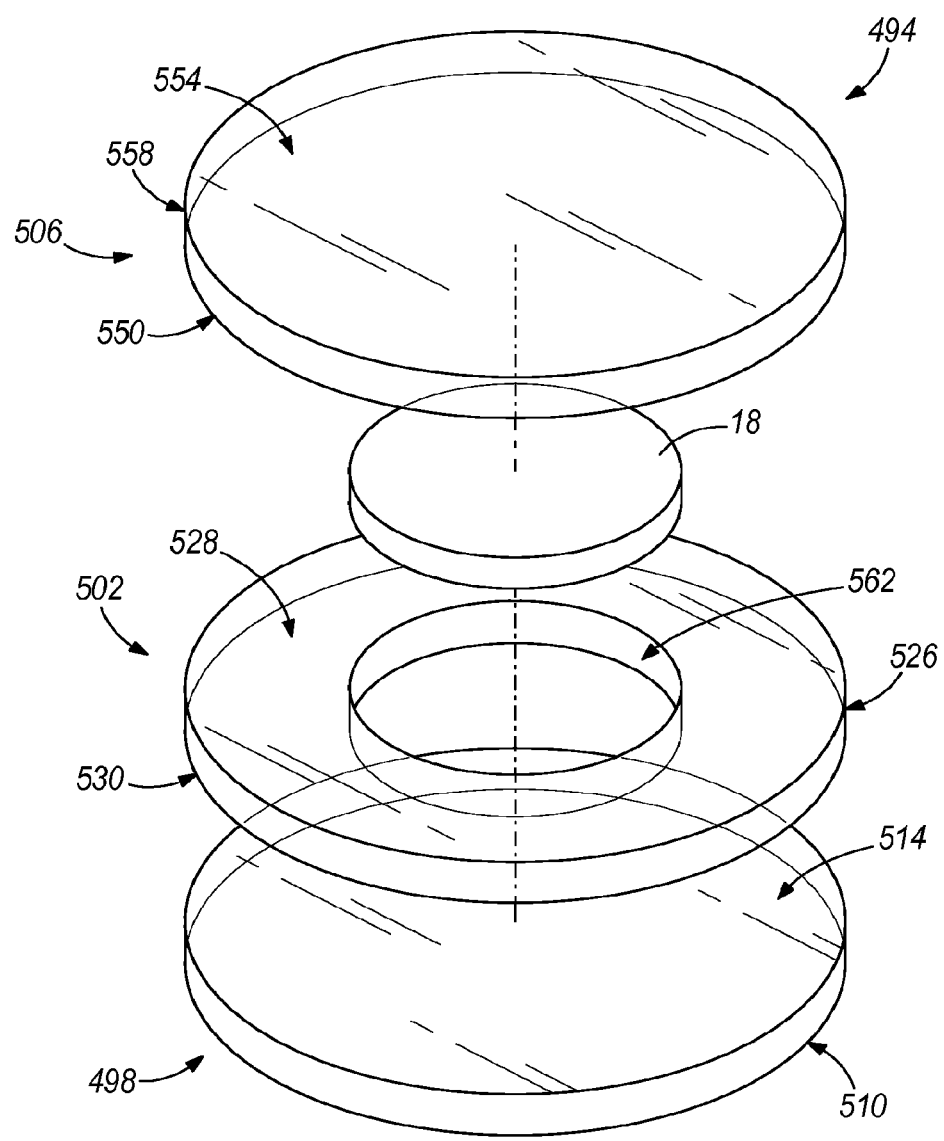
FIG. 42 is an exploded view of the drug delivery device illustrated in FIG. 41.
Figure 43:
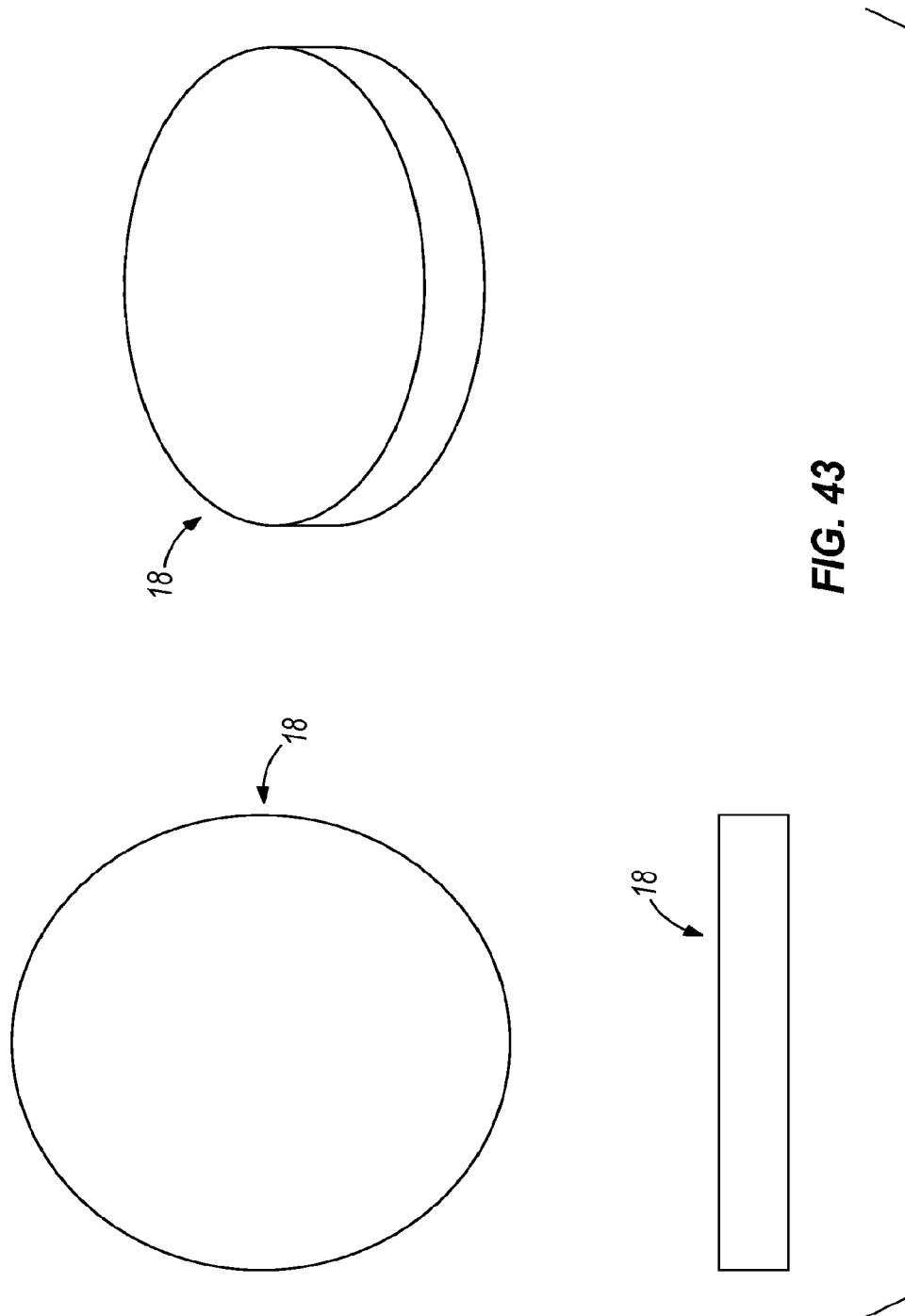
FIG. 43 illustrates several drawings of a composition supported by the drug delivery device illustrated in FIG. 41.
Figure 44:
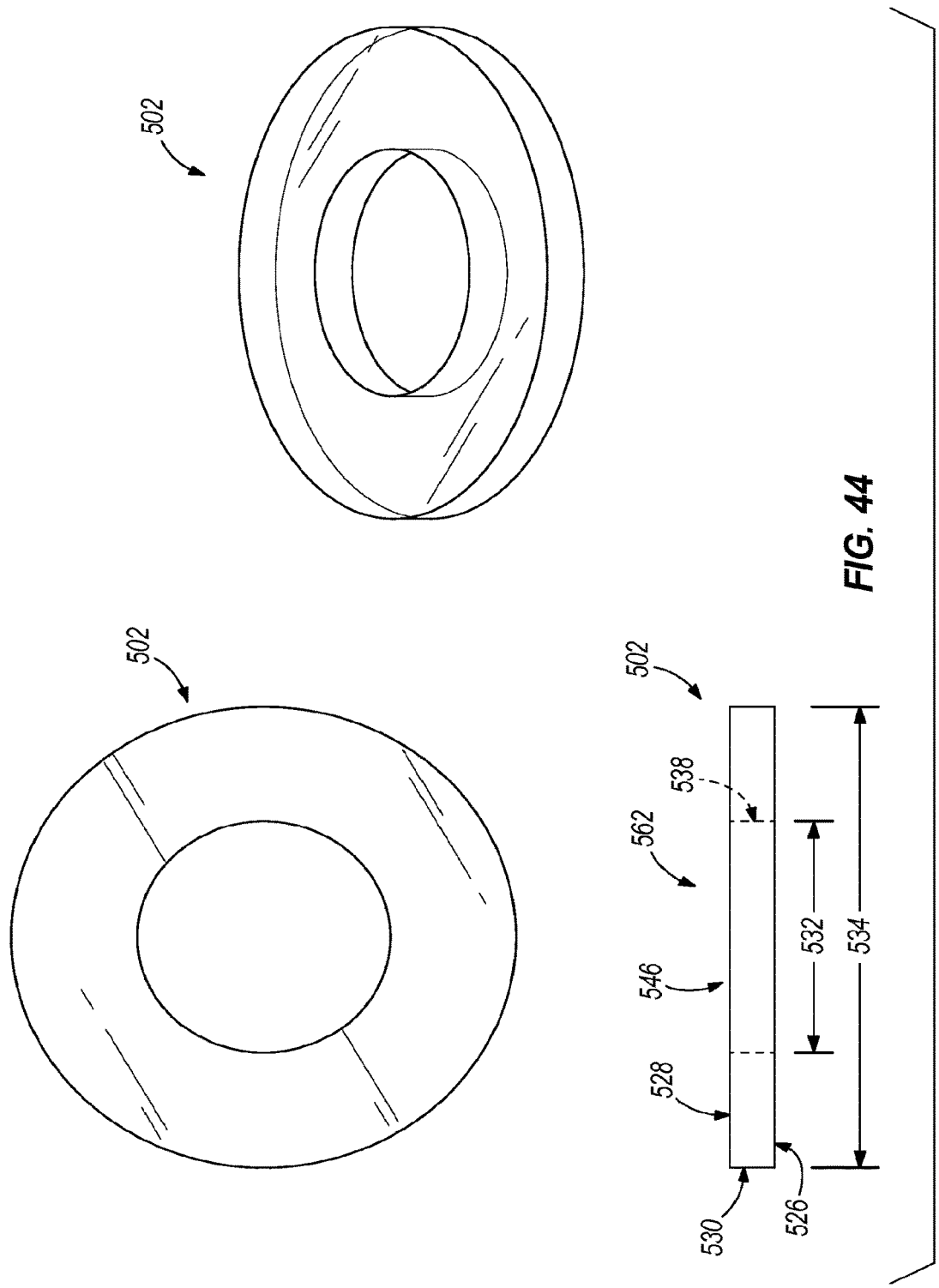
FIG. 44 illustrates several drawings of a portion of the drug delivery device illustrated in FIG. 41.
Figure 45:
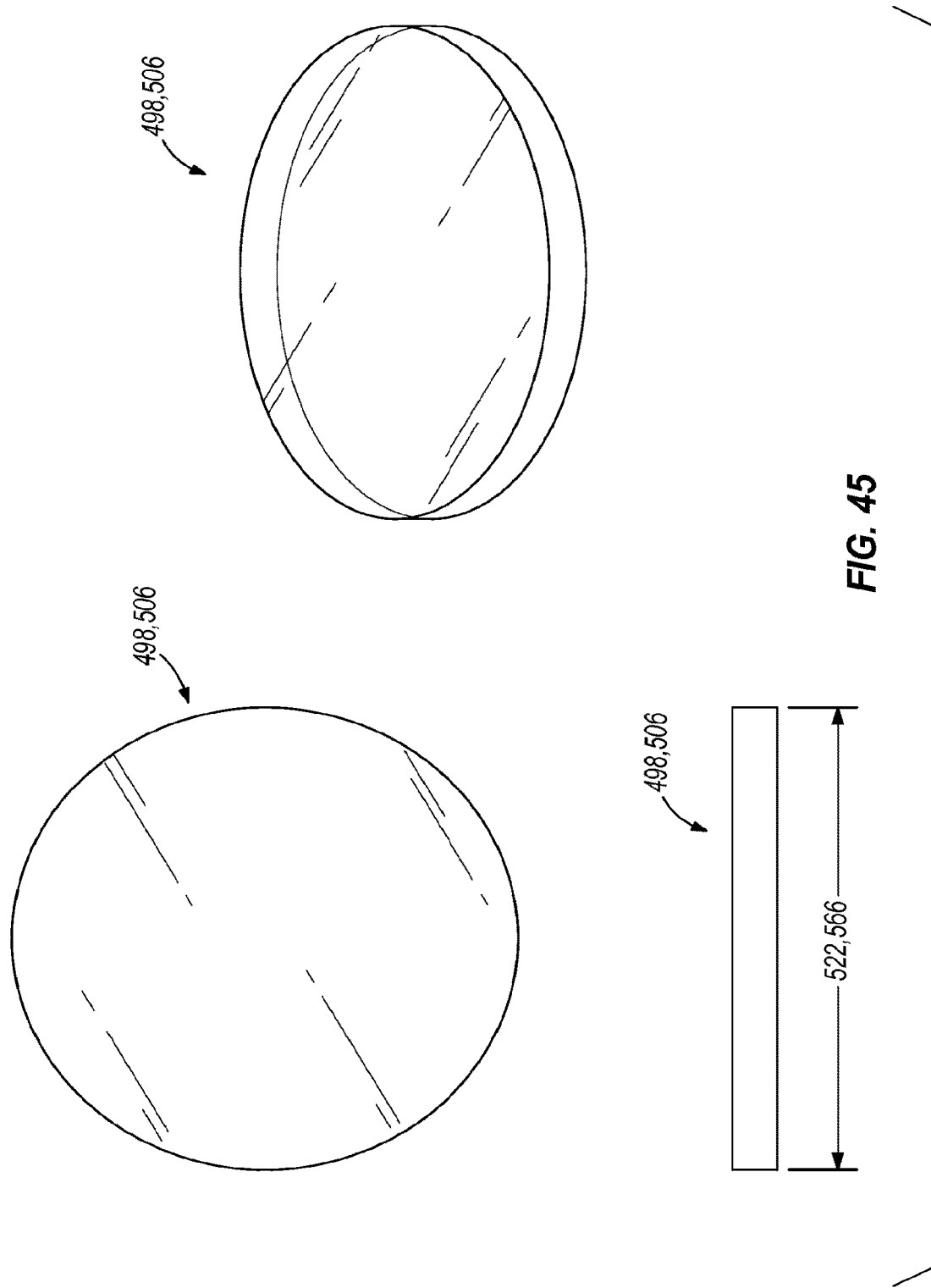
FIG. 45 illustrates several drawings of a portion of the drug delivery device illustrated in FIG. 41.
Figure 46:
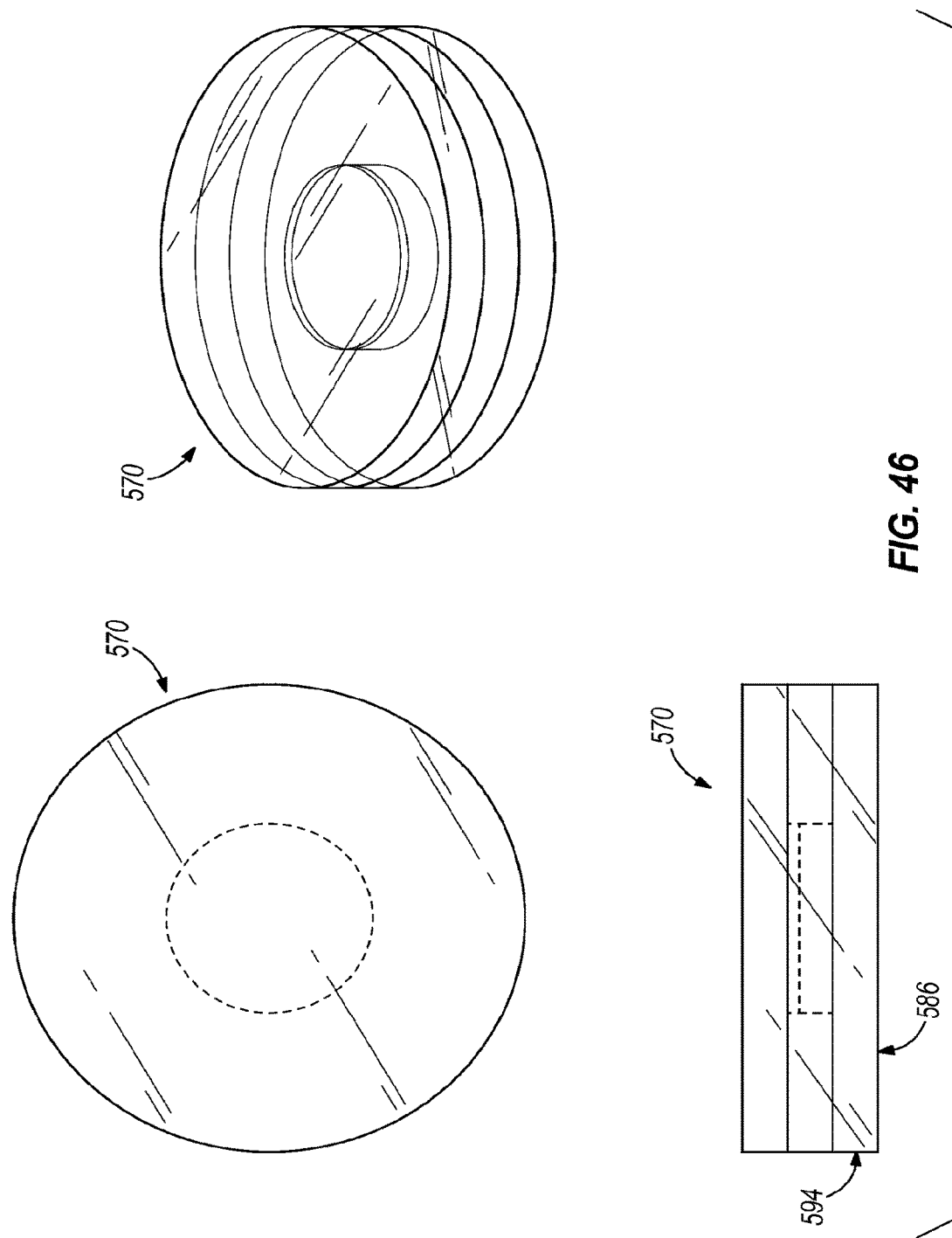
FIG. 46 illustrates several drawings of a drug delivery device according to one embodiment of the present invention.
Figure 47:
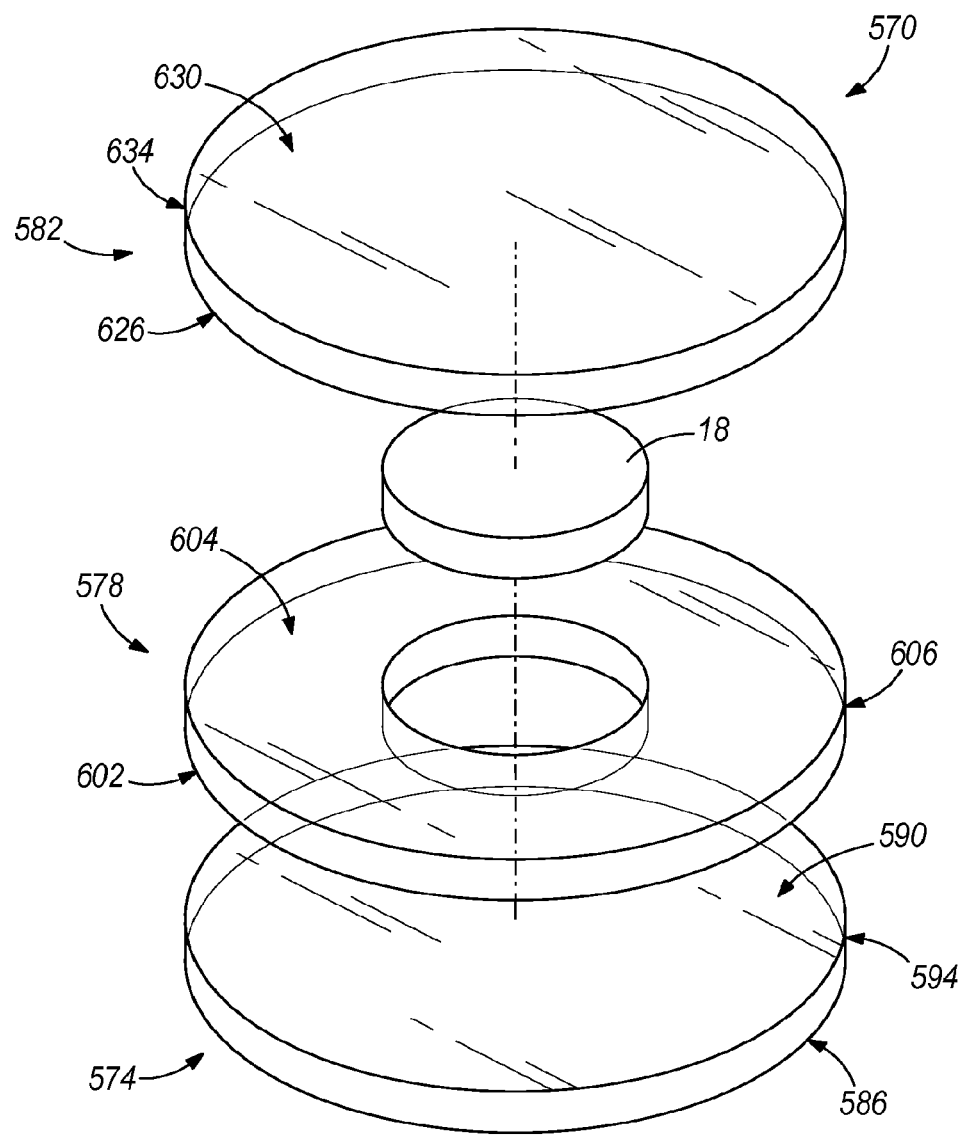
FIG. 47 is an exploded view of the drug delivery device illustrated in FIG. 46.
Figure 48:
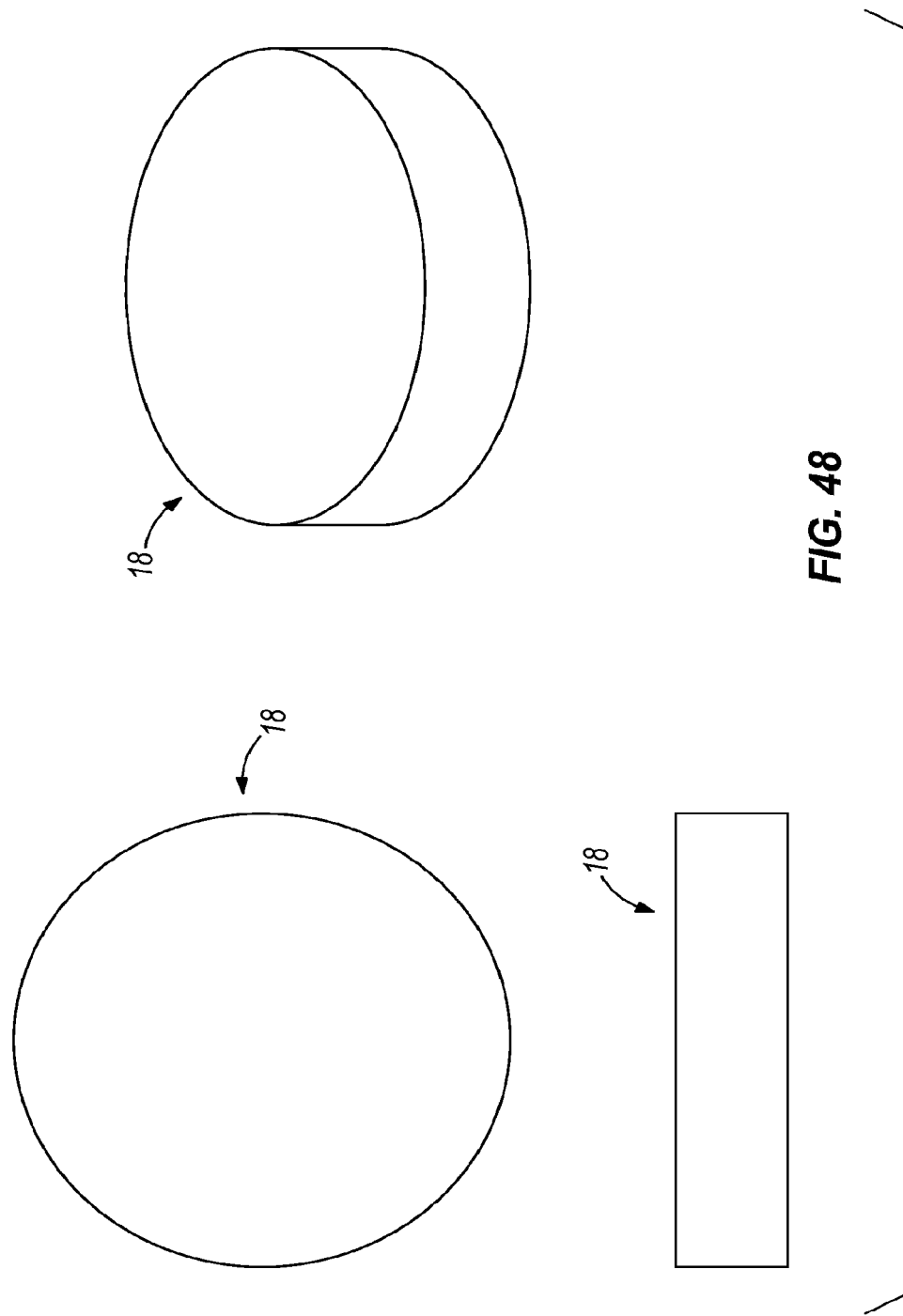
FIG. 48 illustrates several drawings of a composition supported by the drug delivery device illustrated in FIG. 46.
Figure 49:
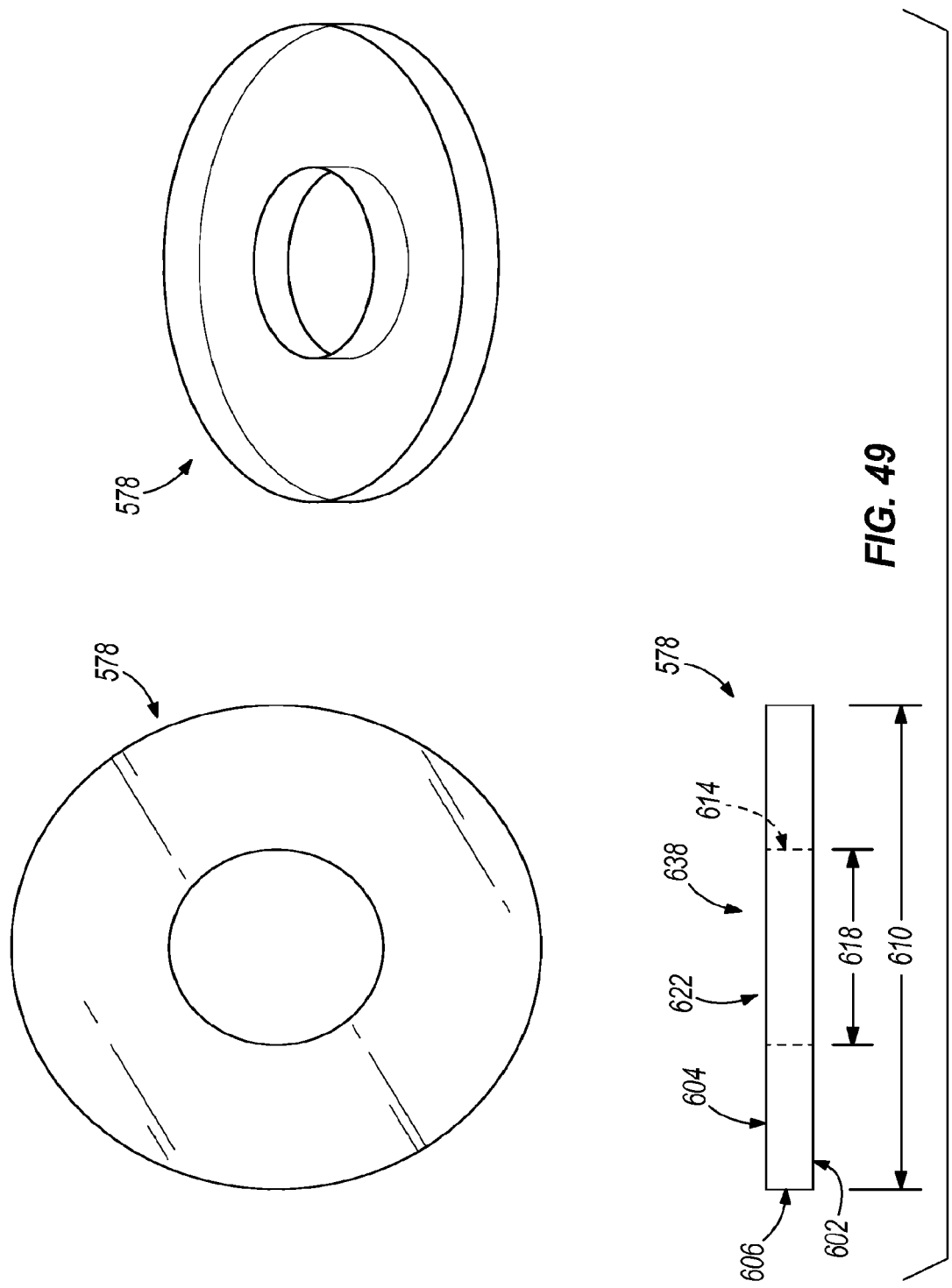
FIG. 49 illustrates several drawings of a portion of the drug delivery device illustrated in FIG. 46.
Figure 50:
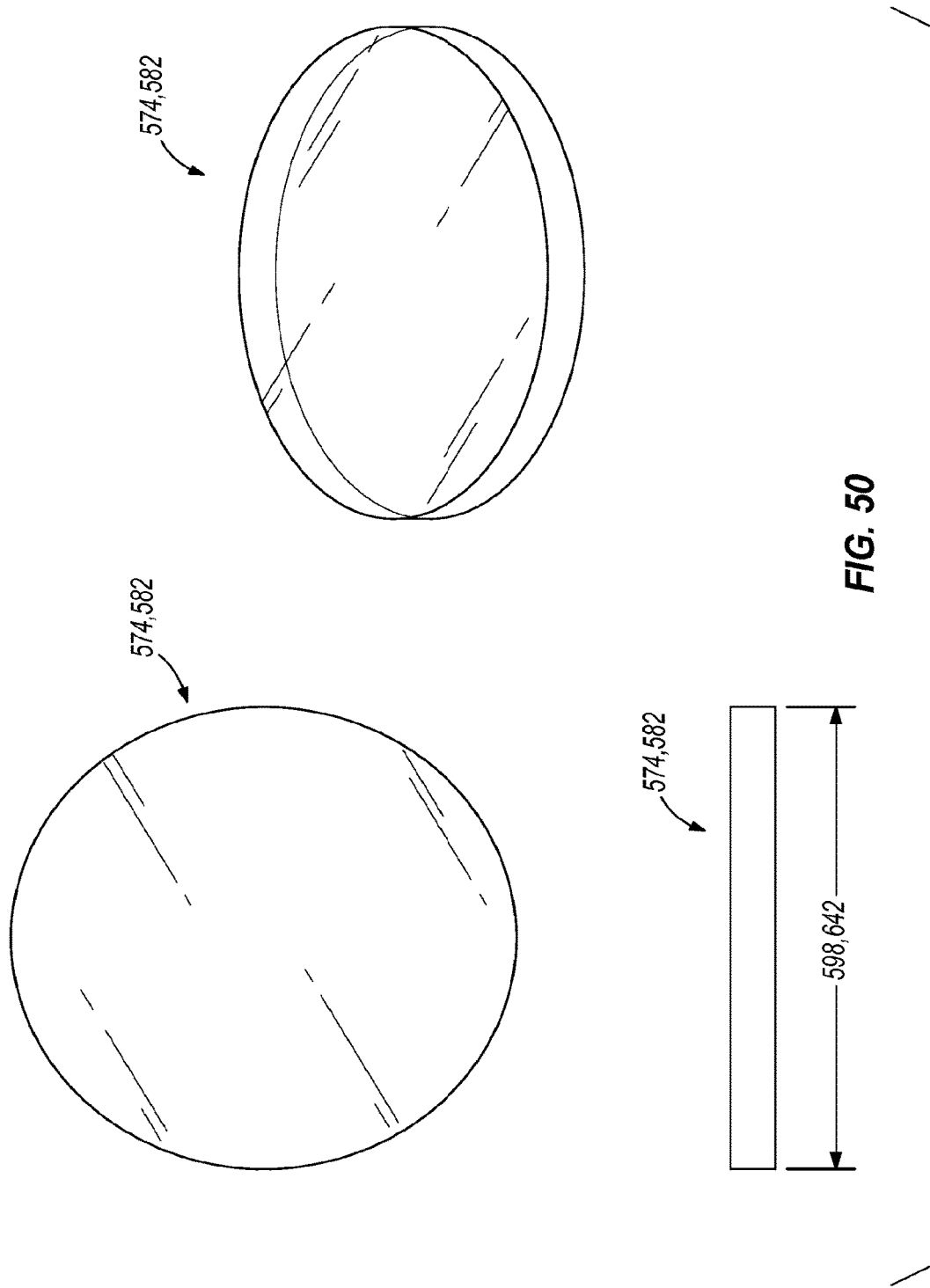
FIG. 50 illustrates several drawings of a portion of the drug delivery device illustrated in FIG. 45.
Figure 51:
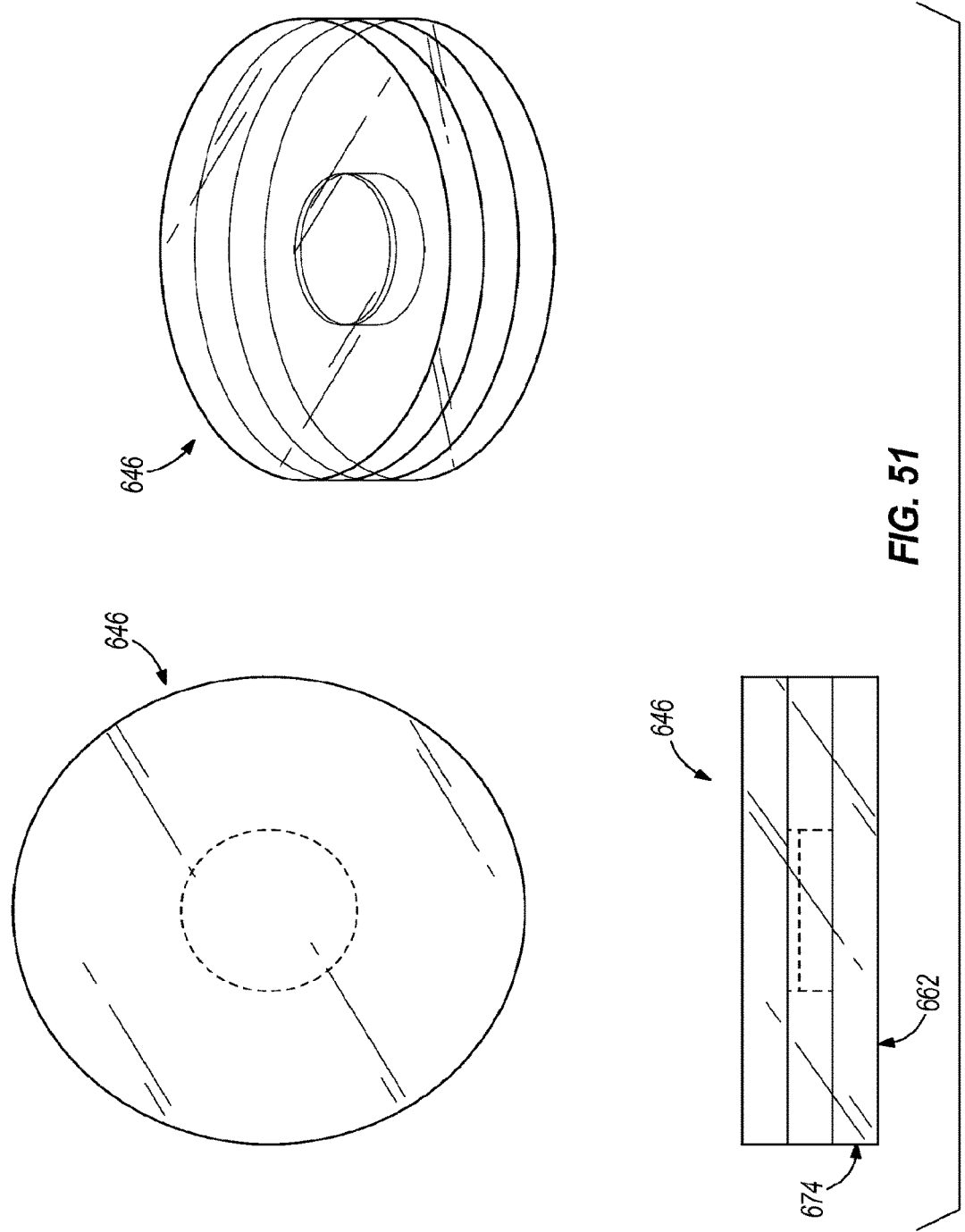
FIG. 51 illustrates several drawings of a drug delivery device according to one embodiment of the present invention.
Figure 52:
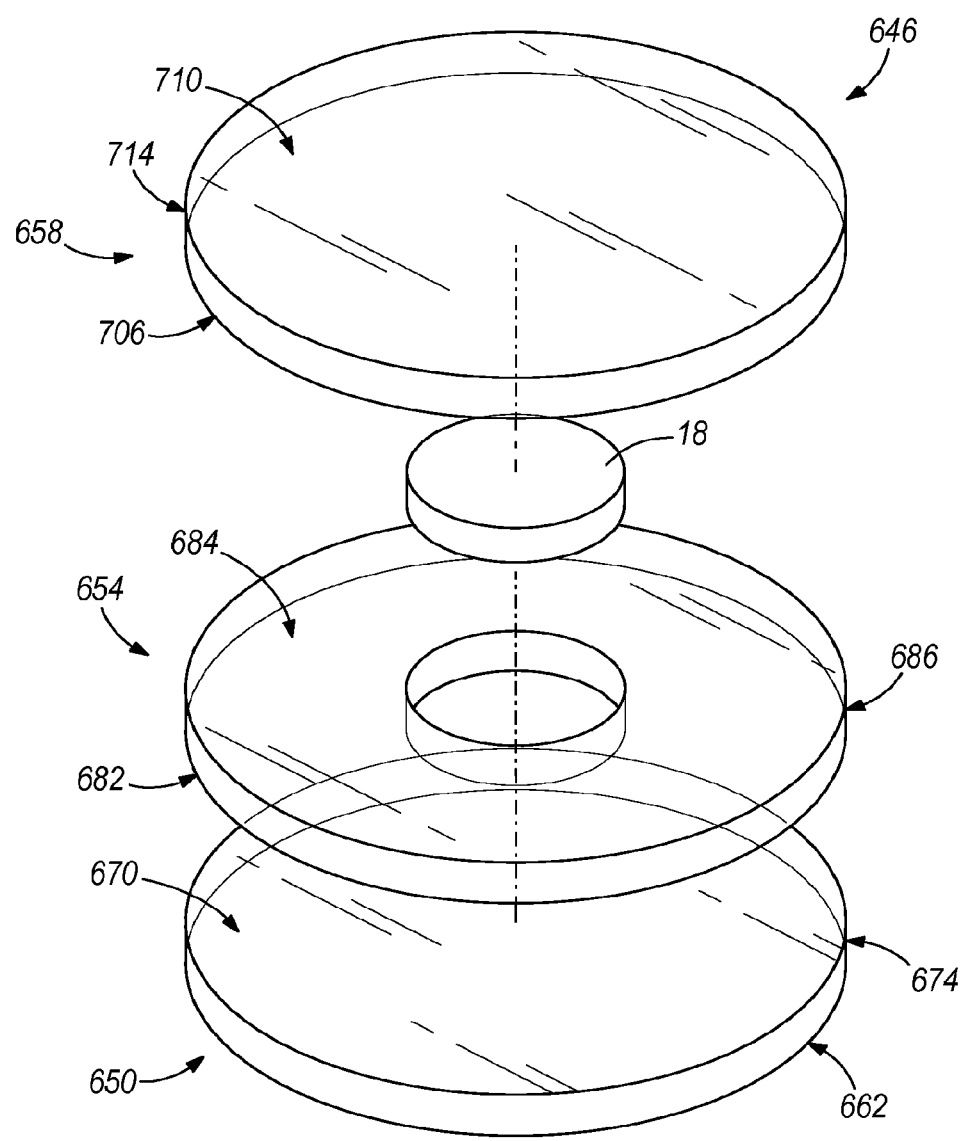
FIG. 52 is an exploded view of the drug delivery device illustrated in FIG. 51.
Figure 53:
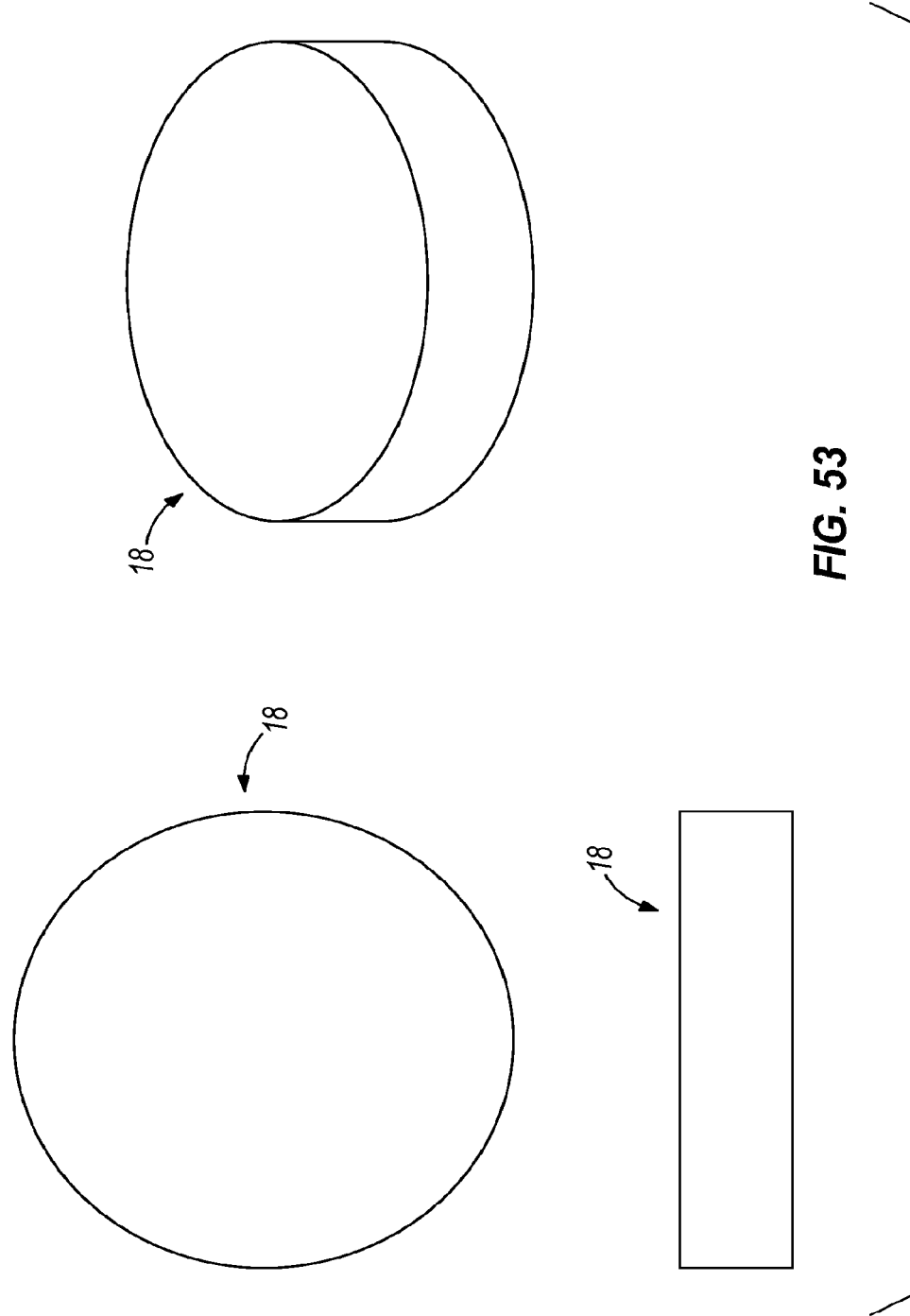
FIG. 53 illustrates several drawings of a composition supported by the drug delivery device illustrated in FIG. 51.
Figure 54:
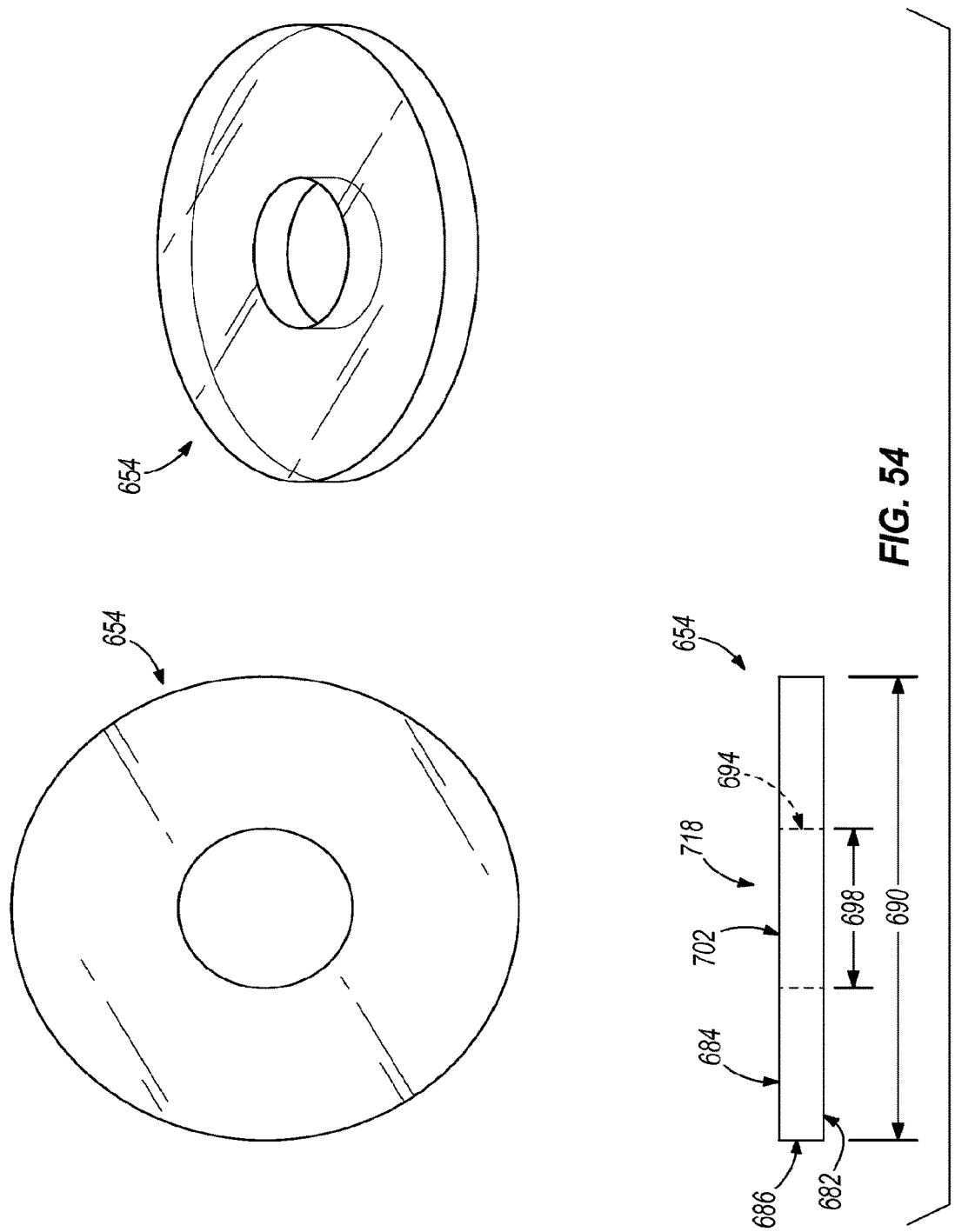
FIG. 54 illustrates several drawings of a portion of the drug delivery device illustrated in FIG. 51.
Figure 55:
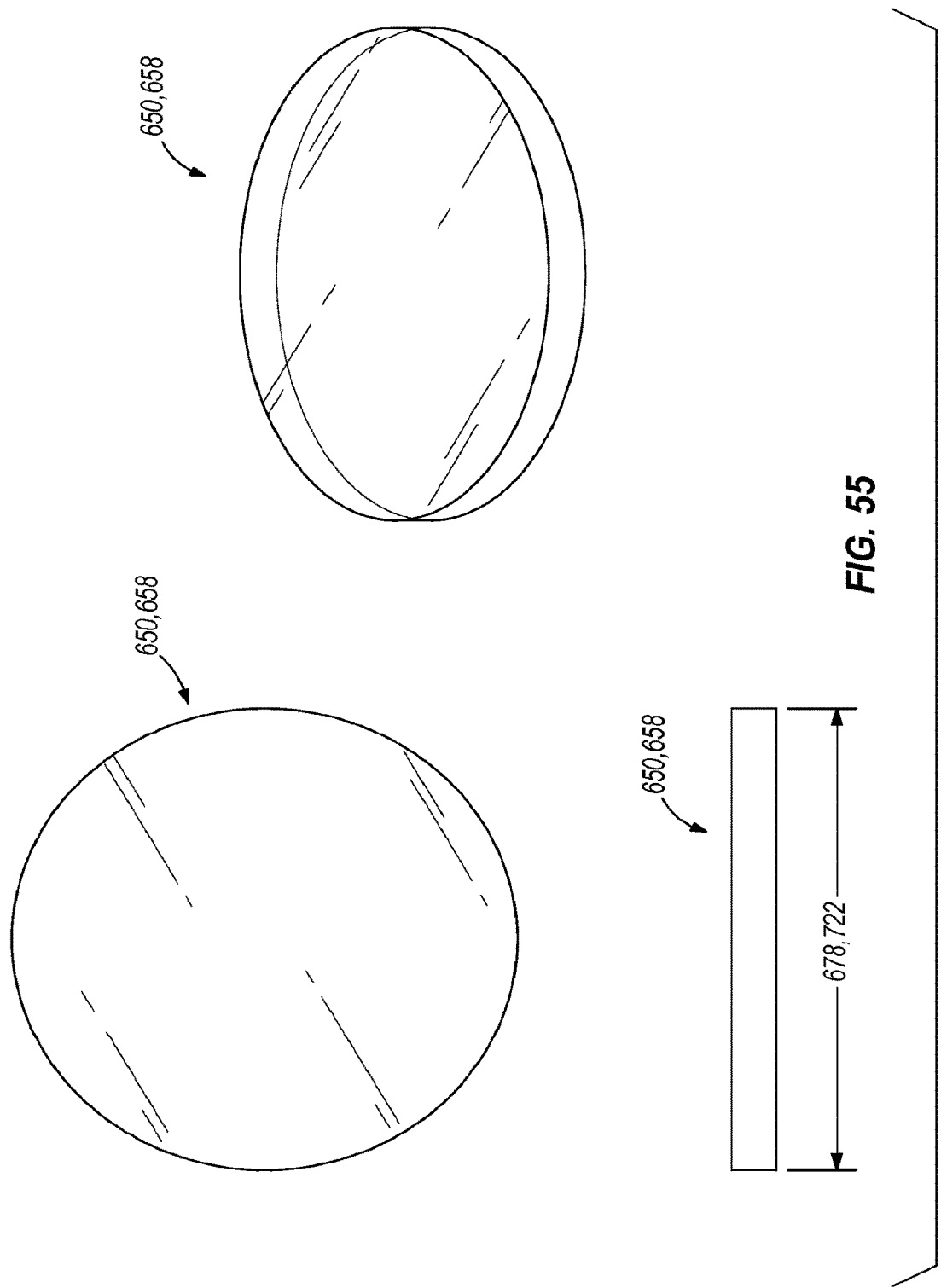
FIG. 55 illustrates several drawings of a portion of the drug delivery device illustrated in FIG. 51.
Figure 56:
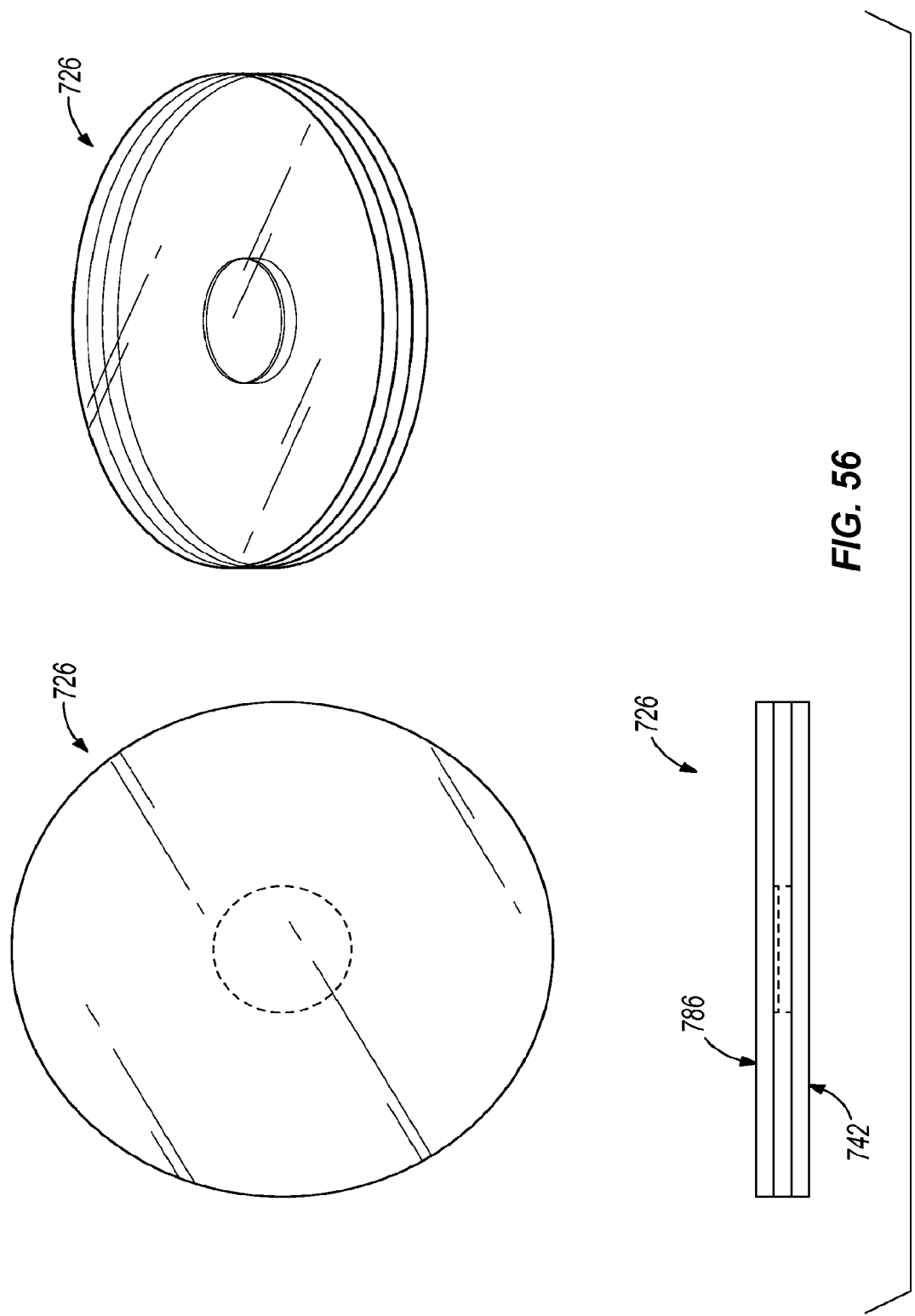
FIG. 56 illustrates several drawings of a drug delivery device according to one embodiment of the present invention.
Figure 57:
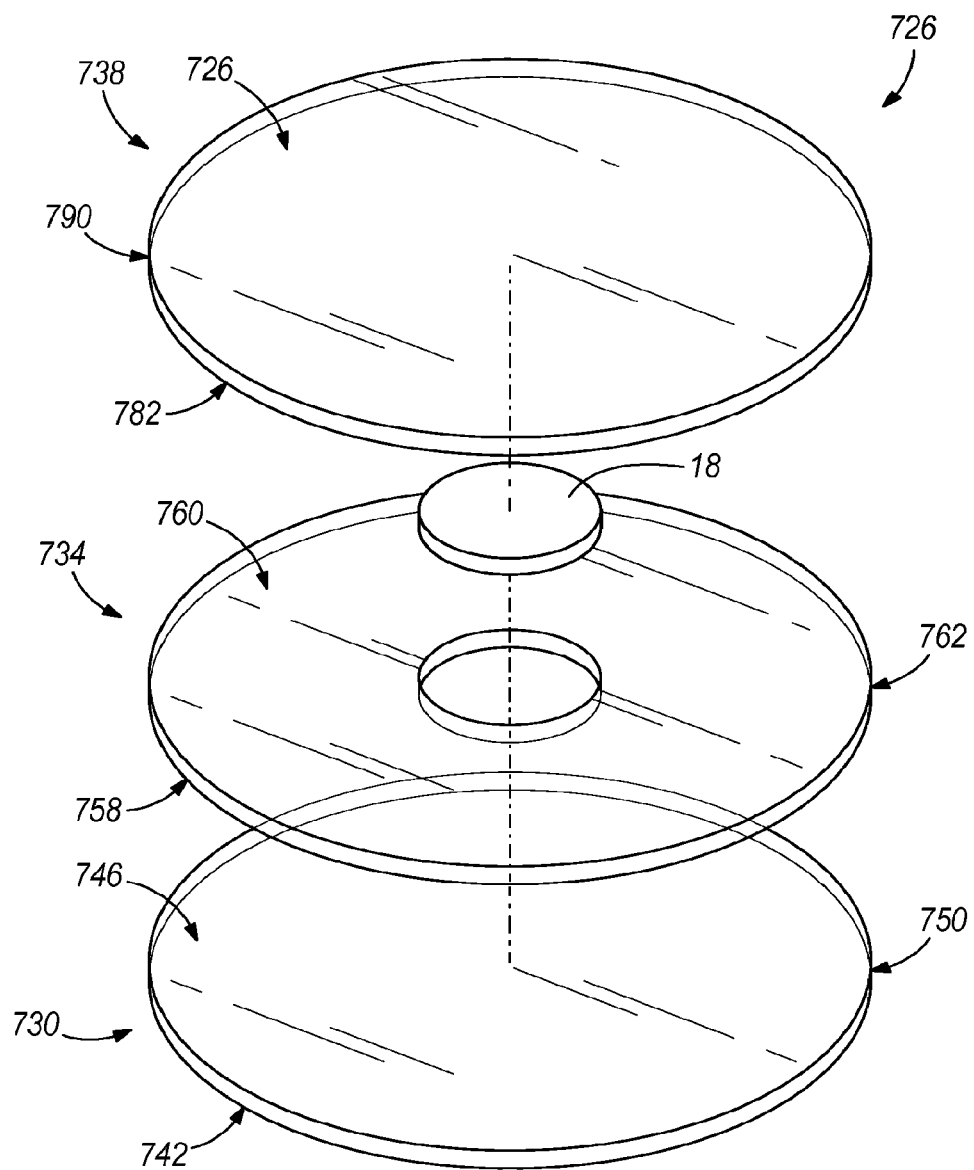
FIG. 57 is an exploded view of the drug delivery device illustrated in FIG. 56.
Figure 58:
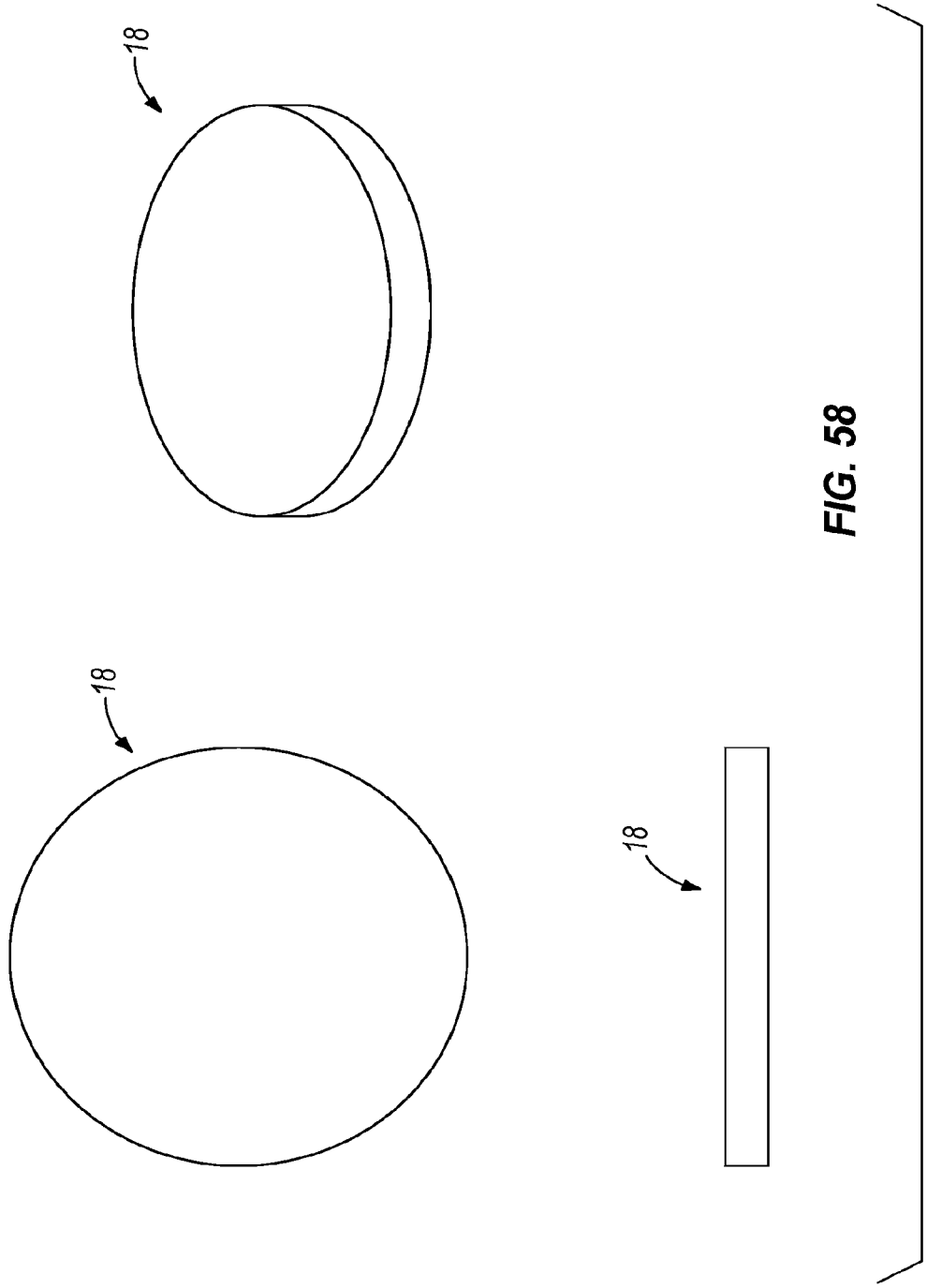
FIG. 58 illustrates several drawings of a composition supported by the drug delivery device illustrated in FIG. 56.
Figure 59:
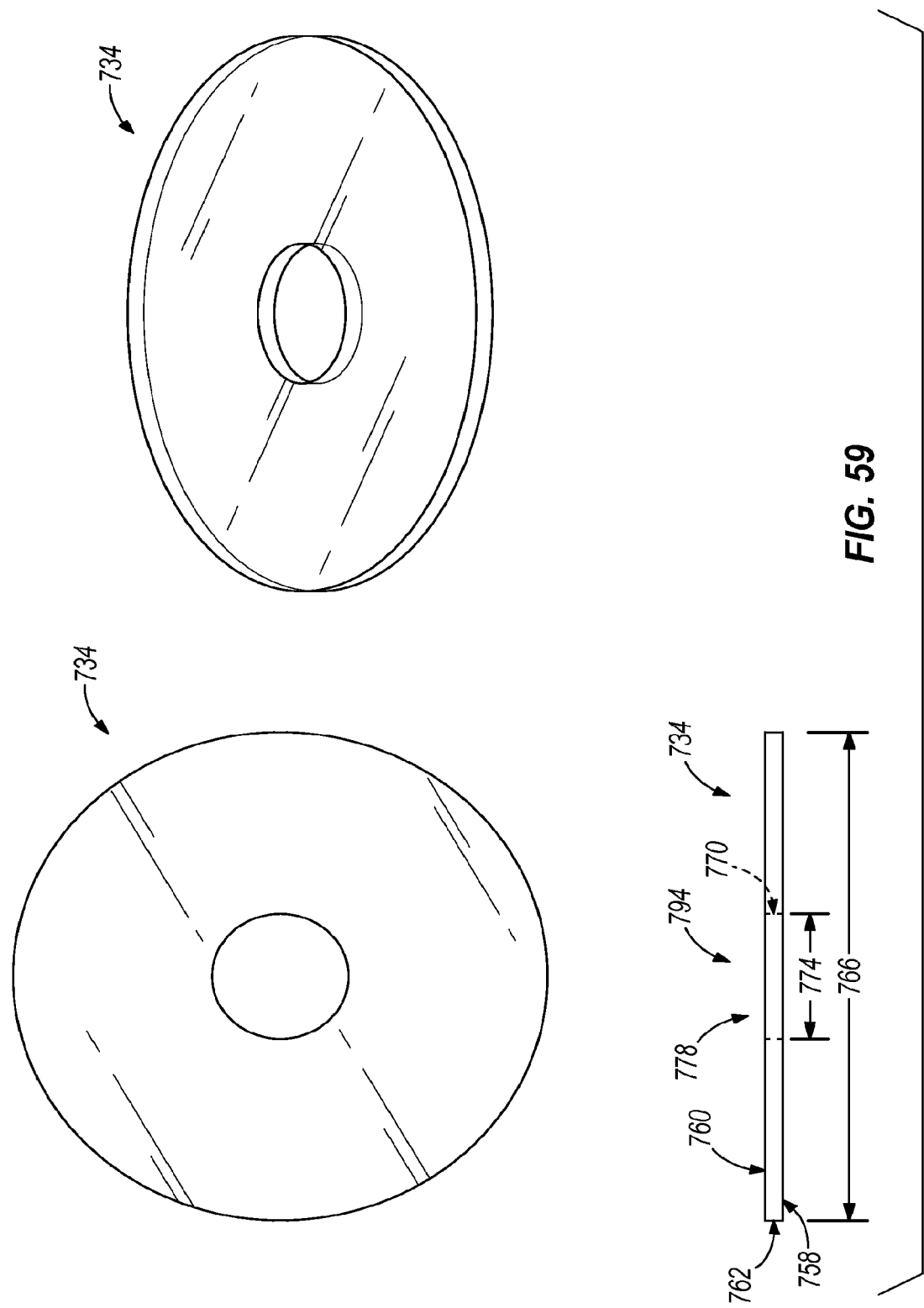
FIG. 59 illustrates several drawings of a portion of the drug delivery device illustrated in FIG. 56.
Figure 60:
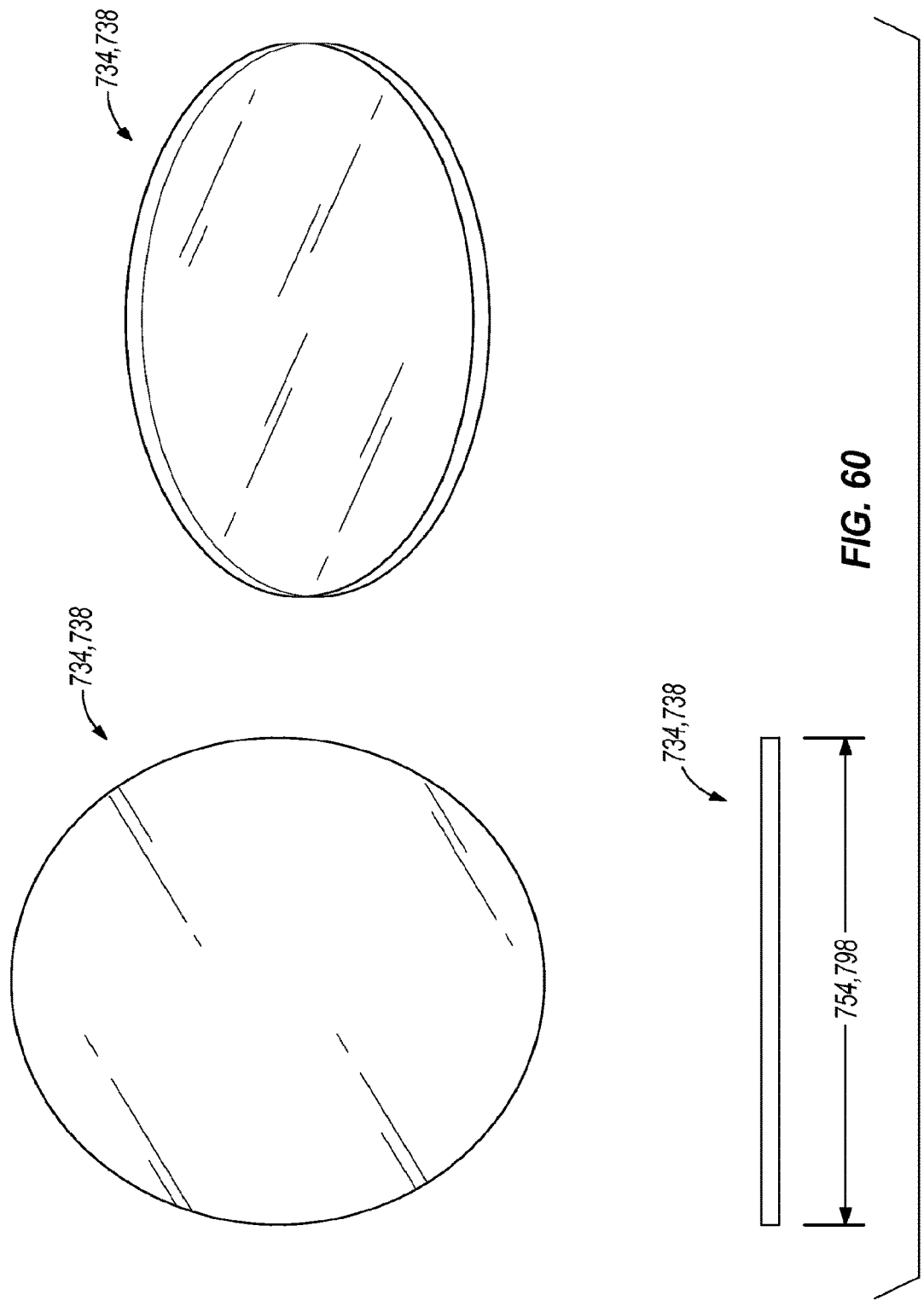
FIG. 60 illustrates several drawings of a portion of the drug delivery device illustrated in FIG. 56.
Figure 61:
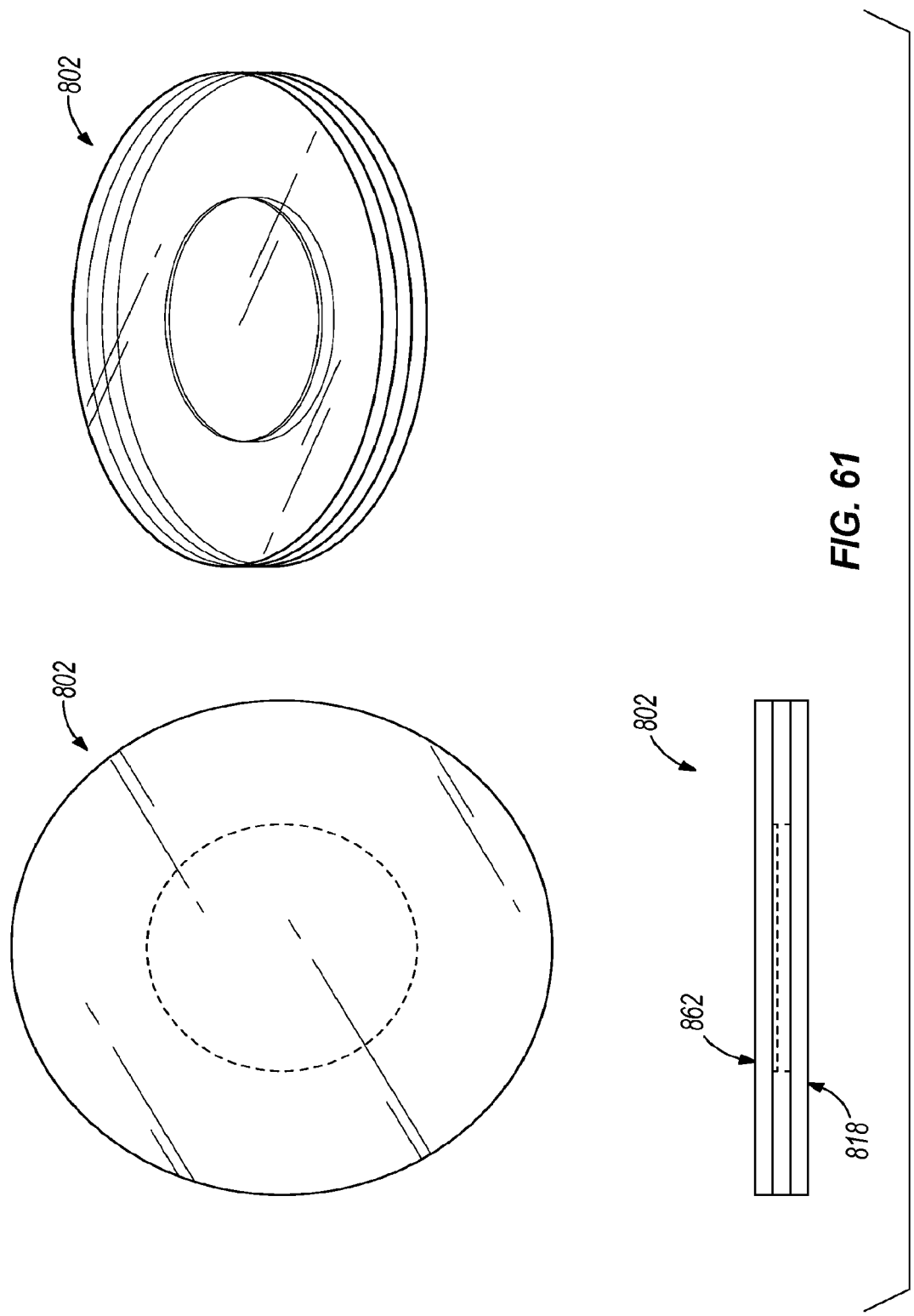
FIG. 61 illustrates several drawings of a drug delivery device according to one embodiment of the present invention.
Figure 62:
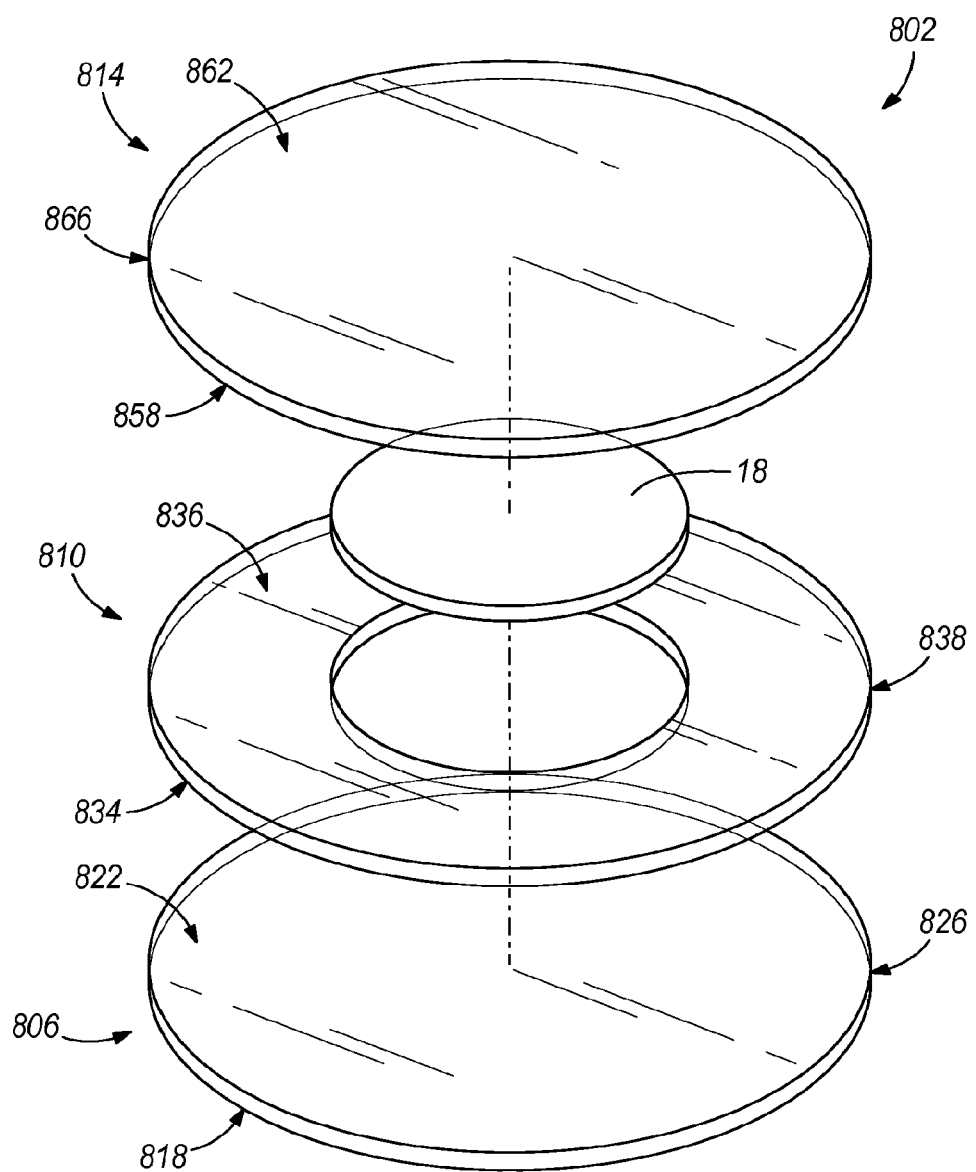
FIG. 62 is an exploded view of the drug delivery device illustrated in FIG. 61.
Figure 63:
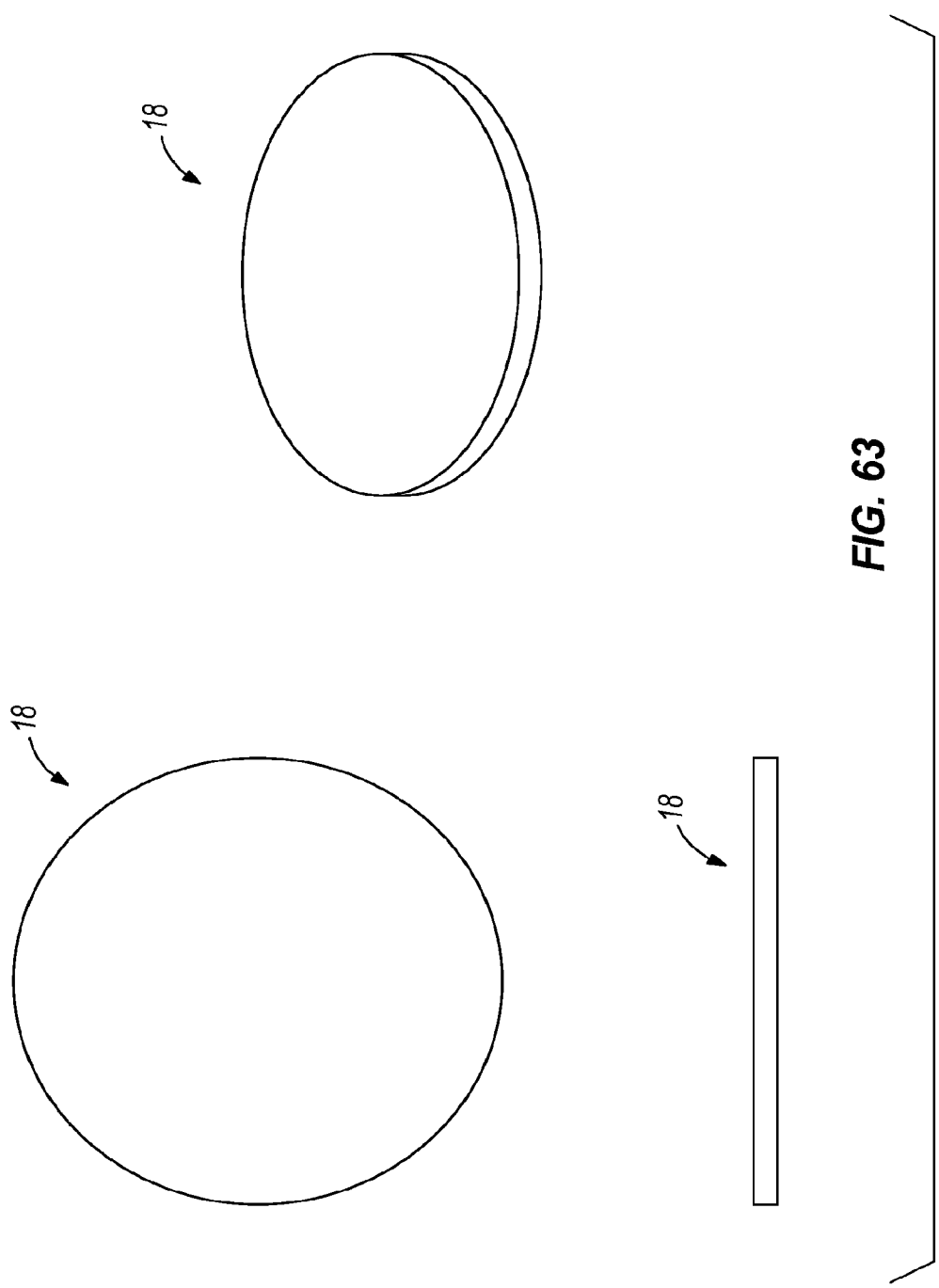
FIG. 63 illustrates several drawings of a composition supported by the drug delivery device illustrated in FIG. 61.
Figure 64:
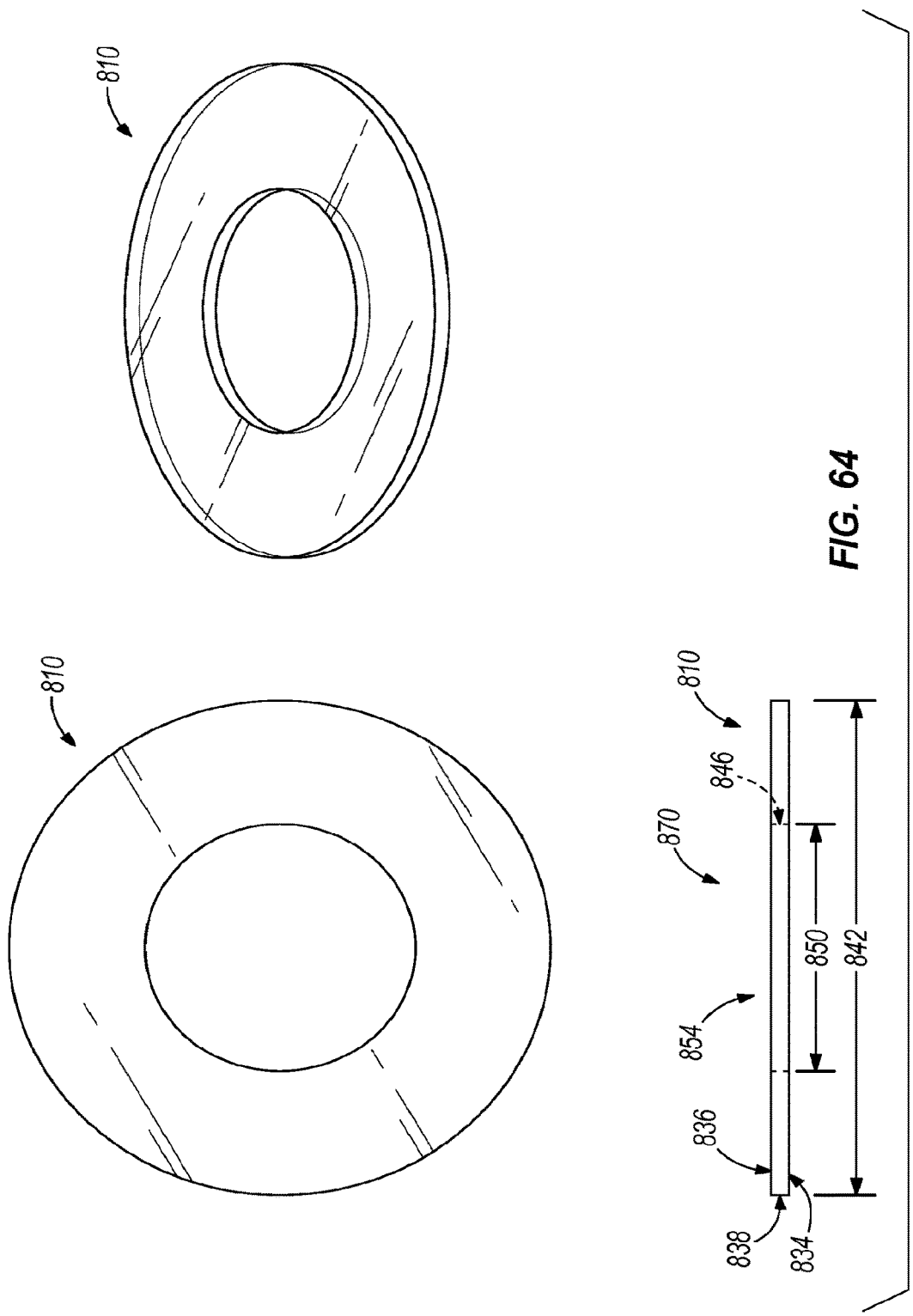
FIG. 64 illustrates several drawings of a portion of the drug delivery device illustrated in FIG. 61.
Figure 65:
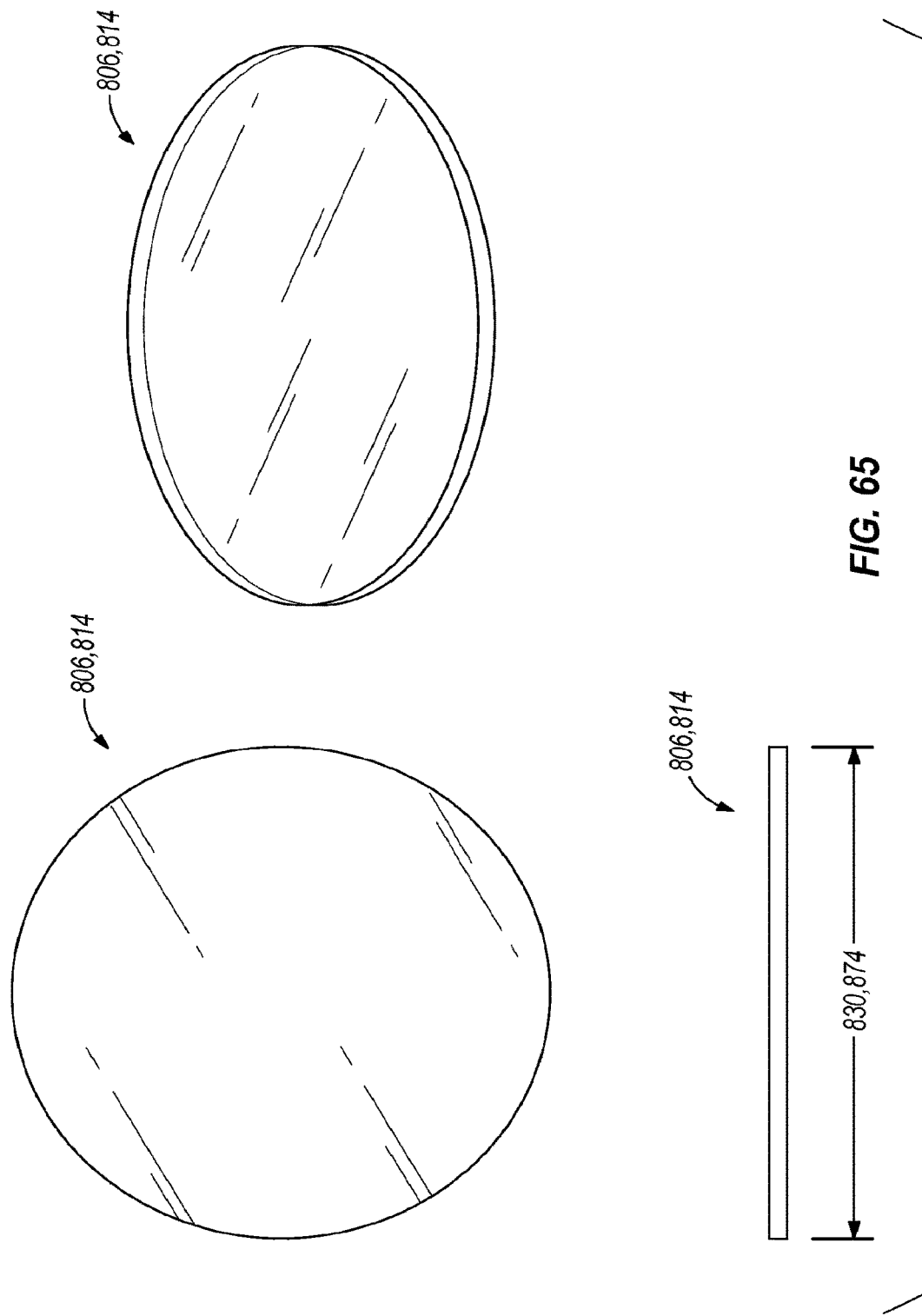
FIG. 65 illustrates several drawings of a portion of the drug delivery device illustrated in FIG. 61.
Figure 66:
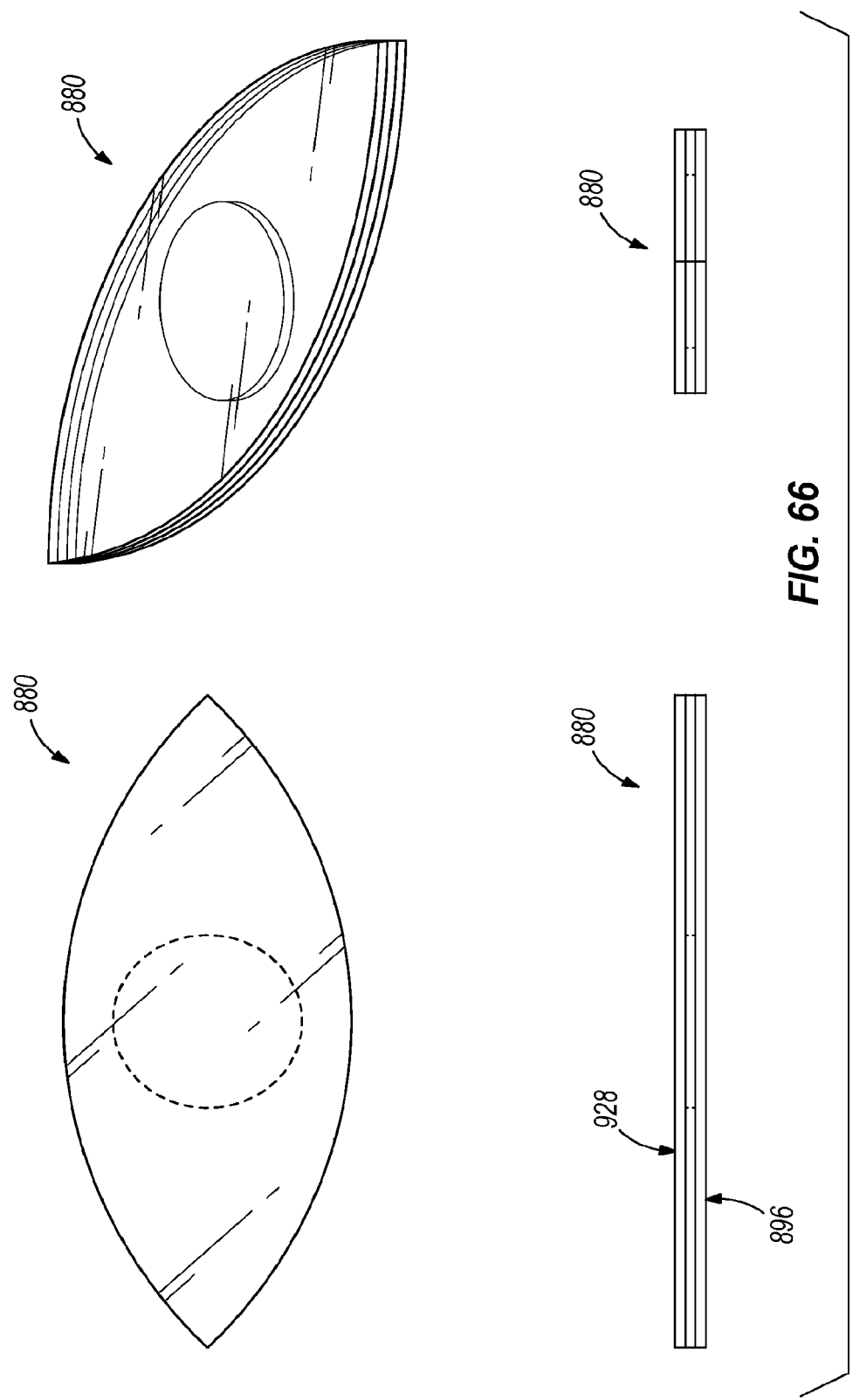
FIG. 66 illustrates several drawings of a drug delivery device according to one embodiment of the present invention.
Figure 67:
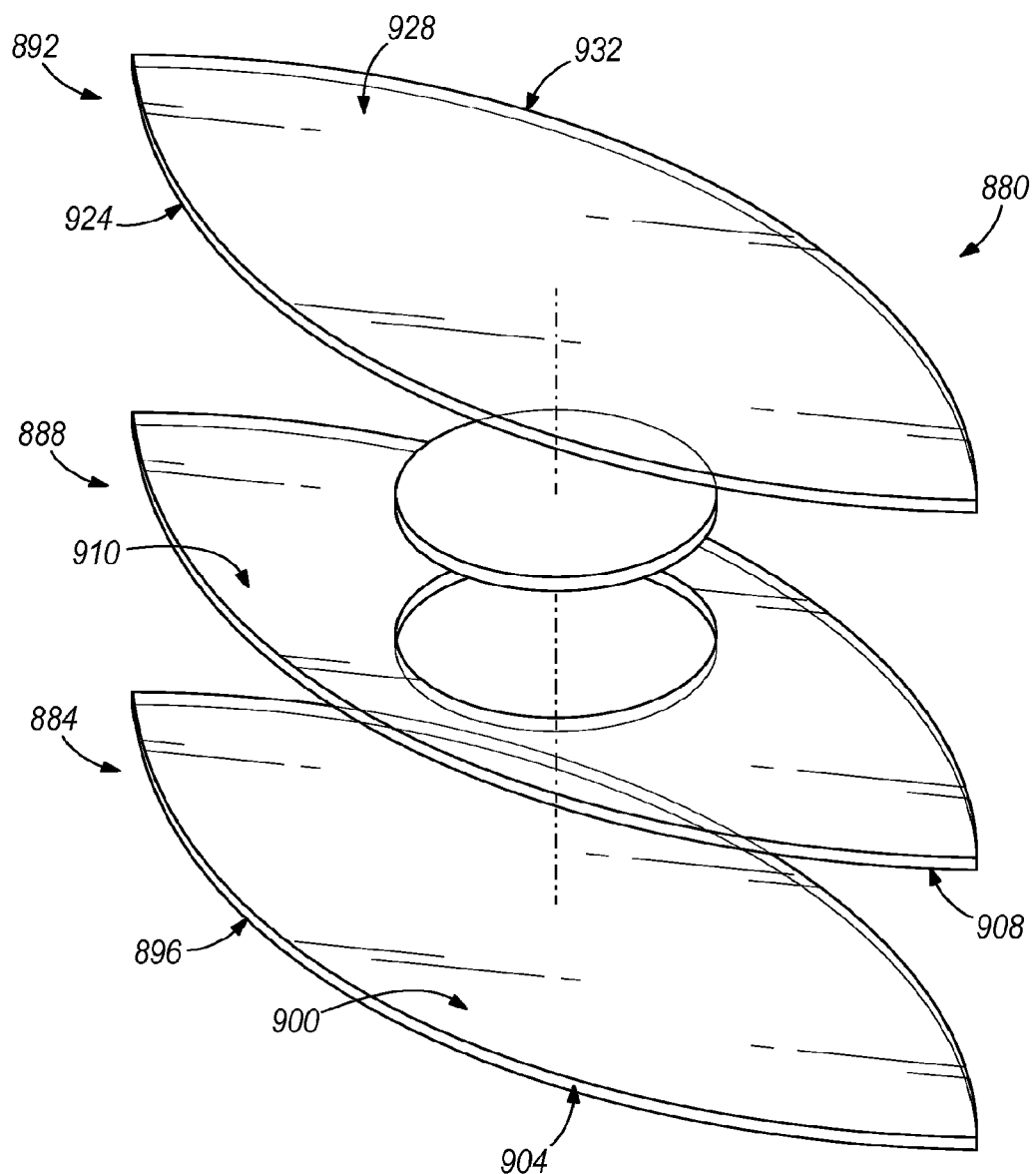
FIG. 67 is an exploded view of the drug delivery device illustrated in FIG. 66.
Figure 68:
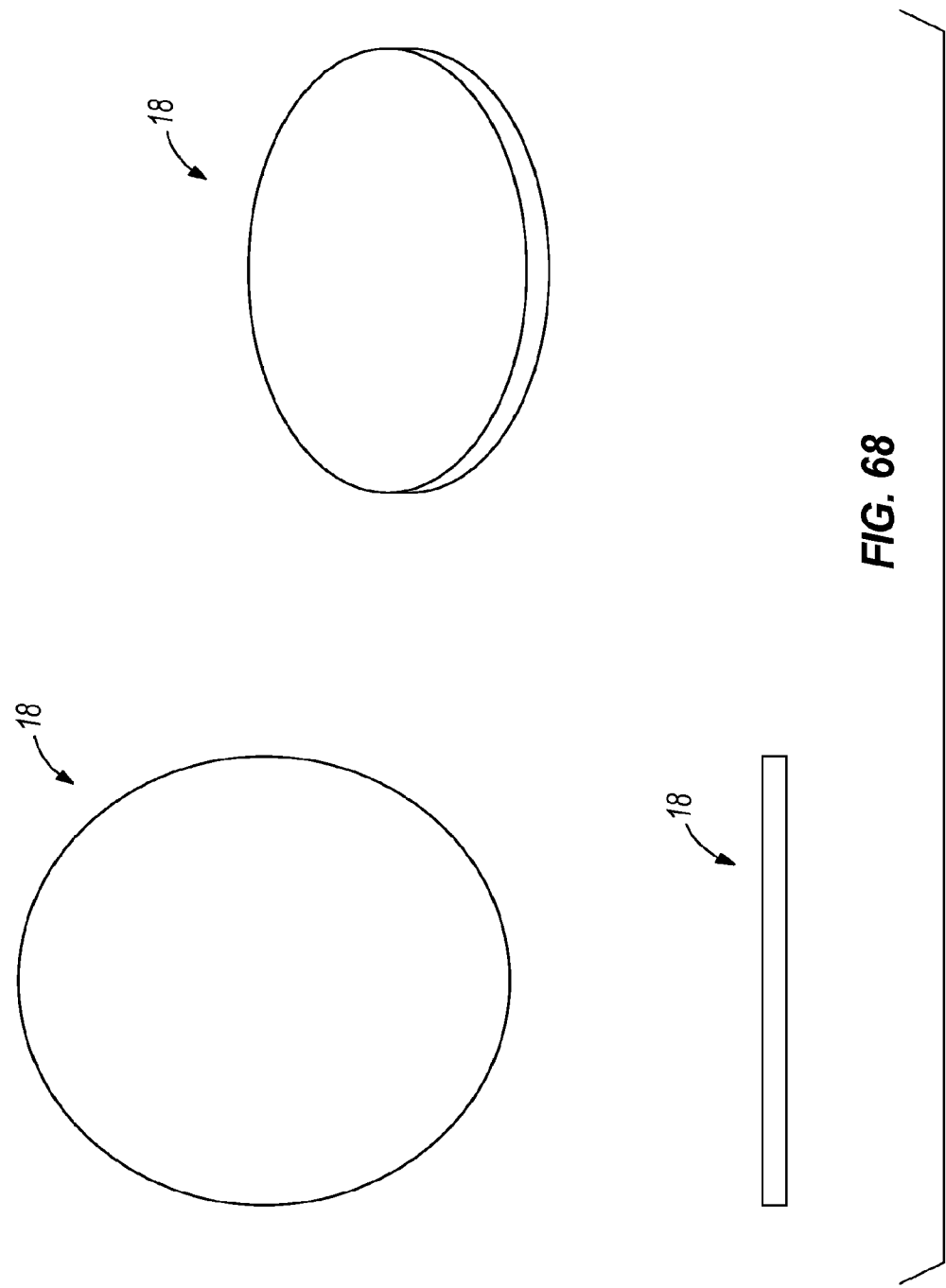
FIG. 68 illustrates several drawings of a composition supported by the drug delivery device illustrated in FIG. 66.
Figure 70:
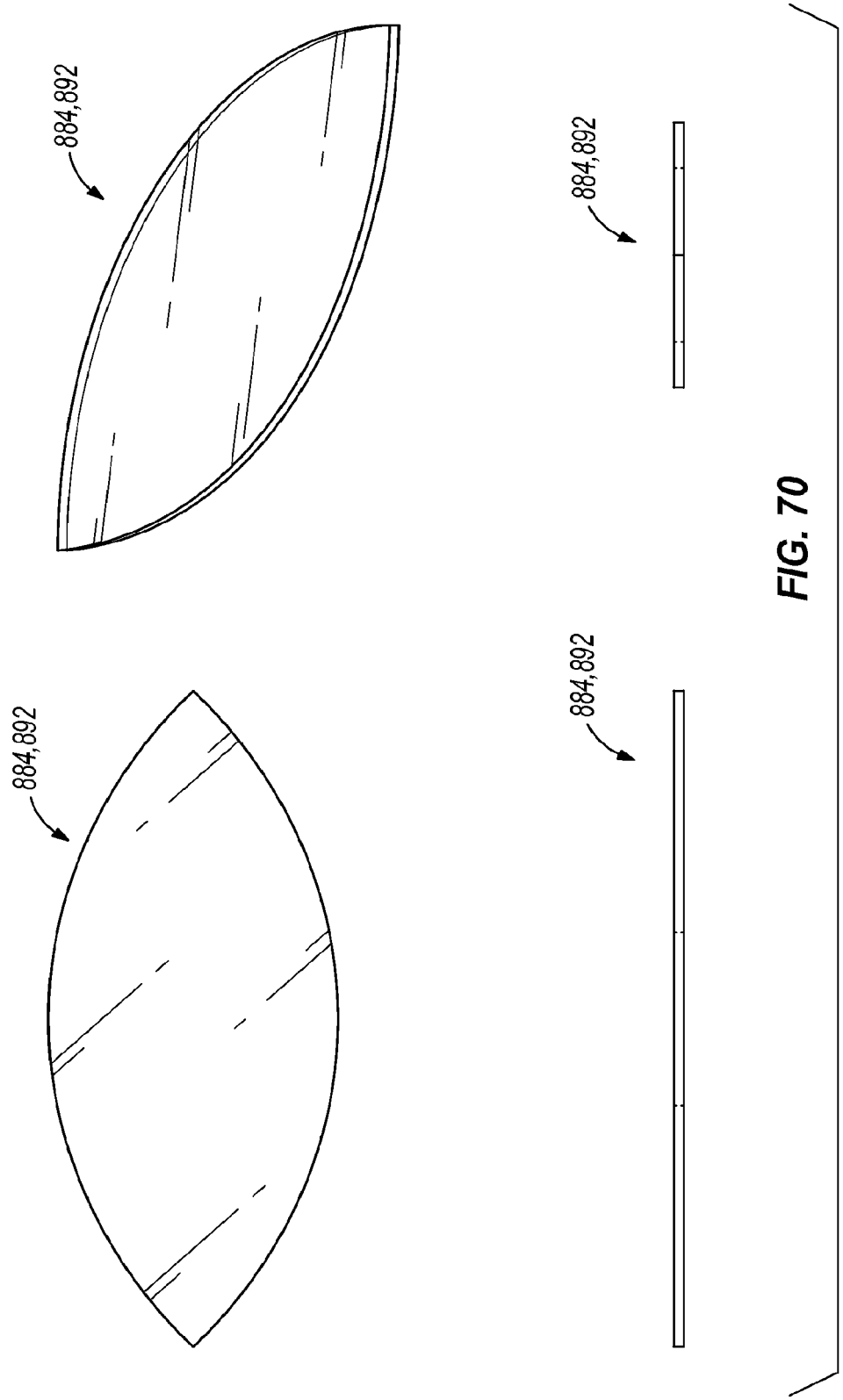
FIG. 70 illustrates several drawings of a portion of the drug delivery device illustrated in FIG. 66.
Figure 71:
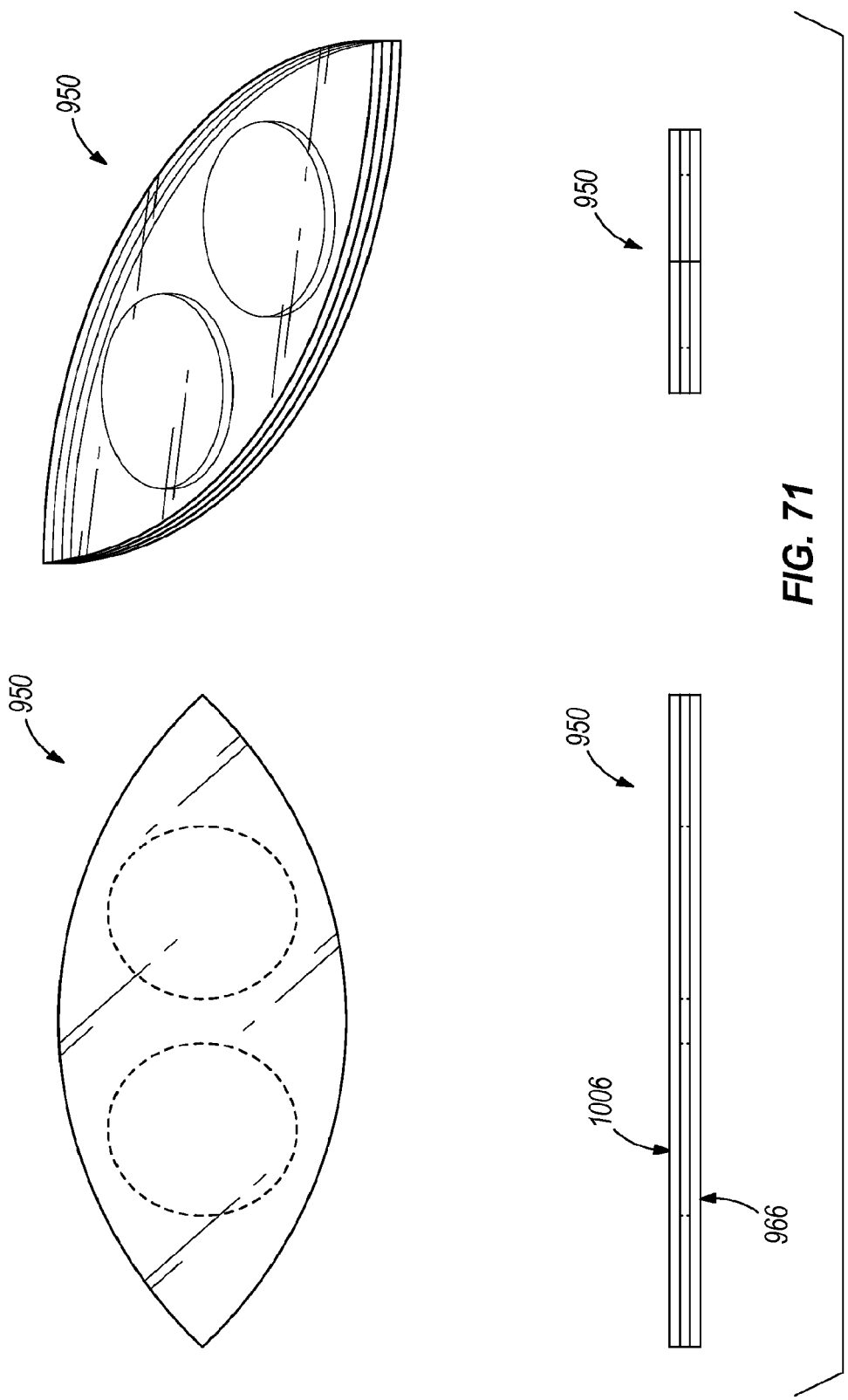
FIG. 71 illustrates several drawings of a drug delivery device according to one embodiment of the present invention.
Figure 72:
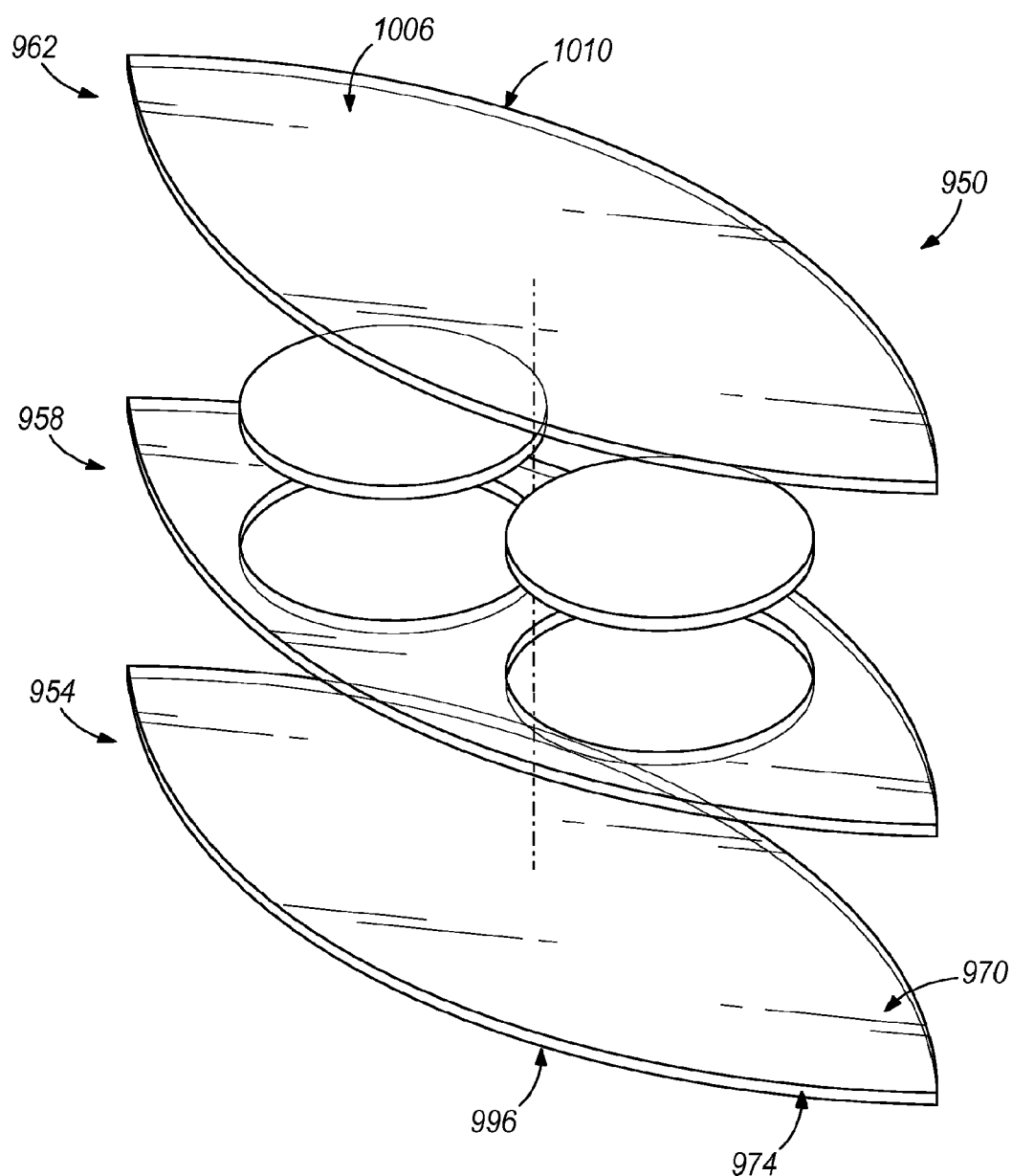
FIG. 72 is an exploded view of the drug delivery device illustrated in FIG. 71.
Figure 73:
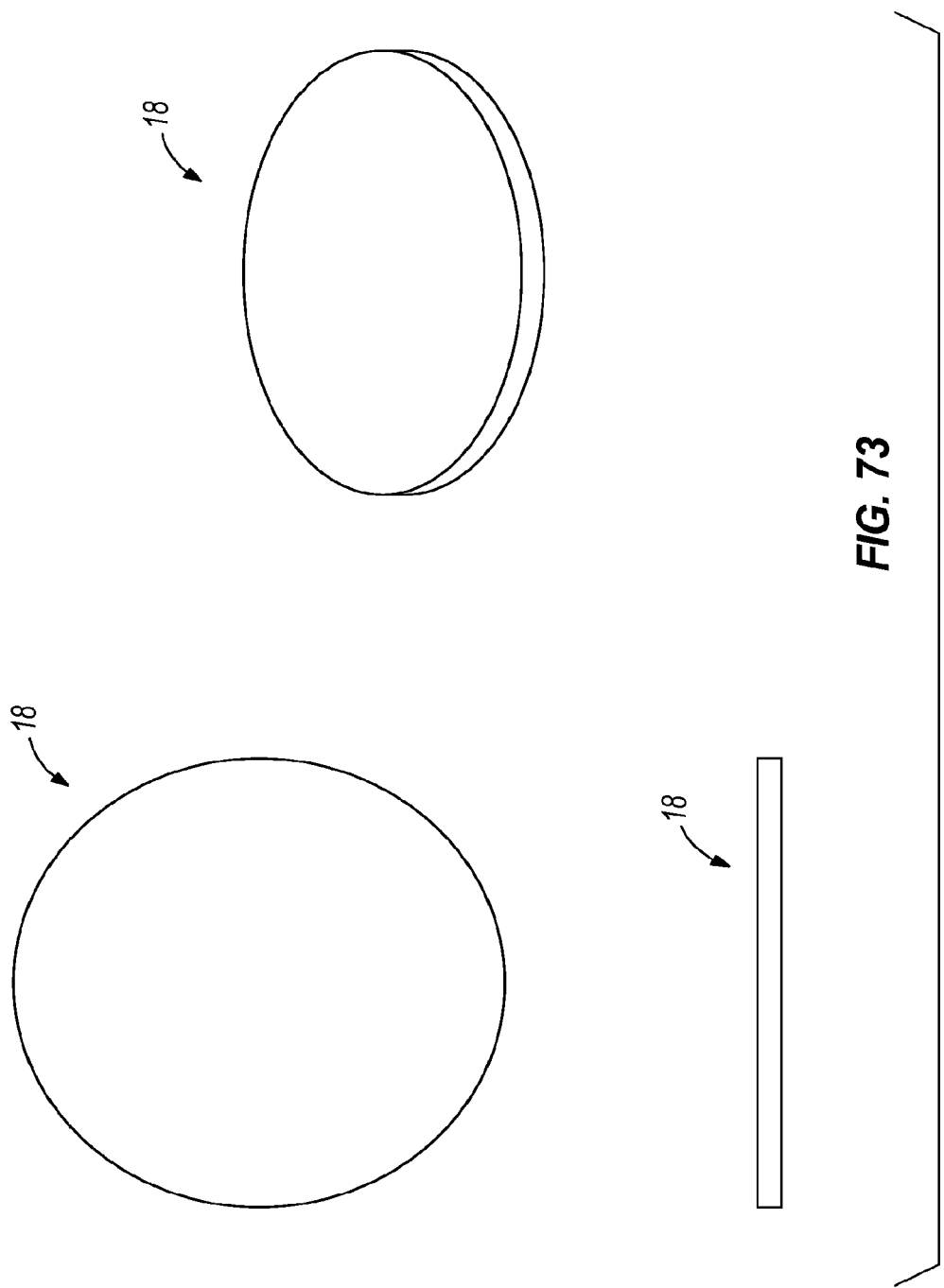
FIG. 73 illustrates several drawings of a composition supported by the drug delivery device illustrated in FIG. 71.
Figure 74:
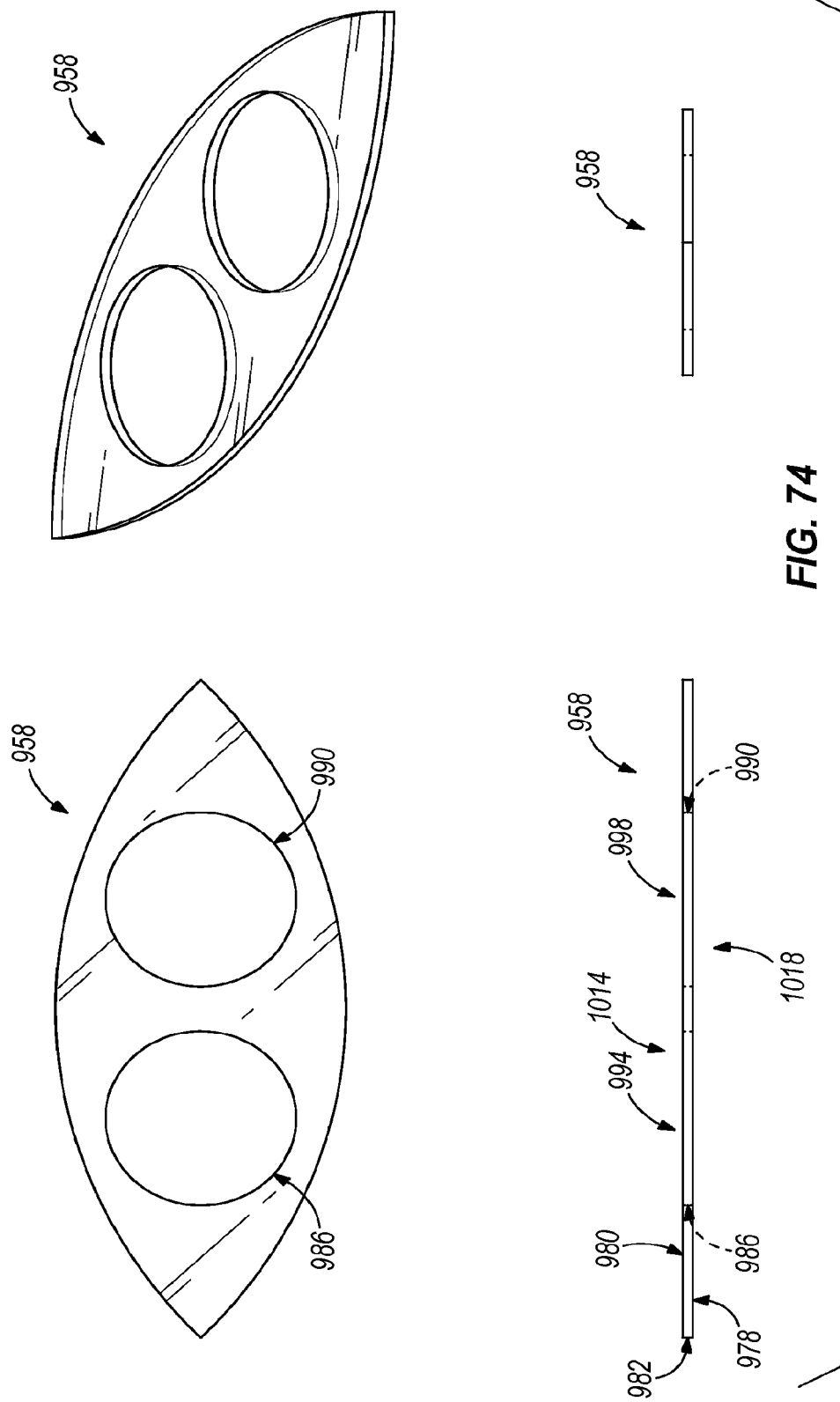
FIG. 74 illustrates several drawings of a portion of the drug delivery device illustrated in FIG. 71.
Figure 75:
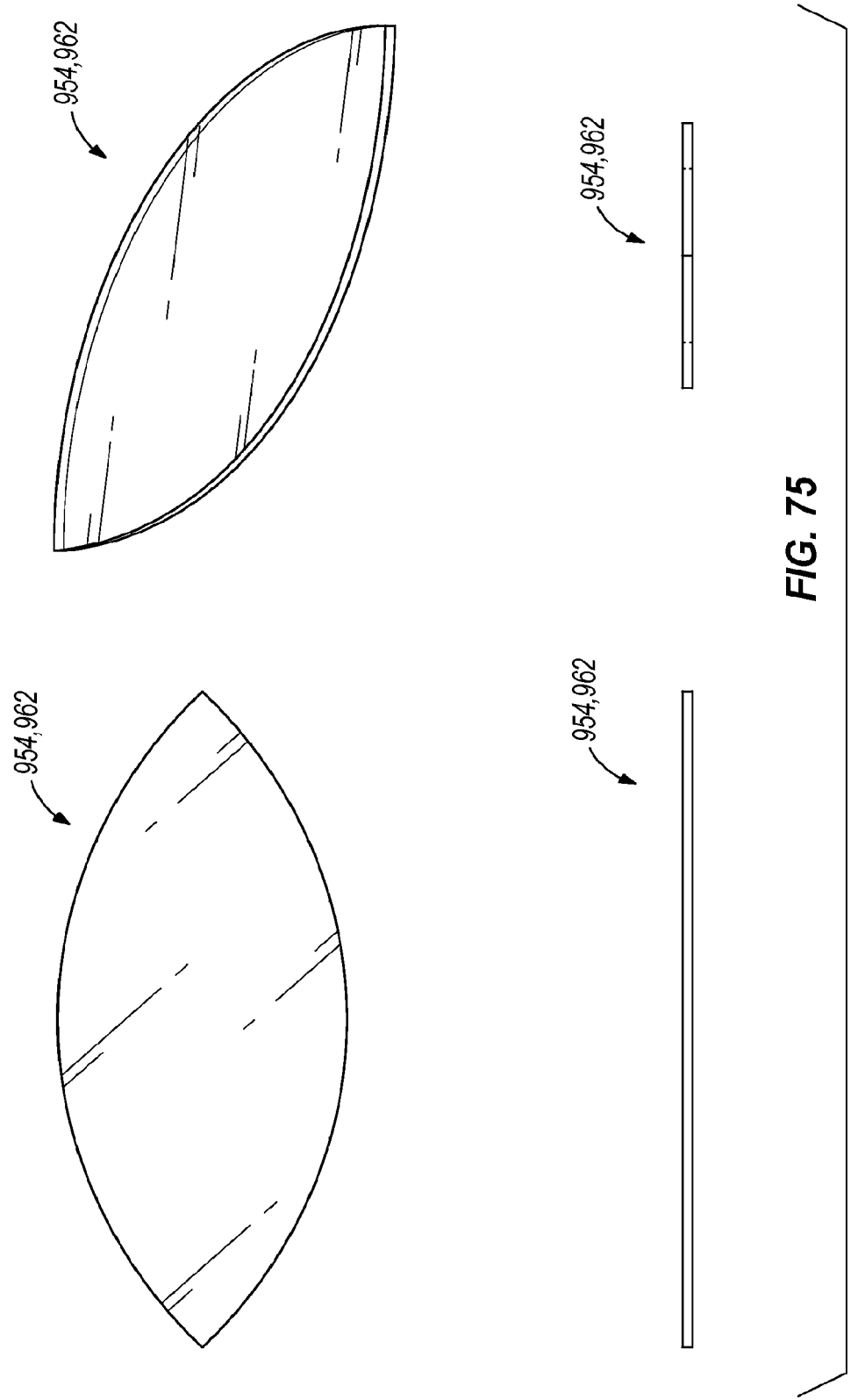
FIG. 75 illustrates several drawings of a portion of the drug delivery device illustrated in FIG. 71.
Figure 76:
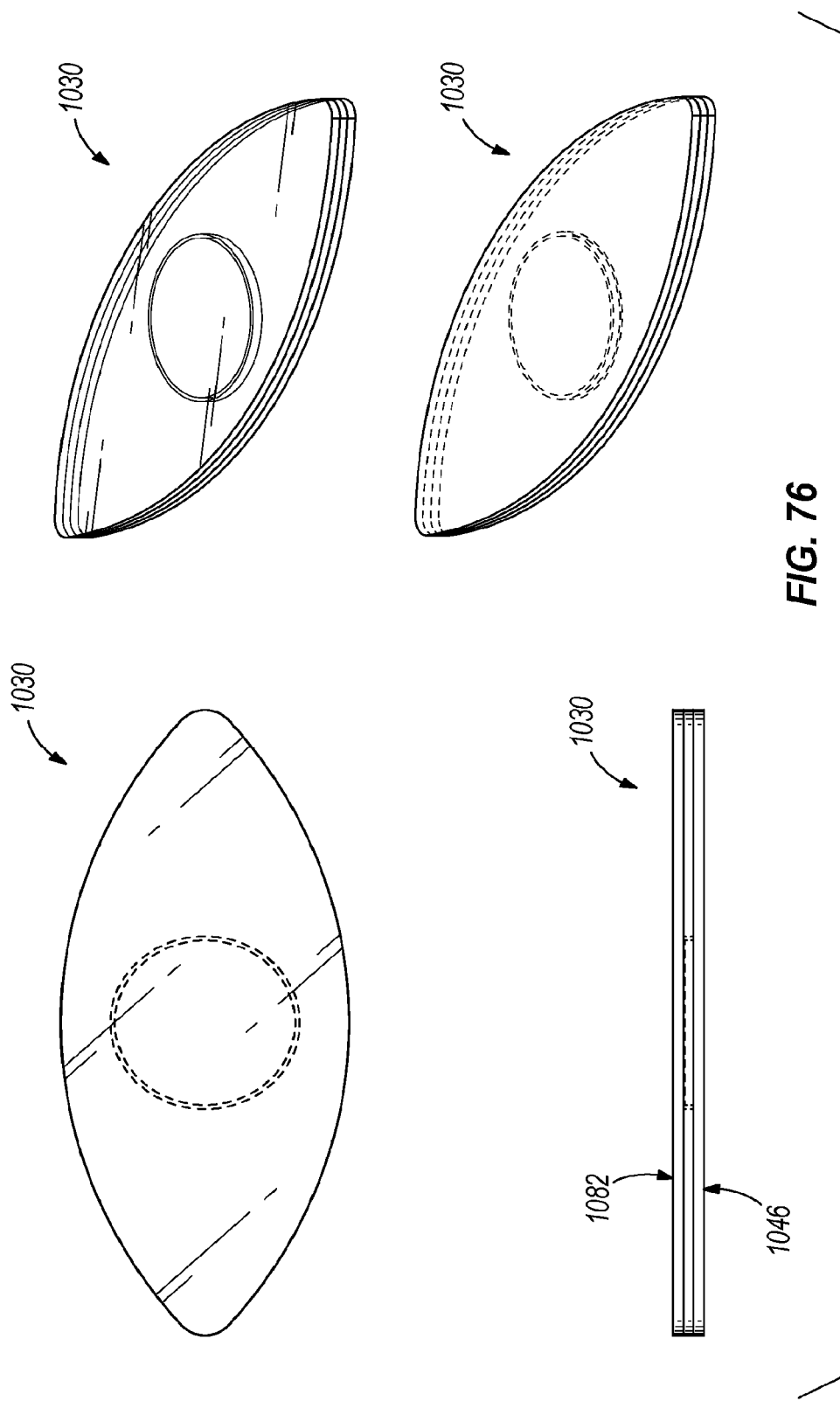
FIG. 76 illustrates several drawings of a drug delivery device according to one embodiment of the present invention.
Figure 77:
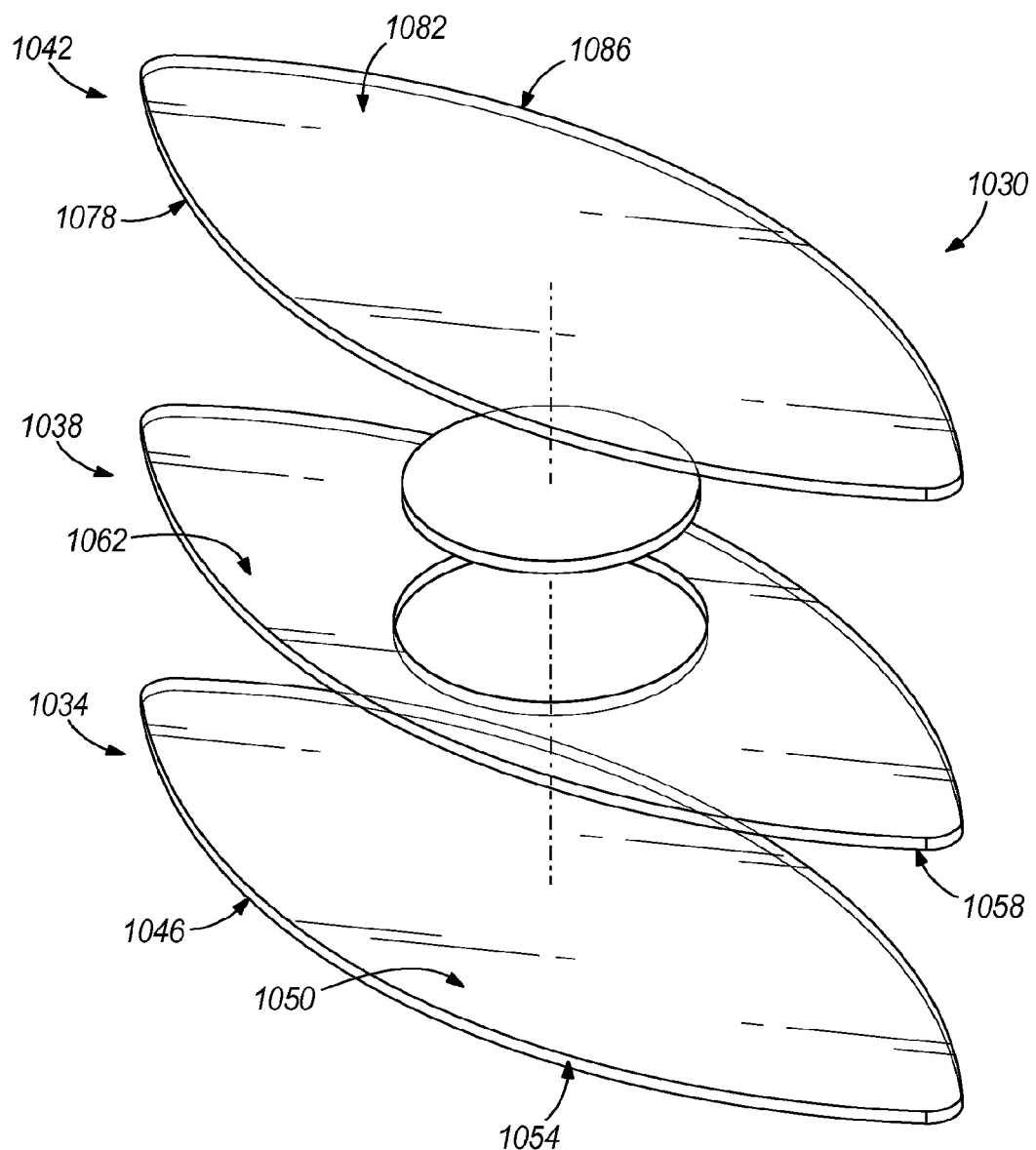
FIG. 77 is an exploded view of the drug delivery device illustrated in FIG. 76.
Figure 78:
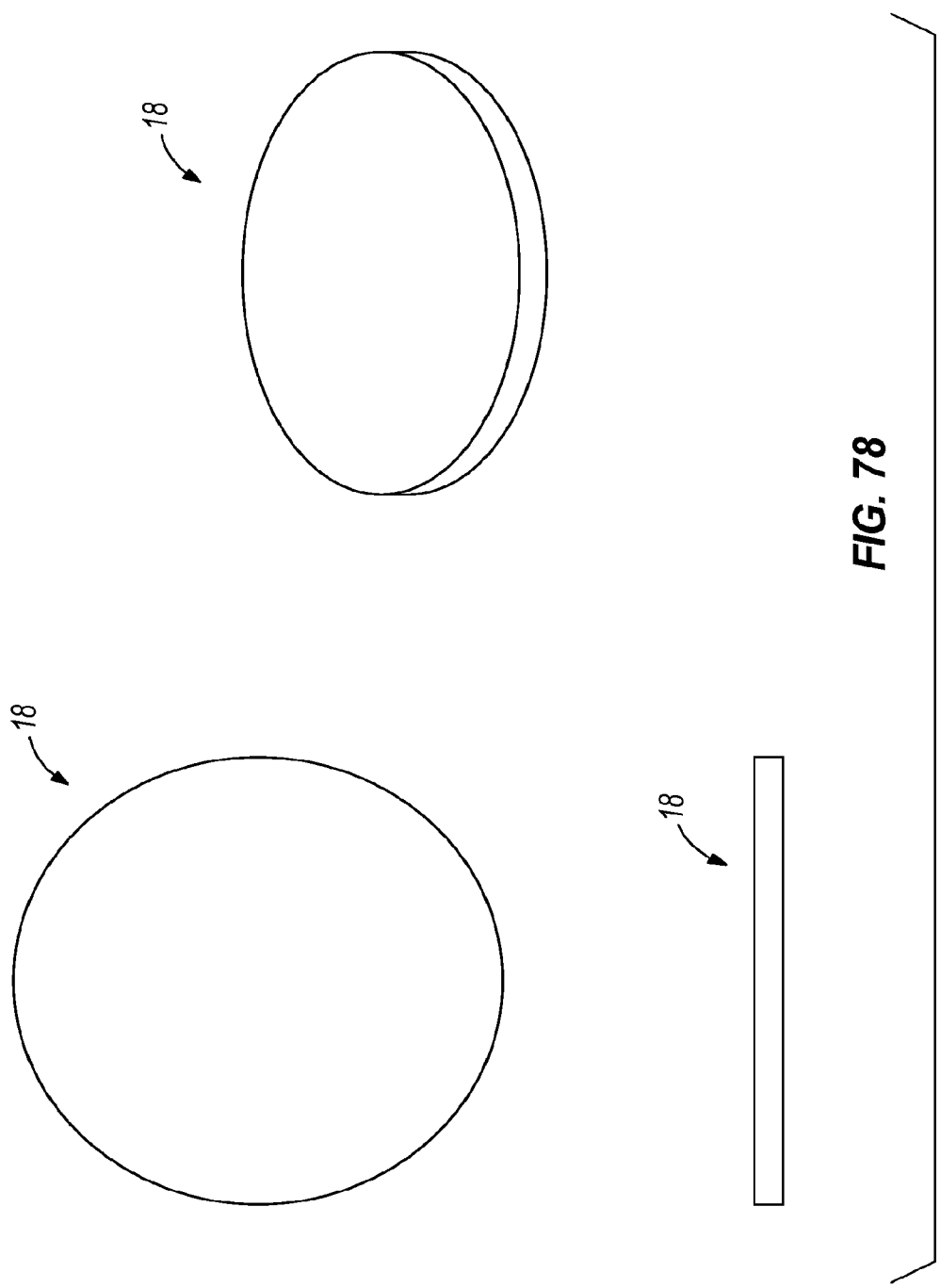
FIG. 78 illustrates several drawings of a composition supported by the drug delivery device illustrated in FIG. 76.
Figure 79:
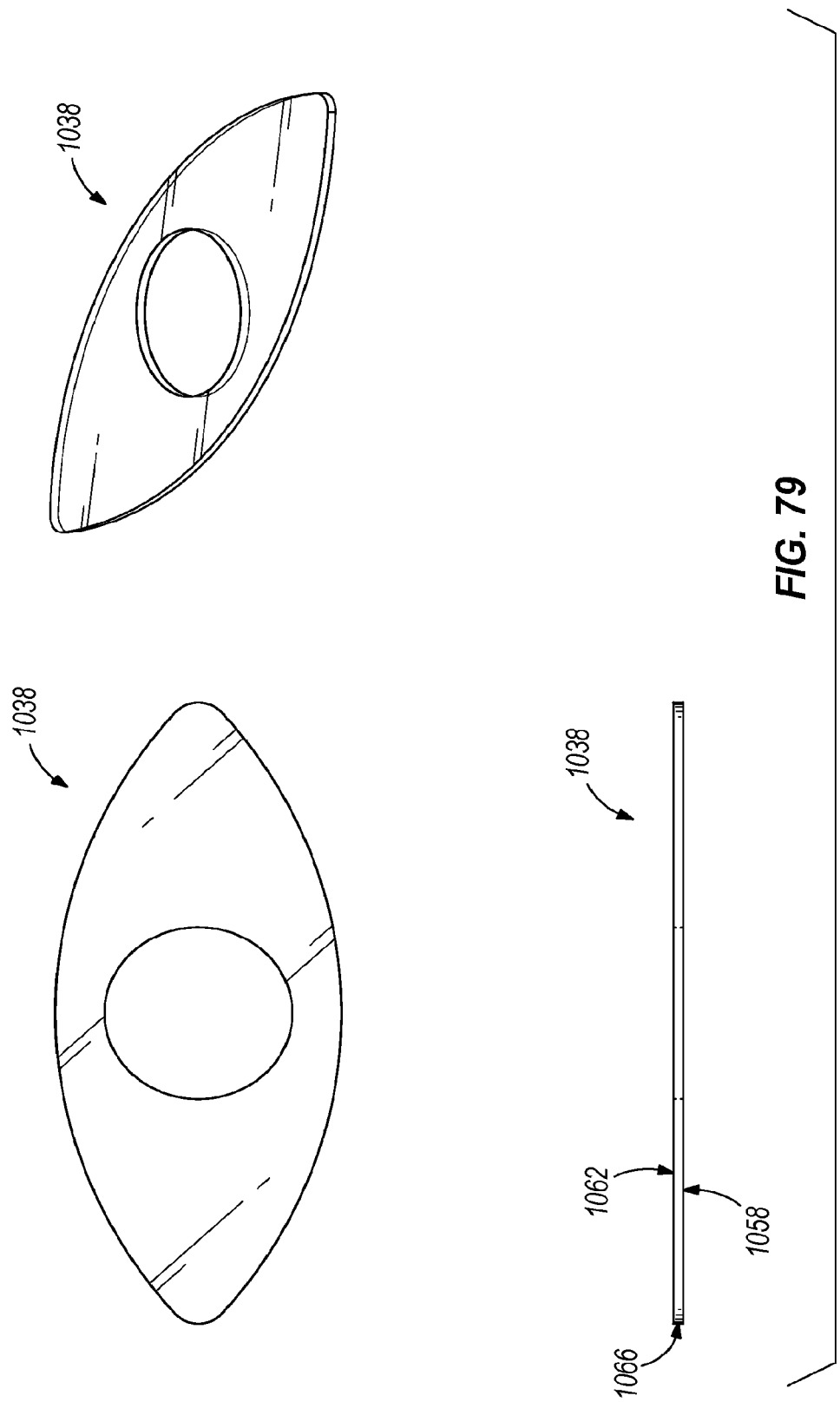
FIG. 79 illustrates several drawings of a portion of the drug delivery device illustrated in FIG. 76.
Figure 80:
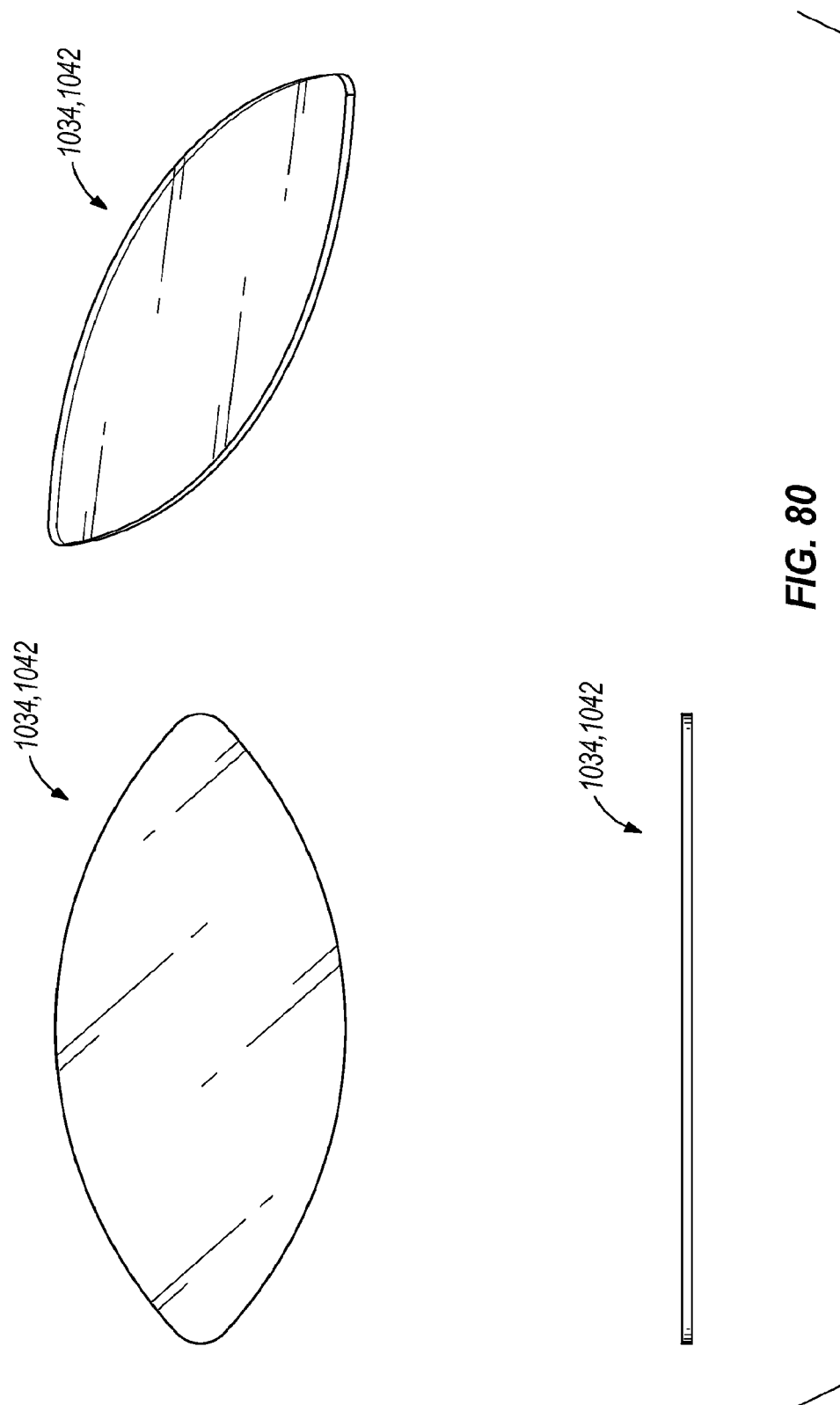
FIG. 80 illustrates several drawings of a portion of the drug delivery device illustrated in FIG. 76.

FIG. 3 illustrates one embodiment of a drug delivery device 10 inserted or implanted in the eye. For episcleral implantation, a small incision (~3 mm) is made in the conjunctiva near the limbus in the superior temporal episcleral zone of the eye, and a drug delivery device 10 according to one embodiment of the present invention is introduced through the incision into the sub-Tenon's space. Closing the conjunctival incision by suture is optional. For supraconjunctival placement, a drug delivery device 10 according to one embodiment of the present invention is gently inserted into the upper or lower fornix of the eye. Depending on the size/shape and desired duration of use, the drug delivery device 10 may be sutured to the conjunctiva to immobilize such device.

Although FIG. 3 illustrates one embodiment of a drug delivery device 10 inserted in the eye, any one of the drug delivery devices disclosed herein can be inserted or implanted in the eye as described above.

FIGS. 4-8 illustrate a drug delivery device 34 according to another embodiment of the present invention. The drug delivery device 34 is generally cylindrical-shaped and includes a first portion 38 and a second portion 42. The first portion 38 includes a bottom surface 46, a top surface 50, and an outer side surface 54 positioned between and extending around a periphery of the bottom surface 46 and the top surface 50. The first portion 38 includes a recess 58 defined by an inner side wall 62 and a bottom surface 66. The bottom surface 66 is positioned a predetermined distance from the bottom surface 46.

The recess 54 is configured to support the composition 18 comprising an active agent (as discussed above). The dimensions of the recess 58 are similar to the dimensions of the composition 18 such that the composition 18 (in its undissolved state or pre-insertion state) cannot move freely within the recess 58. The inner side wall 62 is generally concentric with the outer side surface 54 and is spaced from the outer side surface 54 around its entire circumference. The outer side surface 54 includes a first diameter 70, and the inner side wall 62 includes a second diameter 74. The first diameter 70 is generally greater than the second diameter 74.

The second portion 42 includes a bottom surface 78, a top surface 82, and a side surface 86 positioned between and extending around a periphery of the bottom surface 78 and the top surface 82. The bottom surface 78 of the second portion 42 interfaces with the top surface 50 of the first portion 38 to enclose the composition 18 within the recess 58.

The first portion 38 comprises an impermeable polymer 22 as discussed above. The impermeable polymer 22 does not allow the passage of the active agent and provides mechanical strength for the device 34. The impermeable polymer 22 suitably has a thickness of about 50 micrometers to about 800 micrometers or about 100 micrometers to about 250 micrometers, depending on the overall size and required mechanical strength of the device 34.

The second portion 42 comprises a rate-limiting water-permeable polymer 30 as discussed above. The rate-limiting water-permeable polymer 30 is a polymer that allows for the passage of the active agent and water or tissue fluids. The composition and/or thickness of this polymer determines the rate of release from the drug delivery device. The rate-limiting water-permeable polymer 30 suitably has a thickness of about 20 micrometers to about 500 micrometers, depending on the overall size and required mechanical strength of the device 34.

FIGS. 9-13 illustrate a drug delivery device 90 according to another embodiment of the present invention. The drug delivery device 90 is generally cylindrical-shaped and includes a first portion 94 and a second portion 98. The first portion 94 includes a bottom surface 102, a top surface 106, and an outer side surface 110 positioned between and extending around a periphery of the bottom surface 102 and the top surface 106. The first portion 94 includes a recess 114 defined by an inner side wall 118 and a bottom surface 122. The bottom surface 122 is positioned a predetermined distance from the bottom surface 102.

The recess 114 is configured to support the composition 18 comprising an active agent (as discussed above). The recess 114 includes an axis extending between the bottom surface 122 and the top surface 106. The dimensions of the recess 114 are similar to the dimensions of the composition 18, but extra space exists between the top surface 106 and the composition 18 and/or between the bottom surface 122 and the composition 18, such that the composition 18 (in its undissolved state or pre-insertion state) can move along the axis within the recess 114. The inner side wall 118 is generally concentric with the outer side surface 110 and is spaced from the outer side surface 110 around its entire circumference. The outer side surface 110 includes a first diameter 126, and the inner side wall 118 includes a second diameter 130. The first diameter 126 is generally greater than the second diameter 130.

The second portion 98 includes a bottom surface 134, a top surface 138, and a side surface 142 positioned between and extending around a periphery of the bottom surface 134 and the top surface 138. The bottom surface 134 of the second portion 98 interfaces with the top surface 106 of the first portion 94 to enclose the composition 18 within the recess 114.

The first portion 94 comprises an impermeable polymer 22 as discussed above. The impermeable polymer 22 does not allow the passage of the active agent and provides mechanical strength for the device 90. The impermeable polymer 22 suitably has a thickness of about 50 micrometers to about 800 micrometers or about 100 micrometers to about 250 micrometers, depending on the overall size and required mechanical strength of the device 90.

The second portion 98 comprises a rate-limiting water-permeable polymer 30 as discussed above. The rate-limiting water-permeable polymer 30 is a polymer that allows for the passage of the active agent and water or tissue fluids. The composition and/or thickness of this polymer determines the rate of release from the drug delivery device. The rate-limiting water-permeable polymer 30 suitably has a thickness of about 20 micrometers to about 500 micrometers, depending on the overall size and required mechanical strength of the device 90.

FIGS. 14-18 illustrate a drug delivery device 146 according to another embodiment of the present invention. The drug delivery device 146 is generally cylindrical-shaped and includes a first portion 150 and a second portion 154. The first portion 150 includes a bottom surface 158, a top surface 162, and an outer side surface 166 positioned between and extending around a periphery of the bottom surface 158 and the top surface 162. The first portion 150 includes a recess 170 defined by an inner side wall 174 and a bottom surface 178. The bottom surface 178 is positioned a predetermined distance from the bottom surface 158.

The recess 170 is configured to support the composition 18 comprising an active agent (as discussed above). The dimensions of the recess 170 are similar to the dimensions of the composition 18 such that the composition 18 (in its undissolved state or pre-insertion state) cannot move freely within the recess 170. The inner side wall 174 is generally concentric with the outer side surface 166 and is spaced from the outer side surface 166 around its entire circumference. The outer side surface 166 includes a first diameter 182, and the inner side wall 174 includes a second diameter 186. The first diameter 182 is generally greater than the second diameter 186.

The second portion 154 includes a bottom surface 190, a top surface 194, and a side surface 198 positioned between and extending around a periphery of the bottom surface 190 and the top surface 194. The bottom surface 190 of the second portion 154 interfaces with the top surface 162 of the first portion 150 to enclose the composition 18 within the recess 170.

The first portion 150 comprises an impermeable polymer 22 as discussed above. The impermeable polymer 22 does not allow the passage of the active agent and provides mechanical strength for the device 146. The impermeable polymer 22 suitably has a thickness of about 50 micrometers to about 800 micrometers or about 100 micrometers to about 250 micrometers, depending on the overall size and required mechanical strength of the device 146.

The second portion 154 comprises a rate-limiting water-permeable polymer 30 as discussed above. The rate-limiting water-permeable polymer 30 is a polymer that allows for the passage of the active agent and water or tissue fluids. The composition and/or thickness of this polymer determines the rate of release from the drug delivery device. The rate-limiting water-permeable polymer 30 suitably has a thickness of about 20 micrometers to about 500 micrometers, depending on the overall size and required mechanical strength of the device 146.

FIGS. 19-24 illustrate a drug delivery device 202 according to another embodiment of the present invention. The drug delivery device 202 is generally cylindrical-shaped and includes a first portion 206 and a second portion 210. The first portion 206 includes a bottom surface 214, a top surface 218, and an outer side surface 222 positioned between and extending around a periphery of the bottom surface 214 and the top surface 218. The first portion 206 includes a recess 226 defined by an inner side wall 230 and a bottom surface 234. The bottom surface 234 is positioned a predetermined distance from the bottom surface 214.

The recess 226 is configured to support the composition 18 comprising an active agent (as discussed above). The dimensions of the recess 226 are similar to the dimensions of the composition 18 such that the composition 18 (in its undissolved state or pre-insertion state) cannot move freely within the recess 226. The inner side wall 230 is generally concentric with the outer side surface 222 and is spaced from the outer side surface 222 around its entire circumference. The outer side surface 222 includes a first diameter 234, and the inner side wall 230 includes a second diameter 238. The first diameter 234 is generally greater than the second diameter 238.

The second portion 210 includes a bottom surface 242, a top surface 246, and a side surface 250 positioned between and extending around a periphery of the bottom surface 242 and the top surface 246. The bottom surface 242 of the second portion 210 interfaces with the top surface 246 of the first portion 206 to enclose the composition 18 within the recess 226.

The device 202 also includes a flange 254 such as a surgical suture tab configured to secure the device to an anchor point with a surgical suture(s). The flange 254 is connected to the second portion 210 and extends therefrom. The flange 254 includes a base 258, a first arm 262 extending from the base 258, and a second arm 266 extending from the base 258. The base 258 and the first and second arms 262, 266 are integrally molded and form a recess 270 configured to receive at least a portion of the second portion 210. In one construction, the recess 270 is configured to receive about one-half the circumference of the side surface 250. In other constructions, the recess 270 can be configured to receive more or less than one-half the circumference of the side surface 250. The base 258 can include one or more apertures 274 configured to receive a surgical suture. The apertures 274 are not necessary, however, as a surgical suture needle can penetrate the flange 254 to secure the device 202 in a suitable position. The recess 270 of the flange 254 is connected to side surface 250 of the second portion 210 in a thermal process that involves the application of heat to fuse the flange 254 to the side surface 250. A suitable application of heat is in the range of about 90 degrees C. to about 102 degrees C. to fuse the flange 254 to the side surface 250.

The first portion 206 comprises an impermeable polymer 22 as discussed above. The impermeable polymer 22 does not allow the passage of the active agent and provides mechanical strength for the device 202. The impermeable polymer 22 suitably has a thickness of about 50 micrometers to about 800 micrometers or about 100 micrometers to about 250 micrometers, depending on the overall size and required mechanical strength of the device 202.

The second portion 210 comprises a rate-limiting water-permeable polymer 30 as discussed above. The rate-limiting water-permeable polymer 30 is a polymer that allows for the passage of the active agent and water or tissue fluids. The composition and/or thickness of this polymer determines the rate of release from the drug delivery device. The rate-limiting water-permeable polymer 30 suitably has a thickness of about 20 micrometers to about 500 micrometers, depending on the overall size and required mechanical strength of the device 202.

FIGS. 25-30 illustrate a drug delivery device 278 according to another embodiment of the present invention. The drug delivery device 278 is generally cylindrical-shaped and includes a first portion 282 and a second portion 286. The first portion 282 includes a bottom surface 290, a top surface 294, and an outer side surface 298 positioned between and extending around a periphery of the bottom surface 290 and the top surface 294. The first portion 282 includes a recess 302 defined by an inner side wall 306 and a bottom surface 310. The bottom surface 310 is positioned a predetermined distance from the bottom surface 290.

The recess 302 is configured to support the composition 18 comprising an active agent (as discussed above). The dimensions of the recess 302 are similar to the dimensions of the composition 18 such that the composition 18 (in its undissolved state or pre-insertion state) cannot move freely within the recess 302. The inner side wall 306 is generally concentric with the outer side surface 298 and is spaced from the outer side surface 298 around its entire circumference. The outer side surface 298 includes a first diameter 314, and the inner side wall 306 includes a second diameter 318. The first diameter 314 is generally greater than the second diameter 318.

The second portion 286 includes a bottom surface 322, a top surface 326, and a side surface 330 positioned between and extending around a periphery of the bottom surface 322 and the top surface 326. The bottom surface 322 of the second portion 286 interfaces with the top surface 294 of the first portion 284 to enclose the composition 18 within the recess 302.

The device 278 also includes a flange 334 such as a surgical suture tab configured to secure the device to an anchor point with a surgical suture(s). The flange 334 is connected to the second portion 286 and extends therefrom. The flange 334 includes a base 338, a first arm 342 extending from the base 338, and a second arm 346 extending from the base 338. The base 338 and the first and second arms 342, 346 are integrally molded and form a recess 350 configured to receive at least a portion of the second portion 286. In one construction, the recess 350 is configured to receive about one-half the circumference of the side surface 330. In other constructions, the recess 350 can be configured to receive more or less than one-half the circumference of the side surface 330. The base 338 can include one or more apertures 354 configured to receive a surgical suture. The apertures 354 are not necessary, however, as a surgical suture needle can penetrate the flange 334 to secure the device 278 in a suitable position. The recess 350 of the flange 334 is connected to side surface 330 of the second portion 286 in a thermal process that involves the application of heat to fuse the flange 334 to the side surface 330. A suitable application of heat is in the range of about 90 degrees C. to about 102 degrees C. to fuse the flange 334 to the side surface 330.

The first portion 282 comprises an impermeable polymer 22 as discussed above. The impermeable polymer 22 does not allow the passage of the active agent and provides mechanical strength for the device 278. The impermeable polymer 22 suitably has a thickness of about 50 micrometers to about 800 micrometers or about 100 micrometers to about 250 micrometers, depending on the overall size and required mechanical strength of the device 278.

The second portion 286 comprises a rate-limiting water-permeable polymer 30 as discussed above. The rate-limiting water-permeable polymer 30 is a polymer that allows for the passage of the active agent and water or tissue fluids. The composition and/or thickness of this polymer determines the rate of release from the drug delivery device. The rate-limiting water-permeable polymer 30 suitably has a thickness of about 20 micrometers to about 500 micrometers, depending on the overall size and required mechanical strength of the device 278.

FIGS. 31-35 illustrate a drug delivery device 358 according to another embodiment of the present invention. The drug delivery device 358 is generally cylindrical-shaped and includes a first portion 362 and a second portion 366. The first portion 362 includes a bottom surface 370, a top surface 374, and an outer side surface 378 positioned between and extending around a periphery of the bottom surface 370 and the top surface 374. The first portion 362 includes a recess 382 defined by an inner side wall 386 and a bottom surface 390. The bottom surface 390 is positioned a predetermined distance from the bottom surface 370.

The recess 382 is configured to support the composition 18 comprising an active agent (as discussed above). The dimensions of the recess 382 are similar to the dimensions of the composition 18 such that the composition 18 (in its undissolved state or pre-insertion state) cannot move freely within the recess 382. The inner side wall 386 is generally concentric with the outer side surface 378 and is spaced from the outer side surface 378 around its entire circumference. The outer side surface 378 includes a first diameter 394, and the inner side wall 386 includes a second diameter 398. The first diameter 394 is generally greater than the second diameter 398.

The second portion 366 includes a bottom surface 402, a top surface 406, and a side surface 410 positioned between and extending around a periphery of the bottom surface 402 and the top surface 406. The bottom surface 402 of the second portion 366 interfaces with the top surface 374 of the first portion 362 to enclose the composition 18 within the recess 382. The second portion 366 includes a base 414 and a portion 418 extending from the base 414. The portion 418 also at least partially extends outside of the side surface 378. The portion 418 can include one or more apertures 422 configured to receive a surgical suture. The apertures 422 are not necessary, however, as a surgical suture needle can penetrate the portion 418 to secure the device 358 in a suitable position. The bottom surface 402 of the second portion 366 is connected to the top surface 374 of the first portion 362 in a thermal process that involves the application of heat to fuse the bottom surface 402 to the top surface 374. A suitable application of heat is in the range of about 90 degrees C. to about 102 degrees C. to fuse the bottom surface 402 to the top surface 374.

The first portion 362 comprises an impermeable polymer 22 as discussed above. The impermeable polymer 22 does not allow the passage of the active agent and provides mechanical strength for the device 358. The impermeable polymer 22 suitably has a thickness of about 50 micrometers to about 800 micrometers or about 100 micrometers to about 250 micrometers, depending on the overall size and required mechanical strength of the device 358.

The second portion 366 (including the portion 418) comprises a rate-limiting water-permeable polymer 30 as discussed above. The rate-limiting water-permeable polymer 30 is a polymer that allows for the passage of the active agent and water or tissue fluids. The composition and/or thickness of this polymer determines the rate of release from the drug delivery device. The rate-limiting water-permeable polymer 30 suitably has a thickness of about 20 micrometers to about 500 micrometers, depending on the overall size and required mechanical strength of the device 358.

FIGS. 36-40 illustrate a drug delivery device 426 according to another embodiment of the present invention. The drug delivery device 426 is generally cylindrical-shaped and includes a first portion 430 and a second portion 434. The first portion 430 includes a bottom surface 438, a top surface 442, and an outer side surface 446 positioned between and extending around a periphery of the bottom surface 438 and the top surface 442. The first portion 430 includes a recess 450 defined by an inner side wall 454 and a bottom surface 458. The bottom surface 458 is positioned a predetermined distance from the bottom surface 438.

The recess 450 is configured to support the composition 18 comprising an active agent (as discussed above). The dimensions of the recess 450 are similar to the dimensions of the composition 18 such that the composition 18 (in its undissolved state or pre-insertion state) cannot move freely within the recess 450. The inner side wall 454 is generally concentric with the outer side surface 446 and is spaced from the outer side surface 446 around its entire circumference. The outer side surface 446 includes a first diameter 462, and the inner side wall 454 includes a second diameter 466. The first diameter 462 is generally greater than the second diameter 466.

The second portion 434 includes a bottom surface 470, a top surface 474, and a side surface 478 positioned between and extending around a periphery of the bottom surface 470 and the top surface 474. The bottom surface 470 of the second portion 434 interfaces with the top surface 442 of the first portion 430 to enclose the composition 18 within the recess 450. The second portion 434 includes a base 482 and a portion 486 extending from the base 482. The portion 486 also at least partially extends outside of the side surface 446. The portion 486 can include one or more apertures 490 configured to receive a surgical suture. The apertures 490 are not necessary, however, as a surgical suture needle can penetrate the portion 486 to secure the device 426 in a suitable position. The bottom surface 470 of the second portion 434 is connected to the top surface 442 of the first portion 430 in a thermal process that involves the application of heat to fuse the bottom surface 470 to the top surface 442. A suitable application of heat is in the range of about 90 degrees C. to about 102 degrees C. to fuse the bottom surface 470 to the top surface 442.

The first portion 430 comprises an impermeable polymer 22 as discussed above. The impermeable polymer 22 does not allow the passage of the active agent and provides mechanical strength for the device 426. The impermeable polymer 22 suitably has a thickness of about 50 micrometers to about 800 micrometers or about 100 micrometers to about 250 micrometers, depending on the overall size and required mechanical strength of the device 426.

The second portion 434 (including the portion 486) comprises a rate-limiting water-permeable polymer 30 as discussed above. The rate-limiting water-permeable polymer 30 is a polymer that allows for the passage of the active agent and water or tissue fluids. The composition and/or thickness of this polymer determines the rate of release from the drug delivery device. The rate-limiting water-permeable polymer 30 suitably has a thickness of about 20 micrometers to about 500 micrometers, depending on the overall size and required mechanical strength of the device 426.

FIGS. 41-45 illustrate a drug delivery device 494 according to another embodiment of the present invention. The drug delivery device 494 is generally cylindrical-shaped and includes a base portion 498, a middle portion 502, and an upper portion 506. The base portion 498 includes a bottom surface 510, an upper surface 514, and a side wall 518 positioned between the bottom surface 510 and the upper surface 514 and extending around a periphery of the bottom surface 510 and the upper surface 514. The side wall 518 includes a first diameter 522.

The middle portion 502 includes a bottom wall 526, a top wall 528, an outer side wall 530 having a second diameter 534 substantially the same as the first diameter 522, and an inner side wall 538 having a third diameter 542 less than the second diameter 534. The inner side wall 538 is generally concentric with the outer side wall 530 and is spaced from the outer side wall 530 around its entire circumference. The bottom wall 526 rests upon or is in contact with the upper surface 514 of the base portion 498. The middle portion 502 includes an aperture 546 in the bottom wall 526 and the top wall 528 and is surrounded by the inner side wall 538. The aperture 546 (and the upper surface 514) is configured to support the composition 18 comprising an active agent (as discussed above).

The upper portion 506 includes a bottom surface 550, an upper surface 554, and a side wall 558 positioned between the bottom surface 550 and the upper surface 554 and extending around a periphery of the bottom surface 550 and the upper surface 554. The bottom surface 550 rests on or is in contact with the middle portion 502 such that the composition 18 is housed within an enclosure 562 defined at least partially by the upper surface 514, the inner side wall 538, and at least a portion of the bottom surface 550. The side wall 558 includes a fourth diameter 566 substantially the same as the first diameter 522. The dimensions of the enclosure 562 are similar to the dimensions of the composition 18 such that the composition 18 (in its undissolved state or pre-insertion state) cannot move freely within the enclosure 562.

The base portion 498, the middle portion 502, and the upper portion 506 comprise a rate-limiting water-permeable polymer 30 as discussed above. The rate-limiting water-permeable polymer 30 is a polymer that allows for the passage of the active agent and water or tissue fluids. The composition and/or thickness of this polymer determines the rate of release from the drug delivery device. The rate-limiting water-permeable polymer 30 suitably has a thickness of about 20 micrometers to about 500 micrometers, depending on the overall size and required mechanical strength of the device 494.

FIGS. 46-50 illustrate a drug delivery device 570 according to another embodiment of the present invention. The drug delivery device 570 is generally cylindrical-shaped and includes a base portion 574, a middle portion 578, and an upper portion 582. The base portion 574 includes a bottom surface 586, an upper surface 590, and a side wall 594 positioned between the bottom surface 586 and the upper surface 590 and extending around a periphery of the bottom surface 586 and the upper surface 590. The side wall 594 includes a first diameter 598.

The middle portion 578 includes a bottom wall 602, a top wall 604, an outer side wall 606 having a second diameter 610 substantially the same as the first diameter 598, and an inner side wall 614 having a third diameter 618 less than the second diameter 610. The inner side wall 614 is generally concentric with the outer side wall 606 and is spaced from the outer side wall 606 around its entire circumference. The bottom wall 602 rests upon or is in contact with the upper surface 590 of the base portion 574. The middle portion 578 includes an aperture 622 in the bottom wall 602 and the top wall 604 and is surrounded by the inner side wall 614. The aperture 622 (and the upper surface 590) is configured to support the composition 18 comprising an active agent (as discussed above).

The upper portion 582 includes a bottom surface 626, an upper surface 630, and a side wall 634 positioned between the bottom surface 626 and the upper surface 630 and extending around a periphery of the bottom surface 626 and the upper surface 630. The bottom surface 626 rests on or is in contact with the middle portion 578 such that the composition 18 is housed within an enclosure 638 defined at least partially by the upper surface 590, the inner side wall 614, and at least a portion of the bottom surface 626. The side wall 634 includes a fourth diameter 642 substantially the same as the first diameter 598. The dimensions of the enclosure 638 are similar to the dimensions of the composition 18 such that the composition 18 (in its undissolved state or pre-insertion state) cannot move freely within the enclosure 638.

The base portion 574, the middle portion 578, and the upper portion 582 comprise a rate-limiting water-permeable polymer 30 as discussed above. The rate-limiting water-permeable polymer 30 is a polymer that allows for the passage of the active agent and water or tissue fluids. The composition and/or thickness of this polymer determines the rate of release from the drug delivery device. The rate-limiting water-permeable polymer 30 suitably has a thickness of about 20 micrometers to about 500 micrometers, depending on the overall size and required mechanical strength of the device 570.

FIGS. 51-55 illustrate a drug delivery device 646 according to another embodiment of the present invention. The drug delivery device 646 is generally cylindrical-shaped and includes a base portion 650, a middle portion 654, and an upper portion 658. The base portion 650 includes a bottom surface 662, an upper surface 670, and a side wall 674 positioned between the bottom surface 662 and the upper surface 670 and extending around a periphery of the bottom surface 662 and the upper surface 670. The side wall 674 includes a first diameter 678.

The middle portion 654 includes a bottom wall 682, a top wall 684, an outer side wall 686 having a second diameter 690 substantially the same as the first diameter 678, and an inner side wall 694 having a third diameter 698 less than the second diameter 690. The inner side wall 694 is generally concentric with the outer side wall 686 and is spaced from the outer side wall 686 around its entire circumference. The bottom wall 682 rests upon or is in contact with the upper surface 670 of the base portion 650. The middle portion 654 includes an aperture 702 in the bottom wall 682 and the top wall 684 and is surrounded by the inner side wall 694. The aperture 702 (and the upper surface 670) is configured to support the composition 18 comprising an active agent (as discussed above).

The upper portion 658 includes a bottom surface 706, an upper surface 710, and a side wall 714 positioned between the bottom surface 706 and the upper surface 710 and extending around a periphery of the bottom surface 706 and the upper surface 710. The bottom surface 706 rests on or is in contact with the middle portion 654 such that the composition 18 is housed within an enclosure 718 defined at least partially by the upper surface 670, the inner side wall 694, and at least a portion of the bottom surface 706. The side wall 714 includes a fourth diameter 722 substantially the same as the first diameter 678. The dimensions of the enclosure 718 are similar to the dimensions of the composition 18 such that the composition 18 (in its undissolved state or pre-insertion state) cannot move freely within the enclosure 718.

The middle portion 654 comprises an impermeable polymer 22 as discussed above. The impermeable polymer 22 does not allow the passage of the active agent and provides mechanical strength for the device 646. The impermeable polymer 22 suitably has a thickness of about 50 micrometers to about 800 micrometers or about 100 micrometers to about 250 micrometers, depending on the overall size and required mechanical strength of the device 646.

The base portion 650, the middle portion 654, and the upper portion 658 comprise a rate-limiting water-permeable polymer 30 as discussed above. The rate-limiting water-permeable polymer 30 is a polymer that allows for the passage of the active agent and water or tissue fluids. The composition and/or thickness of this polymer determines the rate of release from the drug delivery device. The rate-limiting water-permeable polymer 30 suitably has a thickness of about 20 micrometers to about 500 micrometers, depending on the overall size and required mechanical strength of the device 646.

FIGS. 56-60 illustrate a drug delivery device 726 according to another embodiment of the present invention. The drug delivery device 726 is generally cylindrical-shaped and includes a base portion 730, a middle portion 734, and an upper portion 738. The base portion 730 includes a bottom surface 742, an upper surface 746, and a side wall 750 positioned between the bottom surface 742 and the upper surface 746 and extending around a periphery of the bottom surface 742 and the upper surface 746. The side wall 750 includes a first diameter 754.

The middle portion 734 includes a bottom wall 758, a top wall 760, an outer side wall 762 having a second diameter 766 substantially the same as the first diameter 754, and an inner side wall 770 having a third diameter 774 less than the second diameter 766. The inner side wall 770 is generally concentric with the outer side wall 762 and is spaced from the outer side wall 762 around its entire circumference. The bottom wall 758 rests upon or is in contact with the upper surface 746 of the base portion 730. The middle portion 734 includes an aperture 778 in the bottom wall 758 and the top wall 760 and is surrounded by the inner side wall 770. The aperture 778 (and the upper surface 746) is configured to support the composition 18 comprising an active agent (as discussed above).

The upper portion 738 includes a bottom surface 782, an upper surface 786, and a side wall 790 positioned between the bottom surface 782 and the upper surface 786 and extending around a periphery of the bottom surface 782 and the upper surface 786. The bottom surface 782 rests on or is in contact with the middle portion 734 such that the composition 18 is housed within an enclosure 794 defined at least partially by the upper surface 746, the inner side wall 770, and at least a portion of the bottom surface 782. The side wall 790 includes a fourth diameter 798 substantially the same as the first diameter 754. The dimensions of the enclosure 794 are similar to the dimensions of the composition 18 such that the composition 18 (in its undissolved state or pre-insertion state) cannot move freely within the enclosure 794.

The base portion 730, the middle portion 734, and the upper portion 738 comprise a rate-limiting water-permeable polymer 30 as discussed above. The rate-limiting water-permeable polymer 30 is a polymer that allows for the passage of the active agent and water or tissue fluids. The composition and/or thickness of this polymer determines the rate of release from the drug delivery device. The rate-limiting water-permeable polymer 30 suitably has a thickness of about 20 micrometers to about 500 micrometers, depending on the overall size and required mechanical strength of the device 726.

FIGS. 61-65 illustrate a drug delivery device 802 according to another embodiment of the present invention. The drug delivery device 802 is generally cylindrical-shaped and includes a base portion 806, a middle portion 810, and an upper portion 814. The base portion 806 includes a bottom surface 818, an upper surface 822, and a side wall 826 positioned between the bottom surface 818 and the upper surface 822 and extending around a periphery of the bottom surface 818 and the upper surface 822. The side wall 826 includes a first diameter 830.

The middle portion 810 includes a bottom wall 834, a top wall 836, an outer side wall 838 having a second diameter 842 substantially the same as the first diameter 830, and an inner side wall 846 having a third diameter 850 less than the second diameter 842. The inner side wall 846 is generally concentric with the outer side wall 838 and is spaced from the outer side wall 838 around its entire circumference. The bottom wall 834 rests upon or is in contact with the upper surface 822 of the base portion 806. The middle portion 810 includes an aperture 854 in the bottom wall 834 and the top wall 836 and is surrounded by the inner side wall 846. The aperture 854 (and the upper surface 822) is configured to support the composition 18 comprising an active agent (as discussed above).

The upper portion 814 includes a bottom surface 858, an upper surface 862, and a side wall 866 positioned between the bottom surface 858 and the upper surface 862 and extending around a periphery of the bottom surface 858 and the upper surface 862. The bottom surface 858 rests on or is in contact with the middle portion 810 such that the composition 18 is housed within an enclosure 870 defined at least partially by the upper surface 822, the inner side wall 846, and at least a portion of the bottom surface 858. The side wall 866 includes a fourth diameter 874 substantially the same as the first diameter 830. The dimensions of the enclosure 870 are similar to the dimensions of the composition 18 such that the composition 18 (in its undissolved state or pre-insertion state) cannot move freely within the enclosure 870.

The base portion 806, the middle portion 810, and the upper portion 814 comprise a rate-limiting water-permeable polymer 30 as discussed above. The rate-limiting water-permeable polymer 30 is a polymer that allows for the passage of the active agent and water or tissue fluids. The composition and/or thickness of this polymer determines the rate of release from the drug delivery device. The rate-limiting water-permeable polymer 30 suitably has a thickness of about 20 micrometers to about 500 micrometers, depending on the overall size and required mechanical strength of the device 802.

FIGS. 66-70 illustrate a drug delivery device 880 according to another embodiment of the present invention. The drug delivery device 880 is generally elliptical-shaped and is adapted to conform to the curvature of the eye. The materials of the drug delivery device 880 include suitable properties that provide flexibility to allow the device 880 to flex and conform to the curvature or shape of the eye. The drug delivery device 880 includes a base portion 884, a middle portion 888, and an upper portion 892. The base portion 884 includes a bottom surface 896, an upper surface 900, and a side wall 904 positioned between the bottom surface 896 and the upper surface 900 and extending around a periphery of the bottom surface 896 and the upper surface 900.

The middle portion 888 includes a bottom wall 908, a top wall 910, an outer side wall 912, and an inner side wall 916. The inner side wall 916 is spaced from the outer side wall 912. The bottom wall 908 rests upon or is in contact with the upper surface 900 of the base portion 884. The middle portion 888 includes an aperture 920 in the bottom wall 908 and the top wall 910 and is surrounded by the inner side wall 916. The aperture 920 (and the upper surface 900) is configured to support the composition 18 comprising an active agent (as discussed above). The aperture 920 is generally circular-shaped as illustrated, however the aperture 920 may have a different but suitable shape to accommodate the shape of the composition 18. For example, the aperture 920 may be elliptical-shaped similar to the outer side wall 912. The aperture 920 may be concentric or non-concentric with the outer side wall 912.

The upper portion 892 includes a bottom surface 924, an upper surface 928, and a side wall 932 positioned between the bottom surface 924 and the upper surface 928 and extending around a periphery of the bottom surface 924 and the upper surface 928. The bottom surface 924 rests on or is in contact with the middle portion 888 such that the composition 18 is housed within an enclosure 936 defined at least partially by the upper surface 900, the inner side wall 916, and at least a portion of the bottom surface 924. The dimensions of the enclosure 936 are similar to the dimensions of the composition 18 such that the composition 18 (in its undissolved state or pre-insertion state) cannot move freely within the enclosure 936.

The base portion 884, the middle portion 888, and the upper portion 892 comprise a rate-limiting water-permeable polymer 30 as discussed above. The rate-limiting water-permeable polymer 30 is a polymer that allows for the passage of the active agent and water or tissue fluids. The composition and/or thickness of this polymer determines the rate of release from the drug delivery device. The rate-limiting water-permeable polymer 30 suitably has a thickness of about 20 micrometers to about 500 micrometers, depending on the overall size and required mechanical strength of the device 880.

FIGS. 71-75 illustrate a drug delivery device 950 according to another embodiment of the present invention. The drug delivery device 950 is generally elliptical-shaped and is adapted to conform to the curvature of the eye. The materials of the drug delivery device 950 include suitable properties that provide flexibility to allow the device 950 to flex and conform to the curvature or shape of the eye. The drug delivery device 950 includes a base portion 954, a middle portion 958, and an upper portion 962. The base portion 954 includes a bottom surface 966, an upper surface 970, and a side wall 974 positioned between the bottom surface 966 and the upper surface 970 and extending around a periphery of the bottom surface 966 and the upper surface 970.

The middle portion 958 includes a bottom wall 978, a top wall 980, an outer side wall 982, a first inner side wall 986 and a second inner side wall 990. The first and second inner side walls 986, 990 are spaced from the outer side wall 982. The bottom wall 978 rests upon or is in contact with the upper surface 970 of the base portion 954. The middle portion 958 includes a first aperture 994 and a second aperture 998 in the bottom wall 978 and the top wall 980 and is surrounded by the first inner side wall 986 and the second inner side wall 990, respectively. The apertures 994, 998 (and the upper surface 970) are configured to support one or more of the composition 18 comprising an active agent (as discussed above). Each of the compositions 18 can comprise the same agents or different agents or other types of elements that comprise the composition(s) 18. The apertures 994, 998 are generally circular-shaped as illustrated, however one or more of the apertures 994, 998 may have a different but suitable shape to accommodate the shape of the composition(s) 18. For example, one or both of the apertures 994, 998 may be elliptical-shaped similar to the outer side wall 982. One or both of the apertures 994, 998 may be concentric or non-concentric with the outer side wall 982.

The upper portion 962 includes a bottom surface 1002, an upper surface 1006, and a side wall 1010 positioned between the bottom surface 1002 and the upper surface 1006 and extending around a periphery of the bottom surface 1002 and the upper surface 1006. The bottom surface 1002 rests on or is in contact with the middle portion 958 such that the compositions 18 are housed within a first enclosure 1014 and a second enclosure 1018 defined at least partially by the upper surface 970, the inner side walls 986, 990, and at least a portion of the bottom surface 1002. The dimensions of the enclosures 1014, 1018 are similar to the dimensions of the compositions 18 such that the compositions 18 (in its undissolved state or pre-insertion state) cannot move freely within the enclosures 1014, 1018.

The base portion 954, the middle portion 958, and the upper portion 962 comprise a rate-limiting water-permeable polymer 30 as discussed above. The rate-limiting water-permeable polymer 30 is a polymer that allows for the passage of the active agent and water or tissue fluids. The composition and/or thickness of this polymer determines the rate of release from the drug delivery device. The rate-limiting water-permeable polymer 30 suitably has a thickness of about 20 micrometers to about 500 micrometers, depending on the overall size and required mechanical strength of the device 950.

FIGS. 76-80 illustrate a drug delivery device 1030 according to another embodiment of the present invention. The drug delivery device 1030 is generally elliptical-shaped and is adapted to conform to the curvature of the eye. In this construction, the ends of the device 1030 are rounded in comparison to the device 880 described (and illustrated in FIGS. 66-70) above. The materials of the drug delivery device 1030 include suitable properties that provide flexibility to allow the device 1030 to flex and conform to the curvature or shape of the eye. The drug delivery device 1030 includes a base portion 1034, a middle portion 1038, and an upper portion 1042. The base portion 1034 includes a bottom surface 1046, an upper surface 1050, and a side wall 1054 positioned between the bottom surface 1046 and the upper surface 1050 and extending around a periphery of the bottom surface 1046 and the upper surface 1050.

The middle portion 1038 includes a bottom wall 1058, a top wall 1062, an outer side wall 1066, and an inner side wall 1070. The inner side wall 1070 is spaced from the outer side wall 1066. The bottom wall 1058 rests upon or is in contact with the upper surface 1050 of the base portion 1034. The middle portion 1038 includes an aperture 1074 in the bottom wall 1058 and the top wall 1062 and is surrounded by the inner side wall 1070. The aperture 1074 (and the upper surface 1050) is configured to support the composition 18 comprising an active agent (as discussed above). The aperture 1074 is generally circular-shaped as illustrated, however the aperture 1074 may have a different but suitable shape to accommodate the shape of the composition 18. For example, the aperture 1074 may be elliptical-shaped similar to the outer side wall 1066. The aperture 1074 may be concentric or non-concentric with the outer side wall 1066.

The upper portion 1042 includes a bottom surface 1078, an upper surface 1082, and a side wall 1086 positioned between the bottom surface 1078 and the upper surface 1082 and extending around a periphery of the bottom surface 1078 and the upper surface 1082. The bottom surface 1078 rests on or is in contact with the middle portion 1038 such that the composition 18 is housed within an enclosure 1090 defined at least partially by the upper surface 1050, the inner side wall 1070, and at least a portion of the bottom surface 1078. The dimensions of the enclosure 1090 are similar to the dimensions of the composition 18 such that the composition 18 (in its undissolved state or pre-insertion state) cannot move freely within the enclosure 1090.

The base portion 1034, the middle portion 1038, and the upper portion 1042 comprise a rate-limiting water-permeable polymer 30 as discussed above. The rate-limiting water-permeable polymer 30 is a polymer that allows for the passage of the active agent and water or tissue fluids. The composition and/or thickness of this polymer determines the rate of release from the drug delivery device. The rate-limiting water-permeable polymer 30 suitably has a thickness of about 20 micrometers to about 500 micrometers, depending on the overall size and required mechanical strength of the device 1030.

In some embodiments, the non-bioabsorbable polymer structure contains a pigment. The pigment is optionally placed into the impermeable polymer. Suitable pigments include, but are not limited to, inorganic pigments, organic lake pigments, pearlescent pigments, fluorescein, and mixtures thereof. Inorganic pigments useful in this invention include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

The organic pigments and lakes useful in this invention include those selected from the group consisting of D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430), the dye or lakes based on Cochineal Carmine (CI 75,570) and mixtures thereof.

The pearlescent pigments useful in this invention include those selected from the group consisting of the white pearlescent pigments such as mica coated with titanium oxide, bismuth oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

In a further embodiment, the drug delivery device comprises a composition comprising an active agent at least partially encompassed by an impermeable membrane and a permeable membrane, wherein the permeable membrane controls release of the active agent episclerally over time.

About 70% to about 90% of the active agent is suitably released from the drug delivery device over a period of about 30 days to about 5 years. Alternatively, about 70% to about 90% of the active agent is released over a period of about 30 days to about 2 years or about 30 days to about 1 year or about 30 days to about 90 days or about 1 year to about 5 years or about 1 year to about 2 years.

In some embodiments, the active agent is released from any one of the drug delivery devices at a rate of about 0.0003 micrograms/hr or from about 0.0001 micrograms/hr to about 200 micrograms/hr, or from about 0.0001 micrograms/hr to about 30 micrograms/hr, or from about 0.001 micrograms/hr to about 30 micrograms/hr, or from about 0.001 micrograms/hr to about 10 micrograms/hr.

Suitably, the rate of release of the active agent does not deviate substantially from linearity (i.e., does not deviate from linearity more than about 5%) until at least about 70% and at most about 95% of the active agent is released from the drug delivery device.

Alternatively, about 2% to about 90% of the active agent is released from the drug delivery device with a coefficient of determination, R-squared or R2, of the linear regression is at least about 0.95.

Dosages may be varied based on the active agent being used, the patient being treated, the condition being treated, the severity of the condition being treated, the route of administration, etc. to achieve the desired effect.

The drug delivery devices of the present invention can be used to treat various conditions including, ocular conditions (such as glaucoma, ocular hypertension, ocular inflammation, uveitis, macular degenerative conditions, retinal degenerative conditions, ocular tumors, ocular allergy, and dry eye), topical fungal infections, topical bacterial infections, dermatitis, peripheral neuropathy, allergic and other rashes, and topical eruptions of t-cell lymphoma. Some of the drug delivery devices of the present invention are also useful in decreasing intraocular pressure. In addition to treatment of ocular conditions, the present invention can be used for local delivery of therapeutics to various types of solid tumors, including tumors of the lung, pancreas, liver, kidney, colon and brain.

The device can also be implanted subcutaneously, intramuscularly or intraperitoneally for systemic delivery of therapeutics, including delivery of contraceptive agents and agents to treat cardiovascular, metabolic, immunological and neurological disorders. The drug delivery device may be implanted at or near a tissue affected by the condition. The drug delivery devices of the present invention are suitably implanted in ocular tissues. In some embodiments, the drug delivery devices are implanted episclerally (inserted between the conjunctiva and sclera) with the permeable portion of the polymer structure facing the sclera. The drug delivery devices of the present invention may also be used as supraconjunctival inserts. In some embodiments, the drug delivery devices are placed on top of the bulbar conjunctiva near the conjunctival fornix. A suture may be used to immobilize the insert.

In some embodiments, the present invention is a method of treating an ocular condition comprising episcleral or supraconjunctival placement of a drug delivery device containing a composition comprising an active agent, wherein the active agent is released at a rate of.

$$Q = 0.001 \times L \times N \times C$$

wherein C is the optimal topically effective concentration (in micrograms/mL) of the active agent, L is the placement constant, and N is the composition constant in mL/hour. L is 1 or 2 when the drug delivery device is placed episclerally or supraconjunctivally, respectively. N=0.005 to 0.15 for prostaglandins in their ester, amide, free acid or salt form, N=0.02-0.6 for rho-kinase inhibitors in their salt or free base form, and N=0.05 to 1.5 for any other active agents. Using the equation, a prostaglandin active agent with a topical effective concentration of 0.05 milligrams/mL (e.g., latanoprost) may be designed to release at a rate of about 0.00025 to about 0.0075 micrograms/hr or about 0.0005 to about 0.015 micrograms/hr when the drug delivery device is placed episclerally or supraconjunctivally, respectively. Using a similar approach, a rho-kinase active agent with a topical effective concentration of 1 milligram/mL (e.g., a Y-39983 salt) may be designed to release at a rate of about 0.02 to about 0.6 micrograms/hr or about 0.04 to about 1.2 micrograms/hr when the drug delivery device is placed episclerally or supraconjunctivally, respectively. Again, using a similar approach, a non-prostaglandin, non-rho-kinase, active agent with a topical effective concentration of 5 milligrams/mL (e.g., a timolol salt) may be designed to release at a rate of about 0.25 to about 7.5 micrograms/hr or about 0.5 to about 15 micrograms/hr when the drug delivery device is placed episclerally or supraconjunctivally, respectively.

Brimonidine or its salts may be designed to release at a rate of about 0.05 to about 60 micrograms/hr, about 0.75 to about 7.5 micrograms/hr, about 0.05 to about 10 micrograms/hr, about 0.05 to about 5 micrograms/hr, about 0.05 to about 4 micrograms/hr, about 0.3 to about 60 micrograms/hr, 0.1 to about 10 micrograms/hr, or 0.7 to about 2.5 micrograms/hr. Brimonidine free base may be designed to release at a rate of about 0.05 to about 4 micrograms/hr, 0.7 to about 2.5 micrograms/hr, or 0.7 to about 2.5 micrograms/hr. Brimonidine tartrate may be designed to release at a rate of about 0.3 to about 60 micrograms/hr, or 0.1 to about 10 micrograms/hr.

Timolol or its salts may be designed to release at a rate of about 0.1 to about 50 micrograms/hr, about 1 to about 50 micrograms/hr, about 2.5 to about 20 micrograms/hr, about 0.1 to about 20 micrograms/hr, about 0.5 to about 5 micrograms/hr, or about 12 to about 18 micrograms/hr. Timolol maleate may be designed to release at a rate of about 1 to about 50 micrograms/hr, about 0.5 to about 5 micrograms/hr, or about 12 to about 18 micrograms/hr.

Latanoprost, latanoprost free acid, or its salts may be designed to release at a rate of about 0.0001 to about 5 micrograms/hr, about 0.0005 to about 0.025 micrograms/hr, about 0.04 to about 5 micrograms/hr, about 0.0001 to about 0.05 micrograms/hr, about 0.001 to about 0.05 micrograms/hr, or about 0.04 to about 5 micrograms/hr. Latanoprost arginine salt may be designed to release at a rate of about 0.04 to about 5 micrograms/hr, or about 0.0001 to about 0.05 micrograms/hr. Latanoprost (the isopropyl ester of latanoprost fee acid) may be designed to release at a rate of about 0.001 to about 0.05 micrograms/hr.

Travoprost, travoprost free acid, or its salts may be designed to release at a rate of about 0.0001 to about 0.05 micrograms/hr, about 0.0004 to about 0.02 micrograms/hr, about 0.0001 to about 0.05 micrograms/hr, or about 0.001 to about 0.02 micrograms/hr. Travoprost (the isopropyl ester of travoprost free acid) may be designed to release at a rate of about 0.001 to about 0.02 micrograms/hr.

Dorzolamide or its salts may be designed to release at a rate of about 0.1 to about 2 micrograms/hr.

Ethacrynic acid or its salts may be designed to release at a rate of about 5 to about 50 micrograms/hr.

AR-102, AR-102 free acid or its salts may be designed to release at a rate of about 0.0005 to about 0.7 micrograms/hr, about 0.04 to about 0.7 micrograms/hr, or about 0.0005 to about 0.1 micrograms/hr. AR-102 free acid may be designed to release at a rate of about 0.04 to about 0.7 micrograms/hr, or about 0.0005 to about 0.1 micrograms/hr.

Dexamethasone or its salts may be designed to release at a rate of about 0.1 to about 200 micrograms/hr, about 0.1 to about 3 micrograms/hr, about 0.1 to about 5 micrograms/hr, or about 2 to about 200 micrograms/hr. Dexamethasone sodium phosphate may be designed to release at a rate of about 2 to about 200 micrograms/hr, or about 0.1 to about 5 micrograms/hr.

Bimatoprost, bimatoprost free acid or its salts may be designed to release at a rate of about 0.0005 to about 0.1 micrograms/hr, or about 0.002 to about 0.1 micrograms/hr.

The active agent may be any active agent suitable to treat the desired condition. In various embodiments, the active agent may be of one of low solubility, moderate solubility or high solubility. "Low solubility" means a solubility of less than or equal to 300 micrograms/mL in phosphate buffered saline (PBS) at pH=7.2-7.4. Examples include, but are not limited to, cyclosporin A, lovastatin, atorvastatin, dexamethasone, and travoprost isopropyl ester, latanoprost isopropyl ester. "Moderate solubility" means a solubility of greater than 300 micrograms/mL, but less than 1000 micrograms/mL in PBS at pH=7.2-7.4. Examples include, but are not limited to, latanoprost free acid (0.8 mg/mL in PBS), brimonidine tartrate (0.6 mg/mL in water at pH 7.7) and brimonidine free base (0.36 mg/mL in PBS). "High solubility" means a solubility of greater than or equal to 1000 micrograms/mL in PBS at pH=7.2-7.4. Examples include, but are not limited to, acetazolamide, dorzolamide HCl, timolol maleate, and ethacrynic acid sodium salt.

For ocular conditions, the active agent is suitably 3-hydroxy-2,2-bis(hydroxymethyl)propyl 7-((1R,2R,3R,5S)-2-((R)-3-(benzo[b]thiophen-2-yl)-3-hydroxypropyl)-3,5-dihydroxycyclopentyl)heptanoate (AR-102), 7-((1R,2R,3R,5S)-2-((R)-3-(benzo[b]thiophen-2-yl)-3-hydroxypropyl)-3,5-dihydroxycyclopentyl)heptanoic acid (AR-102 free acid), dorzolamide, ethacrynic acid, latanoprost, latanoprost free acid, travoprost, travoprost free acid, bimatoprost, bimatoprost free acid, tafluprost, tafluprost free acid, dexamethasone, brimonidine, timolol, or salts thereof. Other suitable ocular active agents are known to those of ordinary skill in the art, such as other prostaglandins and other G-protein coupled receptor ligands, antifungals, antibiotics, enzyme inhibitors including kinase inhibitors, channel blockers, reuptake inhibitors and transporter inhibitors.

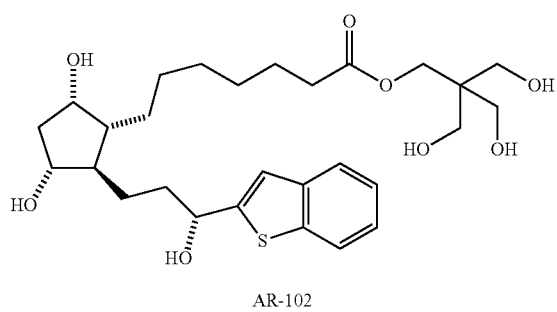

AR-102

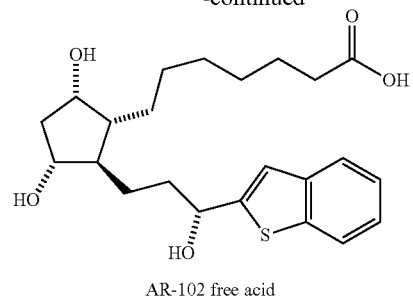

AR-102 free acid

In some embodiments, the composition consists essentially of the active agent. In other embodiments, the composition also includes excipients such as the carriers and other components discussed below. The composition may be in the form of a single compressed pellet. In another embodiment, the composition may be in the form of a matrix of an active agent and a non-water soluble polymer.

Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976). Examples of pharmaceutically acceptable carriers and excipients can, for example, be found in Remington Pharmaceutical Science, 16th Ed.

Suitable carriers include, but are not limited to, phosphate buffered saline (PBS), isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like.

The composition may also contain one or more of the following: a) diluents, b) binders, c) antioxidants, d) solvents, e) wetting agents, f) surfactants, g) emollients, h) humectants, i) thickeners, j) powders, k) sugars or sugar alcohols such as dextrans, particularly dextran 70, l) cellulose or a derivative thereof, m) a salt, n) disodium EDTA (Edetate disodium), and o) non-water soluble polymers.

Ingredient a) is a diluent. Suitable diluents for solid dosage forms include, but are not limited to sugars such as glucose, lactose, dextrose, and sucrose; diols such as propylene glycol; calcium carbonate; sodium carbonate; sugar alcohols, such as glycerin; mannitol; and sorbitol. The amount of diluent in the composition is typically about 0 to about 90%.

Ingredient b) is a binder. Suitable binders for solid dosage forms include, but are not limited to, polyethylene oxide (PEO), polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder in the composition is typically about 0 to about 25%.

Ingredient c) is an antioxidant such as butylated hydroxyanisole ("BHA"), butylated hydroxytoluene ("BHT"), vitamin C and vitamin E. The amount of antioxidant in the composition is typically about 0 to about 15%.

Ingredient d) is a solvent such as water, ethyl alcohol, isopropanol, castor oil, ethylene glycol monoethyl ether, diethylene glycol monobutyl ether, diethylene glycol monoethyl ether, dimethylsulfoxide, dimethyl formamide, and combinations thereof. The amount of ingredient d) in the composition is typically about 0% to about 95%. While a solvent may be used, one discovery of the present invention is that a solvent is generally not needed to ensure substantially linear delivery of the active agent.

Ingredient e) is a wetting agent such as sodium lauryl sulfate, polyoxyethylene sorbitan fatty acid esters, polyoxyethylene alkyl ethers, sorbitan fatty acid esters, polyethylene glycols, polyoxyethylene castor oil derivatives, docusate sodium, quaternary ammonium compounds, sugar esters of fatty acids and glycerides of fatty acids.

Ingredient f) is a surfactant such as lecithin, Polysorbate 80, and sodium lauryl sulfate, and the TWEENS® from Atlas Powder Company of Wilmington, Del. Suitable surfactants include, but are not limited to, those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant in the composition is typically about 0% to about 5%.

Ingredient g) is an emollient. Suitable emollients include, but are not limited to, stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, *arachis* oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. The amount of emollient in the composition is typically about 0% to about 50%.

Ingredient h) is a humectant. Suitable humectants include, but are not limited to, glycerin, sorbitol, sodium 2-pyrrolidone-5-carboxylate, soluble collagen, dibutyl phthalate, gelatin, and combinations thereof. The amount of humectant in the composition is typically about 0% to about 50%.

Ingredient i) is a thickener. The amount of thickener in the composition is typically about 0% to about 50%.

Ingredient j) is a powder. Suitable powders include, but are not limited to, chalk, talc, fullers earth, kaolin, starch, gums, colloidal silicon dioxide, tetra alkyl ammonium smectites, trialkyl aryl ammonium smectites, chemically-modified magnesium aluminum silicate, organically-modified montmorillonite clay, hydrated aluminum silicate, fumed silica, sodium carboxymethyl cellulose, ethylene glycol monostearate, and combinations thereof. The amount of powder in the composition is typically about 0% to about 50%.

Ingredient k) is a sugar or sugar alcohol. Suitable sugars or sugar alcohols include, but are not limited to, dextrans, dextran 70, beta-cyclodextrins, and hydroxypropyl cyclodextrins. The amount of sugars or sugar alcohols in the composition is typically about 0% to about 60%.

Ingredient l) is a cellulose derivative. Suitable cellulose derivatives include, but are not limited to, sodium carboxymethylcellulose, ethylcellulose, methylcellulose, and hydroxypropyl-methylcellulose, particularly, hydroxypropylmethylcellulose.

Ingredient m) is a salt. Suitable salts include, but are not limited to, mono-, di- and trisodium phosphate, sodium chloride, potassium chloride, and combinations thereof.

Ingredient n) is disodium EDTA (Edetate disodium). The amount of disodium EDTA in the composition is typically about 0% to about 1%.

Ingredient o) is a non-water soluble polymer. The non-water soluble polymer may be selected from ethylene vinyl acetate (EVA), silicon rubber polymers, polydimethylsiloxane (PDMS), polyurethane (PU), polyesterurethanes, polyetherurethanes, polyolefins, polyethylenes (PE), low density polyethylene (LDPE), polypropylene (PP), polyetheretherketone (PEEK), polysulfone (PSF), polyphenylsulfone, polyacetals, polymethyl methacrylate (PMMA), polybutymethacrylate, plasticized polyethyleneterephthalate, polyisoprene, polyisobutylene, silicon-carbon copolymers, natural rubber, plasticized soft nylon, polytetrafluoroethylene (PTFE), or combinations thereof. Suitably, the non-water soluble polymer is EVA. The vinyl acetate content may be from about 9% to about 50% by weight (EVA-9-50). In one embodiment, the vinyl acetate content is about 40% by weight (EVA-40). Other suitable non-water soluble polymers are known to those of ordinary skill in the art.

The drug delivery devices of the present invention may be included in kits, which include the drug delivery devices and information, instructions, or both for use of the kit to provide treatment for medical conditions in mammals (particularly humans). The information and instructions may be in the form of words, pictures, or both, and the like.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

The invention will be further explained by the following illustrative examples that are intended to be non-limiting.

Procedures for preparation of the drug delivery devices are described in the following examples. All temperatures are given in degrees Centigrade. Reagents were purchased from commercial sources (given) or prepared following literature procedures.

Example 1

Drug Delivery Device Containing Dorzolamide HCl (a High Solubility Drug)

Parameters Tested
Thickness of permeable EVA film: 40-250 micrometers
Elution rate: 0.1-2 micrograms/hr 30 mg of dorzolamide HCl (which has high solubility) was compressed at 1000 psi to form a compressed drug pellet with a diameter of 5 mm and a thickness of 1 mm. Next, 15 mg of EVA-25 (vinyl acetate content of 25%; Sigma Chemical Company, St. Louis, Mo.) was loaded into a custom-made die set and heated to 100° C. for 1 minute. The polymer was compressed at 100 psi and allowed to cool to room temperature. When prepared in this manner, this EVA-25 polymer membrane is impermeable to water. The molded polymer cup was removed from the die set and the compressed drug pellet was loaded into the cup with the top side uncovered.

EVA-40 (Sigma Chemical Company, St. Louis, Mo.) was loaded into a film maker (International Crystal Laboratory) with a 150-micrometer spacer and heated to 75° C. for 4 minutes. The polymer was compressed at 1500 psi for 1 minute and allowed to cool to room temperature. The polymer membrane thus created with a thickness of 150 micrometers was removed from the base and cut into a discshaped membrane with a diameter of 6 mm using a biopsy punch. This polymer membrane is permeable to water when prepared in this manner. The disc-shaped, permeable membrane was placed on the exposed side of the drug pellet in contact with the EVA-25 "cup", and the two polymers were heat-sealed at 90° C. using a custom-made die set and allowed to cool to room temperature.

Figure 81:
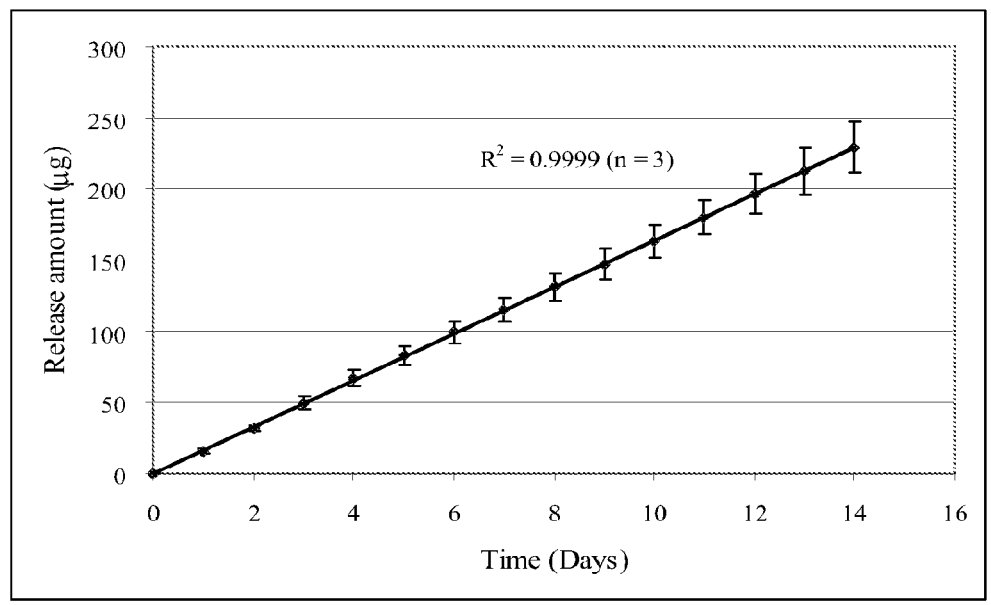
FIG. 81 shows the release profile for a drug delivery device according to the present invention.

In summary, this drug delivery device was composed of a 30 mg core of dorzolamide HCl, the top and sides were composed of the impermeable EVA-25 polymer membrane, and the bottom of the drug delivery device was a 150 micrometer rate-limiting water-permeable membrane composed of EVA-40. The average elution rate in this particular design was 0.66±0.05 micrograms/hr ($R^2$=0.9999) (FIG. 81).

Example 2

Drug Delivery Device Containing Ethacrynic Acid Sodium Salt (a High Solubility Drug)

Parameters Tested
Thickness of EVA film: 100-500 micrometers
Elution rate: 5-50 micrograms/hr 30 mg of ethacrynic acid sodium salt (Sigma Chemical Company, St. Louis, Mo.) (which has high solubility), was compressed at 1000 psi to form a compressed drug pellet with a diameter of 5 mm and a thickness of 1 mm. 15 mg of EVA-25 (Sigma Chemical Company, St. Louis, Mo.) was loaded into a custom-made die set and heated to 100° C. for 1 minute. The polymer was compressed at 100 psi and allowed to cool to room temperature. When prepared in this manner, this polymer membrane was impermeable to water. The molded polymer cup was removed from the die set and the compressed drug pellet was loaded into the cup with the top side uncovered.

EVA-40 (Sigma Chemical Company, St. Louis, Mo.) was loaded into a film maker (International Crystal Laboratory) with a 25-micrometer spacer and heated to 75° C. for 4 minutes. The polymer was compressed at 200 psi for 1 minute and allowed to cool to room temperature. The thus created polymer membrane with a thickness of 75 micrometers was removed from the base and cut into a disc-shaped membrane with a diameter of 6 mm using a biopsy punch. This polymer membrane was permeable to water when prepared in this manner. The disc-shaped, permeable membrane was placed on the exposed side of the drug pellet in contact with the EVA-25 "cup", and the two polymers were heat-sealed at 90° C. using a custom-made die set and allowed to cool to room temperature.

Figure 82:
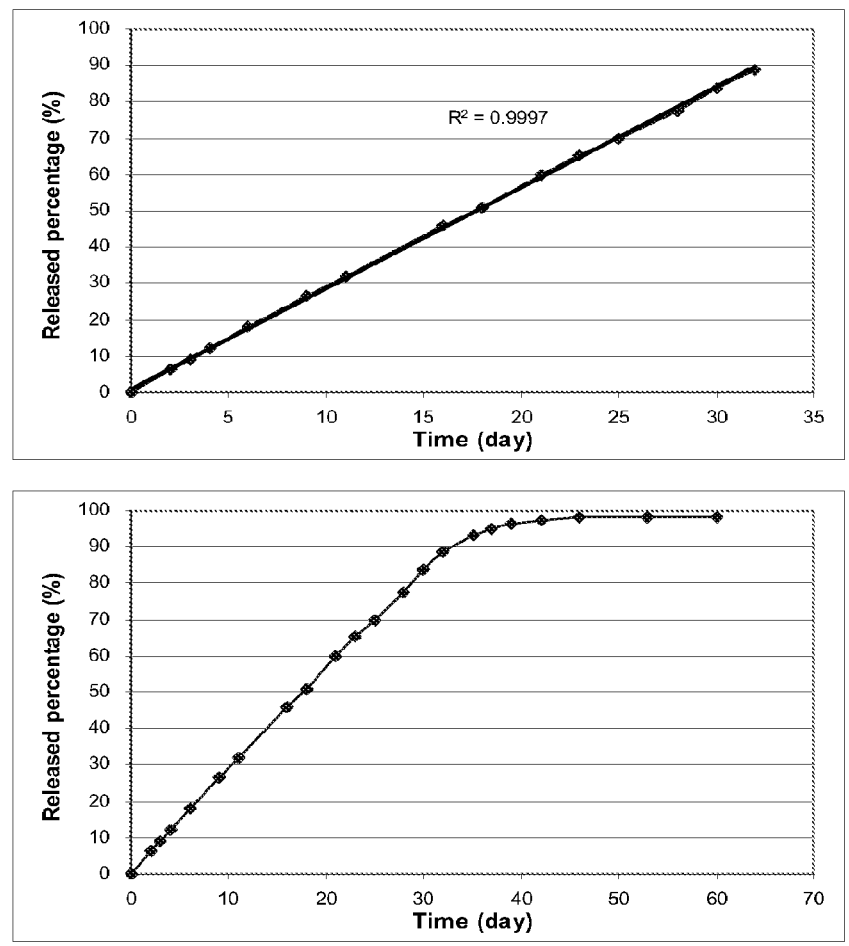
FIG. 82 shows the release profile for a drug delivery device according to the present invention.

In summary, this drug delivery device was composed of a 30 mg core of ethacrynic acid sodium salt, the top and sides were composed of an impermeable EVA-25 polymer membrane, and the bottom of the drug delivery device was a 75 micrometer rate-limiting water-permeable membrane composed of EVA-40. The elution rate in this particular design was 27 micrograms/hr with a zero-order release profile for up to 90% of the contained agent ($R^2$=0.9997) (FIG. 82).

Figure 83:
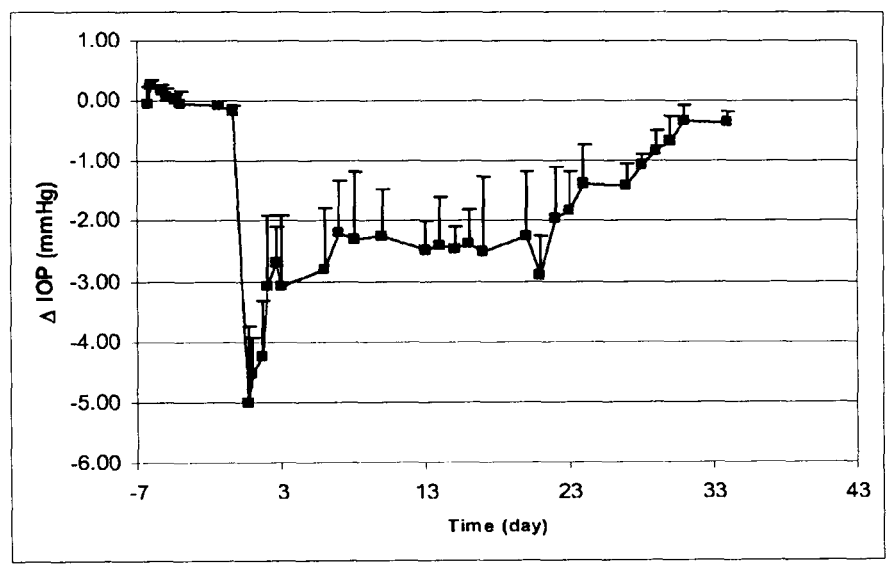
FIG. 83 shows the IOP-lowering effect of a drug delivery device according to the present invention.

Ethacrynic acid sodium salt drug delivery devices falling within the above parameters with an elution rate of approximately 20 micrograms/hr were inserted episclerally in the right eye of Dutch-belted rabbits and the contralateral eye was used as an untreated control. The intraocular pressure was measured at regular intervals. As shown in FIG. 83, the devices provided a sustained IOP-lowering effect for approximately 30 days with >90% elution of the agent achieved.

Example 3

Drug Delivery Device Containing AR-102 Free Acid (a Moderately Soluble Drug)

Parameters Tested
Thickness of EVA film: 120-250 micrometers
Elution rate: 0.04-0.7 micrograms/hr 4 mg of AR-102 free acid (which has moderate solubility) was compressed at 1000 psi to form a compressed drug pellet with a diameter of 3 mm and a thickness of 1 mm. 8 mg of EVA-25 (Sigma Chemical Company, St. Louis, Mo.) was loaded into a custom-made die set and heated to 100° C. for 1 minute. The polymer was compressed at 100 psi and allowed to cool to room temperature. This was the impermeable polymer. The molded polymer cup was removed from the die set and the compressed drug pellet was loaded into the cup with the top side uncovered.

EVA-40 (Sigma Chemical Company, St. Louis, Mo.) was loaded into a film maker (International Crystal Laboratory) with a 200-micrometer spacer and heated to 75° C. for 4 minutes. The polymer was compressed at 200 psi for 1 minute and allowed to cool to room temperature. The polymer membrane with a thickness of 250 micrometers was removed from the base and cut into a disc-shaped membrane with a diameter of 4 mm using a biopsy punch. This polymer membrane was permeable to water when prepared in this manner. The disc-shaped, permeable membrane was placed on the exposed side of the drug pellet in contact with the EVA-25 "cup", and the two polymers were heat-sealed at 90° C. using a custom-made die set and allowed to cool to room temperature.

Figure 84:
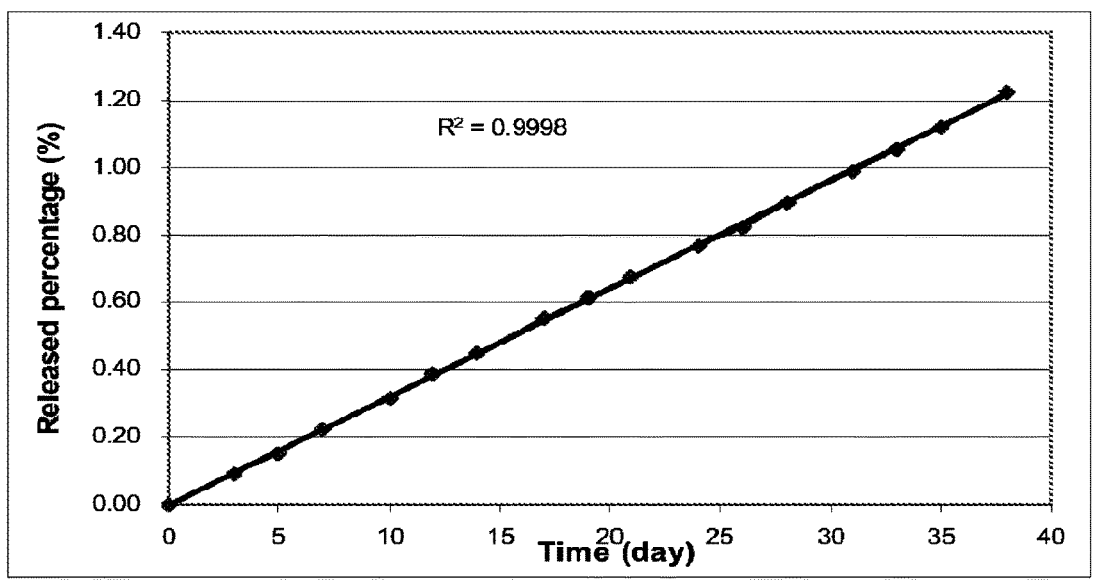
FIG. 84 shows the release profile of a drug delivery device according to the present invention.

In summary, this device was composed of a 4 mg core of AR-102 free acid. The impermeable polymer was EVA-25. The rate-limiting water-permeable polymer was EVA-40, and the thickness of the water-permeable membrane was 250 micrometers. The elution rate in this particular design was 0.16 micrograms/hr (R2=0.9998) (FIG. 84).

Figure 85:
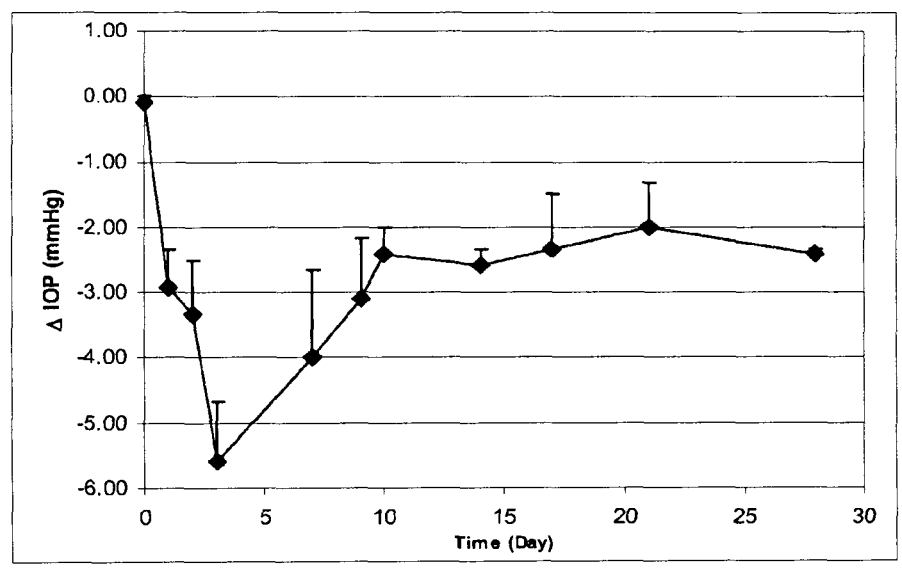
FIG. 85 shows the IOP-lowering effect of a drug delivery device according to the present invention.

AR-102 free acid drug delivery devices falling within the above parameters with an elution rate of approximately 0.03 micrograms/hr were inserted episclerally in the right eye of Dutch-belted rabbits and the contralateral eye was used as an untreated control. The intraocular pressure was measured at regular intervals. As shown in FIG. 85, the devices provided a sustained IOP-lowering effect with a theoretical duration in vivo of approximately 7 years.

Example 4

Drug Delivery Device Containing Latanoprost Arginine Salt (a Moderately Soluble Drug)

Parameters Tested
Thickness of EVA film: 40-300 micrometers
Elution rate: 0.04-5 micrograms/hr 4 mg of latanoprost arginine salt (which has moderate solubility) was compressed at 1000 psi to form a compressed drug pellet with a diameter of 3 mm and a thickness of 1 mm. 8 mg of EVA-25 (Sigma Chemical Company, St. Louis, Mo.) was loaded into a custom-made die set and heated to 100° C. for 1 minute. The polymer was compressed at 100 psi and allowed to cool to room temperature. This was the impermeable polymer. The molded polymer cup was removed from the die set and the compressed drug pellet was loaded into the cup with the top side uncovered.

EVA-40 (Sigma Chemical Company, St. Louis, Mo.) was loaded into a film maker (International Crystal Laboratory) with a 150-micrometer spacer and heated to 75° C. for 4 minutes. The polymer was compressed at 400 psi for 1 minute and allowed to cool to room temperature. The polymer membrane with a thickness of 160 micrometers was removed from the base and cut into a disc-shaped membrane with a diameter of 4 mm using a biopsy punch. This polymer membrane is permeable to water when prepared in this manner. The disc-shaped, permeable membrane was placed on the exposed side of the drug pellet in contact with the EVA-25 "cup", and the two polymers were heat-sealed at 90° C. using a custom-made die set and allowed to cool to room temperature.

Figure 86:
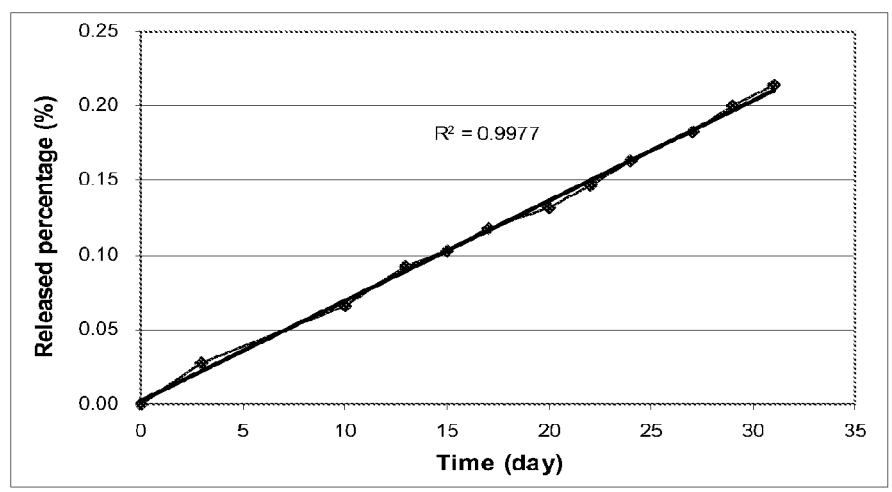
FIG. 86 shows the release profile of a drug delivery device according to the present invention.

In summary, this device was composed of a 4 mg core of latanoprost arginine salt. The impermeable polymer was EVA-25. The rate-limiting waterpermeable polymer was EVA-40, and the thickness of the water-permeable membrane was 160 micrometers. The elution rate in this particular design was approximately 0.01 micrograms/hr (R2=0.9977) (FIG. 86).

Figure 87:
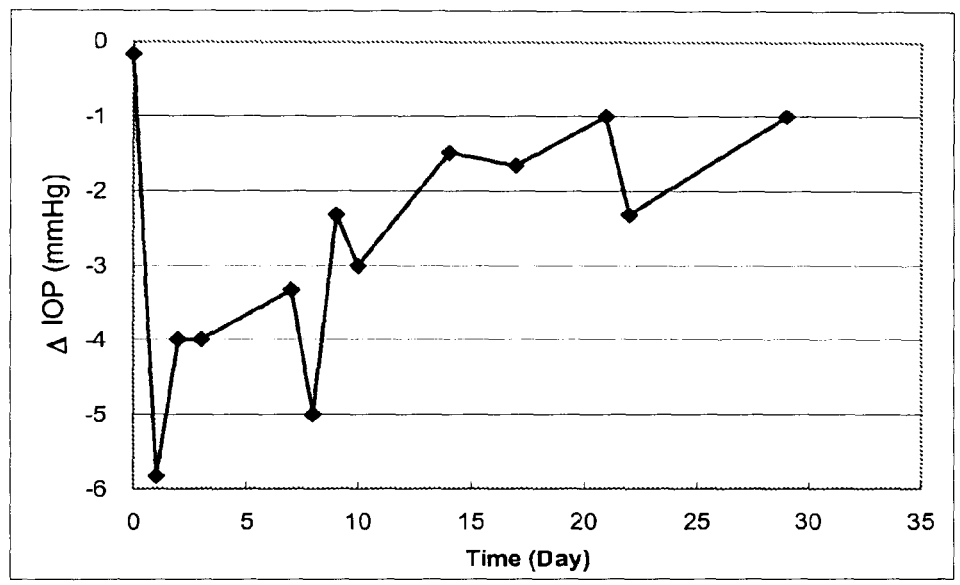
FIG. 87 shows the IOP-lowering effect of a drug delivery device according to the present invention.

A latanoprost free acid arginine salt drug delivery device falling within the above parameters with an elution rate of approximately 0.01 micrograms/hr was inserted episclerally in the right eye of Dutch-belted rabbits and the contralateral eye was used as an untreated control. The intraocular pressure was measured at regular intervals. As shown in FIG. 87, the device provided a sustained IOP-lowering effect for approximately 30 days with a theoretical duration in vivo of approximately 30 years.

Example 5

Drug Delivery Device Containing Dexamethasone (a Low Solubility Drug)

Parameters Tested
Thickness of EVA film: 40-150 micrometers
Elution rate: 0.1-3 micrograms/hr 30 mg of dexamethasone (which has low solubility) was compressed at 1000 psi to form a compressed drug pellet with a diameter of 5 mm and a thickness of 1 mm. 15 mg of EVA-25 (Sigma Chemical Company, St. Louis, Mo.) was loaded into a custom-made die set and heated to 100° C. for 1 minute. The polymer was compressed at 100 psi and allowed to cool to room temperature. This was the impermeable polymer. The molded polymer cup was removed from the die set and the compressed drug pellet was loaded into the cup with the top side uncovered.

EVA-40 (Sigma Chemical Company, St. Louis, Mo.) was loaded into a film maker (International Crystal Laboratory) with a 50-micrometer spacer and heated to 75° C. for 4 minutes. The polymer was compressed at 200 psi for 1 minute and allowed to cool to room temperature. The polymer membrane with a thickness of 75 micrometers was removed from the base and cut into a disc-shaped membrane with a diameter of 6 mm using a biopsy punch. This polymer membrane is permeable to water when prepared in this manner. The disc-shaped, permeable membrane was placed on the exposed side of the drug pellet, and the two polymers were heatsealed at 90° C. using a custom-made die set and allowed to cool to room temperature.

Figure 88:
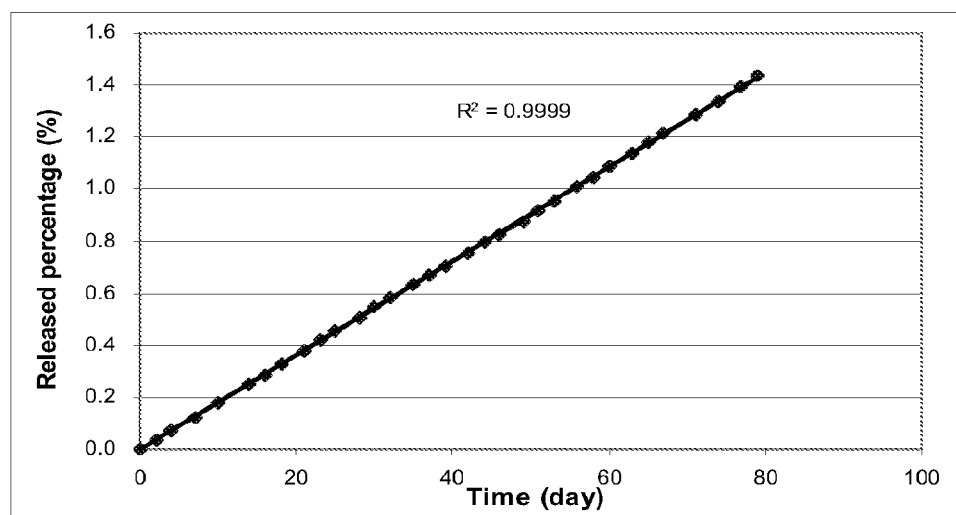
FIG. 88 shows the release profile of a drug delivery device according to the present invention.

In summary, this device was composed of a 30 mg core of dexamethasone. The impermeable polymer was EVA-25. The rate-limiting waterpermeable polymer was EVA-40, and the thickness of the water-permeable membrane was 75 micrometers. The elution rate in this particular design was 0.25 micrograms/hr (R2=0.9999) (FIG. 88).

Example 6

Ethylene Vinyl Acetate/Dextran Film

Standard Methods for Making EVA/Dextran Film

Dextran with an average molecular weight of 5,000-670,000 Daltons (Fluka) was desiccated under vacuum overnight to purge excess moisture. EVA pellets with selected vinyl acetate ratios from 0 to 40% were ground into fine pieces to increase surface area. Dextran and EVA-0-40 were then measured out at a selected weight ratio in a sealed glass vial. Dichloromethane was incrementally added to the dextran/EVA mixture and the mixture was vigorously shaken to prevent clumping of dextran. The mixture was then gently heated to 50° C. and shaken in quick succession to aid EVA-25 dissolution. The mixture was then placed in an ultrasonic bath for 2 minutes. The mixture was allowed to cool to room temperature and inspected for undesirable air bubble formation.

A glass plate or silicon wafer was used as a casting substrate for the evaporative casting of the film. The mixture was uncapped and quickly decanted onto the substrate. Typical drying time was at least 4 hours under low humidity conditions to limit moisture uptake by the hygroscopic dextran. The cast film was then placed in a negative pressure rated flask and the atmosphere was flushed with high purity Argon gas. Air was then evacuated under a high vacuum overnight. The dried film was grounded into fine powder, and a dextran/EVA film with desired thickness was made by heat compression in a film maker. A digital micrometer was used to verify the final film thickness.

Example 7

Drug Delivery Device Containing Dexamethasone Sodium Phosphate (a High Solubility Drug)

Parameters Tested
Dextran molecular weight: 5-12 kDa
Weight ratio of Dextran/EVA film: 1:20 to 1:4
Thickness of Dextran/EVA film: 40-150 micrometers
Elution rate: 2-200 micrograms/hr 30 mg of dexamethasone sodium phosphate (which has high solubility) was compressed at 1000 psi to form a compressed drug pellet with a diameter of 5 mm and a thickness of 1 mm. 15 mg of EVA-25 (Sigma Chemical Company, St. Louis, Mo.) was loaded into a custom-made die set and heated to 100° C. for 1 minute. The polymer was compressed at 100 psi and allowed to cool to room temperature. This was the impermeable polymer. The molded polymer cup was removed from the die set and the compressed drug pellet was loaded into the cup with the top side uncovered.

A mixture of EVA-25 (Sigma Chemical Company, St. Louis, Mo.) and dextran with an average molecular weight of 5 kDa was loaded into a film maker (International Crystal Laboratory) with a 100-micrometer spacer and heated to 100° C. for 4 minutes. The weight ratio of the dextran/EVA film was 1:19. The polymer was compressed at 200 psi for 1 minute and allowed to cool to room temperature. The polymer membrane with a thickness of 120 micrometers was removed from the base and cut into a disc-shaped membrane with a diameter of 6 mm using a biopsy punch. This was the partially-bioerodible membrane. The disc-shape, partially-bioerodible membrane was placed on the exposed side of the drug pellet in contact with the EVA-25 "cup", and the two polymers were heat-sealed at 90° C. using a custom-made die set and allowed to cool to room temperature.

Figure 89:
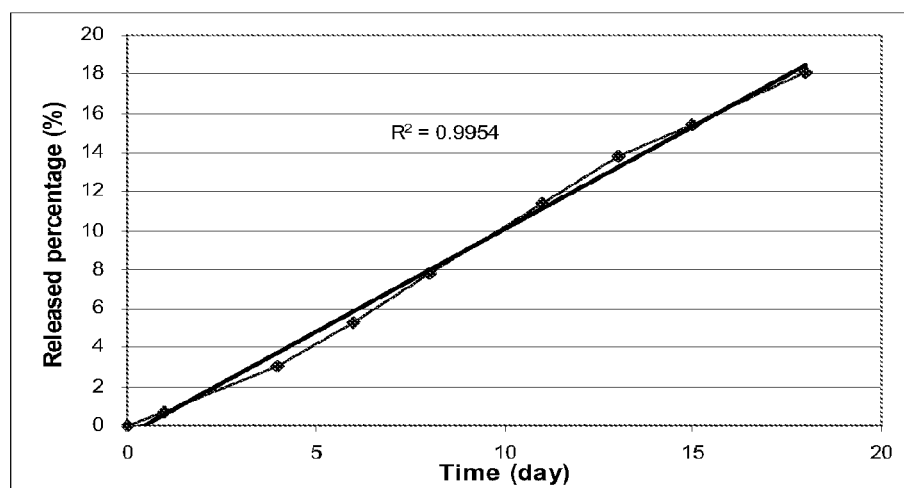
FIG. 89 shows the release profile of a drug delivery device according to the present invention.

In summary, this device was composed of a 30 mg core of dexamethasone sodium phosphate. The impermeable polymer was EVA-25. The partially-bioerodible membrane was dextran with an average weight molecular of 5 kDa and EVA-25 at a weight ratio of 1:19, and the thickness of the partiallybioerodible membrane was 120 micrometers. The elution rate in this particular design was approximately 14 micrograms/hr (R2=0.9954) (FIG. 89).

Example 8

Drug Delivery Device Containing Brimonidine Free Base (a Low Solubility Drug)

Parameters Tested
Dextran molecular weight: 12-670 kDa
Weight ratio of Dextran/EVA film: 1:4 to 1:3
Thickness of Dextran/EVA film: 40-150 micrometers
Elution rate: 0.05-4 micrograms/hr 20 mg of brimonidine free base (which has low solubility) was compressed at 1000 psi to form a compressed drug pellet with a diameter of 5 mm and a thickness of 1 mm. 15 mg of EVA-25 (Sigma Chemical Company, St. Louis, Mo.) was loaded into a custom-made die set and heated to 100° C. for 1 minute. The polymer was compressed at 100 psi and allowed to cool to room temperature. This was the impermeable polymer. The molded polymer cup was removed from the die set and the compressed drug pellet was loaded into the cup with the top side uncovered.

A mixture of EVA-25 (Sigma Chemical Company, St. Louis, Mo.) and dextran with an average molecular weight of 270 kDa was loaded into a film maker (International Crystal Laboratory) with a 50-micrometer spacer and heated to 75° C. for 4 minutes. The weight ratio of the dextran/EVA film was 1:4. The polymer was compressed at 400 psi for 1 minute and allowed to cool to room temperature. The polymer membrane which had a thickness of 65 micrometers was removed from the base and cut into a disc-shaped membrane with a diameter of 6 mm using a biopsy punch. This was the partially-bioerodible membrane. The disc-shaped, partially bioerodible membrane was placed on the exposed side of the drug pellet in contact with the EVA-25 "cup", and the two polymers were heat-sealed at 90° C. using a custom-made die set and allowed to cool to room temperature.

Figure 90:
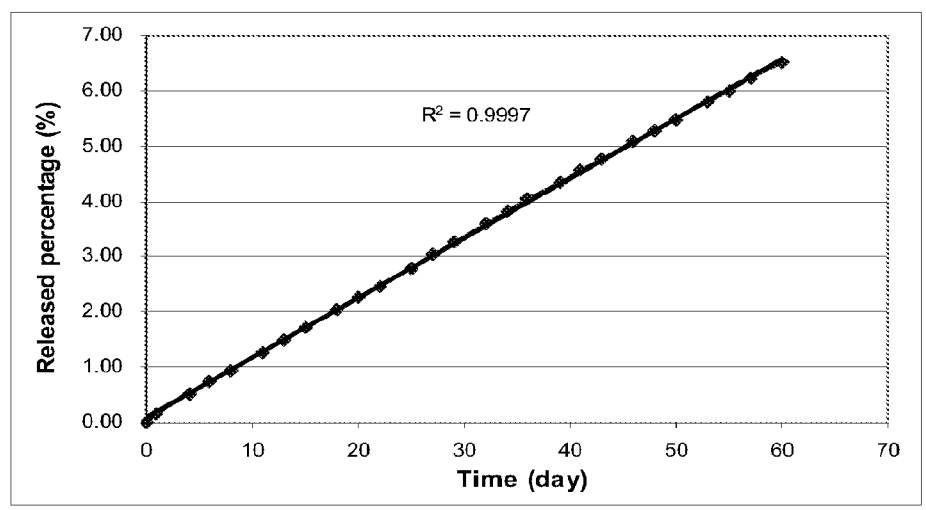
FIG. 90 shows the release profile of a drug delivery device according to the present invention.

In summary, this device was composed of a 20 mg core of brimonidine free base. The impermeable polymer was EVA-25. The partially-bioerodible membrane was synthesized using dextran with an average molecular weight of 270 kDa and EVA-25 at a weight ratio of 1:4, and the thickness of the partially-bioerodible membrane was 65 micrometers. The elution rate in this particular design was 0.7 micrograms/hr (R2=0.9997) (FIG. 90).

Figure 91:
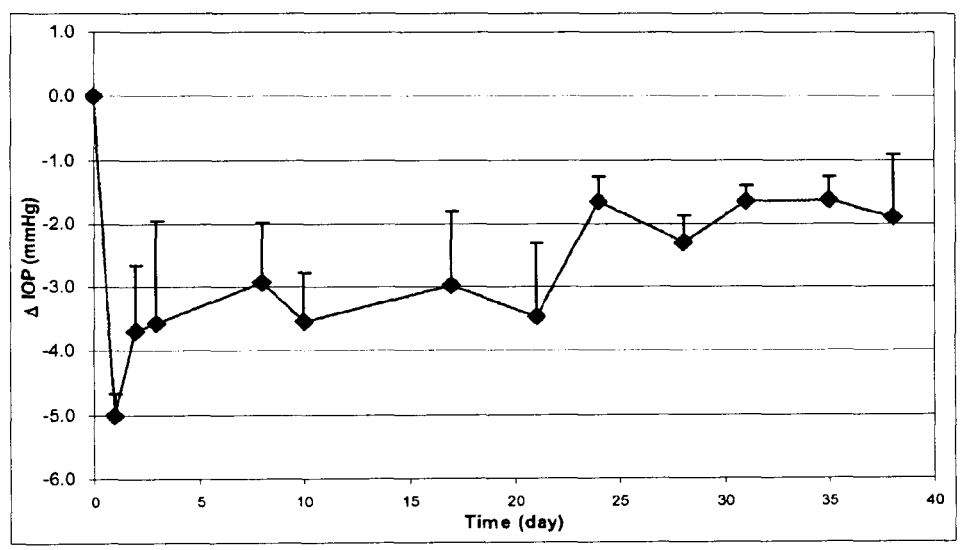
FIG. 91 shows the IOP-lowering effect of a drug delivery device according to the present invention.

Brimonidine free base drug delivery devices falling within the above parameters using a similar design with elution rates of 0.7-2.5 micrograms/hr were inserted below the sclera in the right eye of Dutch-belted rabbits and the contralateral eye was used as an untreated control. The intraocular pressure was measured at regular intervals. As shown in FIG. 91, the device provided a sustained IOP-lowering effect for approximately 38 days with an expected duration in vivo of at least 7 months.

Example 9

Drug Delivery Device Containing Brimonidine D-Tartrate Salt (a High Solubility Drug)

Parameters Tested
Dextran molecular weight: 5-270 kDa
Weight ratio of Dextran/EVA film: 1:20 to 1:4
Thickness of Dextran/EVA film: 95-150 micrometers
Elution rate: 0.3-60 micrograms/hr 30 mg of brimonidine D-tartrate salt (which has high solubility) was compressed at 1000 psi to form a compressed drug pellet with a diameter of 5 mm and a thickness of 1 mm. 15 mg of EVA-25 (Sigma Chemical Company, St. Louis, Mo.) was loaded into a custom-made die set and heated to 100° C. for 1 minute. The polymer was compressed at 100 psi and allowed to cool to room temperature. This was the impermeable polymer. The molded polymer cup was removed from the die set and the compressed drug pellet was loaded into the cup with the top side uncovered.

A mixture of EVA-25 (Sigma Chemical Company, St. Louis, Mo.) and dextran with an average molecular weight of 270 kDa was loaded into a film maker (International Crystal Laboratory) with a 100-micrometer spacer and heated to 100° C. for 4 minutes. The weight ratio of the dextran/EVA film was 1:4. The polymer was compressed at 200 psi for 1 minute and allowed to cool to room temperature. The polymer membrane which had a thickness of 125 micrometers was removed from the base and cut into a disc-shaped membrane with a diameter of 6 mm using a biopsy punch. This was the partially-bioerodible membrane.

The disc-shaped, partially bioerodible membrane was placed on the exposed side of the drug pellet in contact with the EVA-25 "cup", and the two polymers were heat-sealed at 90° C. using a custom-made die set and allowed to cool to room temperature.

Figure 92:
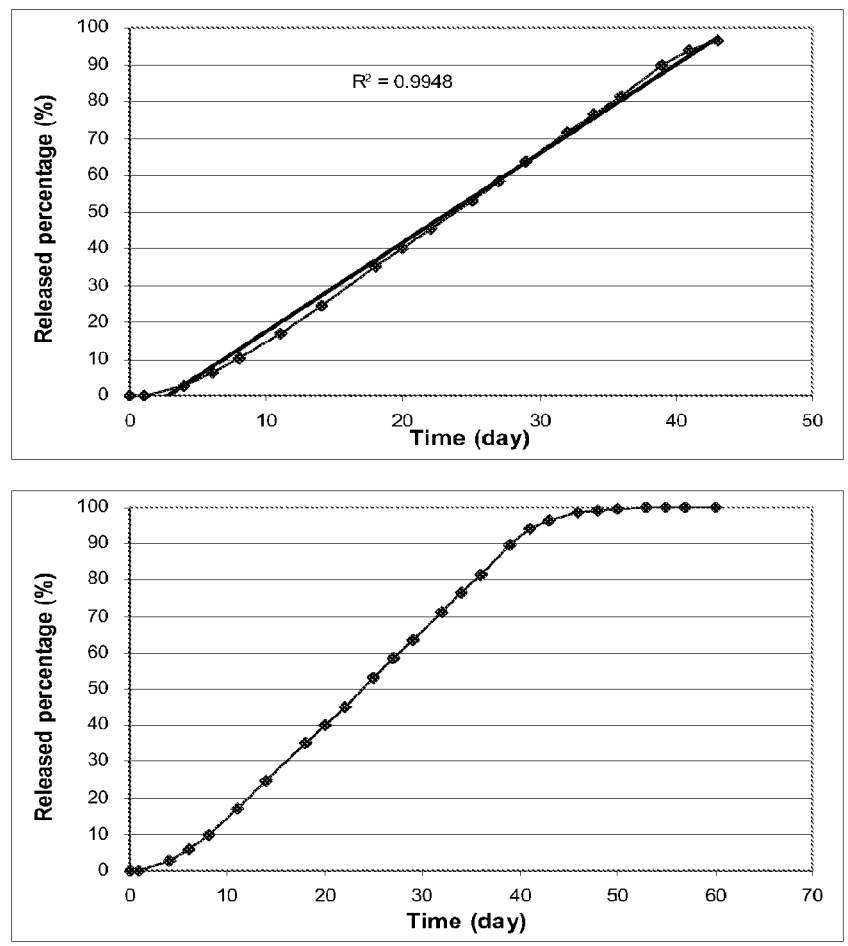
FIG. 92 shows the release profile of a drug delivery device according to the present invention.

In summary, this device was composed of a 30 mg core of brimonidine D-tartrate salt. The impermeable polymer was EVA-25. The partially-bioerodible membrane was dextran with an average molecular weight of 270 kDa and EVA-25 at a weight ratio of 1:4, and the thickness of the partially-bioerodible membrane was 125 micrometers. The elution rate in this particular design was approximately 34 micrograms/hr with a zero-order release profile for up to 95% ($R2 = 0.9948$) (FIG. 92).

Example 10

Drug Delivery Device Containing Timolol Maleate Salt (a High Solubility Drug)

Parameters Tested
Dextran molecular weight: 5-670 kDa
Weight ratio of Dextran/EVA film: 1:20 to 1:3
Thickness of Dextran/EVA film: 40-150 micrometers
Elution rate: 1-50 micrograms/hr 30 mg of timolol maleate (which has high solubility) was compressed at 1000 psi to form a compressed drug pellet with a diameter of 5 mm and a thickness of 1 mm. 15 mg of EVA-25 (Sigma Chemical Company, St. Louis, Mo.) was loaded into a custom-made die set and heated to 100° C. for 1 minute. The polymer was compressed at 100 psi and allowed to cool to room temperature. This was the impermeable polymer. The molded polymer cup was removed from the die set and the compressed drug pellet was loaded into the cup with the top side uncovered.

A mixture of EVA-25 (Sigma Chemical Company, St. Louis, Mo.) and dextran with an average molecular weight of 5 kDa was loaded into a film maker (International Crystal Laboratory) with a 100-micrometer spacer and heated to 75° C. for 4 minutes. The weight ratio of the dextran/EVA film was 1:9. The polymer was compressed at 1500 psi for 1 minute and allowed to cool to room temperature. The polymer membrane which had a thickness of 100 micrometers was removed from the base and cut into a disc-shaped membrane with a diameter of 6 mm using a biopsy punch. This was the partially-bioerodible membrane. The disc-shape, partially bioerodible membrane was placed on the exposed side of the drug pellet in contact with the EVA-25 "cup", and the two polymers were heat-sealed at 90° C. using a custom-made die set and allowed to cool to room temperature.

Figure 93:
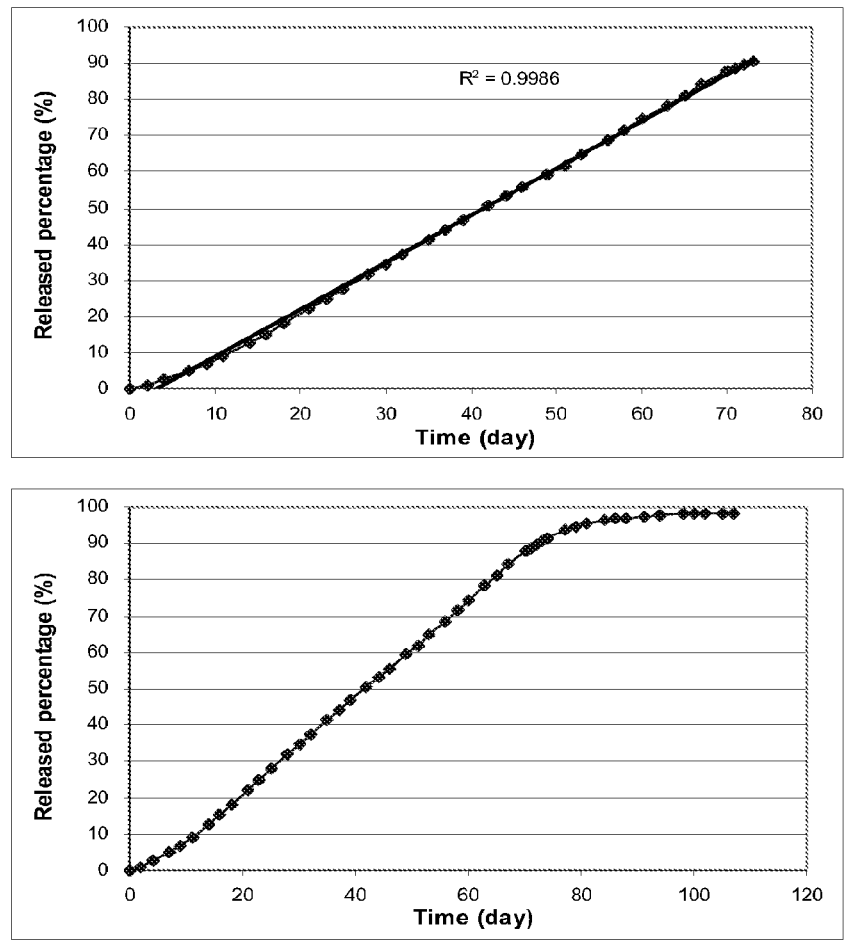
FIG. 93 shows the release profile of a drug delivery device according to the present invention.

In summary, this device was composed of a 30 mg core of timolol maleate salt. The impermeable polymer was EVA-25. The partially-bioerodible membrane was dextran with an average molecular weight of 5 kDa and EVA-25 at a weight ratio of 1:9, and the thickness of the partially-bioerodible membrane was 100 micrometers. The elution rate in this particular design was approximately 15 micrograms/hr with a zero-order release profile for up to 90% of the enclosed agent ($R2=0.9986$) (FIG. 93).

Figure 94:
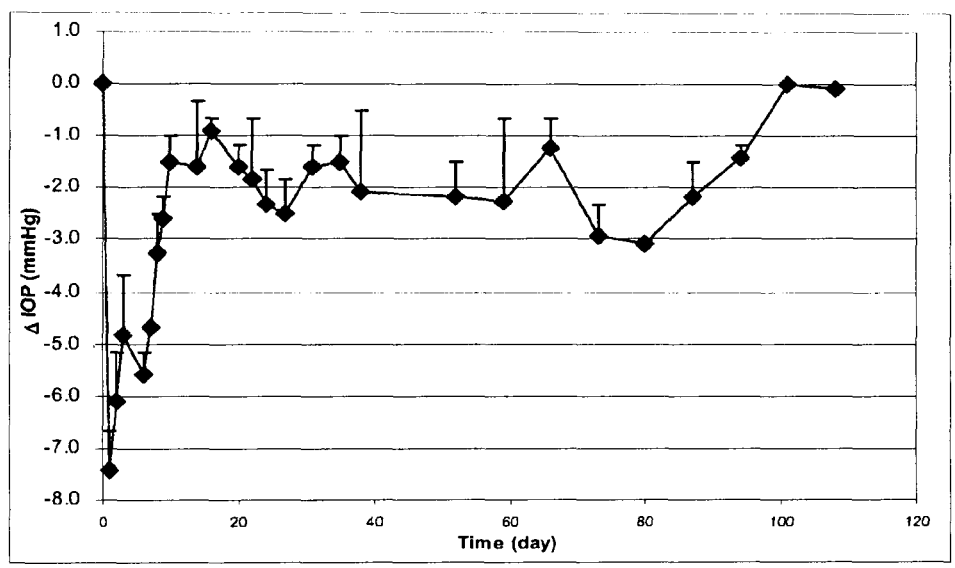
FIG. 94 shows the IOP-lowering effect of a drug delivery device according to the present invention.

Timolol maleate salt drug delivery devices falling within the above parameters with elution rates of about 12 to 18 micrograms/hr were inserted below the sclera in the right eye of Dutch-belted rabbits and the contralateral eye was used as an untreated control. The intraocular pressure was measured at regular intervals. As shown in FIG. 94, the device provided a sustained IOP-lowering effect for approximately 90 days with complete elution achieved.

Example 11

Drug Delivery Device Containing Albumin (a High Molecular Weight, High Solubility Compound)

Parameters Tested
Dextran molecular weight: 270-670 kDa
Weight ratio of Dextran/EVA film: 1:20 to 1:3
Thickness of Dextran/EVA film: 40-150 micrometers 30 mg of albumin (average molecular weight of approximately 67 kDa) that had been labeled with fluorescein isothiocyanate (BSA-FITC, Fluka) (which has high solubility) was mixed with unlabeled albumin at weight ratio of 1:9 and compressed at 1000 psi to form a compressed drug pellet with a diameter of 5 mm and a thickness of 1 mm. 15 mg of EVA-25 (Sigma Chemical Company, St. Louis, Mo.) was loaded into a custom-made die set and heated to 100° C. for 1 minute. The polymer was compressed at 100 psi and allowed to cool to room temperature. This was the impermeable polymer. The molded polymer cup was removed from the die set and the compressed drug pellet was loaded into the cup with the top side uncovered.

A mixture of EVA-25 (Sigma Chemical Company, St. Louis, Mo.) and dextran with an average molecular weight of 670 kDa was loaded into a film maker (International Crystal Laboratory) with a 50-micrometer spacer and heated to 100° C. for 4 minutes. The weight ratio of dextran/EVA film was 1:4. The polymer was compressed at 150 psi for 1 minute and allowed to cool to room temperature. The polymer membrane which had a thickness of 85 micrometers was removed from the base and cut into a disc-shaped membrane with a diameter of 6 mm using a biopsy punch. This was the partially-bioerodible membrane. The disc-shaped, partially-bioerodible membrane was placed on the exposed side of the drug pellet in contact with the EVA-25 "cup", and the two polymers were heat-sealed at 90° C. using a custom-made die set and allowed to cool to room temperature.

In summary, this device was composed of a 30 mg core of albumin with 10% of the core consisting of FITC-labeled albumin. The impermeable polymer was EVA-25. The partially-bioerodible membrane was dextran with an average molecular weight of 670 kDa and EVA-25 at a weight ratio of 1:4, and the thickness of the partially-bioerodible membrane was 85 micrometers. The data showed that albumin was released from the permeable polymer at a controlled rate.

Example 12

General Methods of In Vitro Elution Rate Determination

A drug delivery device, containing a known active agent of interest, is placed in a 20-mL Class A clear borosilicate glass vial with PTFE threaded lid. To the vial is then added 10 mL of sterile 1× phosphate-buffered saline (PBS) without calcium and magnesium salts (Mediatech). The 20-mL glass vial is placed onto a tight fitting polymer rack. The polymer rack is then placed on an adjustable orbital platform shaker set to 60 Hz with infinite duration in a 37° C. incubator. At predetermined time points, 1-2 ml of the incubated solution is transferred from the vial to a sampling vial, and the rest of the solution is aspirated. The predetermined time intervals are usually 48 or 72 hours, and are subject to change based on the target elution rate and the maximum solubility of the active agent in PBS. 10 mL of fresh PBS is added to the 20-mL vial, and the vial is placed back to the incubator. In general, the concentration of active agent in solution is maintained at less than 10% of its maximum solubility in PBS to ensure the near-sink conditions.

The concentration of the solution in the sampling vial is determined using a standard curve obtained from several (usually more than 8) different known concentrations of the same active agent. The total amount of active agent eluted is determined from the original volume of the incubating solution and the elution rate is calculated based on the incubation time.

Example 13

Drug Delivery Device Containing Bimatoprost (a Low Solubility Drug)

Suggested Parameters
Thickness of EVA film: 40-500 micrometers
Elution rate: 0.005-0.3 micrograms/hr
Preferred elution rate: 0.002-0.1 micrograms/hr 4 mg of bimatoprost (which has low solubility) is compressed at 1000 psi to form a compressed drug pellet with a diameter of 3 mm and a thickness of 1 mm. 8 mg of EVA-25 (Sigma) is loaded into a custom-made die set and heated to 100° C. for 1 minute. The polymer is compressed at 100 psi and allowed to cool to room temperature. This is the impermeable polymer. The molded polymer cup is removed from the die set and the compressed drug pellet is loaded into the cup with the top side uncovered.

EVA-40 is loaded into a film maker with a suitable spacer and heated to 75° C. for 4 minutes. The polymer is compressed at constant pressure for 1 minute and allowed to cool to room temperature. The polymer membrane with a thickness of 40-500 micrometers is removed from the base and cut into a disc-shaped membrane with a diameter of 4 mm using a biopsy punch. This polymer membrane is permeable to water when prepared in this manner. The disc-shaped, permeable membrane is placed on the exposed side of the drug pellet in contact with the EVA-25 "cup", and the two polymers are heat-sealed at 90° C. using a custom-made die set and allowed to cool to room temperature.

In summary, this device is composed of a 4 mg core of bimatoprost. The top and sides are composed of an impermeable EVA-25 polymer membrane, and the bottom of the drug delivery device is a 40-500 micrometer permeable membrane composed of EVA-40. The elution rate in this design can be adjusted to the desired elution rate by changing the thickness of the permeable polymer.

Example 14

Drug Delivery Device Containing Latanoprost Isopropyl Ester (a Low Solubility Drug)

Suggested Parameters
Thickness of EVA film: 300-1000 micrometers
Elution rate: 0.005-0.3 micrograms/hr
Preferred elution rate: 0.001-0.05 micrograms/hr 8 mg of EVA-25 is loaded into a custom-made die set and heated to 100° C. for 1 minute. The polymer is compressed at 100 psi and allowed to cool to room temperature. This is the impermeable polymer. The molded polymer cup is removed from the die set and 4 mg of latanoprost isopropyl ester (which has low solubility) is loaded into the EVA-25 cup.

EVA-40 is loaded into a film maker with a suitable spacer and heated to 75° C. for 4 minutes. The polymer is compressed at constant pressure for 1 minute and allowed to cool to room temperature. The polymer membrane with a thickness of 300-800 micrometers is removed from the base and cut into a disc-shaped membrane with a diameter of 4 mm using a biopsy punch. This polymer membrane is permeable to water when prepared in this manner. The disc-shaped, permeable membrane is placed on the exposed side of the drug pellet in contact with the EVA-25 "cup," and the two polymers are heat-sealed at 90° C. using a custom-made die set and allowed to cool to room temperature.

In summary, this device is composed of a 4 mg core of latanoprost isopropyl ester. The top and sides are composed of an impermeable EVA-25 polymer membrane, and the bottom of the drug delivery device is a 40-500 micrometer permeable membrane composed of EVA-40. The elution rate in this design can be adjusted to desired elution rate by changing the thickness of the permeable polymer.

Example 15

Drug Delivery Device Containing Travoprost Isopropyl Ester (a Low Solubility Drug)

Suggested Parameters
Thickness of EVA film: 300-750 micrometers
Elution rate: 0.001-0.04 micrograms/hr
Preferred elution rate: 0.001-0.02 micrograms/hr 8 mg of EVA-25 is loaded into a custom-made die set and heated to 100° C. for 1 minute. The polymer is compressed at 100 psi and allowed to cool to room temperature. This is the impermeable polymer. The molded polymer cup is removed from the die set and 4 mg of travoprost isopropyl ester (which has low solubility) is loaded into the EVA-25 cup.

EVA-40 is loaded into a film maker (International Crystal Laboratory) with a suitable spacer and heated to 75° C. for 4 minutes. The polymer is compressed at constant pressure for 1 minute and allowed to cool to room temperature. The polymer membrane with a thickness of 300-800 micrometers is removed from the base and cut into a disc-shaped membrane with a diameter of 4 mm using a biopsy punch. This polymer membrane is permeable to water when prepared in this manner. The disc-shaped, permeable membrane is placed on the exposed side of the drug pellet in contact with the EVA-25 "cup," and the two polymers are heat-sealed at 90° C. using a custom-made die set and allowed to cool to room temperature.

In summary, this device is composed of a 4 mg core of travoprost isopropyl ester. The top and sides are composed of an impermeable EVA-25 polymer membrane, and the bottom of the drug delivery device is a 40-500 micrometer permeable membrane composed of EVA-40.

Example 16

Drug Delivery Device Containing Non-steroidal Anti-Inflammatory Drugs

Figure 95:
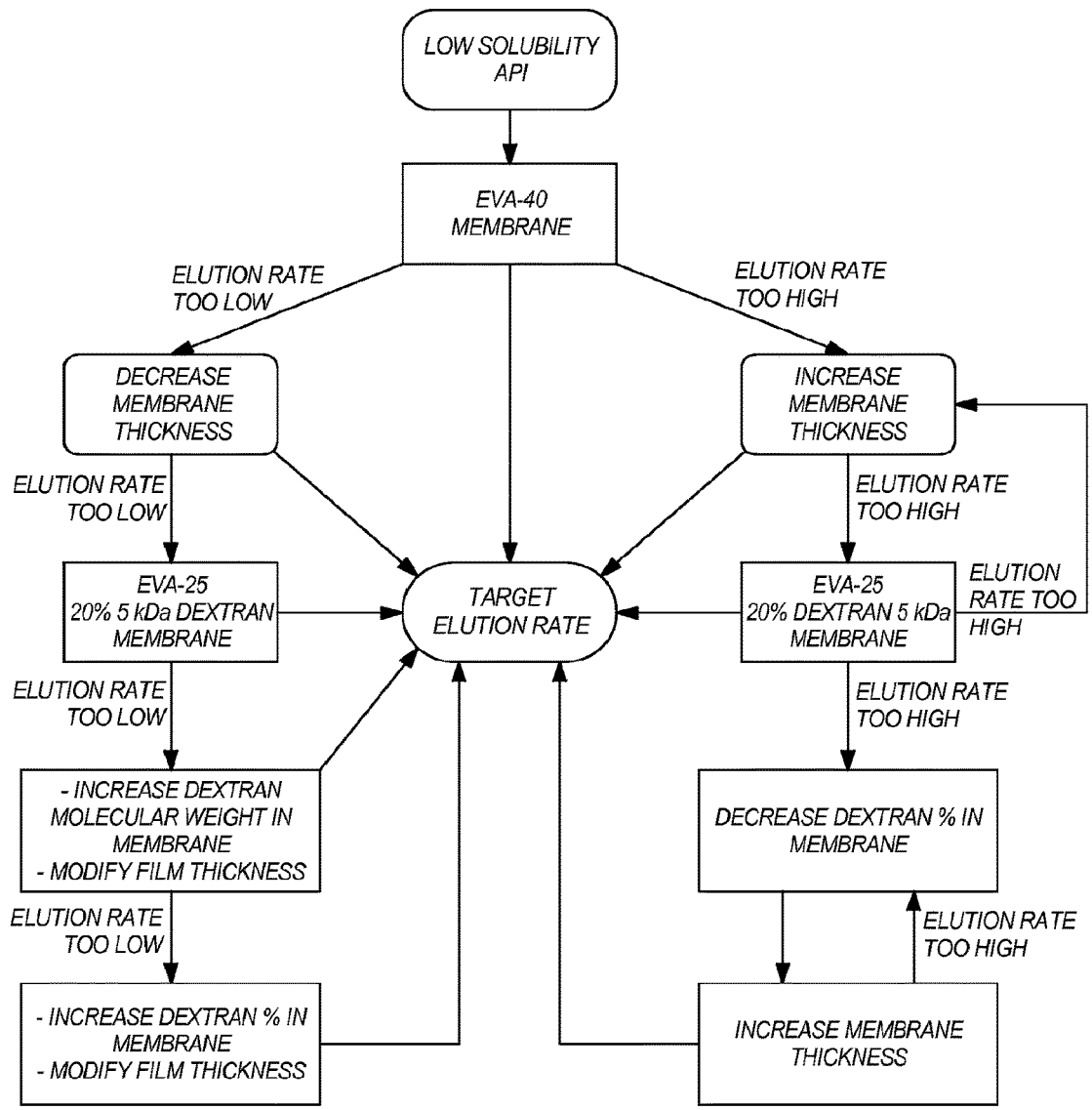
FIG. 95 shows a flowchart for designing drug delivery devices.
Figure 96:
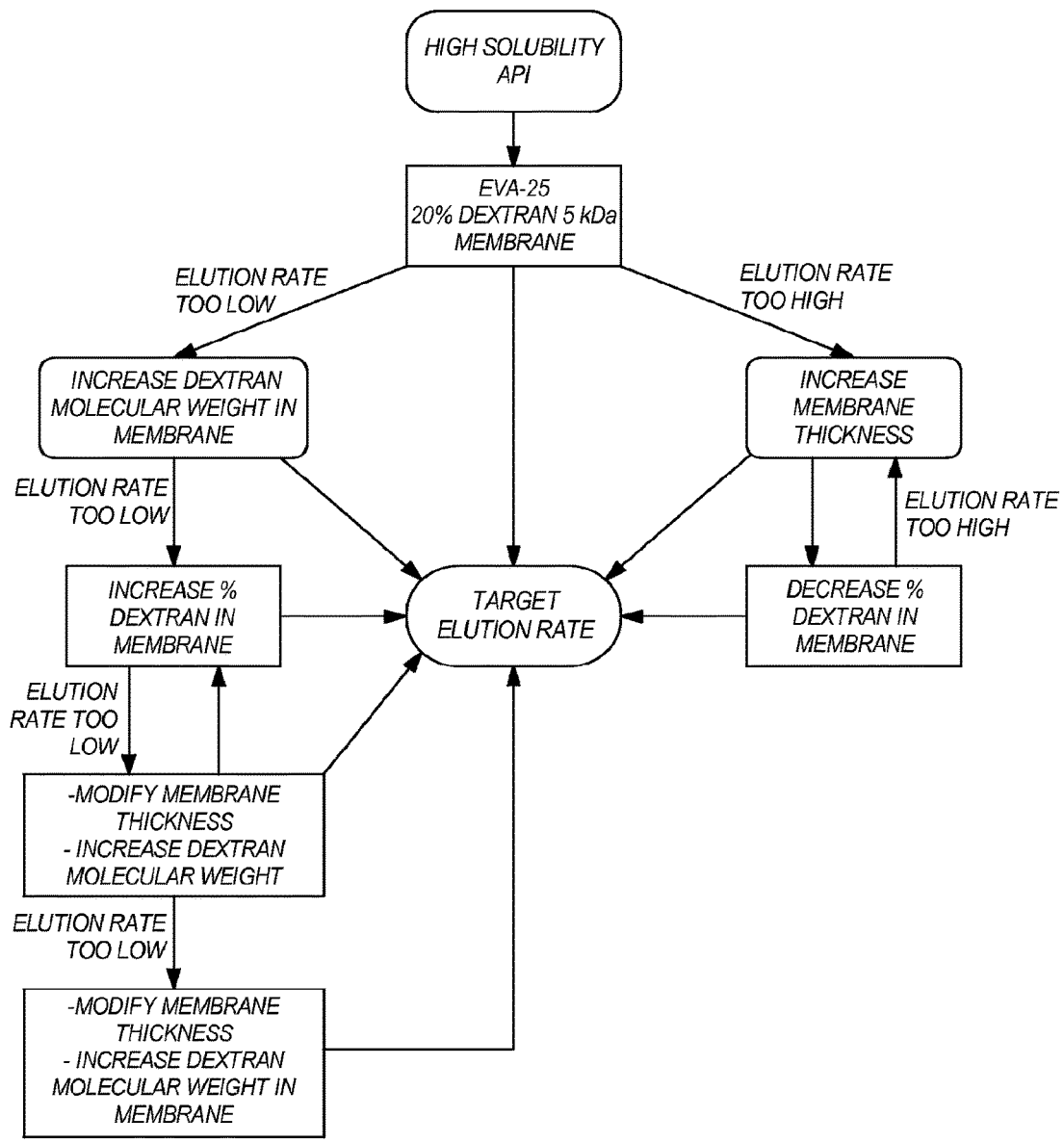
FIG. 96 shows a flowchart for designing drug delivery devices.

A drug delivery device of the invention can be designed to release a selected active agent at a predetermined rate using the flowcharts and table in FIGS. 95-97. Suitably, one would start with EVA-40 as the water permeable membrane

Example 17

Drug Delivery Device Containing Latanoprost Arginine Salt (a Moderately Soluble Drug)

and EVA-25 as the water impermeable membrane, or using partially-bioerodible membranes if the active agent may not release at the predetermined rate. For those skilled in the art, the composition and thickness of the membrane can readily be identified using similar experimental procedures illustrated above.

Parameters Tested
Thickness of EVA film: 40-300 micrometers
Elution rate: 0.00025-0.025 micrograms/hr
Preferred elution rate: 0.00025-0.0075 micrograms/hr The drug core film was prepared using a solvent casting technique. 50 mg of latanoprost arginine salt and 200 mg of EVA-40 (Sigma Chemical Company, St. Louis, Mo.) were dissolved in 3 mL of dichloromethane (DCM). The polymer solution was cast on a custom-made polydimethylsiloxane (PDMS) substrate, and the cast film was dried at ambient temperature in a fume hood for 2 days. The drug core film with a thickness of 100-125 micrometers was removed from the base and cut into disc-shaped pieces with a diameter of 2 mm using a biopsy punch.

EVA-25 (Sigma Chemical Company, St. Louis, Mo.) was loaded into a film maker (International Crystal Laboratory) with a 100-micrometer spacer and heated to 95° C. for 4 minutes. The polymer was compressed at 400 psi for 1 minute and allowed to cool to room temperature. The polymer membrane with a thickness of 125 micrometers was removed from the base and cut into disc-shaped membranes with a diameter of 4 mm using a biopsy punch. This polymer membrane was permeable to water when prepared in this manner. Some of these 4-mm membranes were subsequently manufactured to donut-shaped rings with an outer diameter of 4 mm and an inner diameter of 2 mm. This polymer membrane is the "spacer ring" (FIGS. 46-65). A 2-mm drug core film containing latanoprost argininc salt and EVA-40 was then inserted into the void of a spacer ring, and both sides of the composite film were covered by a 4-mm EVA-25 film (the permeable membrane). The four-piece assembly (2 EVA-25 permeable membranes, 1 spacer ring, and 1 drug core film) was then heat-sealed at 90° C. using a custom-made die set and allowed to cool to room temperature.

In summary, this device was composed of a drug core film of 20% latanoprost arginine salt and 80% of EVA-40. The rate-limiting water permeable polymer was EVA-25, and the thickness of the water-permeable membranes was 125 micrometers. The elution rate in this particular design was approximately 0.005 micrograms/hr.

Example 18

Drug Delivery Device Containing Bimatoprost (a Low Solubility Drug)

Suggested Parameters
Thickness of EVA film: 40-300 micrometers
Elution rate: 0.003-0.3 micrograms/hr
Preferred elution rate: 0.002-0.1 micrograms/hr The drug core film was prepared using a solvent casting technique. 50 mg of bimatoprost and 200 mg of EVA-40 (Sigma Chemical Company, St. Louis, Mo.) were dissolved in 3 mL of dichloromethane (DCM). The polymer solution was cast on a custom-made polydimethylsiloxane (PDMS) substrate, and the cast film was dried at ambient temperature in a fume hood for 2 days. The drug core film with a thickness of 100-125 micrometers was removed from the base and cut into disc-shaped pieces with a diameter of 2 mm using a biopsy punch.

EVA-25 (Sigma Chemical Company, St. Louis, Mo.) was loaded into a film maker (International Crystal Laboratory) with a 100-micrometer spacer and heated to 95° C. for 4 minutes. The polymer was compressed at 400 psi for 1 minute and allowed to cool to room temperature. The polymer membrane with a thickness of 125 micrometers was removed from the base and cut into disc-shaped membranes with a diameter of 4 mm using a biopsy punch. This polymer membrane was permeable to water when prepared in this manner. Some of these 4-mm membranes were subsequently manufactured to donut-shaped rings with an outer diameter of 4 mm and an inner diameter of 2 mm. This polymer membrane is the "spacer ring" (FIGS. 46-65). A 2-mm drug core film containing bimatoprost and EVA-40 was then inserted into the void of a spacer ring, and both sides of the composite film were covered by a 4-mm EVA-25 film (the permeable membrane). The four-piece assembly (2 EVA-25 permeable membranes, 1 spacer ring, and 1 drug core film) was then heat-sealed at 90° C. using a custom-made die set and allowed to cool to room temperature.

In summary, this device was composed of a drug core film of 20% bimatoprost and 80% of EVA-40. The rate-limiting water permeable polymer was EVA-25, and the thickness of the water-permeable membranes was 125 micrometers. The elution rate in this particular design was approximately 0.015-0.020 micrograms/hr.

Example 19

Drug Delivery Device Containing Y-39983 Free Base (a Moderately Soluble Drug)

Parameters Tested
Thickness of EVA film: 40-300 micrometers
Elution rate: 0.01-1.0 micrograms/hr
Preferred elution rate: 0.04-0.6 micrograms/hr The drug core film was prepared using a solvent casting technique. 100 mg of Y-39983 free base and 100 mg of EVA-40 (Sigma Chemical Company, St. Louis, Mo.) were dissolved in 3 mL of dichloromethane (DCM). The polymer solution was cast on a custom-made polydimethylsiloxane (PDMS) substrate, and the cast film was dried at ambient temperature in a fume hood for 2 days. The drug core film with a thickness of 75-90 micrometers was removed from the base and cut into disc-shaped pieces with a diameter of 2.5 mm using a biopsy punch.

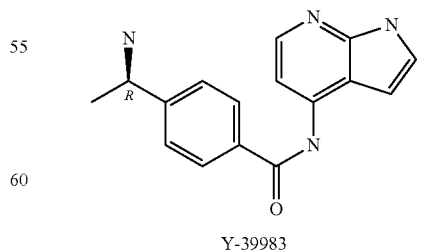

Y-39983

EVA-40 (Sigma Chemical Company, St. Louis, Mo.) was loaded into a film maker (International Crystal Laboratory) with a 50-micrometer spacer and heated to 75° C. for 4 minutes. The polymer was compressed at 300 psi for 1 minute and allowed to cool to room temperature. The polymer membrane with a thickness of 90 micrometers was removed from the base and cut into disc-shaped membranes with a diameter of 4 mm using a biopsy punch. This polymer membrane was permeable to water when prepared in this manner. Some of these 4-mm membranes were subsequently manufactured to donut-shaped rings with an outer diameter of 4 mm and an inner diameter of 2.5 mm. This polymer membrane is the "spacer ring" (FIGS. 46-65). A 2.5-mm drug core film containing Y-39983 free base and EVA-40 was then inserted into the void of a spacer ring, and both sides of the composite film were covered by a 4-mm EVA-40 film (the permeable membrane). The four-piece assembly (2 EVA-40 permeable membranes, 1 spacer ring, and 1 drug core film) was then heat-sealed at 75° C. using a custom-made die set and allowed to cool to room temperature.

In summary, this device was composed of a drug core film of 50% Y-39983 free base and 50% EVA-40. The rate-limiting water permeable polymer was EVA-40, and the thickness of the water-permeable membranes was 90 micrometers. The elution rate in this particular design was approximately 0.015-0.020 micrograms/hr.

Example 20

Drug Delivery Device Containing Latanoprost Arginine Salt (a Moderately Soluble Drug)

Parameters Tested
Thickness of EVA film: 40-300 micrometers
Elution rate: 0.0005-0.03 micrograms/hr
Preferred elution rate: 0.0005-0.015 micrograms/hr The drug core film was prepared using a solvent casting technique. 50 mg of latanoprost arginine salt and 200 mg of EVA-40 (Sigma Chemical Company, St. Louis, Mo.) were dissolved in 3 mL of dichloromethane (DCM). The polymer solution was cast on a custom-made polydimethylsiloxane (PDMS) substrate, and the cast film was dried at ambient temperature in a fume hood for 2 days. The drug core film with a thickness of 90-100 micrometers was removed from the base and cut into disc-shaped pieces with a diameter of 2 mm using a biopsy punch.

EVA-40 (Sigma Chemical Company, St. Louis, Mo.) was loaded into a film maker (International Crystal Laboratory) with a 50-micrometer spacer and heated to 75° C. for 4 minutes. The polymer was compressed at 300 psi for 1 minute and allowed to cool to room temperature. The polymer membrane with a thickness of 100 micrometers was removed from the base and cut into oval-shaped membranes with an aspect ratio of 7.5 mm×3 mm using a biopsy punch. This polymer membrane was permeable to water when prepared in this manner. Some of these 7.5 mm×3 mm oval-shaped membranes were subsequently manufactured to eye-shaped rings with a void of 2 mm at the center of the membrane. This polymer membrane is the "spacer ring" (FIGS. 66-75). A 2-mm drug core film containing latanoprost arginine salt and EVA-40 was then inserted into the void of a spacer ring, and both sides of the composite film were covered by a 7.5 mm×3 mm EVA-40 film (the permeable membrane). The four-piece assembly (2 EVA-40 permeable membranes, 1 spacer ring, and 1 drug core film) was then heat-sealed at 75° C. using a custom-made die set and allowed to cool to room temperature.

In summary, this device was composed of a drug core film of 20% latanoprost arginine salt and 80% of EVA-40. The rate-limiting water permeable polymer was EVA-40, and the thickness of the water-permeable membranes was 100 micrometers. The elution rate in this particular design was approximately 0.012 micrograms/hr.

Various features and advantages of the invention are set forth in the following claims.

What is claimed is:

1. A device, comprising:
   a composition in the form of a matrix of an active agent and a non-water soluble polymer, wherein the active agent comprises a latanoprost free acid salt, and wherein the non-water soluble polymer comprises ethylene vinyl acetate,
   a first polymer portion;
   a second polymer portion fused to the first polymer portion, the second polymer portion including a recess configured to support the composition; and
   a third polymer portion fused to the second polymer portion;
   wherein the total diameter of the device ranges from 3-5 mm, and
   wherein the device is configured to:
   (a) conform to a curvature of the eye,
   (b) yield an elution rate of 0.00025-0.0075 micrograms/hr of the active agent, and
   (c) release 70% to 90% of the active agent over a period of at least 30 days.

2. The device of claim 1, wherein the first polymer portion, the second polymer portion, and the third polymer portion is selected from the group of: ethylene vinyl acetate with a vinyl acetate content from 10% to 50% by weight (EVA-10-50) and ethylene vinyl alcohol with a vinyl alcohol content from 40% to 80% by weight (EVOH40-80).

3. The device of claim 1, wherein the first polymer portion, the second polymer portion, and the third polymer portion are manufactured from the same polymer.

4. The device of claim 1, wherein the first polymer portion, the second polymer portion, and the third polymer portion are manufactured from a non-water soluble polymer.

5. The device of claim 4, wherein the non-water soluble polymer is ethylene vinyl acetate having a vinyl acetate content of from 9% to 50% by weight.

6. The device of claim 5, wherein the ethylene vinyl acetate content in the first polymer portion, the second polymer portion, and the third polymer portion are the same.

7. The device of claim 5, wherein the ethylene vinyl acetate content in the first polymer portion, the second polymer portion, and the third polymer portion are different.

8. The device of claim 1, wherein the non-water soluble polymer of the composition is ethylene vinyl acetate having a vinyl acetate content of from 9% to 50% by weight.

* * * * *